(12) United States Patent
Ebright et al.

(10) Patent No.: US 9,919,998 B2
(45) Date of Patent: Mar. 20, 2018

(54) ANTIBACTERIAL AGENTS: Nα-AROYL-N-ARYL-PHENYLALANINAMIDES

(71) Applicant: Rutgers, The State University of New Jersey, New Brunswick, NJ (US)

(72) Inventors: Richard H. Ebright, New Brunswick, NJ (US); Yon W. Ebright, New Brunswick, NJ (US); Soma Mandal, New Brunswick, NJ (US); Richard Wilde, New Brunswick, NJ (US); Shengjian Li, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/116,787

(22) PCT Filed: Feb. 6, 2015

(86) PCT No.: PCT/US2015/014899
§ 371 (c)(1),
(2) Date: Aug. 4, 2016

(87) PCT Pub. No.: WO2015/120320
PCT Pub. Date: Aug. 13, 2015

(65) Prior Publication Data
US 2016/0347708 A1    Dec. 1, 2016

Related U.S. Application Data

(60) Provisional application No. 61/936,710, filed on Feb. 6, 2014.

(51) Int. Cl.
| | |
|---|---|
| *C07C 233/88* | (2006.01) |
| *A61K 31/167* | (2006.01) |
| *A61K 31/341* | (2006.01) |
| *A61K 31/4402* | (2006.01) |
| *A61K 31/4409* | (2006.01) |
| *C07D 213/75* | (2006.01) |

(Continued)

(52) U.S. Cl.
CPC ............ *C07C 233/88* (2013.01); *A01N 37/22* (2013.01); *A01N 37/24* (2013.01); *A01N 43/10* (2013.01); *A01N 43/30* (2013.01); *A01N 43/32* (2013.01); *A01N 43/36* (2013.01); *A01N 43/38* (2013.01); *A01N 43/40* (2013.01); *A01N 43/48* (2013.01); *A01N 43/50* (2013.01); *A01N 43/52* (2013.01); *A01N 43/56* (2013.01); *A01N 43/60* (2013.01); *A01N 43/62* (2013.01); *A01N 43/647* (2013.01); *A01N 43/653* (2013.01); *A01N 43/713* (2013.01); *A01N 43/78* (2013.01); *A01N 43/84* (2013.01); *A01N 43/90* (2013.01); *A61K 31/167* (2013.01); *A61K 31/341* (2013.01); *A61K 31/4402* (2013.01); *A61K 31/4409* (2013.01); *C07C 237/20* (2013.01); *C07D 207/14* (2013.01); *C07D 209/08* (2013.01); *C07D 209/40* (2013.01); *C07D 209/42* (2013.01); *C07D 211/58* (2013.01); *C07D 213/75* (2013.01); *C07D 213/81* (2013.01); *C07D 213/82* (2013.01); *C07D 215/38* (2013.01); *C07D 215/40* (2013.01); *C07D 217/22* (2013.01); *C07D 231/56* (2013.01); *C07D 235/06* (2013.01); *C07D 237/30* (2013.01); *C07D 241/04* (2013.01); *C07D 249/06* (2013.01); *C07D 249/08* (2013.01); *C07D 249/18* (2013.01); *C07D 257/04* (2013.01); *C07D 265/30* (2013.01); *C07D 277/62* (2013.01); *C07D 295/135* (2013.01); *C07D 295/155* (2013.01); *C07D 295/185* (2013.01); *C07D 295/205* (2013.01); *C07D 307/82* (2013.01); *C07D 317/66* (2013.01); *C07D 319/18* (2013.01); *C07D 333/38* (2013.01); *C07D 333/54* (2013.01); *C07D 333/66* (2013.01); *C07D 401/12* (2013.01); *C07D 405/12* (2013.01); *C07D 409/12* (2013.01); *C07D 471/04* (2013.01); *C07D 487/04* (2013.01); *C07C 2602/08* (2017.05); *C07C 2602/10* (2017.05)

(58) Field of Classification Search
CPC ... C07C 233/88; C07C 237/20; C07D 209/08; C07D 333/54; C07D 295/205; C07D 207/14; C07D 277/62; C07D 209/40; C07D 209/42; C07D 213/75; C07D 295/135; C07D 295/155; C07D 295/185; C07D 333/38
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |

(Continued)

OTHER PUBLICATIONS

Ballell et al (ChemMedChem, 2013, 8(2), 313-321).*
Agarwal, et al., "Synthesis of de novo designed small-molecule inhibitors of bacterial RNA polymerase", Tetrahedron 64, 10049-10054 (2008).
Ballell, et al., "Fueling Open-Source Drug Discovery: 177 Small-Molecule Leads against Tuberculosis", ChemMedChem 8, 313-321 (2013).
Chopra, "Bacterial RNA polymerase: a promising target for the discovery of new antimicrobial agents", Curr. Opin. Investig. Drugs 8, 600-607 (2007).
Collins, et al., "Microplate alamar blue assay versus BACTEC 460 system for high-throughput screening of compounds against *Mycobacterium tuberculosis* and *Mycobacterium avium*", Antimicrob Agents Chemother 41(5), 1004-1009 (1997).

(Continued)

*Primary Examiner* — Sudhakar Katakam
(74) *Attorney, Agent, or Firm* — Viksnins Harris Padys Malen LLP

(57) ABSTRACT

The invention provides compounds having activity as bacterial RNA polymerase inhibitors and antibacterial agents, as well as compositions comprising the compounds and methods for their use. Specifically, phenylalanineamide and tyrosinamide compounds are disclosed that have inhibitory activity toward *mycobacterium tuberculosis* RNA polymerase. Use of these compounds in the treatment or prevention of *M. tuberculosis* infections in a mammal, is disclosed.

23 Claims, 4 Drawing Sheets

(51) Int. Cl.

| | |
|---|---|
| C07D 213/81 | (2006.01) |
| C07D 213/82 | (2006.01) |
| C07D 215/38 | (2006.01) |
| C07D 215/40 | (2006.01) |
| C07D 217/22 | (2006.01) |
| C07D 317/66 | (2006.01) |
| C07D 319/18 | (2006.01) |
| C07D 231/56 | (2006.01) |
| C07D 333/38 | (2006.01) |
| C07D 333/66 | (2006.01) |
| C07D 235/06 | (2006.01) |
| C07D 401/12 | (2006.01) |
| C07D 237/30 | (2006.01) |
| C07D 405/12 | (2006.01) |
| C07D 409/12 | (2006.01) |
| C07D 241/04 | (2006.01) |
| C07D 249/06 | (2006.01) |
| C07D 249/08 | (2006.01) |
| C07D 249/18 | (2006.01) |
| C07D 471/04 | (2006.01) |
| C07D 257/04 | (2006.01) |
| C07D 487/04 | (2006.01) |
| C07D 265/30 | (2006.01) |
| C07D 207/14 | (2006.01) |
| C07D 277/62 | (2006.01) |
| C07D 209/40 | (2006.01) |
| C07D 209/42 | (2006.01) |
| C07D 211/58 | (2006.01) |
| C07D 295/135 | (2006.01) |
| C07D 295/155 | (2006.01) |
| C07D 295/185 | (2006.01) |
| C07D 295/205 | (2006.01) |
| C07D 307/82 | (2006.01) |
| C07C 237/20 | (2006.01) |
| A01N 37/22 | (2006.01) |
| A01N 43/10 | (2006.01) |
| A01N 43/30 | (2006.01) |
| A01N 43/32 | (2006.01) |
| A01N 43/36 | (2006.01) |
| A01N 43/40 | (2006.01) |
| A01N 43/50 | (2006.01) |
| A01N 43/52 | (2006.01) |
| A01N 43/56 | (2006.01) |
| A01N 43/60 | (2006.01) |
| A01N 43/62 | (2006.01) |
| A01N 43/647 | (2006.01) |
| A01N 43/78 | (2006.01) |
| A01N 43/90 | (2006.01) |
| A01N 37/24 | (2006.01) |
| A01N 43/38 | (2006.01) |
| A01N 43/48 | (2006.01) |
| A01N 43/653 | (2006.01) |
| A01N 43/713 | (2006.01) |
| A01N 43/84 | (2006.01) |
| C07D 209/08 | (2006.01) |
| C07D 333/54 | (2006.01) |

(56) References Cited

U.S. PATENT DOCUMENTS

| | | |
|---|---|---|
| 4,820,508 A | 4/1989 | Wortzman |
| 4,938,949 A | 7/1990 | Borch et al. |
| 4,992,478 A | 2/1991 | Geria |
| 2005/0187409 A1 | 8/2005 | Powers et al. |

OTHER PUBLICATIONS

Darst, "New inhibitors targeting bacterial RNA polymerase", Trends Biochem. Sci. 29 (4), 159-162 (2004).
Degen, et al., "Transcription inhibition by the depsipeptide antibiotic salinamide A", Elife 3, e02451, 29 pages (2014).
Hall, "Fluctuation analysis CalculatOR: a web tool for the determination of mutation rate using Luria-Delbruck fluctuation analysis", Bioinformatics 25, 1564-1565 (2009).
Ho, et al., "Structures of RNA polymerase-antibiotic complexes", Curr. Opin. Struct. Biol. 19, 715-723 (2009).
Jones, "Accounting for plating efficiency when estimating spontaneous mutation rates", Mutat Res 292, 187-189 (1993).
Klevens, et al., "Estimating health care-associated infections and deaths in U.S. hospitals, 2002.", Public Health Rep, 122(2), 160-166 (2007).
Lane, et al., "Molecular evolution of multisubunit RNA polymerases: sequence analysis", J. Mol. Biol. 395, 671-85 (2010).
Luria, et al., "Mutations of Bacteria from Virus Sensitivity to Virus Resistance", Genetics 28(6), 491-511 (1943).
Ma, et al., "Analysis of the Luria-Delbrück Distribution Using Discrete Convolution Powers", Journal of Applied Probability vol. 29(2), 255-267 (1992).
Mukhopadhyay, et al., "Translocation of sigma(70) with RNA polymerase during transcription: fluorescence resonance energy transfer assay for movement relative to DNA", Cell 106(4), 453-463 (2001).
Patent Cooperation Treaty, International Searching Authority, Search Report and Written Opinion for PCT/US2015/14899, 13 pages, dated Apr. 22, 2015.
PUBCHEM, CID 2955118, 11 pages, Create Date Jul. 29, 2005.
PUBCHEM, CID 7325930, 10 pages, Create date Jul. 29, 2006.
PUBCHEM, CID 970466, 10 pages, Create Date Jul. 9, 2005.
Sarkar, et al., "On fluctuation analysis: a new, simple and efficient method for computing the expected number of mutants", Genetica 85, 173-179 (1992).
Srivastava, et al., "New Target for Inhibition of Bacterial RNA Polymerase: Switch Region", Curr. Opin. Microbiol. 14, 532-543 (2011).
Stewart, et al., "Fluctuation analysis: the probability distribution of the number of mutants under different conditions", Genetics 124, 175-185 (1990).
Vassylyev, et al., "Crystal structure of a bacterial RNA polymerase holoenzyme at 2.6 Å resolution", Nature 417, 712-719 (2003).
Villain-Guillot, et al., "Progress in targeting bacterial transcription", Drug Discov. Today 12 (5/6), 200-208 (2007).
Zhang, et al., "GE23077 binds to the RNA polymerase 'i ' and 'i+1 ' sites and prevents the binding of initiating nucleotides",eLife 3, e02450 (2014).
Ballell, et al., "Supporting Information Fueling Open-Source Drug Discovery: 177 Small-Molecule Leads against Tuberculosis", ChemMedChem, 116 pages, (Jan. 1, 2013).
European Search Report, for EP Application No. 15745890.2, 15 pages, dated Sep. 25, 2017.
PUBCHEM, "Zinc46085605, C24H25C1N402S", Retrieved from the Internet: https://pubchem.ncbi.nlm.nih.gov/compound/52232232*section=Top [retrieved on Sep. 8, 2017], 10 pages, May 20, 2011.
Zvarec, et al., "5-Benzylidenerhodanine and 5-benzylidene-2-4-thiazolidinedione based antibacterials", Bioorganic & Medicinal Chemistry Letters 22, 2720-2722 (2012).

* cited by examiner

ANTIBACTERIAL AGENTS: Nα-AROYL-N-ARYL-PHENYLALANINAMIDES

CROSS-REFERENCE TO RELATED APPLICATIONS

This application is a 35 U.S.C. § 371 application of International Application No. PCT/US15/14899, filed Feb. 6, 2015, which claims the benefit of U.S. Provisional Application No. 61/936,710, filed Feb. 6, 2014, which applications are hereby incorporated by reference in their entirety.

STATEMENT OF GOVERNMENT SUPPORT

This invention was made with government support under AI072766 and GM041376 awarded by the National Institutes of Health. The government has certain rights in the invention.

BACKGROUND

Bacterial infectious diseases kill 100,000 persons each year in the US and 11 million persons each year worldwide, representing nearly a fifth of deaths each year worldwide (Heron et al., *Final Data for 2006. National Vital Statistics Reports*, Vol. 57 (Centers for Disease Control and Prevention, Atlanta Ga.) and World Health Organization (2008) *The Global Burden of Disease: 2004 Update* (World Health Organization, Geneva)). In the US, hospital-acquired bacterial infections strike 2 million persons each year, resulting in 90,000 deaths and an estimated $30 billion in medical costs (Klevins et al., (2007) Estimating health care-associated infections and deaths in U.S. hospitals. *Public Health Reports*, 122, 160-166; Scott, R. (2009) *The direct medical costs of healthcare-associated infections in U.S. hospitals and benefits of prevention* (Centers for Disease Control and Prevention, Atlanta Ga.)). Worldwide, the bacterial infectious disease tuberculosis kills nearly 2 million persons each year. One third of the world's population currently is infected with tuberculosis, and the World Health Organization projects that there will be nearly 1 billion new infections by 2020, 200 million of which will result in serious illness, and 35 million of which will result in death. Bacterial infectious diseases also are potential instruments of biowarfare and bioterrorism.

For six decades, antibiotics have been a bulwark against bacterial infectious diseases. This bulwark is failing due to the appearance of resistant bacterial strains. For all major bacterial pathogens, strains resistant to at least one current antibiotic have arisen. For several bacterial pathogens, including tuberculosis, strains resistant to all current antibiotics have arisen.

Bacterial RNA polymerase (RNAP) is a target for antibacterial therapy (Darst, S. (2004) *Trends Biochem. Sci.* 29, 159-162; Chopra, I. (2007) *Curr. Opin. Investig. Drugs* 8, 600-607; Villain-Guillot, P., Bastide, L., Gualtieri, M. & Leonetti, J. (2007) *Drug Discov. Today* 12, 200-208; Ho, M., Hudson, B., Das, K., Arnold, E., Ebright, R. (2009) *Curr. Opin. Struct. Biol.* 19, 715-723; and Srivastava et al. (2011) *Curr. Opin. Microbiol.* 14, 532-543). The suitability of bacterial RNA polymerase as a target for antibacterial therapy follows from the fact that bacterial RNA polymerase is an essential enzyme (permitting efficacy), the fact that bacterial RNA polymerase subunit sequences are highly conserved (permitting broad-spectrum activity), and the fact that bacterial RNA polymerase-subunit sequences are highly conserved in human RNA polymerase I, RNA polymerase II, and RNA polymerase III (permitting therapeutic selectivity). Accordingly, new antibacterial agents are needed.

SUMMARY OF CERTAIN EMBODIMENTS OF THE INVENTION

The applicants disclose herein that compounds of general structural formulae (I), (II), (III), and (IV) inhibit mycobacterial RNA polymerase in vitro and inhibit one of the growth and the viability of a *mycobacterium* in culture. For example, the applicants disclose herein that the compounds Nα-(2-methylphenyl)-N-phenyl-phenylalaninamide, Nα-phenyl-N-(2-fluorophenyl)-phenylalaninamide, Nα-phenyl-N-(2-fluorophenyl)-phenylalaninamide, Nα-phenyl-N-phenyl-phenylalaninamide, Nα-phenyl-N-(4-pyridyl)-phenylalaninamide, and Nα-phenyl-N-(2-pyridyl)-phenylalaninamide inhibit *Mycobacterium tuberculosis* RNA polymerase in vitro (IC50s as low as 0.1 µM) and inhibit the growth of *Mycobacterium smegmatis* in culture (MICs as low as ~0.3 µg/ml).

The applicants have shown, through the isolation, sequencing, and characterization of resistant mutants of *Mycobacterium smegmatis*, that compounds of general structural formulae (I), (II), (III), and (IV) function through a site on RNA polymerase located at the base of the RNA polymerase "β lobe."

The applicants have shown, through the isolation, sequencing, and characterization of resistant mutants of *Mycobacterium smegmatis*, that compounds of general structural formulae (I), (II), (III), and (IV) function through a site on RNA polymerase that is different from, and does not overlap, the binding sites for the prior-art RNA polymerase inhibitors rifampin, myxopyronin, and lipiarmycin.

The applicants have shown that compounds of general structural formulae (I), (II), (III), and (IV) do not exhibit target-based cross-resistance with the prior-art RNA polymerase inhibitors rifampin, myxopyronin, and lipiarmycin.

The applicants have demonstrated that they are able to discover new compositions of matter according to general structural formulae (I), (II), (III), and (IV) that inhibit a bacterial RNA polymerase or that inhibit one of the growth of a bacterium and the viability of a bacterium. For example, the applicants have discovered that Nα-phenyl-N-(2-pyridyl)-phenylalaninamide, a new composition of matter according to general structural formula (I), (II), (III), or (IV), inhibits *Mycobacterium tuberculosis* RNA polymerase in vitro (IC50~1 µM) and inhibits the growth of *Mycobacterium smegmatis* in culture (MIC~3 µg/ml).

Certain embodiments of the invention provide for use of an Nα-aroyl-N-aryl-phenylalaninamide to inhibit an RNA polymerase from a bacterium or to inhibit growth or viability of a bacterium.

In certain embodiments, the invention provides for use of an Nα-aroyl-N-aryl-phenylalaninamide to inhibit an RNA polymerase from a *mycobacterium* or to inhibit growth of viability of a *mycobacterium*.

In certain embodiments, the invention provides for use of an Nα-aroyl-N-aryl-phenylalaninamide to inhibit RNA polymerase from one of *Mycobacterium tuberculosis, Mycobacterium bovis, Mycobacterium leprae, Mycobacterium avium*, and *Mycobacterium smegmatis* or to inhibit growth or viability of *Mycobacterium tuberculosis, Mycobacterium bovis, Mycobacterium leprae, Mycobacterium avium*, and *Mycobacterium smegmatis*.

The invention has applications, e.g., in antibacterial prophylaxis, antibacterial therapy, and drug discovery.

Compounds of general structural formulae (I), (II), (III), and (IV) have utility as inhibitors of a bacterial RNA polymerase, as antibacterial agents, as antimycobacterial agents and as antituberculosis agents.

In particular, the applicants disclose herein that compounds of general structural formula (V) or (VI) highly potently inhibit mycobacterial RNA polymerase in vitro and inhibit one of the growth and the viability of a *mycobacterium* in culture. For example, the applicants disclose herein that the compounds 2-fluoro-N-(1-((5-fluoro-2-(piperazin-1-yl)phenyl)amino)-1-oxo-3-phenylpropan-2-yl)benzamide (IX-214), (R)-2-fluoro-N-(1-((5-fluoro-2-(piperazin-1-yl)phenyl)amino)-1-oxo-3-phenylpropan-2-yl)benzamide (IX-214a) (R)—N-(1-((5-chloro-2-(piperazin-1-yl)phenyl)amino)-1-oxo-3-phenylpropan-2-yl)-2-fluorobenzamide (IX-274), and (R)—N-(1-((5-chloro-2-(piperazin-1-yl)phenyl)amino)-1-oxo-3-phenylpropan-2-yl)-2-fluorobenzamide (IX-274a) highly potently inhibit *Mycobacterium tuberculosis* RNA polymerase in vitro (IC50s as low as 0.01 μM) and highly potently inhibit the growth of *Mycobacterium smegmatis*, *Mycobacterium tuberculosis*, and *Mycobacterium avium* in culture (MICs as low as 0.073 μg/ml).

The applicants have shown, through analysis of cross-resistance patterns, that compounds of general structural formula (V) or (VI) function through a site on RNA polymerase located at the base of the RNA polymerase "β lobe."

The applicants have shown, through further analysis of cross-resistance patterns, that compounds of general structural formula (V) or (VI) function through a site on RNA polymerase that is different from, and does not overlap, the binding sites for the prior-art RNA polymerase inhibitors rifampin, myxopyronin, and lipiarmycin.

The applicants have shown that compounds of general structural formula (V) or (VI) do not exhibit target-based cross-resistance with the prior-art RNA polymerase inhibitors rifampin, myxopyronin, and lipiarmycin.

The applicants have demonstrated that they are able to discover new compositions of matter according to general structural formula (V) or (VI) that inhibit a bacterial RNA polymerase or that inhibit one of the growth of a bacterium and the viability of a bacterium. For example, the applicants have discovered that 2-fluoro-N-(1-((5-fluoro-2-(piperazin-1-yl)phenyl)amino)-1-oxo-3-phenylpropan-2-yl)benzamide (IX-214), (R)-2-fluoro-N-(1-((5-fluoro-2-(piperazin-1-yl)phenyl)amino)-1-oxo-3-phenylpropan-2-yl)benzamide (IX-214a) (R)—N-(1-((5-chloro-2-(piperazin-1-yl)phenyl)amino)-1-oxo-3-phenylpropan-2-yl)-2-fluorobenzamide (IX-274), and (R)—N-(1-((5-chloro-2-(piperazin-1-yl)phenyl)amino)-1-oxo-3-phenylpropan-2-yl)-2-fluorobenzamide (IX-274a), new compositions of matter according to general structural formula (V) or (VI), highly potently inhibit *Mycobacterium tuberculosis* RNA polymerase in vitro (IC50s=0.01-0.074 μM) and highly potently inhibit the growth of *Mycobacterium smegmatis Mycobacterium tuberculosis*, and *Mycobacterium avium* in culture (MICs=0.073-0.78 g/ml).

Certain embodiments of the invention provide for use of a compound according to general structural formula (V) or (VI) to inhibit an RNA polymerase from a bacterium or to inhibit growth or viability of a bacterium.

In certain embodiments, the invention provides for use of a compound according to general structural formula (V) or (VI) to inhibit an RNA polymerase from a *mycobacterium* or to inhibit growth of viability of a *mycobacterium*.

In certain embodiments, the invention provides for use of a compound according to general structural formula (V) or (VI) to inhibit an RNA polymerase from one of *Mycobacterium tuberculosis, Mycobacterium bovis, Mycobacterium leprae, Mycobacterium avium, Mycobacterium abscessus, Mycobacterium ulcerans*, and *Mycobacterium smegmatis*, or to inhibit growth or viability of *Mycobacterium tuberculosis, Mycobacterium bovis, Mycobacterium leprae, Mycobacterium avium, Mycobacterium abscessus, Mycobacterium ulcerans*, and *Mycobacterium smegmatis*.

In certain embodiments, the invention provides for use of a compound according to general structural formula (V) or (VI) to prevent or treat an infection by a bacterium.

In certain embodiments, the invention provides for use of a compound according to general structural formula (V) or (VI) to prevent or treat an infection by a *mycobacterium*.

In certain embodiments, the invention provides for use of a compound according to general structural formula (V) or (VI) to prevent or treat an infection by one of *Mycobacterium tuberculosis, Mycobacterium bovis, Mycobacterium leprae, Mycobacterium avium, Mycobacterium abscessus, Mycobacterium ulcerans*, and *Mycobacterium smegmatis*, or to inhibit growth or viability of *Mycobacterium tuberculosis, Mycobacterium bovis, Mycobacterium leprae, Mycobacterium avium, Mycobacterium abscessus, Mycobacterium ulcerans*, and *Mycobacterium smegmatis*.

In certain embodiments, the invention provides a method of inhibiting a bacterial RNA polymerase, comprising contacting a bacterial RNA polymerase with a compound according to any of general structural formulae (V) and (VI).

In certain embodiments, the invention provides a method of inhibiting one of the growth and the viability of a bacterium, comprising contacting a bacterium with a compound according to any of general structural formulae (V) and (VI).

In certain embodiments, the invention provides a method of preventing or treating a bacterial infection, comprising administering to a mammal a compound according to any of general structural formulae (V) and (VI).

DETAILED DESCRIPTION OF THE INVENTION

Figure 1:
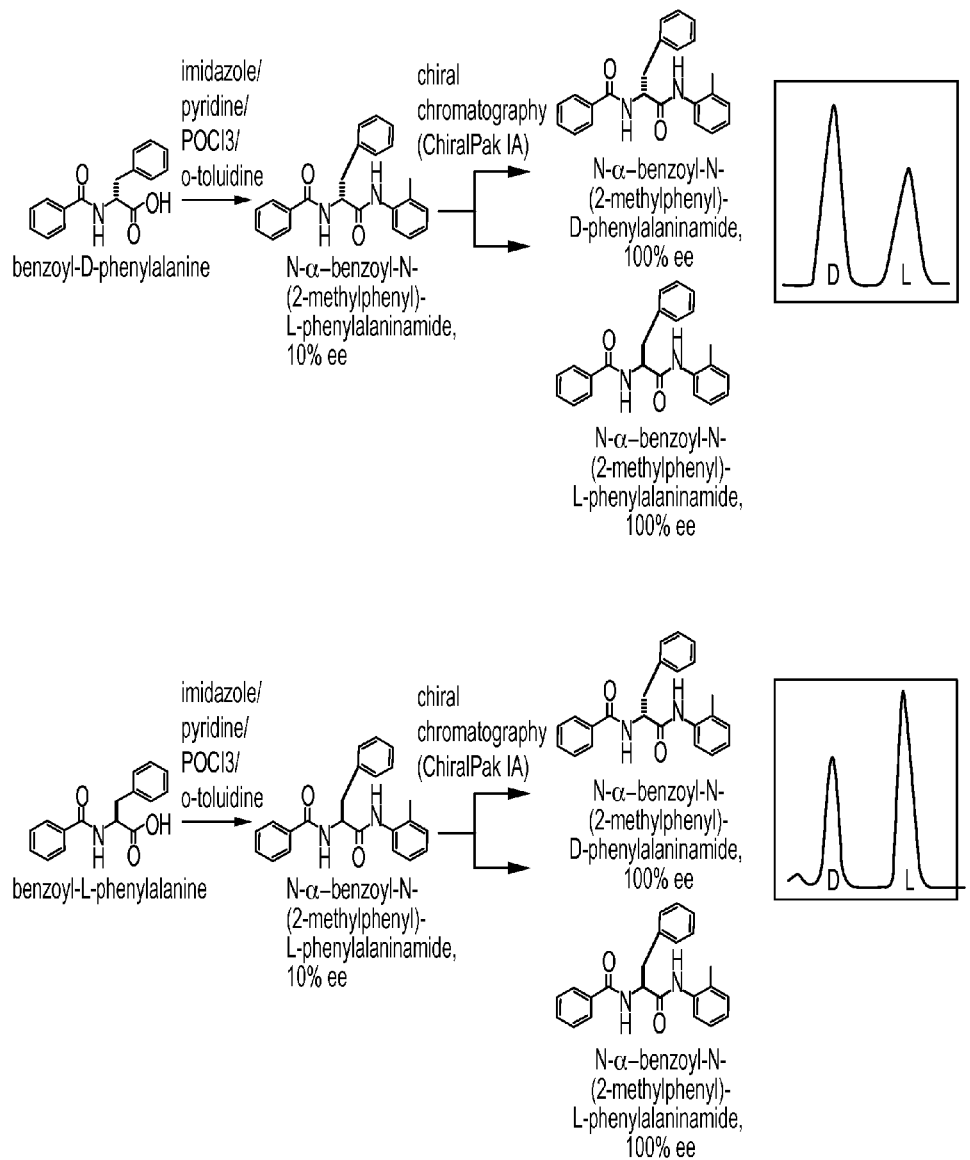
FIG. 1. (Upper panel) Preparation of the D stereoisomer of Nα-benzoyl-N-(2-methylphenyl)-phenylalaninamide (AAP1a) in enantiomeric excess (ee) by synthesis from D-benzoyl phenylalanine, and resolution of the D stereoisomer (peak eluting first) and the L stereoisomer (peak eluting second) by chiral chromatography on ChiralPak IA. (Lower panel) Preparation of the L stereoisomer of Nα-benzoyl-N-(2-methylphenyl)-phenylalaninamide (AAP1b) in enantiomeric excess (ee) by synthesis from L-benzoyl phenylalanine, and resolution of the D stereoisomer (peak eluting first) and the L stereoisomer (peak eluting second) by chiral chromatography on ChiralPak IA.

Certain embodiments of the invention provide the use of a compound according to general structural formula (I), or a salt thereof, to inhibit an RNA polymerase from a bacterium:

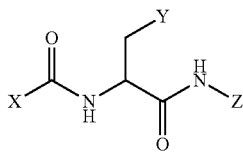

(I)

where X, Y, and Z are each independently aryl or heteroaryl.

In certain embodiments, where X is unsubstituted 2-thiophenyl and Y is unsubstituted phenyl, Z is not 2-morpholino-phenyl.

In certain embodiments, where X is unsubstituted 2-thiophenyl and Y is unsubstituted phenyl, Z is not 2-ethoxy-phenyl.

In certain embodiments, where X and Y are unsubstituted phenyl, Z is not 2-methyl-phenyl.

In certain embodiments, where X and Y are unsubstituted phenyl, Z is not 4-methyl-phenyl.

In certain embodiments, where X is unsubstituted 2-furyl and Y is unsubstituted phenyl, Z is not 4-methyl-phenyl.

In certain embodiments, where X is unsubstituted 2-furyl and Y is unsubstituted phenyl, Z is not 4-acetyl-phenyl.

Certain embodiments of the invention provide the use of a compound according to general structural formula (II), or a salt thereof, to inhibit an RNA polymerase from a bacterium:

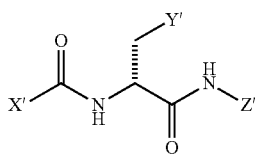

(II)

where X', Y', and Z' are each independently aryl or heteroaryl; and where the configuration of the Cα atom of the amino acid moiety containing Y' is D.

In certain embodiments, where X' is unsubstituted 2-thiophenyl and Y' is unsubstituted phenyl, Z' is not 2-morpholino-phenyl.

In certain embodiments, where X' is unsubstituted 2-thiophenyl and Y' is unsubstituted phenyl, Z' is not 2-ethoxy-phenyl.

In certain embodiments, where X' and Y' are unsubstituted phenyl, Z' is not 2-methyl-phenyl.

In certain embodiments, where X' and Y' are unsubstituted phenyl, Z' is not 4-methyl-phenyl.

In certain embodiments, where X' is unsubstituted 2-furyl and Y' is unsubstituted phenyl, Z' is not 4-acetyl-phenyl.

In certain embodiments, where X' is unsubstituted 2-furyl and Y' is unsubstituted phenyl, Z' is not 4-methyl-phenyl.

Certain embodiments of the invention provide the use of a compound according to general structural formula (III), or a salt thereof, to inhibit an RNA polymerase from a bacterium:

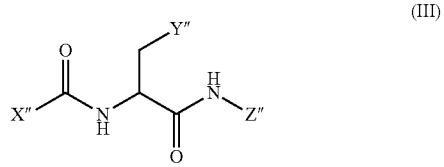

(III)

where X", Y", and Z" are each independently phenyl, pyridyl, pyrazinyl, furyl, thiophenyl, pyrrolyl, oxazoyl, thioxazoyl, isoxazoyl, thioisoxazoyl, napthyl, benzofuranyl, benzothiofuranyl, or indoyl, each optionally substituted with C1-C5 acyl, C1-C5-O-acyl, C1-C5-NH-acyl, carboxy, C1-C5 ester, C1-C5 amide, C1-C5 alkoxy, C1-C5-monoalkylamino, C1-C5 dialkylamino, amino, hydroxy, or halogen.

In certain embodiments, where X" is unsubstituted 2-thiophenyl and Y" is unsubstituted phenyl, Z" is not 2-morpholino-phenyl.

In certain embodiments, where X" is unsubstituted 2-thiophenyl and Y" is unsubstituted phenyl, Z" is not 2-ethoxy-phenyl.

In certain embodiments, where X" and Y" are unsubstituted phenyl, Z" is not 2-methyl-phenyl.

In certain embodiments, where X" and Y" are unsubstituted phenyl, Z" is not 4-methyl-phenyl.

In certain embodiments, where X" is unsubstituted 2-furyl and Y" is unsubstituted phenyl, Z" is not 4-acetyl-phenyl.

In certain embodiments, where X" is unsubstituted 2-furyl and Y" is unsubstituted phenyl, Z" is not 4-methyl-phenyl.

Certain embodiments of the invention provide the use of a compound according to general structural formula (IV), or a salt thereof, to inhibit an RNA polymerase from a bacterium:

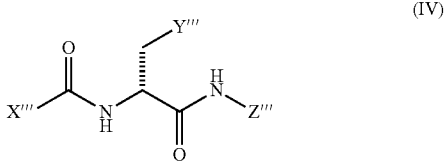

(IV)

where X''', Y''', and Z''' each independently is one of phenyl, pyridyl, pyrazinyl, furyl, thiophenyl, pyrrolyl, oxazoyl, thioxazoyl, isoxazoyl, thioisoxazoyl, napthyl, benzofuranyl, benzothiofuranyl, or indoyl, each optionally substituted with C1-C5 acyl, C1-C5-O-acyl, C1-C5-NH-acyl, carboxy, C1-C5 ester, C1-C5 amide, C1-C5 alkoxy, C1-C5-monoalkylamino, C1-C5 dialkylamino, amino, hydroxy, or halogen; and where the configuration of the Cα atom of the amino acid moiety containing Y is D.

In certain embodiments, where X''' is unsubstituted 2-thiophenyl and Y''' is unsubstituted phenyl, Z''' is not 2-morpholino-phenyl.

In certain embodiments, where X''' is unsubstituted 2-thiophenyl and Y''' is unsubstituted phenyl, Z''' is not 2-ethoxy-phenyl.

In certain embodiments, where X''' and Y''' are unsubstituted phenyl, Z''' is not 2-methyl-phenyl.

In certain embodiments, where where X''' and Y''' are unsubstituted phenyl, Z''' is not 4-methyl-phenyl.

In certain embodiments, where X''' is unsubstituted 2-furyl and Y''' is unsubstituted phenyl, Z''' is not 4-acetyl-phenyl.

In certain embodiments, where X''' is unsubstituted 2-furyl and Y''' is unsubstituted phenyl, Z''' is not 4-methyl-phenyl.

In certain embodiments, the compound according to general structural formula (I), (II), (III), or (IV), or a salt thereof, has an IC50 of less than about 25 micromolar for inhibiting an RNA polymerase from a bacterium.

In certain embodiments, the compound according to general structural formula (I), (II), (III), or (IV) is

AAP1

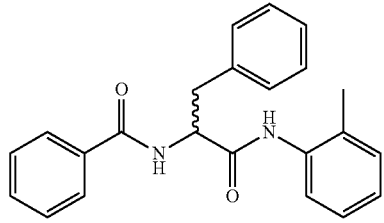

AAP1a

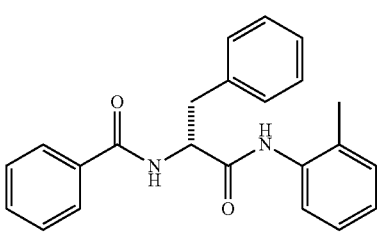

AAP1b

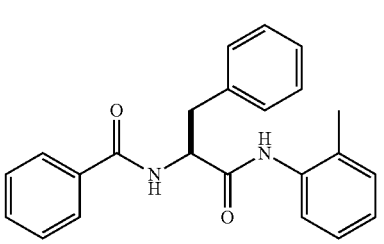

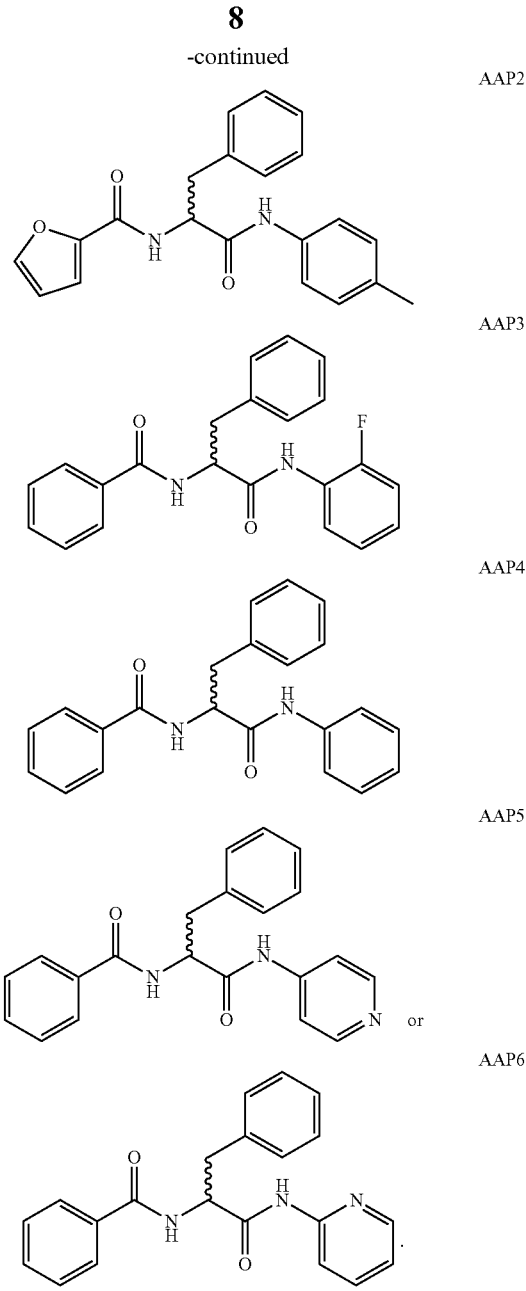

Certain embodiments of the invention provide the use of a compound according to general structural formula (I), (II), (III), or (IV), or a salt thereof, to inhibit an RNA polymerase from a *mycobacterium*.

Certain embodiments of the invention provide the use of a compound according to general structural formula (I), (II), (III), or (IV), or a salt thereof, to inhibit an RNA polymerase from one of *Mycobacterium tuberculosis, Mycobacterium bovis, Mycobacterium leprae, Mycobacterium avium*, and *Mycobacterium smegmatis.*

Certain embodiments of the invention provide the use of a compound according to general structural formula (I), (II), (III), or (IV), or a salt thereof, to inhibit the growth and/or the viability of a bacterium.

Certain embodiments of the invention provide the use of a compound according to general structural formula (I), (II), (III), or (IV), or a salt thereof, to inhibit the growth and/or the viability of a *mycobacterium*.

Certain embodiments of the invention provide the use of a compound according to general structural formula (I), (II), (III), or (IV), or a salt thereof, to inhibit the growth and/or the viability of one of *Mycobacterium tuberculosis, Mycobacterium bovis, Mycobacterium leprae, Mycobacterium avium*, and *Mycobacterium smegmatis*.

Certain embodiments of the invention provide the use of a compound according to general structural formula (I), (II), (III), or (IV), or a salt thereof, to prevent an infection by a bacterium.

Certain embodiments of the invention provide the use of a compound according to general structural formula (I), (II), (III), or (IV), or a salt thereof, to prevent an infection by a *mycobacterium*.

Certain embodiments of the invention provide the use of a compound according to general structural formula (I), (II), (III), or (IV), or a salt thereof, to prevent an infection by one of *Mycobacterium tuberculosis, Mycobacterium bovis, Mycobacterium leprae, Mycobacterium avium*, and *Mycobacterium smegmatis*.

Certain embodiments of the invention provide the use of a compound according to general structural formula (I), (II), (III), or (IV, or a salt thereof, to treat an infection by a bacterium.

Certain embodiments of the invention provide the use of a compound according to general structural formula (I), (II), (III), or (IV), or a salt thereof, to treat an infection by a *mycobacterium*.

Certain embodiments of the invention provide the use of a compound according to general structural formula (I), (II), (III), or (IV), or a salt thereof, to treat an infection by one of *Mycobacterium tuberculosis, Mycobacterium bovis, Mycobacterium leprae, Mycobacterium avium*, and *Mycobacterium smegmatis*.

Certain embodiments of the invention provide a method of inhibiting a bacterial RNA polymerase, comprising contacting a bacterial RNA polymerase with a compound according to general structural formula (I), (II), (III), or (IV), or a salt thereof.

Certain embodiments of the invention provide a method of inhibiting one of the growth and the viability of a bacterium, comprising contacting a bacterium with a compound according to general structural formula (I), (II), (III), or (IV), or a salt thereof.

Certain embodiments of the invention provide a method of preventing a bacterial infection, comprising administering to a mammal a compound according to general structural formula (I), (II), (III), or (IV), or a salt thereof.

Certain embodiments of the invention provide a method of treating a bacterial infection, comprising administering to a mammal a compound according to general structural formula (I), (II), (III), or (IV), or a salt thereof.

Certain embodiments of the invention provide a formulation comprising a compound according to general structural formula (I), (II), (III), or (IV), or a salt thereof, for administration to a mammal to prevent a bacterial infection.

Certain embodiments of the invention provide a formulation comprising a compound according to general structural formula (I), (II), (III), or (IV), or a salt thereof, for administration to a mammal to treat a bacterial infection.

Certain embodiments of the invention provide the administration of a formulation comprising a compound according to general structural formula (I), (II), (III), or (IV), or a salt thereof, to prevent a bacterial infection.

Certain embodiments of the invention provide the administration of a formulation comprising a compound according to general structural formula (I), (II), (III), or (IV), or a salt thereof, to treat a bacterial infection.

Certain embodiments of the invention provide a composition of matter according to general structural formula (V), or a salt thereof:

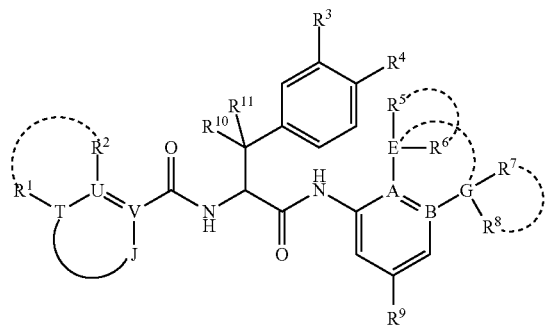

(V)

wherein T and U each is one of carbon and nitrogen;

V is carbon;

A and B each is one of carbon and nitrogen;

E is one of carbon (CH), nitrogen, oxygen, and sulfur;

G is absent or is one of hydrogen, halogen, carbon (CH), nitrogen, oxygen, and sulfur;

J is one of carbon and nitrogen, and J, together with T, U, V, and two additional atoms, forms a 6-membered cycle; or J is one of nitrogen, oxygen, and sulfur, and J, together with T, U, V, and one additional atom, forms a 5-membered cycle;

$R^1$ and $R^2$ each independently is absent, hydrogen, or halogen, or is alkyl, alkoxy-substituted alkyl, amino-substituted alkyl, aryl-substituted alkyl, or alkoxy, each optionally substituted by halogen; or $R^1$ and $R^2$, together with T and U, form a cycle containing 4 to 9 atoms selected from carbon, nitrogen, oxygen, and sulfur;

$R^3$ and $R^4$ each independently is hydrogen, halogen, hydroxyl, amine, amide, ester, phosphate, or O-methylphosphate; and $R^5$, $R^6$, $R^7$, and $R^8$ each independently is absent, hydrogen, or halogen, or is alkyl, alkoxy-substituted alkyl, hydroxy-substituted alkyl, amino-substituted alkyl, aryl-substituted alkyl, or alkoxy, each optionally substituted by halogen; or $R^5$ and $R^6$, together with E, form a cycle containing 3 to 9 atoms selected from carbon, nitrogen, oxygen, and sulfur, said cycle optionally substituted with halogen or alkyl, hydroxy-substituted alkyl, alkoxy-substituted alkyl, amino-substituted alkyl, aryl-substituted alkyl, alkoxy, acyl, or carbamidyl, each optionally substituted by halogen; or $R^7$ and $R^8$, together with G, form a cycle containing 3 to 8 atoms selected from carbon, nitrogen, oxygen, and sulfur, said cycle optionally substituted with alkyl, alkoxy-substituted alkyl, hydroxy-substituted alkyl, amino-substituted alkyl, or aryl-substituted alkyl, alkoxy, acyl, or carbamidyl, each optionally substituted by halogen; or $R^6$ and $R^7$ are absent and E and G, together with A and B, form a cycle containing 4 to 9 atoms selected from carbon, nitrogen, oxygen, and sulfur, said cycle optionally substituted with halogen or alkyl, hydroxy-substituted alkyl, alkoxy-substituted alkyl, amino-substituted alkyl, aryl-substituted alkyl, alkoxy, acyl, or carbamidyl, each optionally substituted by halogen; and $R^9$, $R^{10}$, and $R^{11}$ each independently is hydrogen or halogen;

provided that; when T, U, A, B, and E are carbon, G is hydrogen or is the carbon atom of an unsubstituted methyl group, J is carbon, oxygen, or sulfur, and $R^1$, $R^2$, $R^3$, $R^4$, $R^9$, $R^{10}$, and $R^{11}$ are hydrogen; then E is bonded to no more than two hydrogen atoms and no more than two fluorine atoms;

provided that; when T, U, A, B, and E are carbon, G is hydrogen, J is oxygen, $R^1$, $R^2$, $R^3$, $R^4$, $R^{10}$, and $R^1$ are hydrogen, and $R^9$ is halogen; then E is bonded to no more than two hydrogen atoms;

provided that; when T, U, A, B, E, and G are carbon, J is carbon or sulfur, $R^1$ is hydrogen or methoxy, $R^2$ is hydrogen or methyl, and $R^3$, $R^4$, $R^9$, $R^{10}$, and $R^{11}$ are hydrogen; then A, B, E, and G are not part of a phenyl cycle;

provided that; when T, U, A, and B, are carbon, E is nitrogen, G is carbon, J is oxygen, and $R^1$, $R^2$, $R^3$, $R^4$, $R^9$, $R^{10}$, and $R^{11}$ are hydrogen; then A, B, E, and G are not part of a pyridine cycle.

provided that; when T, U, A, B, are carbon, E is nitrogen, G is hydrogen, J is sulfur, and $R^1$, $R^2$, $R^3$, $R^4$, $R^9$, $R^{10}$, and $R^{11}$ are hydrogen; then E, $R^5$, and $R^6$ are not part of a morpholine cycle;

provided that; when T, U, A, and B, are carbon, E is oxygen, G is hydrogen, J is carbon or sulfur, and $R^1$, $R^3$, $R^9$, $R^{10}$, and $R^{11}$ are hydrogen; then E is not bonded to hydrogen or unsubstituted ethyl;

provided that; when T, U, A, and B, are carbon, E is oxygen, G is hydrogen, J is carbon or sulfur, and $R^1$, $R^2$, $R^3$, $R^9$, $R^{10}$, and $R^{11}$ are hydrogen, and $R^9$ is chlorine; then E is not bonded to hydrogen or unsubstituted methyl;

provided that; when T, U, A, and B, are carbon, E is oxygen, G is hydrogen, J is oxygen, and $R^1$, $R^2$, $R^3$, $R^4$, $R^9$, $R^{10}$, and $R^{11}$ are hydrogen; then E is not bonded to unsubstituted methyl; and provided that; when T, U, A, B, and E are carbon, G is hydrogen, J is carbon, and $R^3$, $R^4$, $R^9$, $R^{10}$, and $R^{11}$ are hydrogen; then E, $R^5$, and $R^6$ are not part of a phenyl cycle.

Certain embodiments of the invention provide compound of formula (V), which is a compound of formula (VI), or a salt thereof:

(VI)

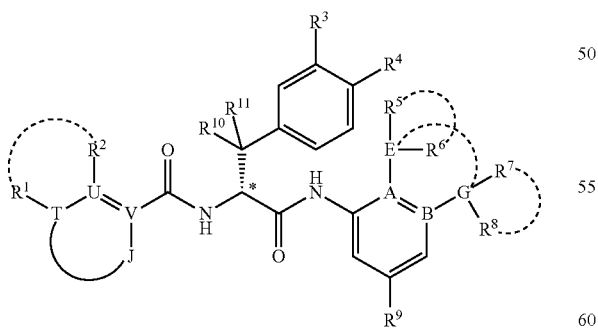

wherein where the configuration of the Cα atom of the central amino acid moiety, the carbon identified with the *, has the indicated, D, absolute configuration.

In certain embodiments, the compound according to general structural formula (V) or (VI) is

I-12

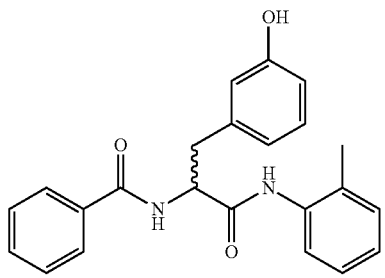

I-13

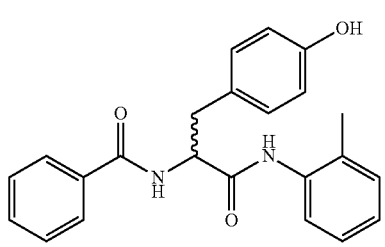

I-17

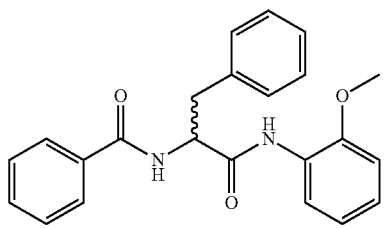

I-18

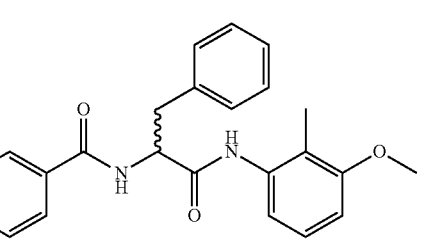

I-25

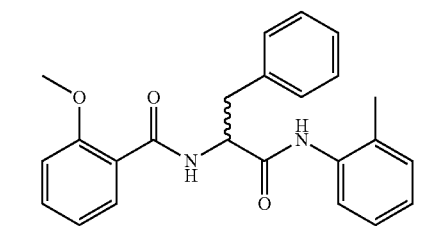

I-37

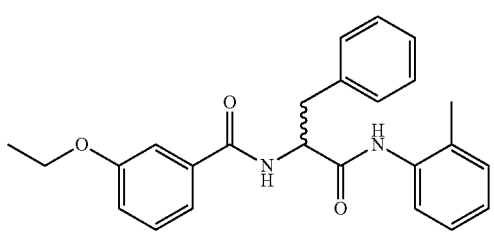

I-39
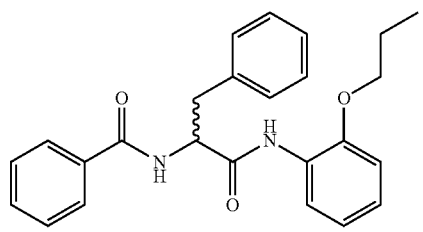
I-50
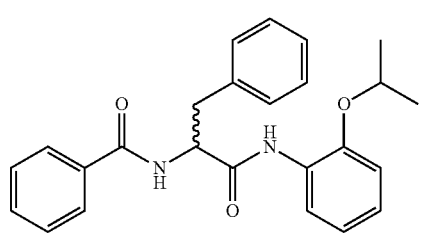
I-51
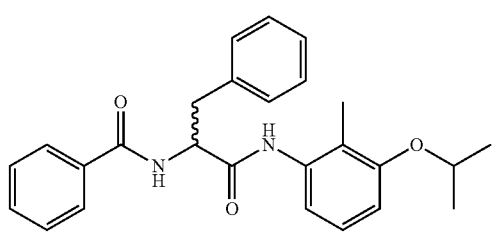
I-61
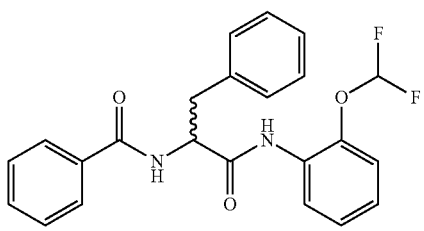
I-70
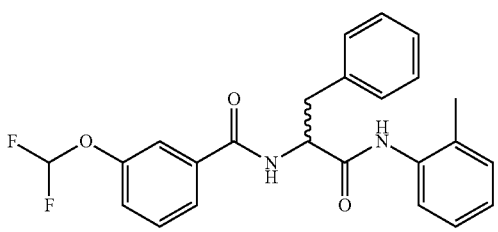
I-73
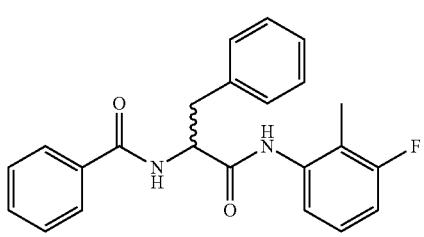
I-75
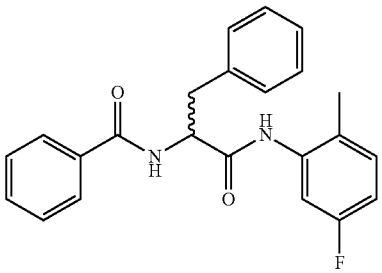
I-80
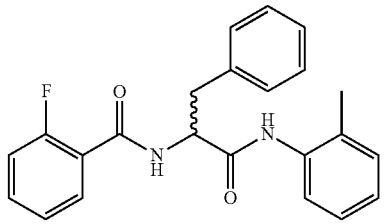
I-86
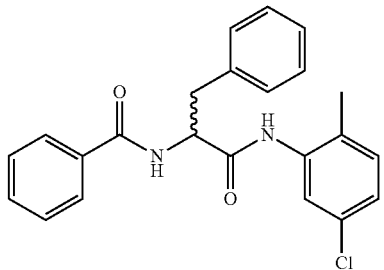
I-91
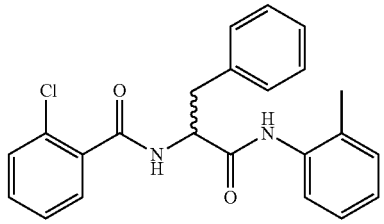
I-97
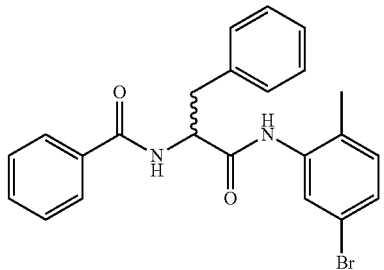
I-102
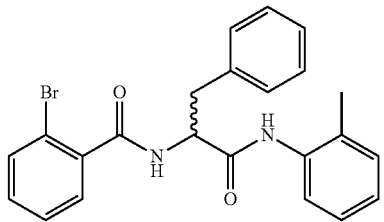

I-105
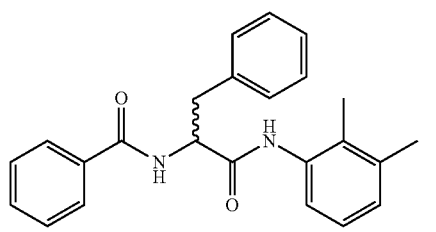
I-112
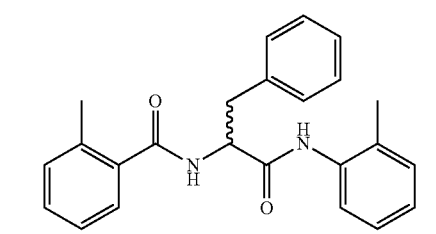
I-113
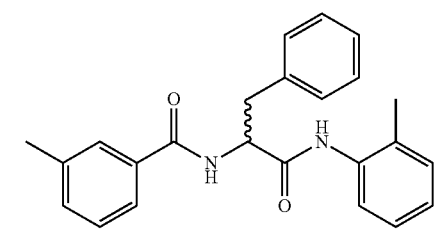
I-115
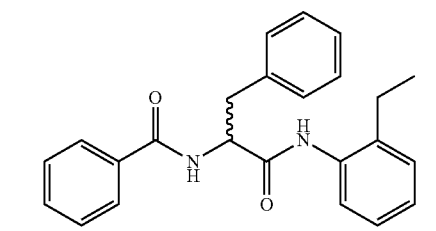
I-116
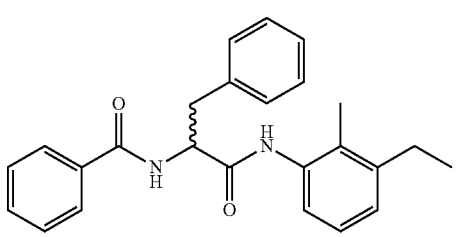
I-123
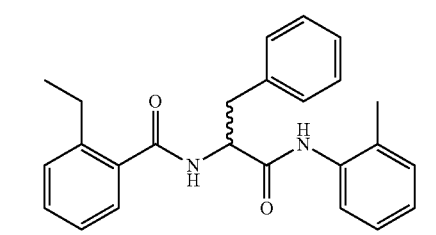
I-124
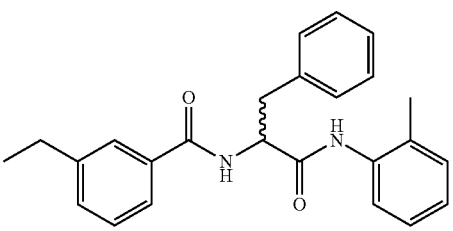
I-126
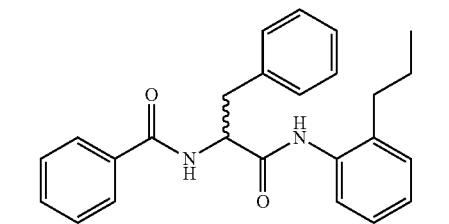
I-127
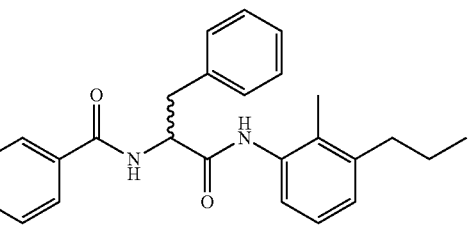
I-138
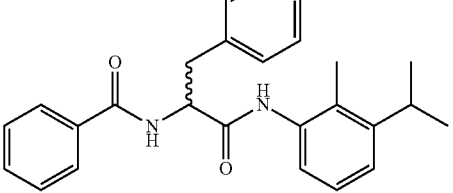
I-148
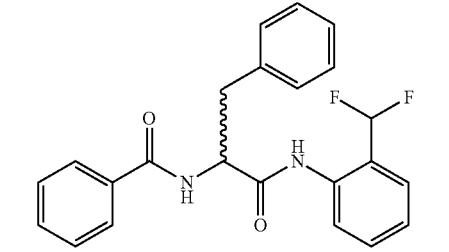
I-149
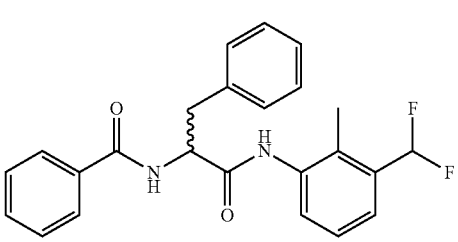

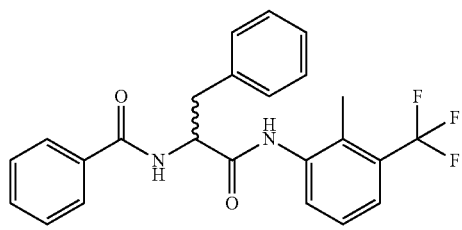
I-160
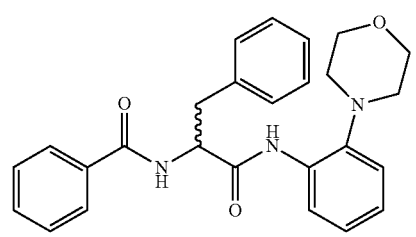
I-181
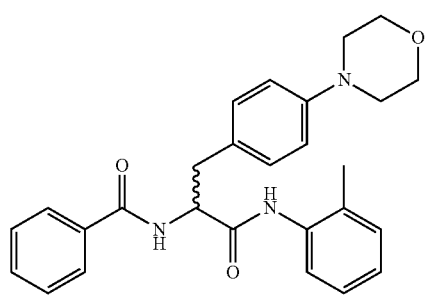
I-188
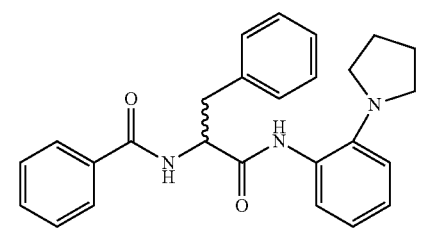
I-192
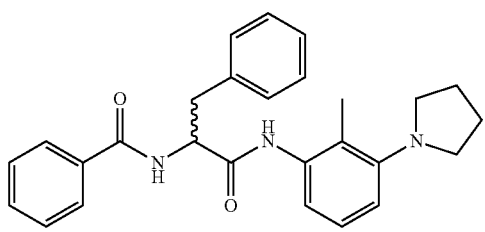
I-193
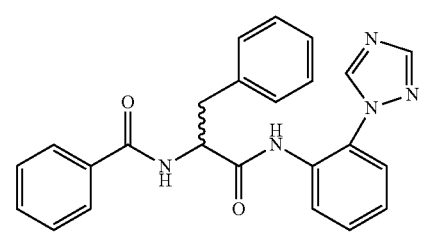
I-203
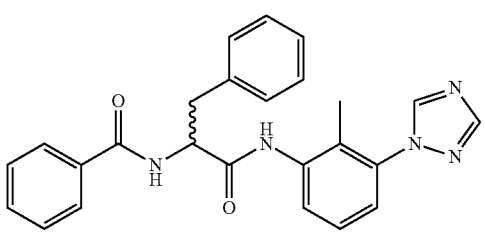
I-204
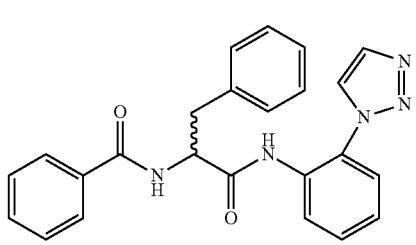
I-214
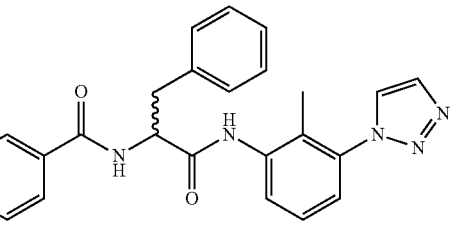
I-215
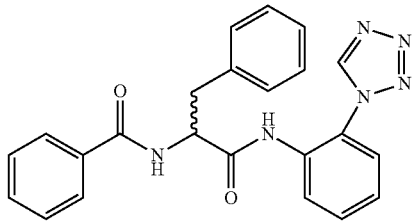
I-225
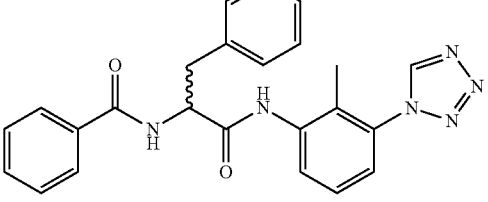
I-226
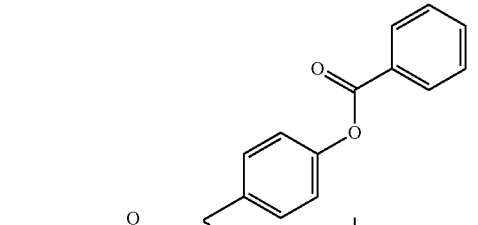
I-236

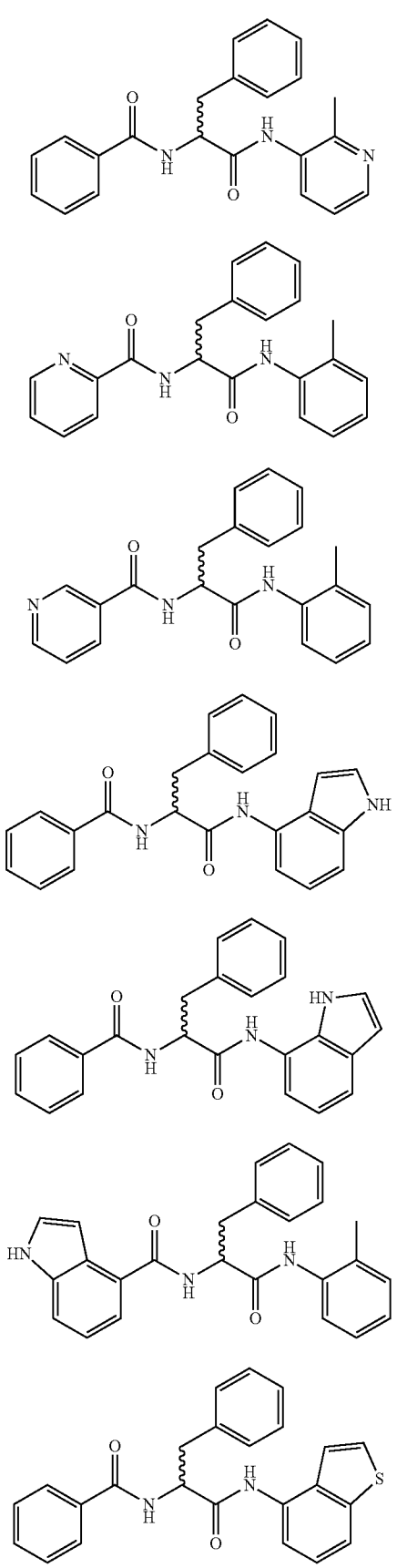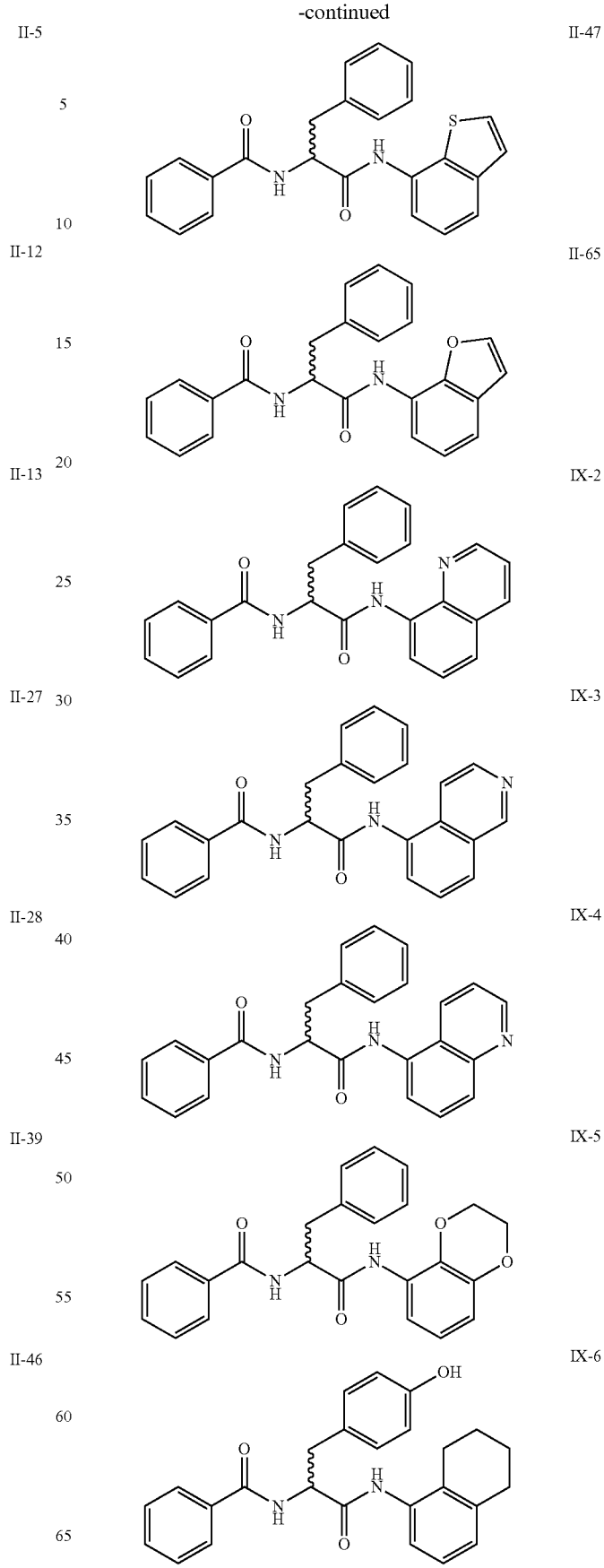

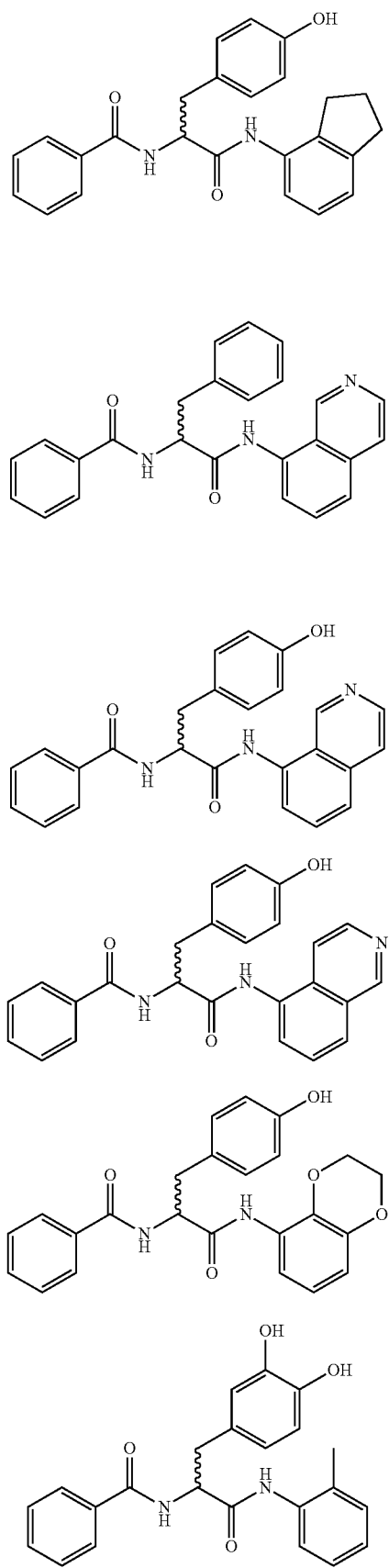
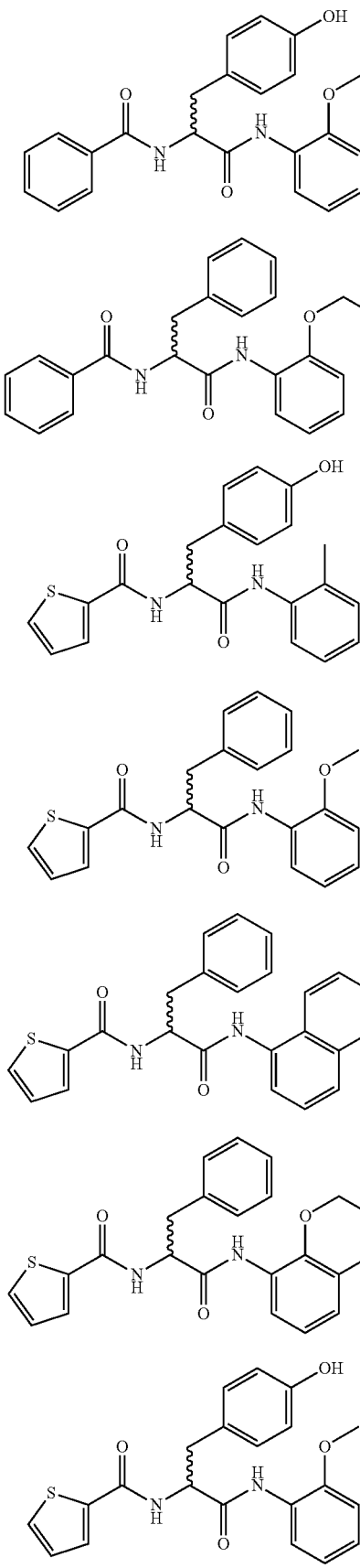

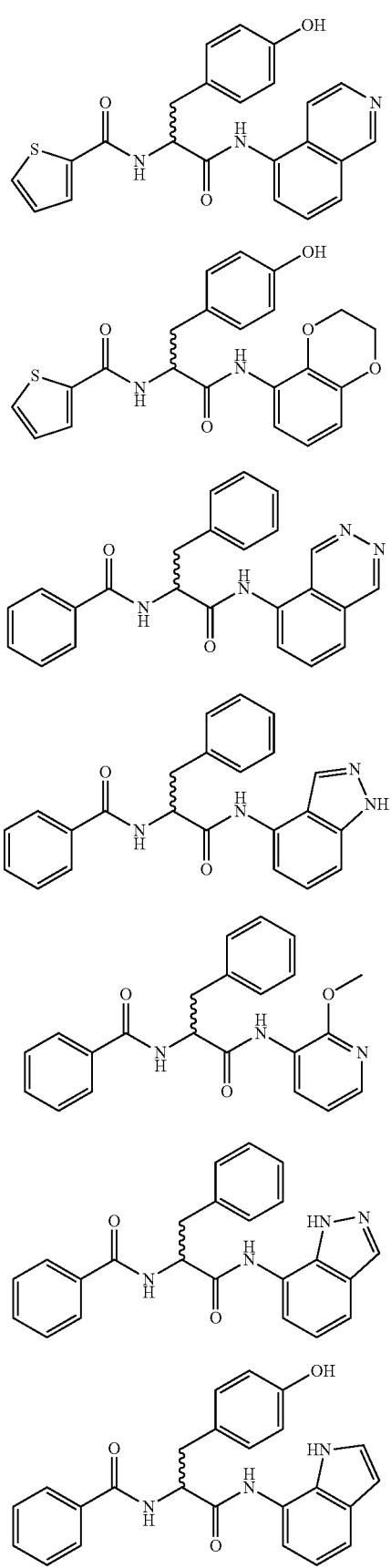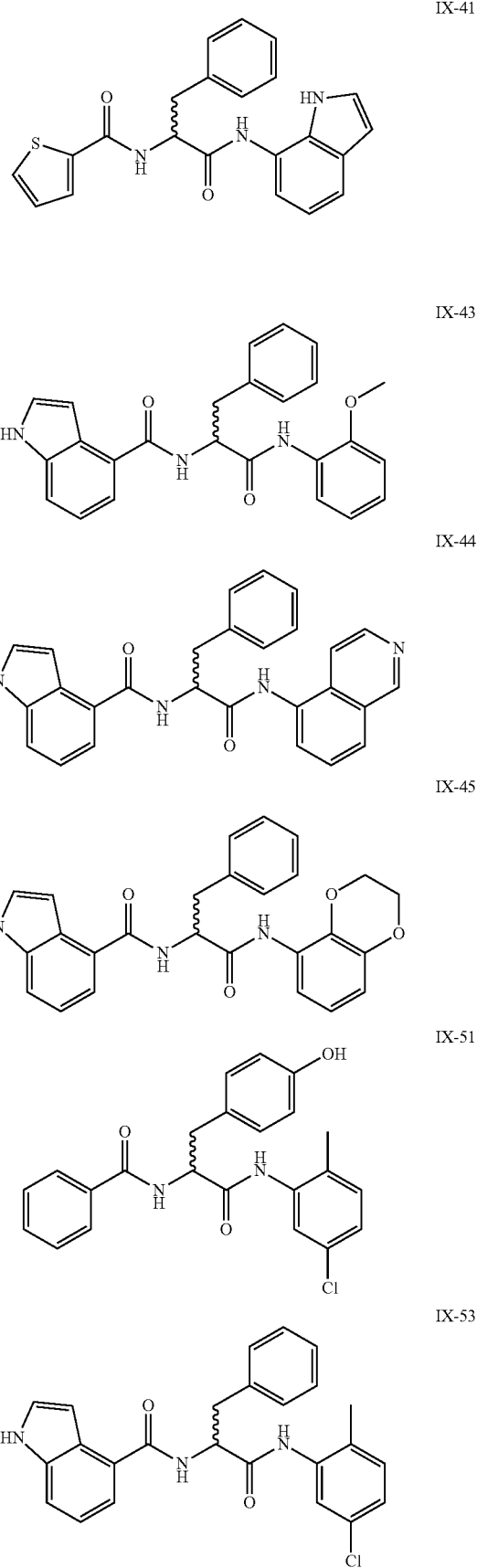

IX-54 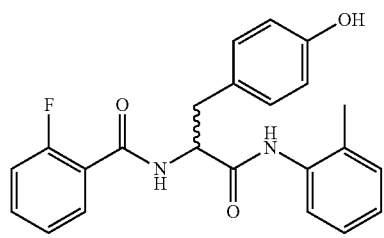
IX-55 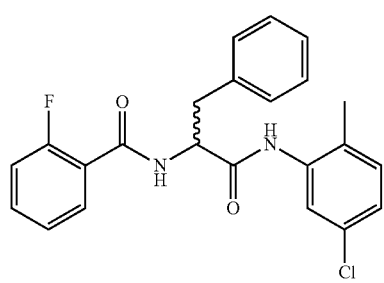
IX-55a 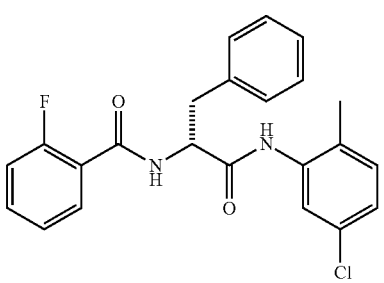
IX-55b 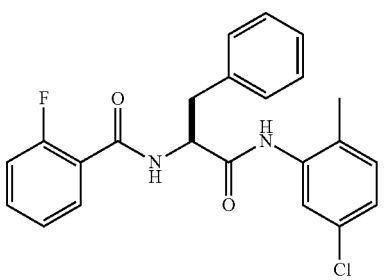
IX-56 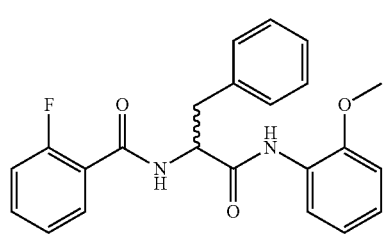
IX-57 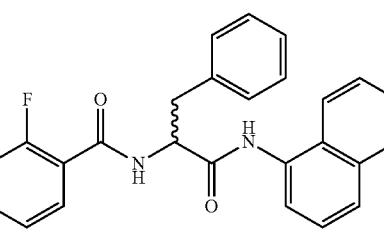
IX-58 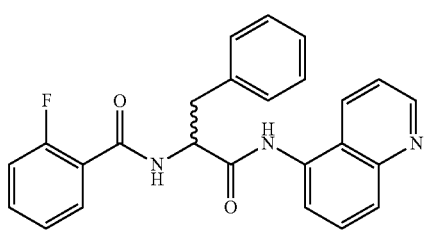
IX-59 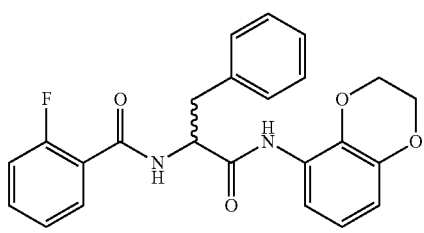
IX-60 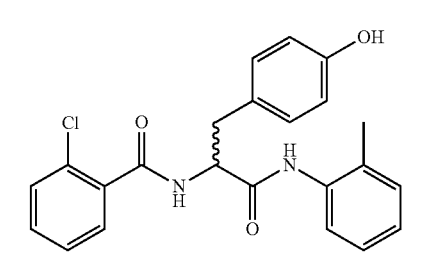
IX-61 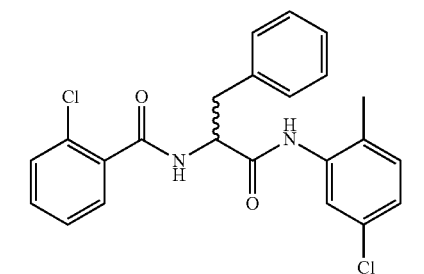
IX-62 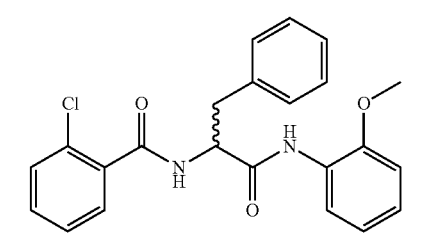
IX-63 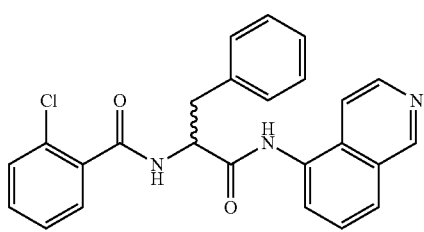

IX-64
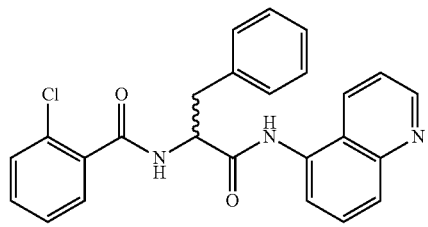
IX-65
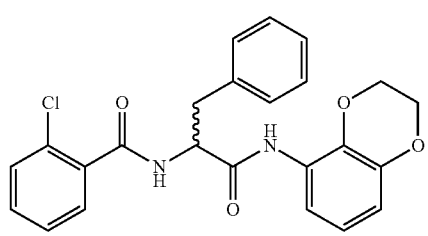
IX-66
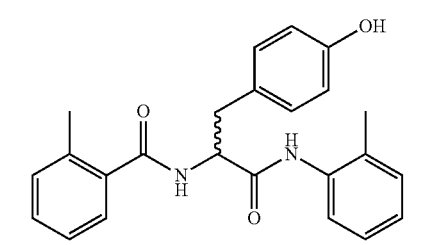
IX-67
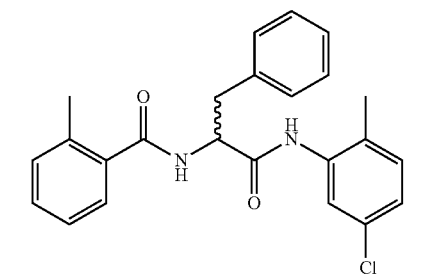
IX-68
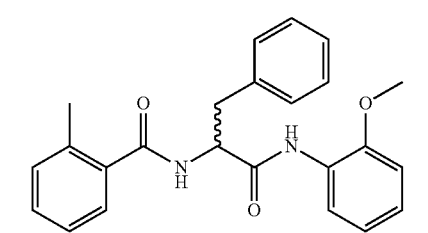
IX-69
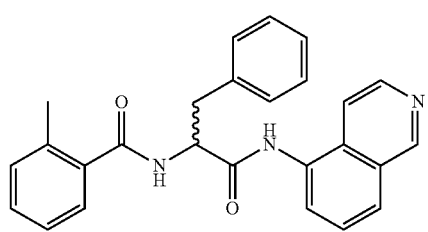
IX-70
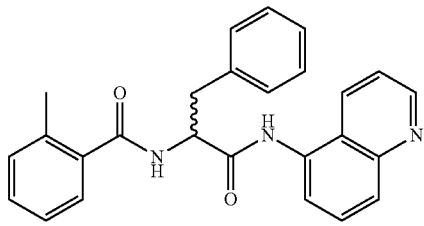
IX-71
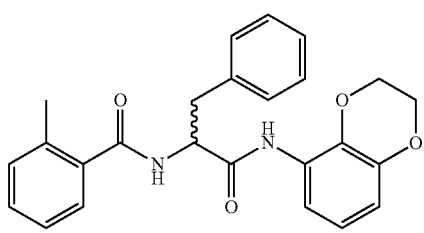
IX-72
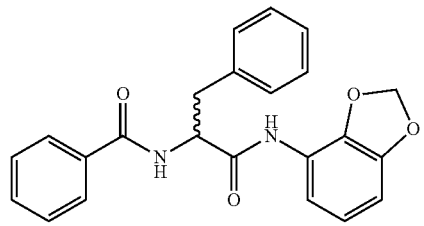
IX-73
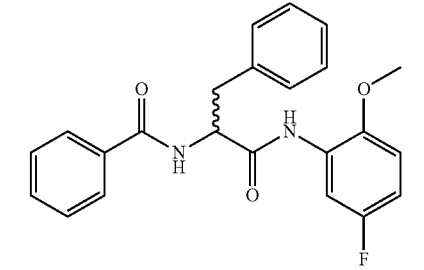
IX-75
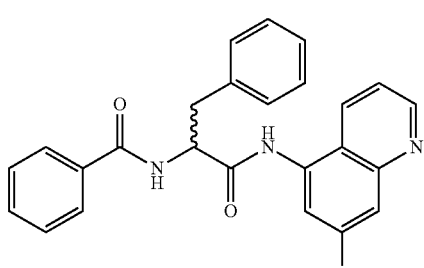
IX-79
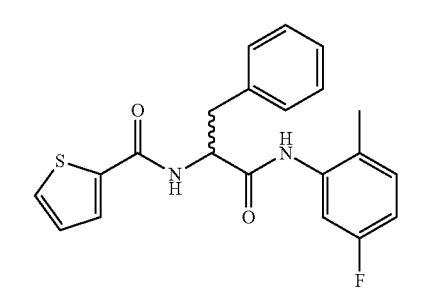

IX-80
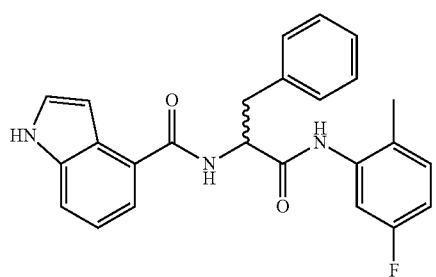
IX-81
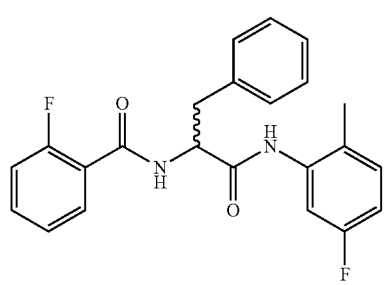
IX-82
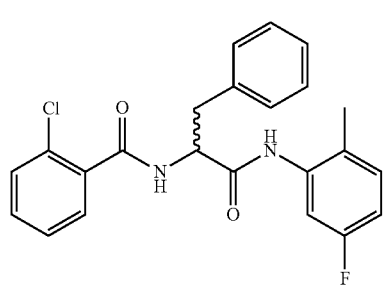
IX-83
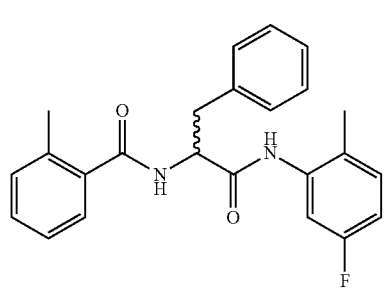
IX-85
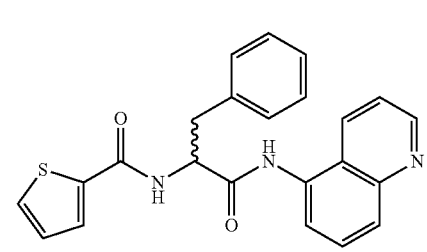
IX-86
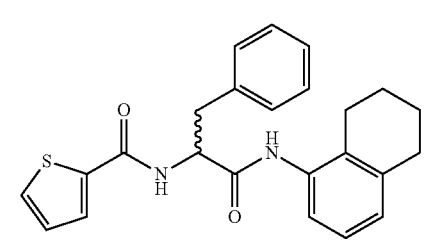
IX-91
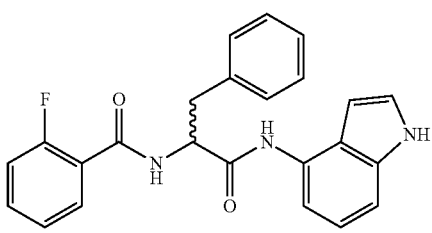
IX-94
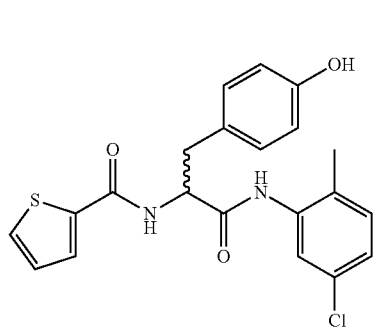
IX-95
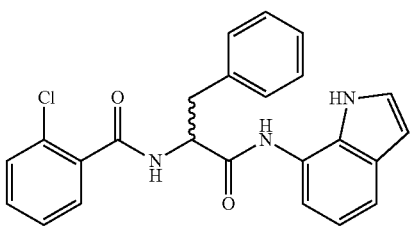
IX-96
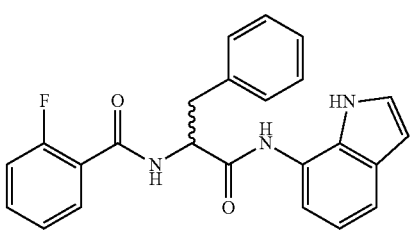
IX-97
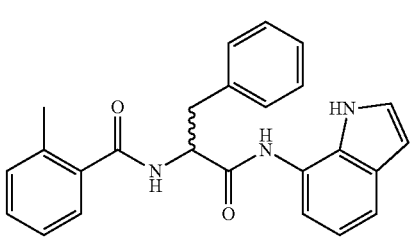
IX-98
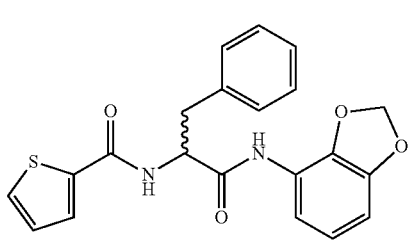

IX-99
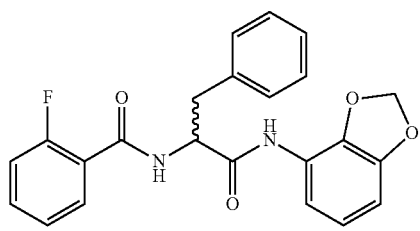
IX-107
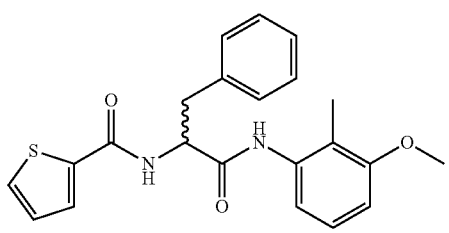
IX-100
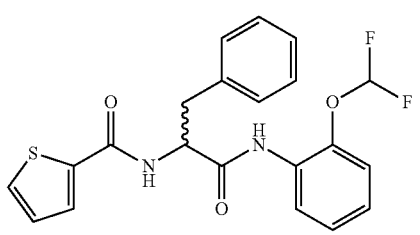
IX-108
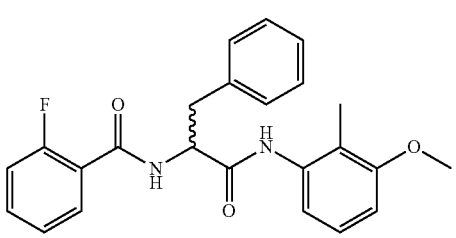
IX-101
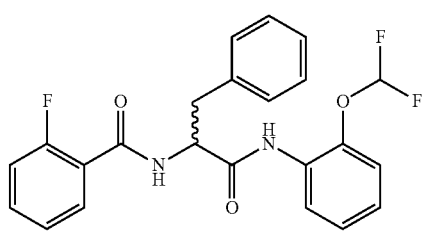
IX-111
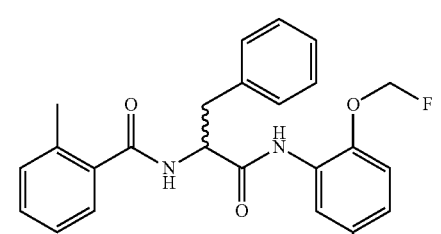
IX-103
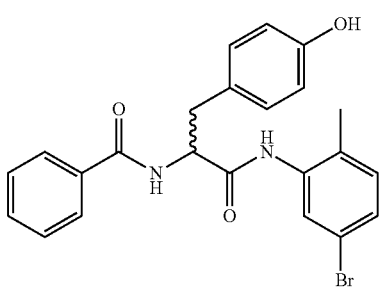
IX-119
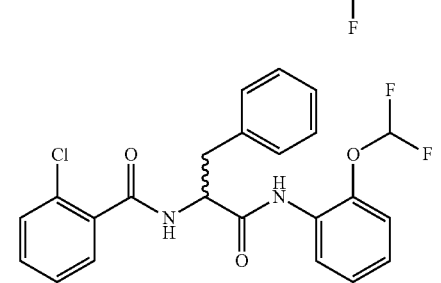
IX-104
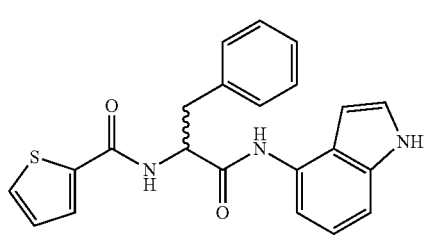
IX-120
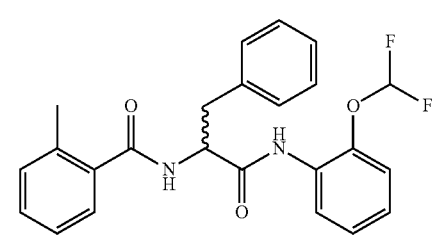
IX-105
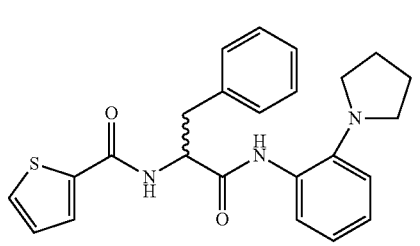
IX-122
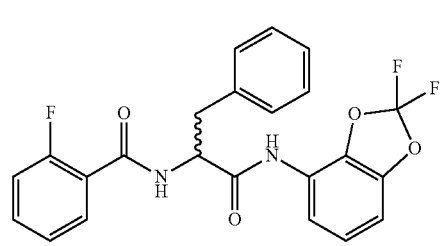

IX-124
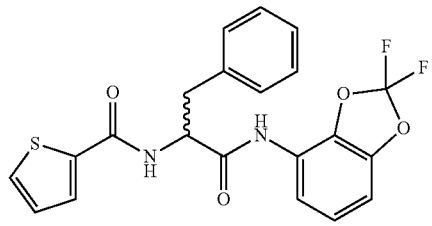
IX-125
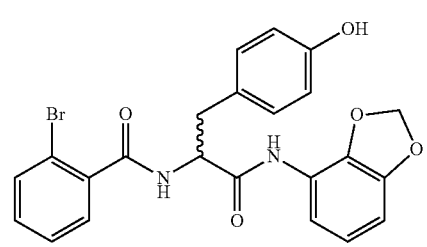
IX-128
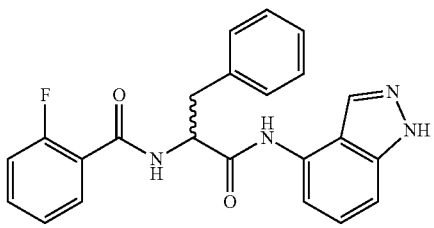
IX-149
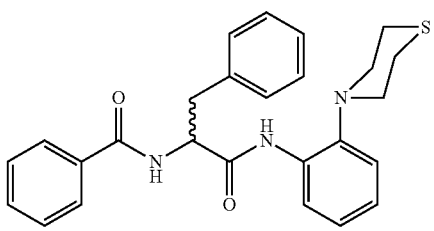
IX-150
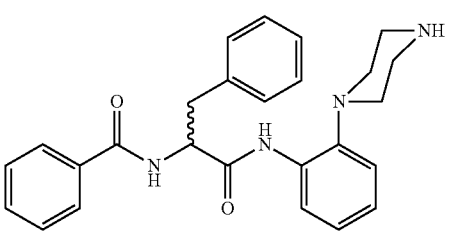
IX-151
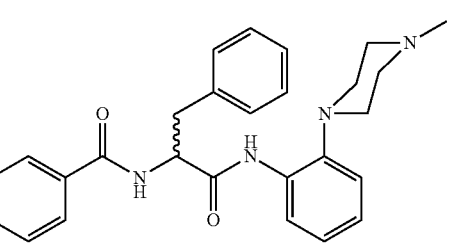
IX-152
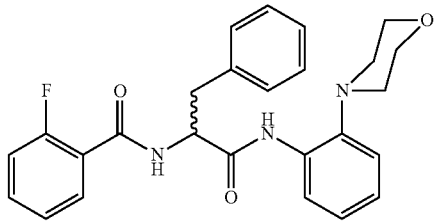
IX-153
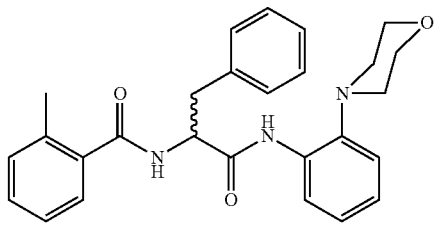
IX-154
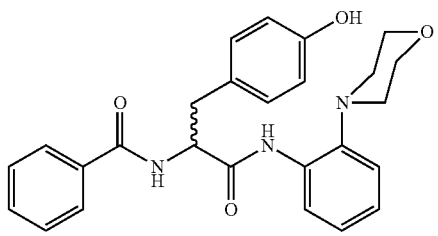
IX-155
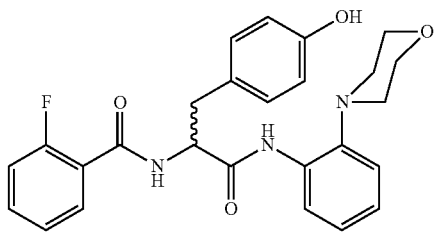
IX-156
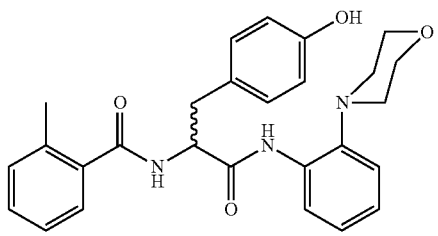
IX-157
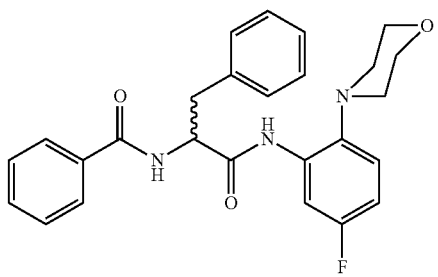

IX-158
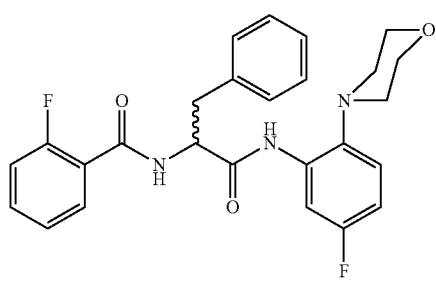
IX-159
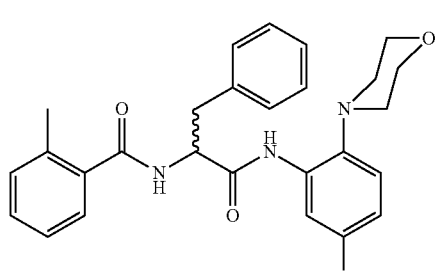
IX-160
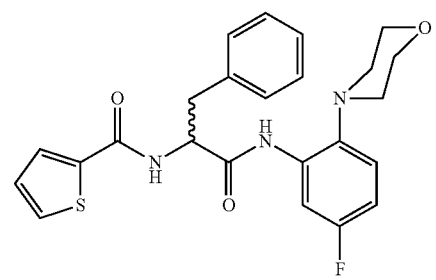
IX-176
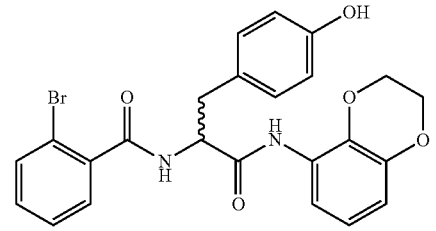
IX-177
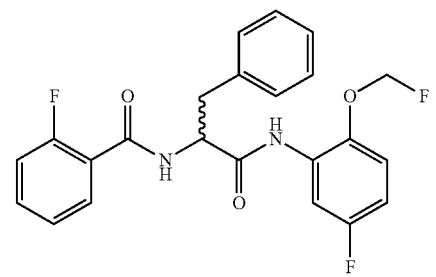
IX-180
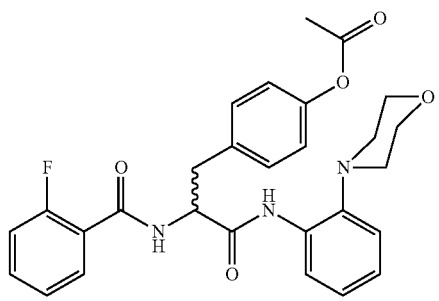
IX-181
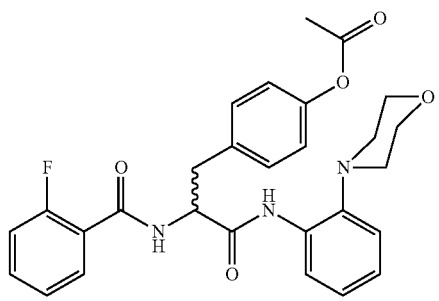
IX-182
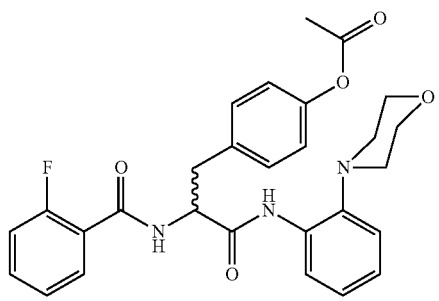
IX-183
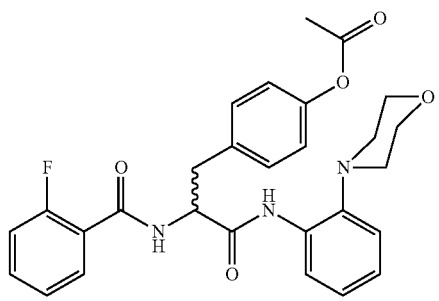
IX-184
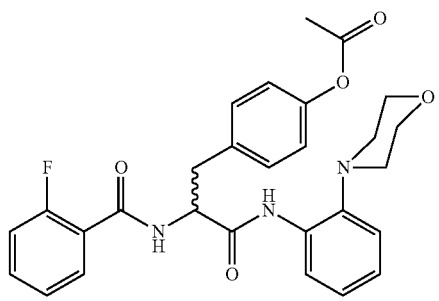

IX-186
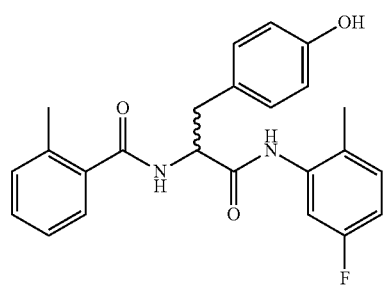
IX-188
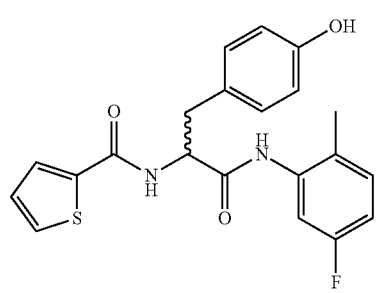
IX-191
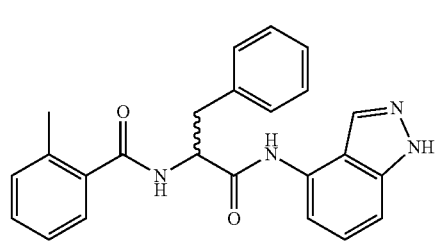
IX-201
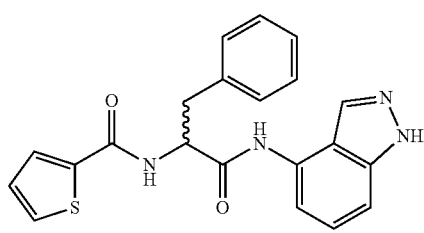
IX-203
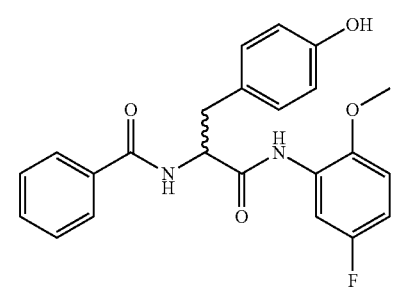
IX-204
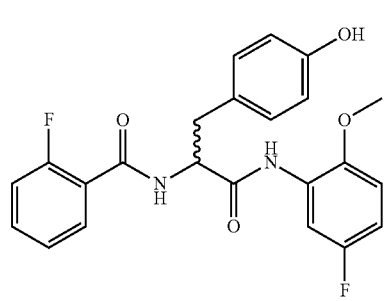
IX-205
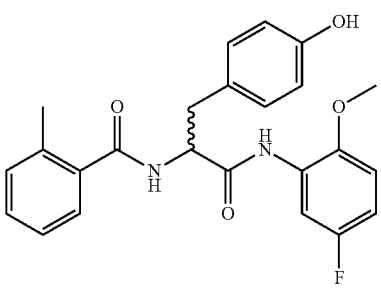
IX-206
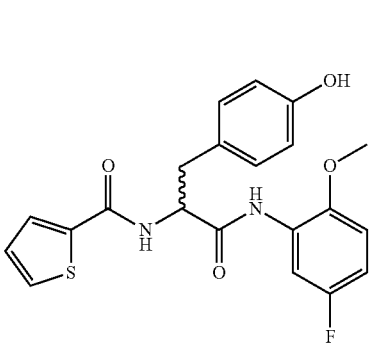
IX-211
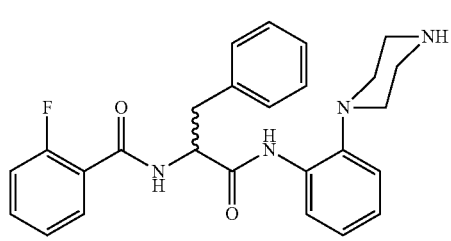
IX-212
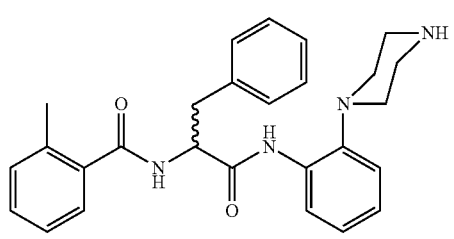
IX-213
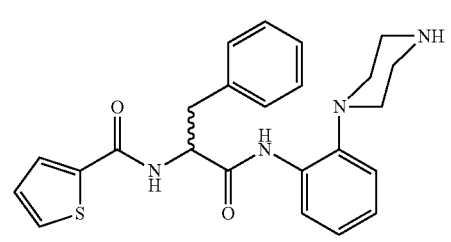
IX-214
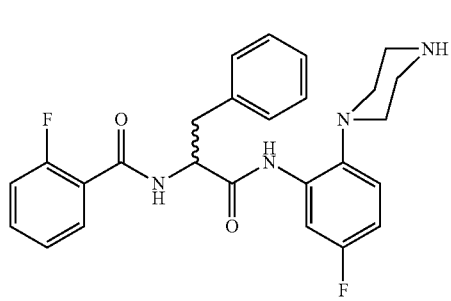

IX-214a
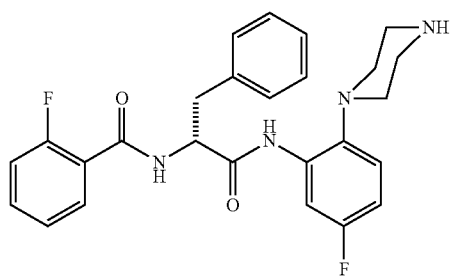
IX-222
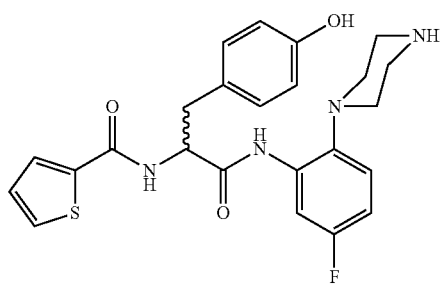
IX-214b
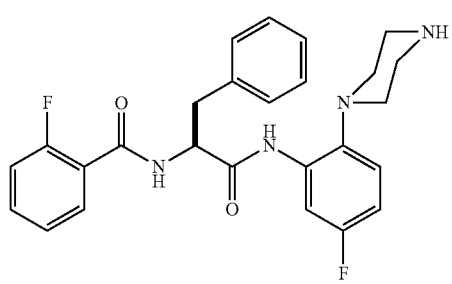
IX-223
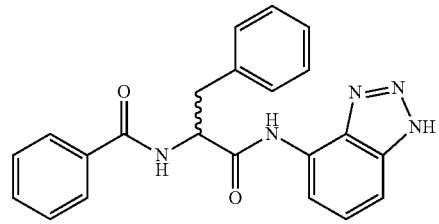
IX-215
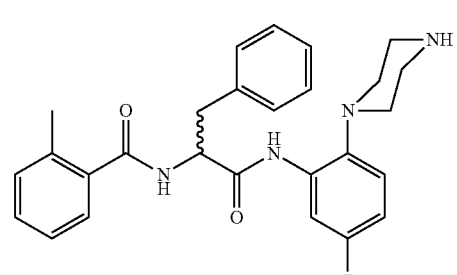
IX-224
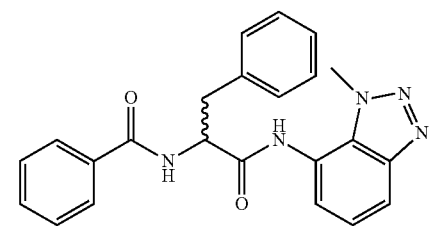
IX-216
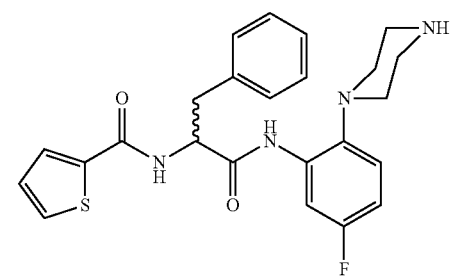
IX-225
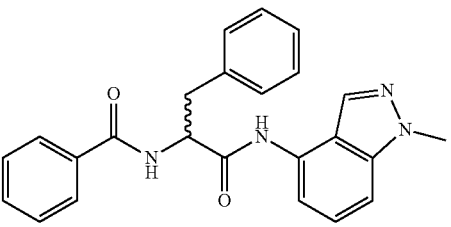
IX-219
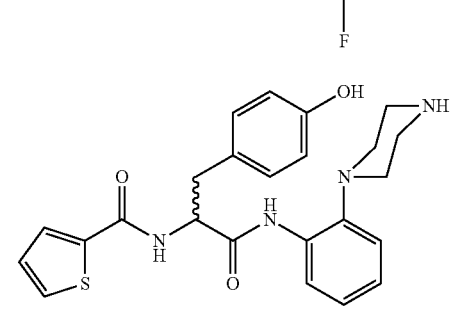
IX-230
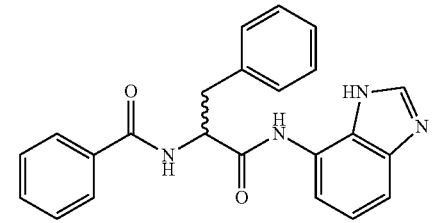
IX-231
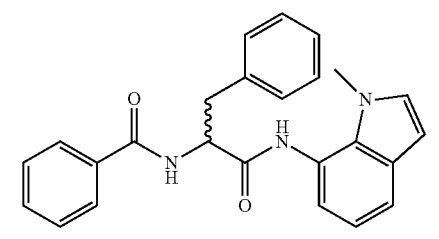

IX-232
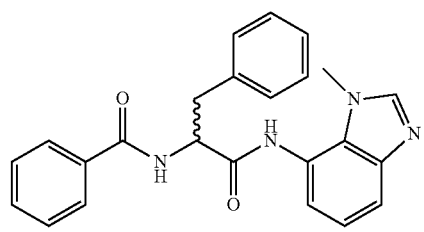
IX-234
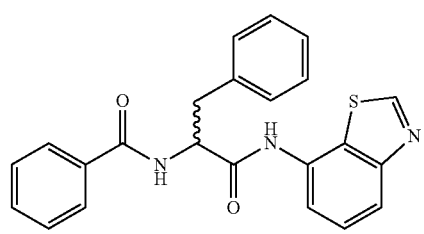
IX-235
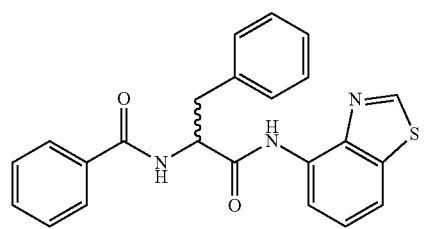
IX-236
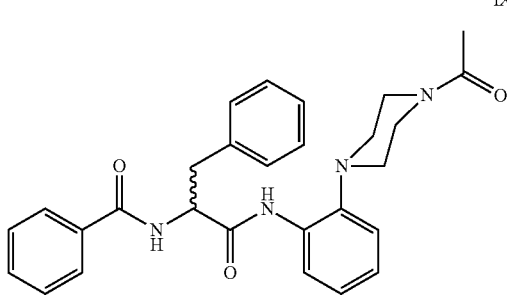
IX-238
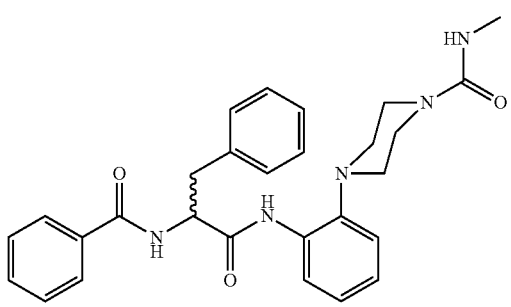
IX-241
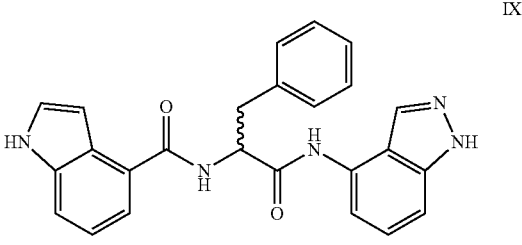
IX-242
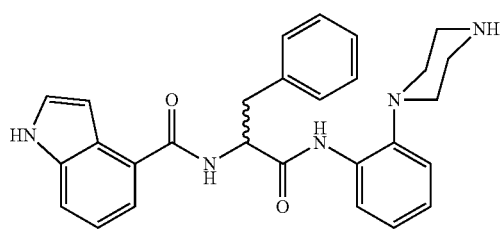
IX-243
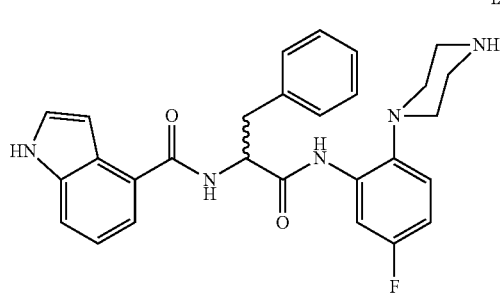
IX-244
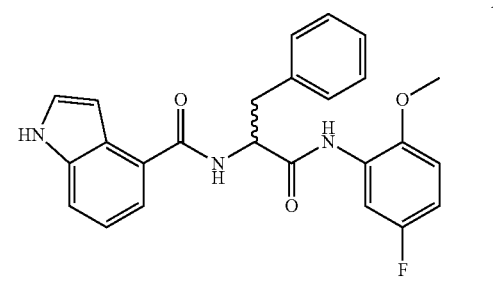
IX-245
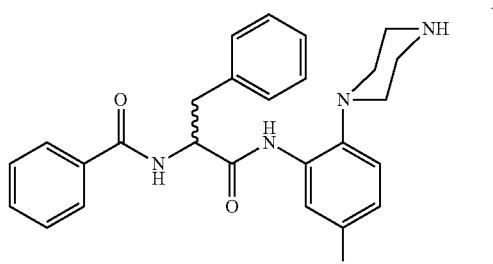
IX-246
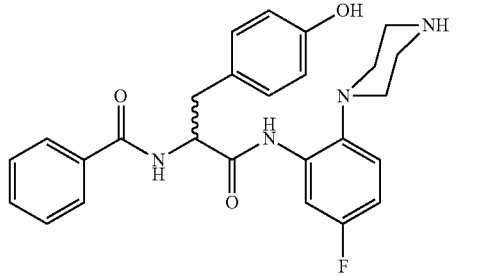

-continued
IX-247
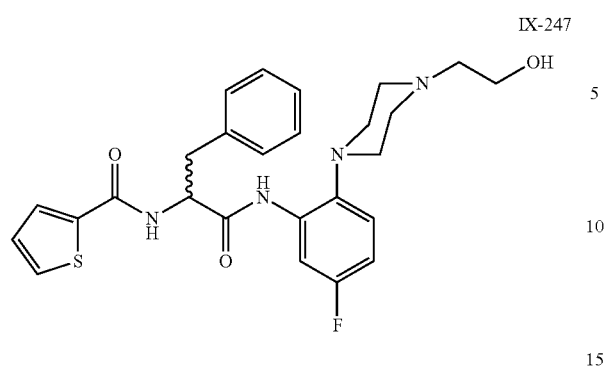
IX-265
IX-266
IX-274
IX-274a
-continued
IX-274b
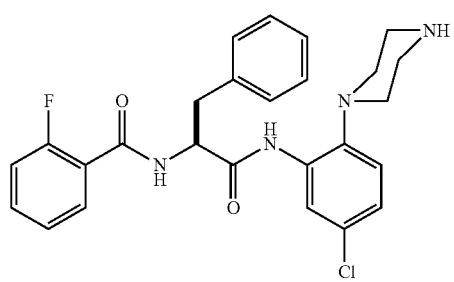
IX-275
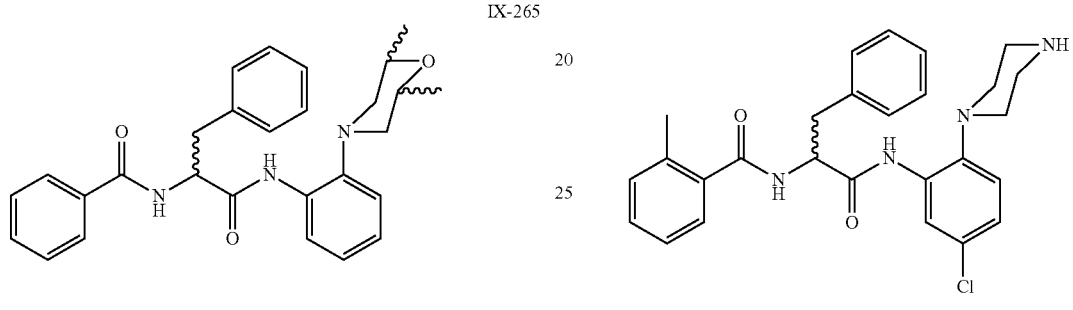
IX-276
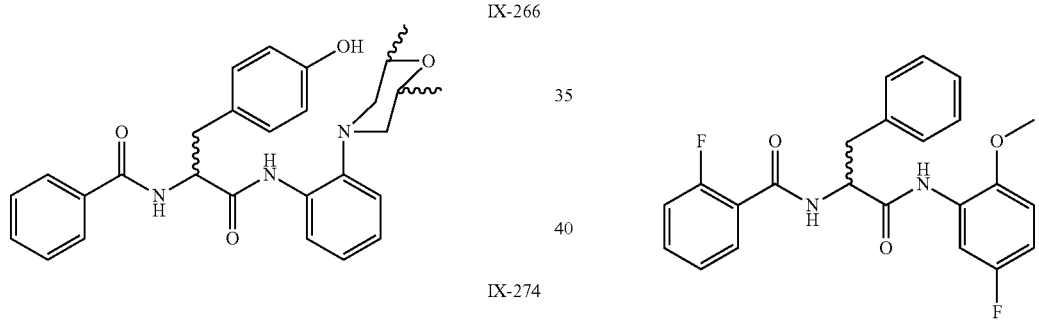
IX-277
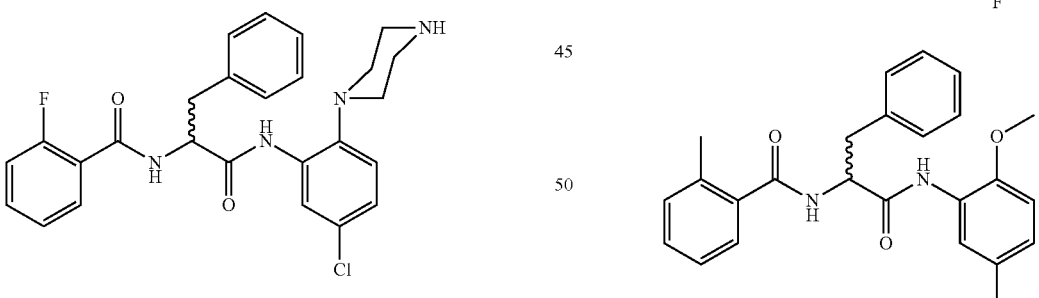
IX-278
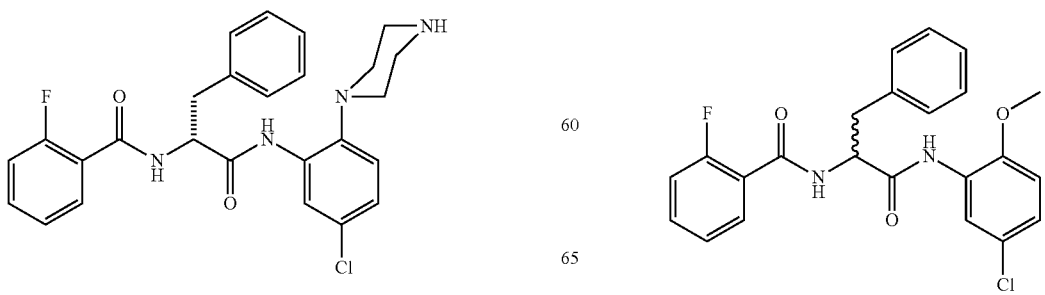

IX-279
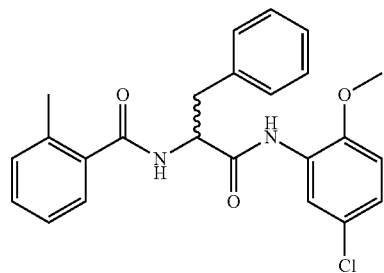
IX-280
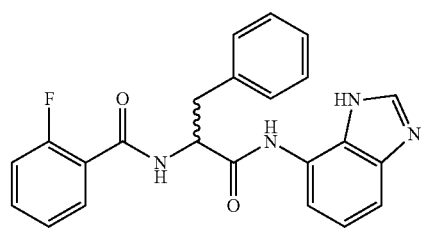
IX-281
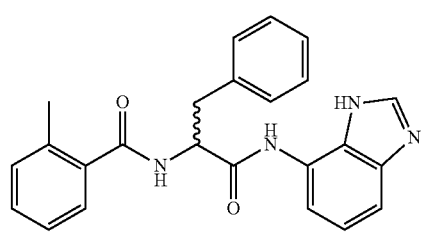
IX-296
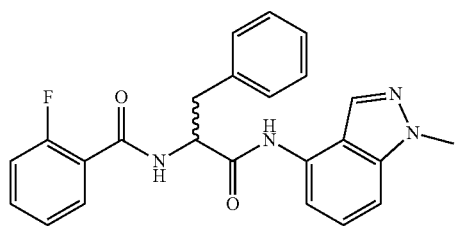
IX-297
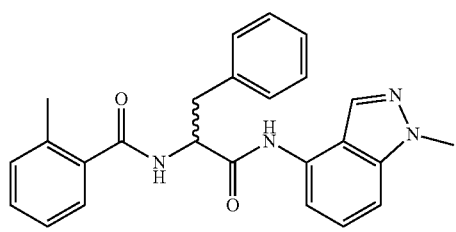
IX-300
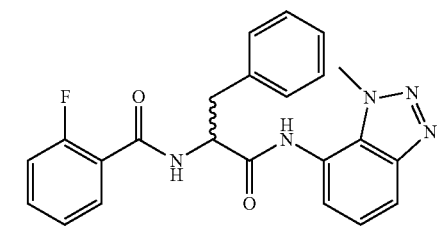
IX-301
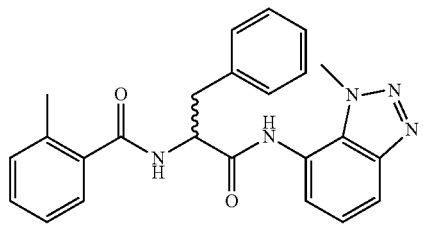
IX-305
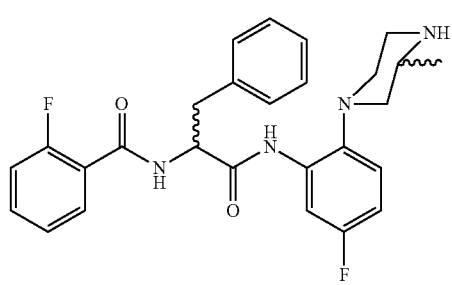
IX-306
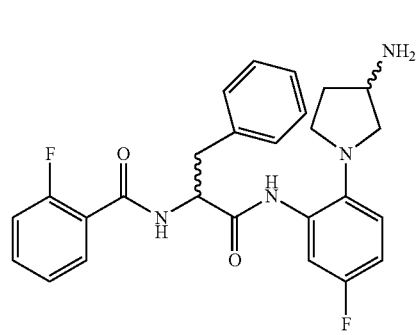
IX-307
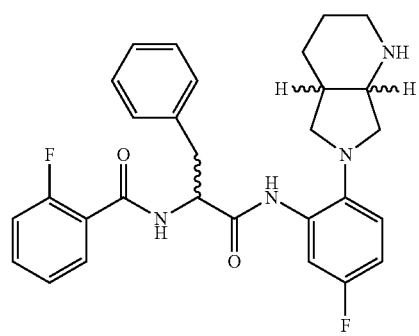
IX-308
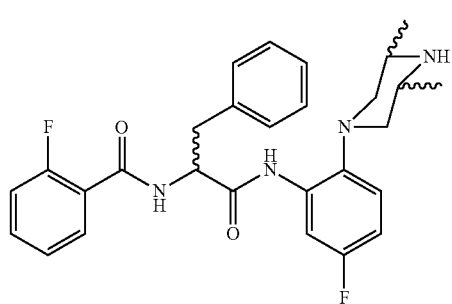

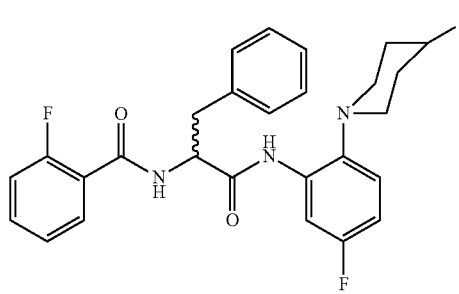

IX-312

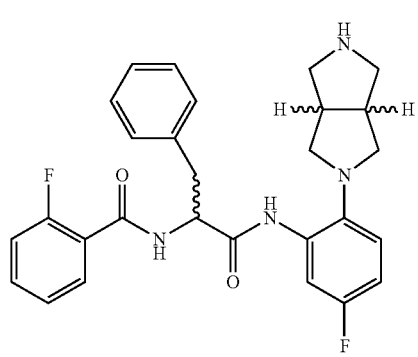

IX-313

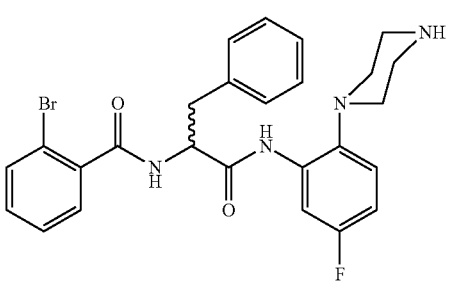

IX-315


IX-316

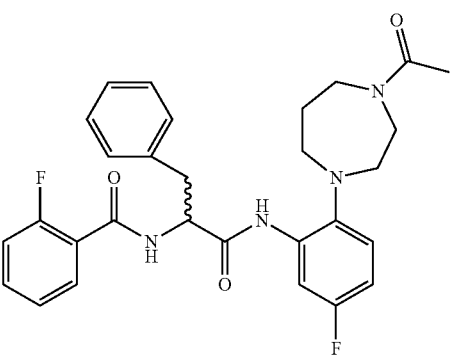

IX-319

Certain embodiments of the invention provide the synthesis of a compound according to any of general structural formulae (V) and (VI), or a salt thereof.

Compounds of general structural formula (V) or (VI) may be prepared by synthetic Schemes 1-2 shown below, by reference to the Examples, or by reference to analogous chemistry known in the art.

Schemes 1-2 show two general routes for preparing compounds of general structural formula (V) or (VI). Schemes 1-2 are illustrated for a compound of general structural formula (V) or (VI) where the cycle containing T, U, and V is unsubstituted phenyl, the cycle containing substituents $R^3$ and $R^4$ is unsubstituted phenyl, and the cycle containing A and B is 2-methoxy-phenyl.

One skilled in the art will understand how the Schemes 1 and 2 may be modified to obtain other compounds of general structural formula (V) or (VI).

By way of example, Scheme 1 may be modified by the use of a different phenylalanine building block, the use of a different aryl acid chloride building block, the use of a different aniline building block, the use of a different carboxyl-activated aryl acid in place of the aryl acid chloride, the use of an aryl acid and a condensing agent in place of the aryl acid chloride, the use of a different condensing agent, the use of a different base or acid, the use of a different solvent, the use of a protecting group for a heteroatom in a cycle or in a substituent of a cycle, or the inclusion of an additional protection or de-protection step.

By way of example, Scheme 2 may be modified by the use of a different protected phenylalanine building block, the use of a different aryl acid chloride building block, the use of a different aniline building block, the use of an amino-protected phenylalanine acid chloride or other carboxyl-activated amino-protected phenylalanine in place of the amino-protected phenylalanine, the use of a different carboxyl-activated aryl acid in place of the aryl acid chloride, the use of an aryl acid and a condensing agent in place of the aryl acid chloride, the use of a different condensing agent, the use of a different base or acid, the use of a different solvent, the use of a different protecting group for the phenylalanine amine, the use of a protecting group for a heteroatom in a cycle or in a substituent of a cycle, or the inclusion of an additional protection or de-protection step.

Furthermore, one skilled in the art will appreciate that compounds 3, 7, and 8 in Schemes 1-2 are useful intermediates for obtaining further compounds of general structural formula (V) or (VI) by methods known in the art.

Scheme 1: General Scheme for Preparing Certain Compounds of the General Structural Formulae: Method A

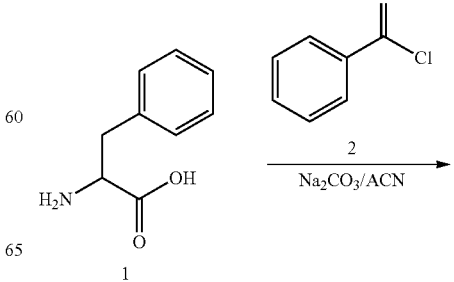

-continued

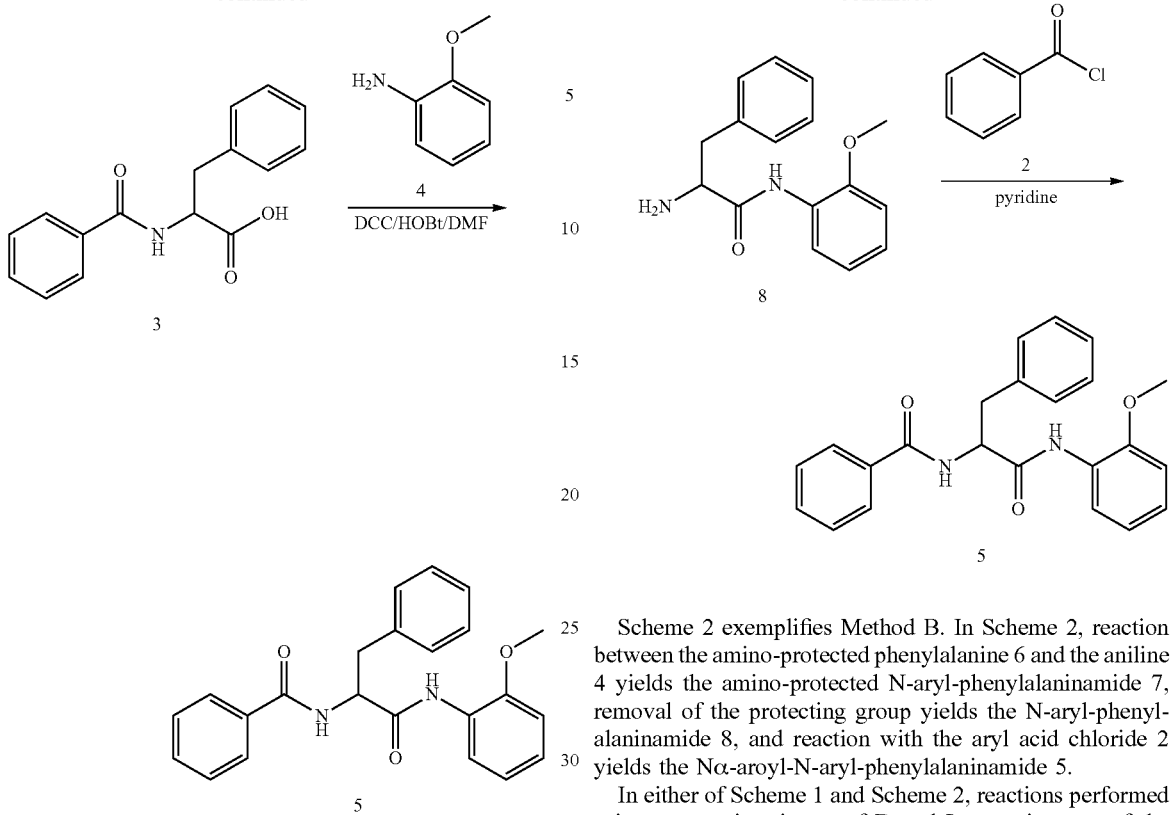

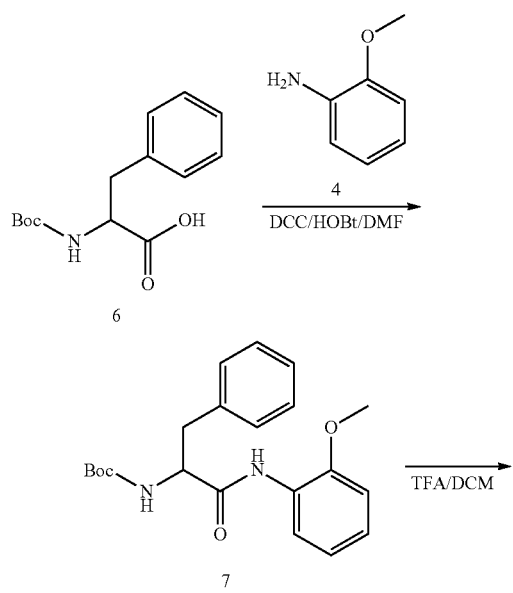

Scheme 1 exemplifies Method A.

In Scheme 1, reaction between the phenylalanine 1 and the aryl acid chloride 2 yields the Nα-aroyl-phenylalanine 3, and reaction with the aniline 4 yields the Nα-aroyl-N-aryl-phenylalaninamide 5.

Scheme 2: General Scheme for Preparing Certain Compounds of of the General Structural Formulae: Method B

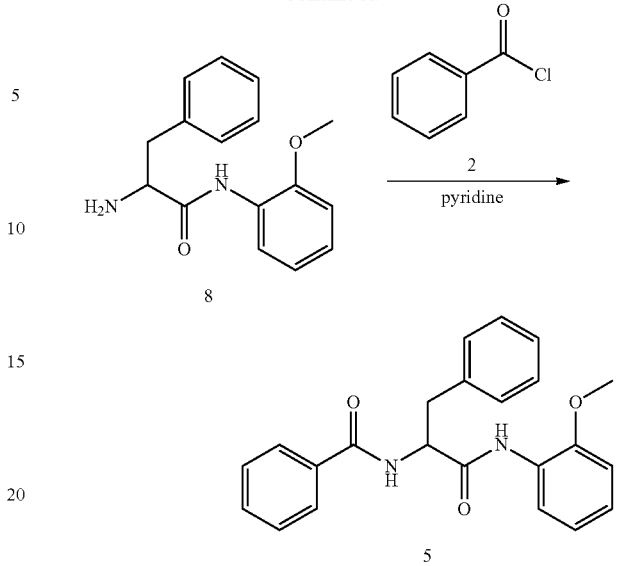

-continued

Scheme 2 exemplifies Method B. In Scheme 2, reaction between the amino-protected phenylalanine 6 and the aniline 4 yields the amino-protected N-aryl-phenylalaninamide 7, removal of the protecting group yields the N-aryl-phenylalaninamide 8, and reaction with the aryl acid chloride 2 yields the Nα-aroyl-N-aryl-phenylalaninamide 5.

In either of Scheme 1 and Scheme 2, reactions performed using a racemic mixture of D and L stereoisomers of the phenylalanine 1 or the protected phenylalanine 6 will yield a racemic mixture of D and L stereoisomers of the Nα-aroyl-N-aryl-phenylalaninamide 5.

In either of Scheme 1 and Scheme 2, reactions performed using a single stereoisomer (D or L) of the phenylalanine 1 or the protected phenylalanine 6 and using conditions under which complete racemization occurs likewise will yield a racemic mixture of D and L stereoisomers of the Nα-aroyl-N-aryl-phenylalaninamide 5.

In either of Scheme 1 and Scheme 2, reactions performed using a single stereoisomer (D or L) of the phenylalanine 1 or the protected phenylalanine 6 and using conditions under which partial racemization occurs will yield a mixture of stereoisomers, containing a majority of the starting stereoisomer (D or L, respectively) and a minority of the other stereoisomer (L or D, respectively), of the Nα-aroyl-N-aryl-phenylalaninamide 5.

In either of Scheme 1 and Scheme 2, reactions performed using a single stereoisomer (D or L) of the phenylalanine 1 or the protected phenylalanine 6 and using conditions under which no racemization occurs will yield a single stereoisomer (D or L, respectively) of the Nα-aroyl-N-aryl-phenylalaninamide 5.

In either of Scheme 1 and Scheme 2, in cases in which mixtures of stereoisomers are obtained, preparations containing single stereoisomers (D or L) optionally can be obtained therefrom by chiral chromatography using methods known in the art.

In some embodiments, the compound of general structural formula (V) or (VI) is prepared according to Scheme 1 or Scheme 2 using a racemic mixture of D and L stereoisomers of the phenylalanine 1 or the protected phenylalanine 6, yielding a racemic mixture of D and L stereoisomers of the Nα-aroyl-N-aryl-phenylalaninamide 5.

In some embodiments, the compound of general structural formula (V) or (VI) is prepared according to Scheme 1 or Scheme 2 using a single stereoisomer (D or L) of the phenylalanine 1 or the protected phenylalanine 6 and using conditions under which complete, or essentially complete, racemization occurs, yielding a racemic mixture of D and L stereoisomers of the Nα-aroyl-N-aryl-phenylalaninamide 5.

In some embodiments, the compound of general structural formula (V) or (VI) is prepared according to Scheme 1 or Scheme 2 using a single stereoisomer (D or L) of the phenylalanine 1 or the protected phenylalanine 6 and using conditions under which partial, but not complete or essentially complete, racemization occurs, yielding a mixture of stereoisomers, containing a majority of the starting stereoisomer (D or L, respectively) and a minority of the other stereoisomer (L or D, respectively), of the Nα-aroyl-N-aryl-phenylalaninamide 5.

In some embodiments, the compound of general structural formula (V) or (VI) is prepared according to Scheme 1 or Scheme 2 using a single stereoisomer (D or L) of the phenylalanine 1 or the protected phenylalanine 6 and using conditions under which no, or essentially no, racemization occurs, yielding only, or essentially only, a single stereoisomer (D or L, respectively) of the Nα-aroyl-N-aryl-phenylalaninamide 5.

In some embodiments, in cases in which mixtures of stereoisomers are obtained, preparations containing single stereoisomers (D or L) are obtained therefrom by chiral chromatography using methods known in the art.

Embodiments that provide predominantly the single stereoisomer of general structural formula (VI) are preferred.

Embodiments that provide only, or essentially only, the single stereoisomer of general structural formula (VI) are especially preferred.

Certain embodiments of the invention provide the use of a compound according to any of general structural formulae (V) and (VI), or a salt thereof, to inhibit an RNA polymerase from a bacterium.

Certain embodiments of the invention provide the use of a compound according to any of general structural formulae (V) and (VI), or a salt thereof, to inhibit an RNA polymerase from a *mycobacterium*.

Certain embodiments of the invention provide the use of a compound according to any of general structural formulae (V) and (VI), or a salt thereof, to inhibit an RNA polymerase from one of *Mycobacterium tuberculosis, Mycobacterium bovis, Mycobacterium leprae, Mycobacterium avium, Mycobacterium abscessus, Mycobacterium ulcerans*, and *Mycobacterium smegmatis*.

Certain embodiments of the invention provide the use of a compound according to any of general structural formulae (V) and (VI), or a salt thereof, to inhibit one of the growth and the viability of a bacterium.

Certain embodiments of the invention provide the use of a compound according to any of general structural formulae (V) and (VI), or a salt thereof, to inhibit one of the growth and the viability of a *mycobacterium*.

Certain embodiments of the invention provide the use of a compound according to any of general structural formulae (V) and (VI), or a salt thereof, to inhibit one of the growth and the viability of one of *Mycobacterium tuberculosis, Mycobacterium bovis, Mycobacterium leprae, Mycobacterium avium, Mycobacterium abscessus, Mycobacterium ulcerans*, and *Mycobacterium smegmatis*.

Certain embodiments of the invention provide the use of a compound according to any of general structural formulae (V) and (VI), or a salt thereof, to prevent an infection by a bacterium.

Certain embodiments of the invention provide the use of a compound according to any of general structural formulae (V) and (VI), or a salt thereof, to prevent an infection by a *mycobacterium*.

Certain embodiments of the invention provide the use of a compound according to any of general structural formulae (V) and (VI), or a salt thereof, to prevent an infection by one of *Mycobacterium tuberculosis, Mycobacterium bovis, Mycobacterium leprae, Mycobacterium avium, Mycobacterium abscessus, Mycobacterium ulcerans*, and *Mycobacterium smegmatis*.

Certain embodiments of the invention provide the use of a compound according to any of general structural formulae (V) and (VI), or a salt thereof, to treat an infection by a bacterium.

Certain embodiments of the invention provide the use of a compound according to any of general structural formulae (V) and (VI), or a salt thereof, to treat an infection by a *mycobacterium*.

Certain embodiments of the invention provide the use of a compound according to any of general structural formulae (V) and (VI), or a salt thereof, to treat an infection by one of *Mycobacterium tuberculosis, Mycobacterium bovis, Mycobacterium leprae, Mycobacterium avium, Mycobacterium abscessus, Mycobacterium ulcerans*, and *Mycobacterium smegmatis*.

Certain embodiments of the invention provide a method of inhibiting a bacterial RNA polymerase, comprising contacting a bacterial RNA polymerase with a compound according to any of general structural formulae (V) and (VI), or a salt thereof.

Certain embodiments of the invention provide a method of inhibiting one of the growth and the viability of a bacterium, comprising contacting a bacterium with a compound according to any of general structural formulae (V) and (VI), or a salt thereof.

Certain embodiments of the invention provide a method of preventing a bacterial infection, comprising administering to a mammal a compound according to any of general structural formulae (V) and (VI), or a salt thereof.

Certain embodiments of the invention provide a method of treating a bacterial infection, comprising administering to a mammal a compound according to any of general structural formulae (V) and (VI), or a salt thereof.

Certain embodiments of the invention provide a formulation according to any of general structural formulae (V) and (VI), or a salt thereof, for administration to a mammal to prevent a bacterial infection.

Certain embodiments of the invention provide a formulation according to any of general structural formulae (V) and (VI), or a salt thereof, for administration to a mammal to treat a bacterial infection.

Certain embodiments of the invention provide the administration of a formulation according to any of general structural formulae (V) and (VI), or a salt thereof.

Certain embodiments of the invention provide the administration of a formulation according to any of general structural formulae (V) and (VI), or a salt thereof, to a mammal to treat a bacterial infection.

Figure 4:
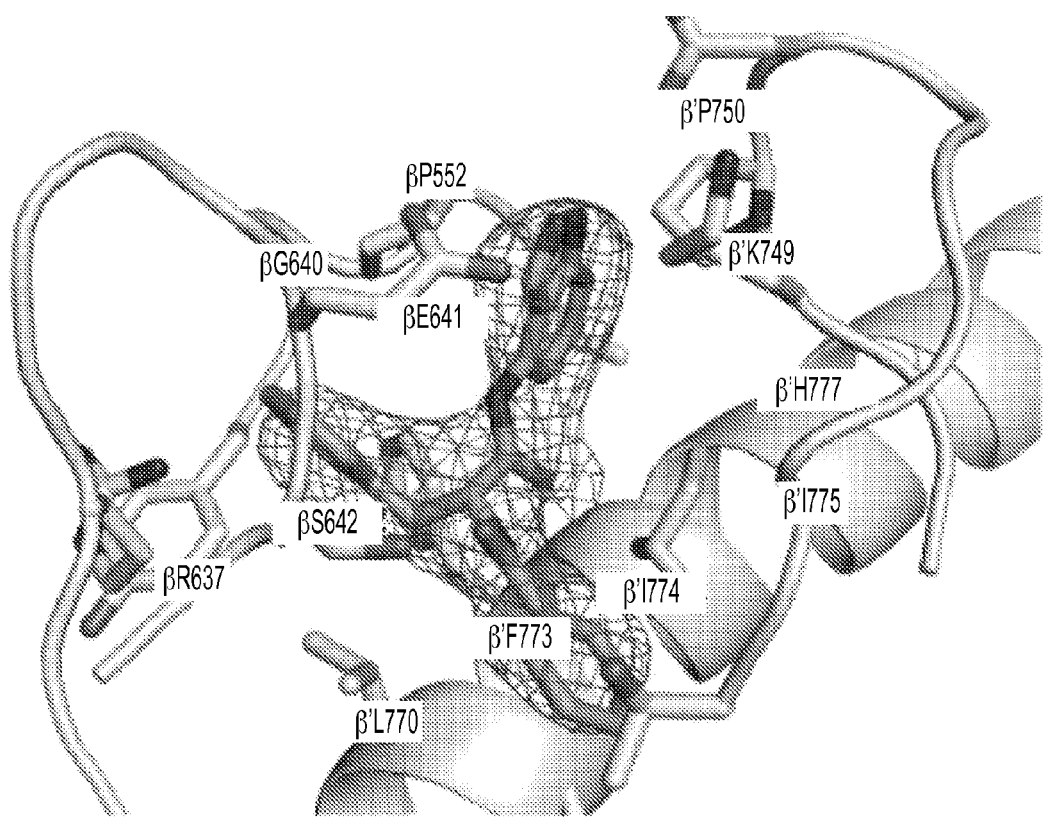
FIG. 4. Crystal structure of *Escherichia coli* RNA polymerase $\sigma^{70}$ holoenzyme in complex with IX-37. Experimental electron density for IX-37 is shown as a mesh ($2\sigma$ $F_o$–$F_c$ difference electron density for *Escherichia coli* RNA polymerase $\sigma^{70}$ holoenzyme with IX-37 vs. *E. coli* RNA polymerase holoenzyme without IX-37). Fitted atoms of IX-37 are shown in a stick representation (medium gray for carbon atoms; dark gray for nitrogen and oxygen atoms). The RNA polymerase bridge helix is shown in a ribbon representation in (light gray). Amino acids of RNA polymerase that contact IX-37 in the crystal structure are shown in a stick representation (light gray for carbon atoms; dark gray for nitrogen and oxygen atoms) and are labelled to indicate the RNA polymerase subunit (β or β') and the residue number within the RNA polymerase subunit.

The invention also provides a crystal structure of a compound according to general structural formula (V) or (VI) in complex with a bacterial RNA polymerase (FIG. 4).

The applicants have determined a crystal structure of a compound according to general structural formula (V) or (VI), compound IX-37 (Example 39), in complex with *Escherichia coli* RNA polymerase holoenzyme at a resolution of 4.1 Å and an $R_{free}$ of 0.269 (FIG. 4).

The crystal structure was determined by soaking a preformed crystal of *Escherichia coli* RNA polymerase holoenzyme with IX-37, collecting x-ray diffraction data at a synchroton beamline, solving the structure by molecular replacement using atomic coordinates for the structure of *Escherichia coli* RNA polymerase holoenzyme in the absence of IX-37 as the search model, and refining the structure (method for crystal growth, crystal soaking, data collection, structure solution, and structure refinement essentially as in [Degen, D., Feng, Y., Zhang, Y., Ebright, K., Ebright, Y., Gigliotti, M., Vahedian-Movahed, H., Mandal, S., Talaue, M., Connell, N., Arnold, E., Fenical, W., Ebright, R. (2014) eLife 3, e02451]).

IX-37 exhibits an $IC_{50}$ of 10 µM for inhibition of *Escherichia coli* RNA polymerase, and IX-37 exhibits an aqueous solubility of >>10 µM. The relatively high aqueous solubility of IX-37 enabled crystals of *Escherichia coli* RNA polymerase to be soaked with IX-37 at IX-37 concentrations sufficiently high to yield efficient complex formation.

The crystal structure shows that a compound according to general structural formula (V) or (VI) binds to a bacterial RNA polymerase at a binding site located at the base of the RNA polymerase "β lobe" (*Escherichia coli* RNA polymerase β subunit residues 552, 637, 640, 641, 642, 749, 750, and 777, and β' subunit residues 770, 773, 774, 755, and 777; FIG. 4).

The crystal structure further shows that a compound according to general structural formula (V) or (VI) bound at said "β lobe" binding site contacts RNA polymerase residues in the N-terminal portion part of the RNA polymerase "bridge helix" (*Escherichia coli* RNA polymerase β' subunit residues 770, 773, 774, 755, and 777; FIG. 4).

Figure 2:
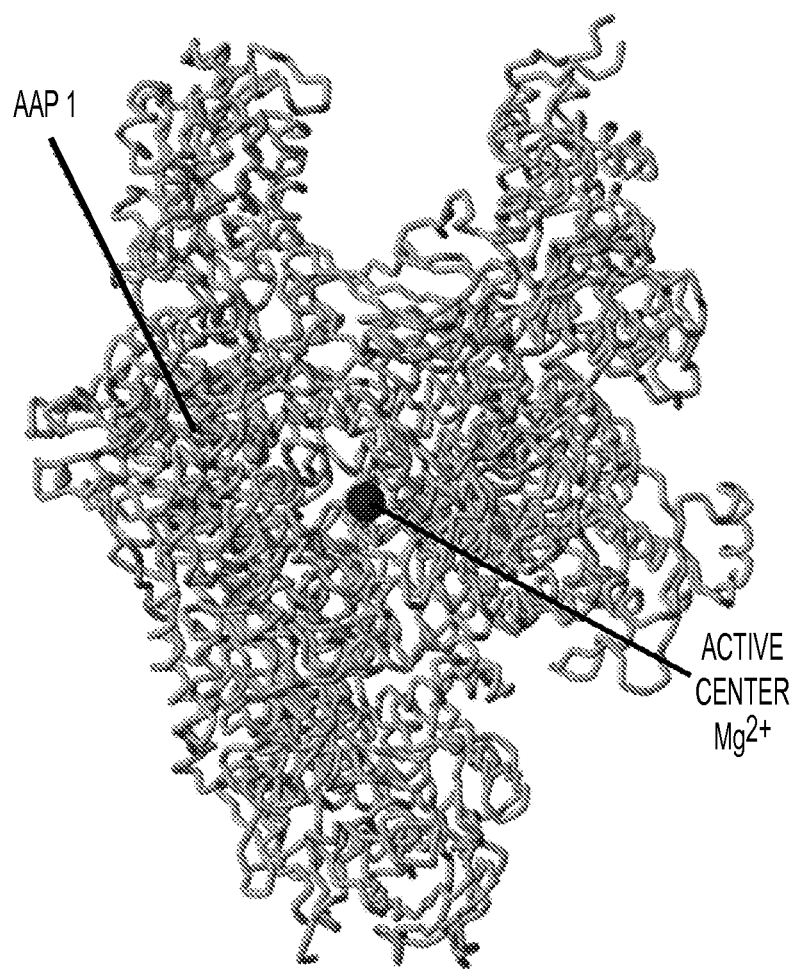
FIG. 2. Structure of a bacterial RNA polymerase, showing residues at which substitutions conferring AAP1-resistance are obtained (light gray surfaces; identities of residues from Example 11 and Table 6). The residues constitute a discrete cluster in the structure ("AAP1 target"), herein disclosed to define a determinant of RNA polymerase required for inhibition of RNA polymerase and inhibition of bacterial growth by AAP1, and herein disclosed to define the probable binding site of AAP1 on RNA polymerase. For reference, the RNA polymerase active-center $Mg^{2+}$ ion is shown as a sphere.
Figure 3:
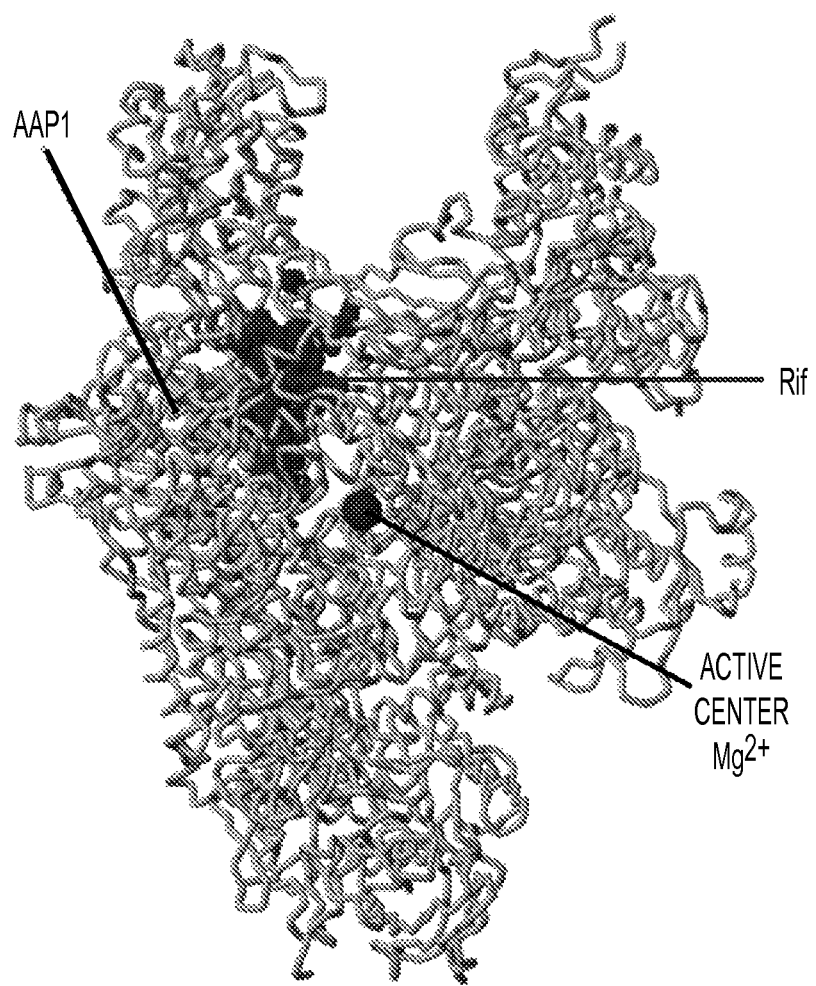
FIG. 3. Structure of a bacterial RNA polymerase, showing the relationship between residues at which substitutions conferring AAP1-resistance are obtained ("AAP1 target"; light gray surfaces; identities of residues from Example 11 and Table 6) and residues at which substitutions conferring rifampin-resistance are obtained ("Rif target"; dark gray surfaces; identities of residues from [Ho, M., Hudson, B., Das, K., Arnold, E., Ebright, R. (2009) *Curr. Opin. Structl. Biol.* 19, 715-723]). In the structure of a bacterial RNA polymerase, the AAP1 target is located close to, but does not overlap, the Rif target. For reference, the RNA polymerase active-center $Mg^{2+}$ ion is shown as a sphere.

The crystal structure further shows that a compound according to general structural formula (V) or (VI) bound at said "β lobe" binding site contacts, or is close to, RNA polymerase residues corresponding to, and alignable with, the RNA polymerase residues for which the applicants have identified substitutions that confer resistance to compounds of the general structural formulae (AAP1-resistant substitutions and "AAP1 target" of Examples 11-12 and FIGS. 2-3).

The crystal structure is consistent with, and corroborates, the conclusion of Examples 11-12, based on analysis of resistance substitutions, that compounds of the general structural formulae function through a binding site located at the base of the RNA polymerase "β lobe."

The crystal structure further is consistent with, and corroborates, the conclusion of Examples 11-12, based on analysis of resistance substitutions, that compounds of the general structural formulae function through a binding site that is close to, but does not overlap, the binding sites of the RNA polymerase inhibitors rifampin, streptolydigin, GE23077, and salinamide.

The crystal structure further is consistent with, and corroborates, the conclusion of Examples 11-12, based on analysis of resistance substitutions, that compounds of the general structural formulae function through a binding site that is distant from to, and does not overlap, the binding sites of the RNA polymerase inhibitors myxopyronin, corallopyronin, ripostatin, and lipiarmycin.

The crystal structure further is consistent with, and corroborates, the conclusion of Examples 11-12, based on analysis of resistance substitutions, that compounds of the general structural formulae function through a binding site that does not overlap the RNA polymerase active center.

Accordingly, the crystal structure indicates that compounds according to the general structural formulae inhibit a bacterial RNA polymerase through an allosteric mechanism, rather than through a steric mechanism.

The crystal structure suggests that compounds according to the general structural formulae inhibit a bacterial RNA polymerase allosterically through an effect on a conformation of the RNA polymerase "β lobe" or of the RNA polymerase "bridge helix."

The crystal structure defines the interactions between individual atoms of a compound according to the general structural formulae and individual atoms of a bacterial RNA polymerase.

The crystal structure defines the roles in RNA polymerase-inhibitor interaction of individual atoms of a compound according to the general structural formulae, and enables estimation of the energetic contributions to RNA polymerase-inhibitor interaction of individual atoms of a compound according to the general structural formulae.

The crystal structure defines the roles in RNA polymerase-inhibitor interaction of individual atoms in the variables in general structural formula (V) or (VI), and enables estimation of the energetic contributions to RNA polymerase-inhibitor interaction of individual atoms in the variables in general structural formula (V) or (VI).

The crystal structure enables structure-based design of new compounds according to general structural formula (V) or (VI) that can be predicted to have improved interactions with a bacterial RNA polymerase and therefore can be predicted to have increased potency of inhibition of a bacterial RNA polymerase.

Definitions

The following definitions are used, unless otherwise indicated.

The term "halo" means fluoro, chloro, bromo, or iodo.

The term "alkyl" used alone or as part of a larger moiety, includes both straight and branched chains.

Aryl denotes a phenyl radical or an ortho-fused bicyclic carbocyclic radical having about nine to ten ring atoms in which at least one ring is aromatic. In certain embodiments, aryl can be phenyl, indenyl, or naphthyl.

Heteroaryl denotes a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1$-$C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X). In certain embodiments, heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Unless otherwise noted, aryl and heteroaryl groups can be optionally substituted. For example, in one embodiment, the groups aryl and heteroaryl can each be optionally substituted with one or more groups independently selected from C1-C5 alkyl, C1-C5 acyl, C1-C5-O-acyl, C1-C5-NH-acyl, carboxy, C1-C5 ester, C1-C5 amide, C1-C5 alkoxy, C1-C5-monoalkylamino, C1-C5 dialkylamino, amino, hydroxy, halogen, —C(═O)—O—$C_1$-$C_4$phenyl, and —O—C(═O)-phenyl.

The term C1-C5 acyl as used herein includes —C(=O)—$C_1$-$C_4$alkyl.

The term C1-C5-O-acyl as used herein includes —O—C(=O)—$C_1$-$C_4$alkyl.

The term C1-C5-NH-acyl as used herein includes —NH—C(=O)—$C_1$-$C_4$alkyl.

The term C1-C5 ester as used herein includes —C(=O)—O—$C_1$-$C_4$alkyl.

The term C1-C5 amide as used herein includes —C(=O)—N(H)—$C_1$-$C_4$alkyl.

The term C1-C5 alkoxy as used herein includes —O—$C_1$-$C_5$alkyl.

The term C1-C5-monoalkylamino as used herein includes —N(H)($C_1$-$C_5$alkyl).

The term C1-C5 dialkylamino as used herein includes —N($C_1$-$C_5$alkyl)$_2$, wherein each alkyl can be the same or different.

The term amino as used herein includes —$NH_2$.

The term amine as used herein includes —$NH_2$, C1-C5-monoalkylamino, and C1-C5 dialkylamino.

The term amide as used herein includes —C(=O)—$NH_2$—, —C(=O)—N(H)—$C_1$-$C_4$alkyl and —NH—C(=O)—$C_1$-$C_4$alkyl.

The term ester as used herein includes —C(=O)—O—$C_1$-$C_4$alkyl, —C(=O)—O—$C_1$-$C_4$aryl, —O—C(=O)—$C_1$-$C_4$alkyl, and —O—C(=O)-aryl.

The term phosphate as used herein includes —OP(=O)(OH)$_2$.

The term O-methylphosphate as used herein includes —O—$CH_2$—P(=O)(OH)$_2$.

The term cycle as used herein includes mono- and bicyclic-ring systems that can be saturated, partially unsaturated, or aromatic.

The term acyl as used herein includes —C(=O)—$C_1$-$C_4$alkyl.

The term carbamidyl as used herein includes —C(=O)—N(H)—$C_1$-$C_4$alkyl and —C(=O)—N($C_1$-$C_5$alkyl)$_2$, wherein each alkyl can be the same or different.

A combination of substituents or variables is permissible only if such a combination results in a stable or chemically feasible compound. The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents.

Unless otherwise stated, structures depicted herein are also meant to include all stereochemical forms of the structure (i.e., the R and S configurations for each asymmetric center). Therefore, single stereochemical isomers, as well as enantiomeric and diastereomeric mixtures, of the present compounds are within the scope of the invention. Similarly, E- and Z-isomers, or mixtures thereof, of olefins within the structures also are within the scope of the invention.

Unless otherwise stated, structures depicted herein also are meant to include compounds that differ only by the presence of one or more isotopically enriched atoms. For example, compounds having the present structures except for the replacement of a hydrogen atom by a deuterium or tritium, or the replacement of a carbon by a $^{13}$C- or $^{14}$C-enriched carbon, are within the scope of this invention.

Compounds of this invention may exist in tautomeric forms, such as keto-enol tautomers. The depiction of a single tautomer is understood to represent the compound in all of its tautomeric forms.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. Accordingly, certain embodiments of the invention are directed to salts of the compounds described herein, e.g., pharmaceutically acceptable salts.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Administration of Pharmaceutical Compositions

The compounds described herein may be formulated as pharmaceutical compositions and administered to a mammalian host, such as a human male or female patient in a variety of forms adapted to the chosen route of administration (e.g., orally or parenterally, by intravenous, intramuscular, topical or subcutaneous routes).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 10 to about 125 mg/kg of body weight per day, such as 3 to about 75 mg per kilogram body weight of the recipient per day, preferably in the range of 6 to 120 mg/kg/day, most preferably in the range of 15 to 90 mg/kg/day.

The compound may be conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting examples.

EXAMPLES

Example 1. Preparation of Nα-benzoyl-N-(2-methylphenyl)-D/L-phenylalaninamide (AAP1)

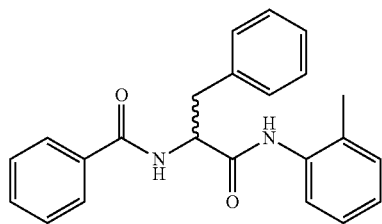

AAP1

D/L-Benzoyl phenylalanine (32.2 mg; 120 μmol; Chem-Impex, Inc.) was dissolved in 2 ml anhydrous DMF at 25° C. To the solution, was added PS-carbodiimide (180 mg, 240 μmol; Biotage, Inc.) and hydroxybenzotriazole (24.3 mg; 180 μmol; Aldrich, Inc.). The reaction mixture was stirred for 15 min under argon, o-toluidine (10.63 μl, 100 μmol; Aldrich, Inc.) was added, and stirring was continued for 2 h. The mixture was filtered through a plug of glass wool and evaporated to dryness. The sample was re-dissolved in chloroform and purified by silica chromatography with chloroform as eluent.

Yield: 31.9 mg, 89%. $^1$H-NMR (500 MHz, CDCl$_3$): δ 2.18 (s, 3H), 3.25 (dd, 1H), 3.35 (dd, 1H), 5.05 (dd, 1H), 6.8-7.8 (m; 14H, aryl protons). MS (MALDI): calculated: m/z 359.43 (MH$^+$); found: 359.35, 381.33 (M+Na$^+$).

A second, alternative, method of preparation was as follows: D-Benzoyl phenylalanine (269 mg; 1 mmol; Chem-Impex, Inc.) and imidazole (102 mg, 1.5 mmole; Aldrich, Inc.) were dissolved in 5 ml anhydrous pyridine at 0° C. To the solution was added o-toluidine (106 μl, 1 mmol; Aldrich, Inc.) and phosphorus oxychloride (137 μl, 1.5 mmol; Aldrich, Inc.). The reaction mixture was stirred at 25° C. for 90 min, poured into 25 ml 10% sodium bicarbonate, and extracted with 3×25 ml ethyl acetate. The organic extract was washed with a saturated copper sulfate solution, washed with brine, dried with magnesium sulfate, and evaporated to an oil. The oil was purified by silica chromatography (ethyl acetate/hexane gradient).

Yield: 10 mg, 2.8%. $^1$H-NMR (500 MHz, CDCl$_3$): δ 2.18 (s, 3H), 3.25 (dd, 1H), 3.35 (dd, 1H), 5.05 (dd, 1H), 6.8-7.8 (m; 14H, aryl protons). MS (MALDI): calculated: m/z 359.43 (MH$^+$); found: 359.35, 381.33 (M+Na$^+$).

Example 2. Preparation of Nα-benzoyl-N-(2-methylphenyl)-D-phenylalaninamide (AAP1a; FIG. 1, Upper Panel)

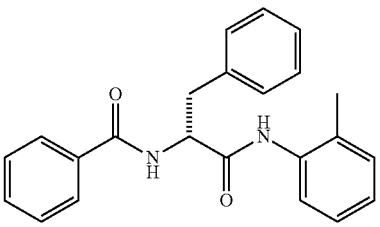

AAP1a

AAP1a was prepared as in Example 1, but using D-benzoyl phenylalanine (Chem-Impex, Inc.) in place of D/L-benzoyl phenylalanine. The product (100 μg) was dissolved in isopropanol (100 μl) and purified by chiral HPLC on a 4.6×250 mm ChiralPak IA column (ChiralPak, Inc.) in 10% isopropanol in hexanes at 1 ml/min. Two peaks were observed, one exhibiting a retention time of 14 min and an integrated area of 1.1 arbitrary units (assigned as the D stereoisomer, AAP1a; 10% enantiomeric excess), and another exhibiting a retention time of 17 min and an integrated area of 1.0 arbitrary unit (assigned as the L stereoisomer, AAP1b). The peak assigned as the D stereoisomer was collected.

MS (MALDI): calculated: m/z 359.43 (MH$^+$); found: 359.35, 381.33 (M+Na$^+$). Optical rotation in DMF, $[\alpha]_{589}^{22°\,C.}=+19$.

Example 3. Preparation of Nα-benzoyl-N-(2-methylphenyl)-L-phenylalaninamide (AAP1b; FIG. 1, Lower Panel)

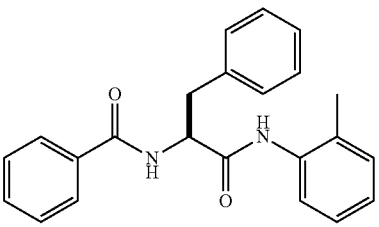

AAP1b

AAP1b was prepared as in Example 2, but using L-benzoyl phenylalanine (Chem-Impex) in place of D-benzoyl phenylalanine. Two peaks were observed, one exhibiting a retention time of 14 min and an integrated area of 1.0 arbitrary unit (assigned as the D stereoisomer, AAP1a), and another exhibiting a retention time of 17 min and an integrated area of 1.1 arbitrary units (assigned as the L stereoisomer, AAP1b; 10% enantiomeric excess). The peak assigned as the L stereoisomer was collected.

MS (MALDI): calculated: m/z 359.43 (MH$^+$); found: 359.35, 381.33 (M+Na$^+$). Optical rotation in DMF, $[\alpha]_{589}^{22°\,C.}=-22$.

Example 4. Preparation of Nα-benzoyl-N-(2-fluoro-phenyl)-D/L-phenylalaninamide (AAP3)

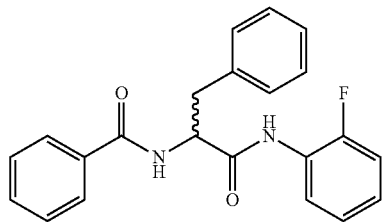

AAP3

D/L-Benzoyl phenylalanine (200 mg; 0.74 mmol; Chem-Impex, Inc.) and imidazole (75 mg, 1.11 mmol; Aldrich, Inc.) were dissolved in 5 ml anhydrous pyridine at 0° C. To the solution was added 2-fluoroaniline (71.4 µl, 0.74 mmol; Aldrich, Inc.) and phosphorus oxychloride (101 µl, 1.11 mmol; Aldrich, Inc.). The reaction mixture was stirred at 25° C. for 90 min, poured into 10 ml 10% sodium bicarbonate, and extracted with 3×10 ml ethyl acetate. The organic extract was washed with a saturated copper sulfate solution, washed with brine, dried with magnesium sulfate, and evaporated to an oil. The oil was purified by silica chromatography (ethyl acetate/hexane gradient).

Yield: 8 mg, 22%. MS (MALDI): calculated: m/z 363.40 (MH$^+$); found: 363.21, 385.25 (M+Na$^+$).

Example 5. Preparation of Nα-benzoyl-N-phenyl-D/L-phenylalaninamide (AAP4)

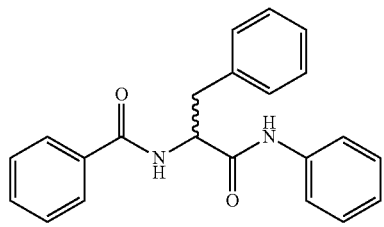

AAP4

D/L Benzoyl phenylalanine (32.2 mg; 120 µmol; Chem-Impex, Inc.) was dissolved in 2 ml anhydrous dimethylformamide at 25° C. To the solution was added PS-carbodiimide (180 mg, 240 µmol; Biotage, Inc.) and hydroxybenzotriazole (24.3 mg; 180 µmol; Aldrich, Inc.). The reaction mixture was stirred for 15 min under argon, aniline (9.1 µl, 100 µmol; Aldrich, Inc.) was added, and stirring was continued for 2 h. The mixture was filtered through a plug of glass wool and evaporated to dryness. The sample was re-dissolved in chloroform and purified by silica chromatography with chloroform as the eluent.

Yield: 16 mg, 46%. MS (MALDI): calculated: m/z 345.41 (MH$^+$); found: 367.35 (M+Na$^+$).

Example 6. Preparation of Nα-benzoyl-N-(4-pyridyl)-D/L-phenylalaninamide (AAP5)

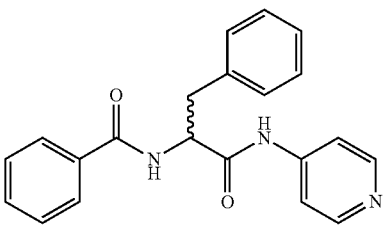

AAP5

D/L-Benzoyl phenylalanine (269 mg; 1 mmol; Chem-Impex, Inc.) was dissolved in 10 ml anhydrous dimethylformamide at 25° C. To the solution, was added DIPEA (0.435 ml, 2.5 mmol; Aldrich, Inc.) and 4-aminopyridine (94 mg, 1 mmol; Aldrich, Inc.). The reaction mixture was stirred for 10 min under argon, 1-propane phosphonic anhydride (0.763 ml, 1.2 mmol; Aldrich, Inc.) was added dropwise over 10 min, and stirring was continued for 18 h. The mixture was quenched with 2 ml ice water and evaporated to approximately half volume. Another 5 ml water was added to the mixture, and the pH was adjusted to pH=8 with 15% sodium hydroxide. The mixture was extracted with 20 ml dichloromethane. The organic extract was dried with brine, dried with sodium sulfate, and evaporated to dryness. The sample was re-dissolved in chloroform and purified by silica chromatography (methanol gradient in chloroform) followed by HPLC (Lux Cellulose-1, 10% isopropanol in hexanes, 0.5 ml/min; Phenomenex, Inc.).

Yield: 2 mg, 0.58%. MS (MALDI): calculated: m/z 345.39 (MH$^+$); found: 367.35 (M+Na).

Example 7. Preparation of Nα-benzoyl-N-(2-pyridyl)-D/L-phenylalaninamide (AAP6)

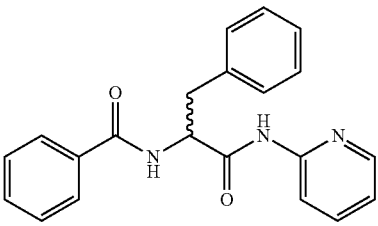

AAP6

D/L-Benzoyl phenylalanine (32.2 mg; 120 µmol; Chem-Impex, Inc.) was dissolved in 2 ml anhydrous dimethylformamide at 25° C. To the solution, was added PS-carbodiimide (180 mg, 240 µmol; Biotage, Inc.) and hydroxybenzotriazole (24.3 mg; 180 µmol; Aldrich, Inc.). The reaction mixture was stirred for 15 min under argon, 2-aminopyridine (9.4 mg, 100 µmol; Aldrich, Inc.) was added, and stirring was continued for 2 h. The mixture was filtered through a plug of glass wool and evaporated to dryness. The sample was re-dissolved in chloroform and purified by silica chromatography (methanol gradient in chloroform).

Yield: 10 mg, 29%. MS (MALDI): calculated: m/z 345.39 (MH$^+$); found: 367.35 (M+Na$^+$).

Example 8. Assay of Inhibition of Mycobacterial RNA Polymerase

Run-off transcription assays with *Mycobacterium tuberculosis* RNA polymerase were performed using reaction mixtures containing (10 µl): 0-100 µM test compound, 75 nM *Mycobacterium tuberculosis* RNA polymerase core enzyme, 300 nM *Mycobacterium tuberculosis* $\sigma^A$, 20 nM 130 bp DNA fragment containing positions −100 to −1 of the bacteriophage T4 N25 promoter followed by positions +1 to +30 of the lacUV5-15 promoter of [Mukhopadhyay, J., Kapanidis, A., Mekler, V., Kortkhonjia, E., Ebright, Y., Ebright, R. (2001) *Cell* 106, 453-463], 25 nM [alpha-$^{32}$P]UTP (600 Bq/pmol) for an initial 2 min at 37° C. and 100 µM [alpha-$^{32}$P]UTP (6 Bq/pmol) for a subsequent 5 min at 37° C., 100 µM ATP, 100 µM GTP, 100 µM UTP, 100 µM CTP, 40 mM Tris-HCl, pH 8.0, 80 mM NaCl, 5 mM MgCl$_2$, 2.5 mM DTT, and 12.7% glycerol. Reactions were terminated by addition of 2 1 80% formamide, 10 mM EDTA, 0.04% bromophenol blue, and 0.04% xylene cyanol, followed by heating for 5 min at 90° C. Reaction products were resolved by 15% urea-PAGE, and quantified using a storage-phosphor scanner. IC50 was defined as the concentration of inhibitor resulting in 50% inhibition of RNA polymerase activity.

Certain compounds according to the general structural formulae were found to potently inhibit mycobacterial RNA polymerase (IC50s=0.01 to 12 µM; Tables 1, 9).

In particular, certain compounds according to general structural formula (V) or VI) were found to highly potently inhibit mycobacterial RNA polymerase (IC50s=0.01 to 3.5 µM; Tables 9, 10).

For the series AAP1 (DL racemic mixture), AAP1a (D stereoisomer), and AAP1b (L stereoisomer), the D stereoisomer inhibited mycobacterial RNA polymerase more potently that the DL racemic mixture, and the DL racemic mixture inhibited mycobacterial RNA polymerase more potently than the L stereoisomer (Table 1).

Similarly, for the series IX-214 (DL racemic mixture) and IX-214a (D stereoisomer), the D stereoisomer inhibited mycobacterial RNA polymerase more potently than the DL racemic mixture (Tables 9, 10).

Similarly, for the series IX-274 (DL racemic mixture) and IX-274a (D stereoisomer), the D stereoisomer inhibited mycobacterial RNA polymerase more potently than the DL racemic mixture (Tables 9, 10).

By comparison to their potent inhibition of mycobacterial RNA polymerase polymerase (IC50s as low as 0.01 µM; Tables 1, 9, 10), tested compounds according to the general structural formulae less potently inhibited *Escherichia coli* RNA polymerase in analogous run-off transcription assays with *Escherichia coli* RNA polymerase (IC50s≥10 µM).

Example 9. Assay of Inhibition of Mycobacterial Growth

Minimal inhibitory concentrations (MICs) in *Mycobacterium tuberculosis* H37Rv and *Mycobacterium avium* ATCC 25291 were quantified using microplate Alamar Blue assays as described (MABA; [Collins, L. & Franzblau, S. (1997) Microplate Alamar Blue assay versus BACTEC 460 system for high-throughput screening of compounds against *Mycobacterium tuberculosis* and *Mycobacterium avium*. *Antimicrob. Agents Chemother.* 41, 1004-1009]).

MICs in *Mycobacterium smegmatis* ATCC 19420 and *Mycobacterium smegmatis* ATCC 19420 derivatives were quantified using broth microdilution assays as described [Clinical and Laboratory Standards Institute (CLSI/NCCLS) (2009) *Methods for Dilution Antimicrobial Susceptibility Tests for Bacteria That Grow Aerobically; Approved Standard, Eighth Edition. CLIS Document M07-A8* (CLIS, Wayne Pa.)].

Certain compounds according to the general structural formulae were found to potently inhibit mycobacterial growth (MICs=0.073 to 50 µg/ml; Tables 2-3, 9, 10).

In particular, certain compounds according to general structural formula (V) or VI) were found to highly potently inhibit mycobacterial growth (MICs=0.073 to 50 µg/ml; Tables 9, 10).

For the series AAP1 (DL racemic mixture), AAP1a (D stereoisomer), and AAP1b (L stereoisomer), the D stereoisomer inhibited mycobacterial growth more potently that the DL racemic mixture, and the DL racemic mixture inhibited mycobacterial growth more potently than the L stereoisomer (Table 1).

Similarly, for the series IX-214 (DL racemic mixture), IX-214a (D stereoisomer), and IX-214b (L stereoisomer), the D stereoisomer inhibited mycobacterial growth more potently than the DL racemic mixture, and the DL racemic mixture inhibited mycobacterial growth more potently than the L stereoisomer (Tables 9, 10).

Similarly, for the series IX-274 (DL racemic mixture), IX-274a (D stereoisomer), and IX-274b (L stereoisomer), the D stereoisomer inhibited mycobacterial growth more potently than the DL racemic mixture, and the DL racemic mixture inhibited mycobacterial growth more potently than the L stereoisomer (Tables 9, 10).

By comparison to their potent inhibition of mycobacterial growth (MICs as low as 0.073 g/ml; Tables 2-3, 9, 10), tested compounds according to the general structural formulae less potently inhibited growth of *Staphylococcus aureus*, *Enterococcus faecalis*, *Pseudomonas aeruginosa*, *Acinetobacter baumannii*, *Klebsiella pneumoniae*, or *Escherichia coli* in analogous MIC assays with these organisms (MICs≥6.25 ug/ml).

Example 10. Determination of AAP1 Spontaneous Resistance Rates

Resistance rates were determined using fluctuation assays [Luria, S., Delbrück, M. (1943) *Genetics* 28, 491-511.]. Defined numbers of cells of *Mycobacterium smegmatis* ATCC 19420 (0.7×10$^9$-2×10$^9$ cfu/plate) were plated on Middlebrook Seven H11 agar base (BD, Inc.) containing Middlebrook ADC enrichment (BD, Inc.) and 0.5% glycerol, and also containing 2×MIC, 4×MIC, or 8×MIC of test compound on this medium (1.56, 3.13, or 6.25 µg/ml for AAP1), and numbers of colonies were counted after 96 h at 37° C. (at least 3 independent determinations for each concentration of each test compound). Resistance rates and 95% confidence intervals were calculated using the Ma-Sandri-Sarkar Maximum Likelihood Estimator (MSS-MLE [Ma, W., Sandri, GvH., Sarkar, S. (1992.) *J. Appl. Probab.* 29, 255-267; Sarkar, S., Ma, W., Sandri, GvH. (1992) *Genetica* 85, 173-179]) as implemented on the Fluctuation Analysis Calculator (FALCOR; www.keshavsingh.org/protocols/FALCOR.html [Hall, B., Ma, C., Liang, P., Singh, K (2009) *Bioinformatics* 25, 1564-1565]). Sampling correction was performed as in [Stewart, F., Gordon, D., Levin, B. (1990) *Genetics* 124, 175-185; Jones, M. (1993) *Mutat. Res.* 292, 187-189].

The spontaneous resistant rate for AAP1 was found to be $4\text{-}5\times10^{-9}$ per generation (Table 4).

Example 11. Isolation and Characterization of AAP1-Resistant Mutants

*Mycobacterium smegmatis* ATCC 19420 ($0.7\times10^9$-$2\times10^9$ cfu/plate) were plated on Middlebrook Seven H11 agar base (BD, Inc.) containing Middlebrook ADC enrichment (BD, Inc.), 0.5% glycerol, and 1.56, 3.13, or 6.25 µg/ml for AAP1, and colonies were isolated after 96 h at 37° C.

A total of 19 independent AAP1-resistant mutants were isolated (Table 5).

For each of the 19 independent AAP1-resistant mutants, the rpoB gene encoding the RNA polymerase second-largest subunit, beta, and the rpoC gene encoding the RNA polymerase largest subunit, beta', were isolated and sequenced as follows: Cells were lysed using 10 mg/ml lysozyme (Sigma, Inc.). Genomic DNA was isolated using the Wizard Genomic DNA Purification Kit (Promega, Inc.; procedures as specified by the manufacturer), and genomic DNA was quantified by measurement of UV-absorbance. The rpoB and rpoC genes were PCR-amplified in 50 µl reactions containing 50-200 ng genomic DNA, 0.5 µM forward and reverse oligonucleotide primers (5'-GTGCTGGAAGGATG-CATCTTGGCAGT-3' (SEQ ID NO:1) and 5'-TT-GCGGGACAGGTTGATTCCCAGGTTCGCG-3' (SEQ ID NO:2) for rpoB; 5'-GTGCTAGACGTCAACTTCTTCG-3' (SEQ ID NO:3) and 5'-TTAGCGGTAATCCGAGTAGCC-3' for rpoC) (SEQ ID NO:4), 25 µl 2× Phusion High-Fidelity PCR Master Mix with GC Buffer (New England Biolabs, Inc.) (initial denaturation step of 30 s at 98° C.; 30 cycles of 10 s at 99° C., 30 s at 60° C. for rpoB or 30 s at 55° C. for rpoC, and 4 min at 72° C.; final extension step of 10 min at 72° C.). PCR products containing the rpoB gene (3.5 kB) or the rpoC gene (4.0 kB) were isolated by electrophoresis on 0.8% agarose, extracted from gel slices using the QIAquick Gel Extraction Kit (Qiagen, Inc.; procedures as specified by the manufacturer), and sequenced (Sanger sequencing; nine sequencing primers for rpoB and ten sequencing primers for rpoC).

All 19 independent AAP1-resistant mutants were found to contain mutations in RNA polymerase genes (Table 5). 17 contained mutations in the rpoB gene encoding RNA polymerase beta subunit, and 2 contained mutations in the rpoC gene encoding RNA polymerase beta' subunit (Table 5). The fact that 100% of spontaneous AAP1-resistant mutants map to RNA polymerase subunit genes indicates that RNA polymerase is the functional cellular target of AAP1 and indicates that inhibition of mycobacterial RNA polymerase by AAP1 accounts for inhibition of mycobacterial growth by AAP1.

A total of 12 different substitutions conferring AAP1-resistance were identified (Table 6). Substitutions were obtained at 7 sites in *Mycobacterium smegmatis* RNA polymerase beta subunit (residues 466, 470, 477, 553, 557, 571, and 576) and at 2 sites in *Mycobacterium smegmatis* RNA polymerase beta' subunit (residues 833 and 850) (Table 6). The results indicate that residues 466, 470, 477, 553, 557, 571, and 576 of *Mycobacterium smegmatis* RNA polymerase beta subunit and residues 833 and 850 of *Mycobacterium smegmatis* RNA polymerase beta' subunit are important for inhibition of mycobacterial RNA polymerase and inhibition of mycobacterial growth by AAP1.

Resistance levels of AAP1-resistant mutants were quantified by measurement of MICs (methods as in Example 9). Tested AAP1-resistant mutants were found to exhibit >60-fold resistance (Table 6).

AAP1-resistant mutants were found to exhibit cross-resistance to all tested other compounds of the general structural formulae, including I-13, IX-37, IX-55, IX-73, IX-207, IX-211, IX-212, IX-213, IX-214, IX-215, IX-216, IX-235, IX-274, IX-275, IX-276, IX-312, and IX-313.

The existence of cross-resistance between AAP1 and all tested other compounds of the general structural formulae indicates that AAP1 and other compounds of the general structural formulae function through the same molecular target within RNA polymerase.

Example 12. Analysis of Locations of AAP1-Resistant Mutants within Structure of RNA Polymerase Sites of substitutions conferring AAP1-resistance (Table 6; Example 11) were mapped onto the crystal structure of *Thermus thermophilus* RNA polymerase holoenzyme (PDB accession code 1L9U [Vassylyev, D., Sekine, S., Laptenko, O., Lee, J., Vassylyeva, M., Borukhov, S., Yokoyama, S. (2002) Nature, 417, 712-719]). Correspondences between residues of *Mycobacterium smegmatis* RNA polymerase and *Thermus thermophilus* RNA polymerase were based on amino acid sequence alignments [Lane, W., Darst, S. (2010) J. Mol. Biol. 395, 671-685].

In the three-dimensional structure of RNA polymerase, the sites of substitutions conferring AAP1-resistance form a tight cluster (the "AAP1 target"; FIG. 2).

The dimensions of the AAP1 target are ~23 Å×~23 Å×~10 Å (FIG. 2). The AAP1 target is sufficiently large to be able to encompass AAP1 (~12 Å×~8 Å×~4 Å). Based on the resistance properties and the size of the AAP1 target, it is proposed herein that the AAP1 target is the binding site for AAP1 on RNA polymerase.

The AAP1 target is located distant from the RNA polymerase active center (FIG. 2). Based on the absence of overlap between the AAP1 target and the RNA polymerase active, it is proposed herein that AAP1 is an allosteric inhibitor of RNA polymerase.

The AAP1 target is located at the base of an RNA polymerase structural element referred to as the "beta lobe." Based on the location of the AAP1 target at the base of the "beta lobe," it is proposed herein that AAP1 is an allosteric inhibitor of RNA polymerase that functions through effects on a conformation of the beta lobe or a conformation of a structural element of RNA polymerase that interacts with the beta lobe.

The AAP1 target is located close to, but does not overlap, the target of the prior-art RNA polymerase inhibitor and antimycobacterial agent rifampin (FIG. 3; identities of residues of rifampin target as in [Ho, M., Hudson, B., Das, K., Arnold, E., Ebright, R. (2009) *Curr. Opin. Structl. Biol.* 19, 715-723]). Based on the absence of overlap between the AAP1 target and the rifampin target, it is proposed herein that AAP1 is unlikely to exhibit cross-resistance with rifampin.

The AAP1 target also is located close to, but does not overlap, the targets of the prior-art RNA polymerase inhibitor streptolydigin (identities of residues of streptolydigin target as in [Ho, M., Hudson, B., Das, K., Arnold, E., Ebright, R. (2009) *Curr. Opin. Structl. Biol.* 19, 715-723]).

Based on the absence of overlap between the AAP1 target and the streptolydigin target, it is proposed herein that AAP1 is unlikely to exhibit cross-resistance with streptolydigin.

The AAP1 target also is located close to, but does not overlap, the targets of the prior-art RNA polymerase inhibitors GE23077 and salinamide (identities of residues of GE23077 and salinamide targets as in [Zhang, Y., Degen, D., Ho, M., Sineva, E., Ebright, K., Ebright., Y., Mekler, V., Vahedian-Movahed, H., Feng, Y., Yon, R., Tuske, S., Irschik, H., Jansen, R., Maffioli, S., Donadio, S., Arnold, E., Ebright, R. (2014) eLife 3, e02450; Degen, D., Feng, Y., Zhang, Y., Ebright, K., Ebright, Y., Gigliotti, M., Vahedian-Movahed, H., Mandal, S., Talaue, M., Connell, N., Arnold, E., Fenical, W., Ebright, R. (2014) eLife 3, e02451]). Based on the absence of overlap between the AAP1 target and the GE23077 and salinamide targets, it is proposed herein that AAP1 is unlikely to exhibit cross-resistance with GE23077 and salinamide.

The AAP1 target is distant from, and does not overlap, the target of the prior-art RNA polymerase inhibitors myxopyronin, corallopyronin, and ripostatin and the target of the prior-art RNA polymerase inhibitor lipiarmycin (identities of residues of the myxopyronin/corallopyronin/ripostatin and lipiarmycin targets as in [Ho, M., Hudson, B., Das, K., Arnold, E., Ebright, R. (2009) Curr. Opin. Structl. Biol. 19, 715-723; Srivastava, A., Talaue, M., Liu, S., Degen, D., Ebright, R. Y., Sineva, E., Chakraborty, A., Druzhinin, S., Chatterjee, S., Mukhopadhyay, J., Ebright, Y., Zozula, A., Shen, J., Sengupta, S., Niedfeldt, R., Xin, C., Kaneko, T., Irschik, H., Jansen, R., Donadio, S., Connell, N., Ebright, R. (2011) Curr. Opin. Microbiol. 14, 532-543]). Based on the absence of overlap between the AAP1 target and the myxopyronin/corallopyronin/ripostatin and lipiarmycin targets, it is proposed herein that AAP1 is unlikely to exhibit cross-resistance with myxopyronin, corallopyronin, ripostatin, and lipiarmycin.

Example 13. Analysis of Cross-Resistance Between AAP1 and Rifampin

To determine whether AAP1-resistant mutants exhibit cross-resistance to the prior-art RNA polymerase inhibitor and antimycobacterial agent rifampin, MICs for rifampin were measured (methods as in Example 9). No AAP1-resistant mutant was found to exhibit cross-resistance to rifampin (Table 7). Some AAP1 resistant mutants were found to be hypersensitive to rifampin (Table 7).

To determine whether rifampin-resistant mutants exhibit cross-resistance to AAP1, MICs of rifampin-resistant mutants for AAP1 were measured (methods as in Example 9). No rifampin-resistant mutant was found to exhibit cross-resistance to AAP1 (Table 8). One rifampin-resistant mutant was found to be hypersensitive to AAP1 (Table 8).

The absence of cross-resistance between AAP1 and rifampin, and the reciprocal absence of cross-resistance between rifampin and AAP1, are consistent with the absence of overlap between the AAP1 target and the rifampin target (see Example 12).

To determine whether rifampin-resistant mutants exhibit cross-resistance to other compounds of the general structural formulae, MICs of rifampin-resistant mutants for other compounds of the general structural formulae, including I-13, I-17, I-25, I-39, I-80, I-86, I-91, I-97, I-102, I-112, I-115, I-125, I-160, I-236, II-5, II-12, II-13, II-28, II-39, IX-2, IX-3, IX-4, IX-5, IX-14, IX-37, IX55, IX-214, IX-215, and IX-216, were measured (methods as in Example 9). No rifampin-resistant mutant was found to exhibit cross-resistance with the tested other compounds of the general structural formulae.

The absence of cross-resistance between rifampin and the tested other compounds of the general structural formulae is consistent with the finding that other compounds of the general structural formulae function through AAP1 target (see Example 11) and the absence of overlap between the AAP1 target and the rifampin target (see Example 12).

Example 14. Assay of Mammalian-Cell Cytotoxicity

Minimal cytotoxic concentrations (MCCs) against mammalian cells in culture were determined using Vero E6 ATCC CRL1586 cells and the CellTiter96 assay kit (Promega, Inc.).

Therapeutic indices (TIs) were calculated as the ratio $MIC_{Mycobacterium\_sp.}/MCC_{Vero}$.

A TI of at least 10 is considered desirable.

Certain compounds according to the general structural formula (V) or (VI) were found to inhibit mycobacterial growth in culture at least 10 times more potently than they inhibited mammalian cells in culture (TIs≥10; Tables 9, 10).

Certain compounds according to the general structural formula (V) or (VI) were found to inhibit mycobacterial growth in culture at least 100 times more potently than they inhibited mammalian cells in culture (TIs≥100; Tables 9, 10).

Certain compounds according to the general structural formula (V) or (VI) were found to inhibit mycobacterial growth in culture at least 1000 times more potently than they inhibited mammalian cells in culture (TIs≥1000; Tables 9, 10).

Example 15. Preparation of N-(3-(4-hydroxyphenyl)-1-oxo-1-(o-tolylamino)propan-2-yl)benzamide (I-13)

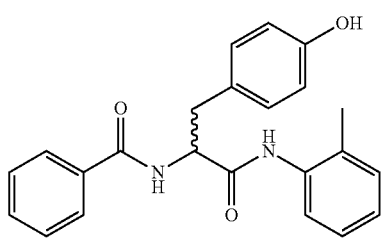

I-13

Example 15.1. Preparation of 2-benzamido-3-(4-(benzoyloxy)phenyl)propanoic acid

DL-Tyrosine (1 g; 5.52 mmol; Aldrich) was dissolved in 20 mL 1 M sodium hydroxide and cooled on an ice bath. To the cooled solution was added benzoyl chloride (1.28 mL, 11.04 mol; Aldrich) over 30 minutes followed by addition of 20 mL water. The reaction mixture was stirred for another 90 minutes on ice after which another 50 mL cold water was added. The suspension was made to pH 2 with 3 N HCl. The suspension was allowed to stand at ice temperature until precipitation was deemed over. The solid was collected via vacuum filtration, washed with water and ether and dried under vacuum to afford 2-benzamido-3-(4-(benzoyloxy) phenyl)propanoic acid.

Yield: 1.5 g, 70%.

Example 15.2. Preparation of I-13

2-Benzamido-3-(4-(benzoyloxy)phenyl)propanoic acid (Example 15.1; 1 g; 2.56 mmol), o-toluidine (0.21 mL; 2 mmol; Aldrich, Inc.) was dissolved in 40 mL anhydrous dimethylformamide at 25° C. To the solution was added PS-carbodiimide (3.1 g; 4 mmol; Biotage, Inc.) and hydroxybenzotriazole (405 mg, 3 mmol; Aldrich). The reaction mixture was stirred for 16 hours. The mixture was filtered through a plug of glass wool and evaporated to dryness. The sample was re-dissolved in chloroform and purified by silica chromatography (methanol gradient in chloroform) to afford 4-(2-benzamido-3-oxo-3-(o-tolylamino)propyl)phenyl benzoate (I-236).

4-(2-Benzamido-3-oxo-3-(o-tolylamino)propyl)phenyl benzoate (Example 17; 180 mg, 0.37 mmol) was dissolved in 72 mL of 1:1 methanol-concentrated ammonium hydroxide. The solution was microwaved at 80° C. (Biotage Initiator, Biotage) for 20 minutes. Upon cooling, the reaction mixture was evaporated and purified by silica chromatography (methanol gradient in chloroform) to afford I-13.

Yield: 75 mg, 27%.

MS (MALDI): calculated: m/z 376.43 (MH$^+$); found: 397.24 (M+Na$^+$).

Example 16. Preparation of N-(1-((2-(difluoromethoxy)phenyl)amino)-1-oxo-3-phenylpropan-2-yl)benzamide (I-61)

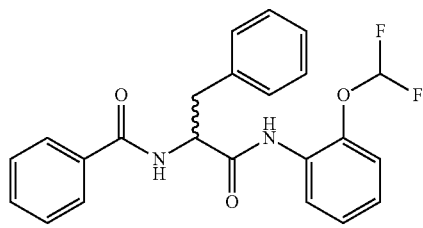

I-61

DL-Benzoyl-phenylalanine (164.4 mg; 0.61 mmol; Chem-Impex), 2-(difluoromethoxy)aniline (87 µl; 0.674 mmol; Aldrich), pyridine (0.5 mL; 6.18 mmol; Aldrich) were dissolved in 1 mL ethyl acetate at 25° C. To the solution was added T3P solution (0.72 mL; 1.21 mmol; Aldrich) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford the product I-61.

MS (MALDI): calculated: m/z 411.41 (MH$^+$); found: 411.13, 433.13 (M+Na$^+$).

Example 17. Preparation of 4-(2-benzamido-3-oxo-3-(o-tolylamino)propyl)phenyl benzoate (I-236)

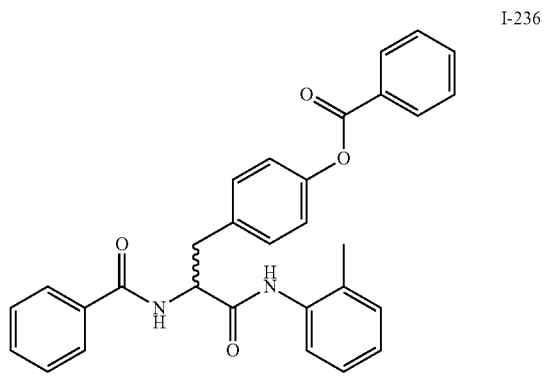 [SMILES: Cc1ccccc1NC(=O)C(Cc1ccc(OC(=O)c2ccccc2)cc1)NC(=O)c1ccccc1]

I-236

2-Benzamido-3-(4-(benzoyloxy)phenyl)propanoic acid (Example 15.1; 1 g; 2.56 mmol), o-toluidine (0.212 mL; 2 mmol; Aldrich, Inc.), was dissolved in 40 ml anhydrous dimethylformamide at 25° C. To the solution was added PS-carbodiimide (3.1 g; 4 mmol; Biotage) and hydroxybenzotriazole (405 mg, 3 mmol; Aldrich, Inc). The reaction mixture was stirred for 16 hours. The mixture was filtered through a plug of glass wool and evaporated to dryness. The sample was re-dissolved in chloroform and purified by silica chromatography (methanol gradient in chloroform) to afford I-236.

Yield: 0.6 g, 49%.

MS (MALDI): calculated: m/z 479.19 (MH$^+$); found: 501.20 (M+Na$^+$).

Example 18. Preparation of N-(1-oxo-3-phenyl-1-(quinolin-8-ylamino)propan-2-yl)benzamide (IX-2)

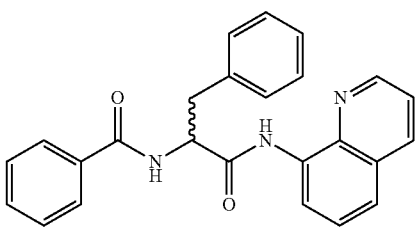

IX-2

DL-Benzoyl-phenylalanine (122.2 mg; 0.454 mmol; Chem-Impex, Inc.), 8-aminoquinoline (79.8 mg; 0.553 mmol; Aldrich), pyridine (0.5 mL; 6.18 mmol; Aldrich) were dissolved in 1 mL ethyl acetate at 25° C. To the solution was added T3P solution (0.5 mL; 0.86 mmol; Aldrich) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford the product IX-2.

MS (MALDI): calculated: m/z 396.45 (MH$^+$); found: 396.07, 418.04 (M+Na$^+$).

Example 19. Preparation of N-(1-(isoquinolin-5-ylamino)-1-oxo-3-phenylpropan-2-yl)benzamide (IX-3)

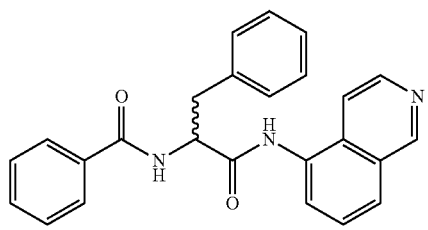

IX-3

IX-3 was prepared according to procedures in Example 18, but using 5-aminoisoquinoline (77.7 mg; 0.539 mmol; Aldrich) in place of 8-aminoquinoline.

MS (MALDI): calculated: m/z 396.45 (MH$^+$); found: 396.21, 418.08 (M+Na$^+$).

Example 20. Preparation of N-(1-oxo-3-phenyl-1-(quinolin-5-ylamino)propan-2-yl)benzamide (IX-4)

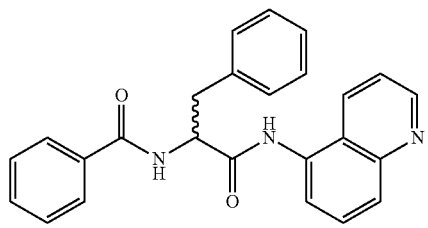

IX-4

IX-4 was prepared as in according to procedures in Example 18, but using 5-aminoquinoline (81.6 mg; 0.566 mmol; Aldrich) in place of 8-aminoquinoline.

MS (MALDI): calculated: m/z 396.41 (MH$^+$); found: 396.06, 418.06 (M+Na$^+$).

Example 21. Preparation of N-(1-((2,3-dihydrobenzo[b][1,4]dioxin-5-yl)amino)-1-oxo-3-phenylpropan-2-yl)benzamide (IX-5)

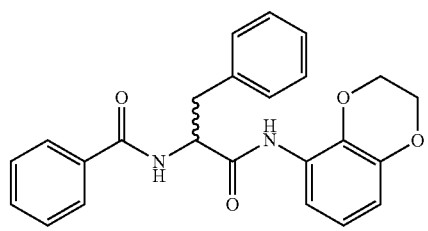

IX-5

IX-5 was prepared according to procedures in Example 18, but using 5-amino-1,4-benzodioxane (78.7 mg; 0.521 mmol; Aldrich) in place of 8-aminoquinoline.

MS (MALDI): calculated: m/z 403.44 (MH$^+$); found: 403.07, 425.07 (M+Na$^+$).

Example 22. Preparation of N-(3-(4-hydroxyphenyl)-1-oxo-1-((5,6,7,8-tetrahydronaphthalen-1-yl)amino)propan-2-yl)benzamide (IX-6)

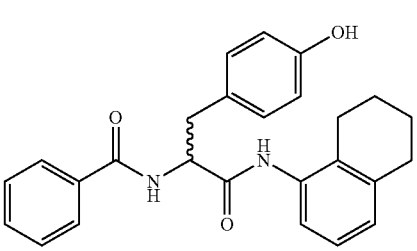

IX-6

2-Benzamido-3-(4-(benzoyloxy)phenyl)propanoic acid (Example 15.1; 161.3 mg; 0.414 mmol), 5,6,7,8-tetrahydro-1-naphthylamine (64 µl; 0.456 mmol; Aldrich), pyridine (0.5 mL; 6.18 mmol, Aldrich) were dissolved in 1 mL ethyl acetate at 25° C. To the solution was added T3P solution (0.5 mL; 0.86 mmol; Aldrich) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford a solid. The solid (66 mg) was re-dissolved in 2 mL of 3:3:1 THF-MeOH-water. Lithium hydroxide hydrate (12 mg; 0.29 mmol; Aldrich) was added and the mixture was stirred overnight at 50° C. The reaction mixture was cooled to 0° C. and poured into 5 mL dilute aqueous HCl. The solid that precipitated was collected by vacuum filtration, washed with water and ether, and dried under vacuum.

MS (MALDI): calculated: m/z 415.50 (MH$^+$); found: 421.35 (M+Li$^+$), 437.32 (M+Na$^+$).

Example 23. Preparation of N-(1-((2,3-dihydro-1H-inden-4-yl)amino)-3-(4-hydroxyphenyl)-1-oxopropan-2-yl)benzamide (IX-14)

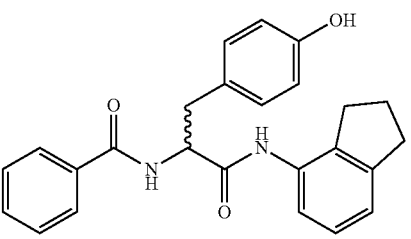

IX-14

IX-14 was prepared according to procedures in Example 22, but using 4-aminoindan (85 µl; 0.456 mmol; Aldrich) in place of 5,6,7,8-tetrahydro-1-naphthylamine.

MS (MALDI): calculated: m/z 401.47 (MH$^+$); found: 401.21, 423.22 (M+Na$^+$).

Example 24. Preparation of N-(1-(isoquinolin-8-ylamino)-1-oxo-3-phenylpropan-2-yl)benzamide (IX-15)

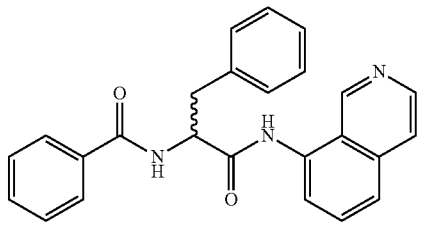

IX-15

IX-15 was prepared according to procedures in Example 18, but using 8-aminoisoquinoline (73.2 mg; 508 μmol; Aldrich) in place of 8-aminoquinoline.

Yield: 96.5 mg, 57%. MS (MALDI): calculated: m/z 396.45 (MH$^+$); found: 396.21, 418.18 (M+Na$^+$).

Example 25. Preparation of N-(3-(4-hydroxyphenyl)-1-(isoquinolin-8-ylamino)-1-oxopropan-2-yl)benzamide (IX-18)

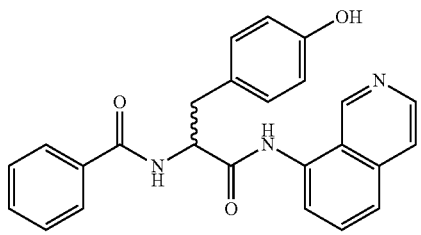

IX-18

IX-18 was prepared according to procedures in Example 22, but using 8-aminoisoquinoline (66 mg; 0.458 mmol; Aldrich) in place of 5,6,7,8-tetrahydro-1-naphthylamine.

Yield: 23.9 mg, 37%.

MS (MALDI): calculated: m/z 412.45 (MH$^+$); found: 412.27, 434.27 (M+Na$^+$).

Example 26. Preparation of N-(3-(4-hydroxyphenyl)-1-(isoquinolin-5-ylamino)-1-oxopropan-2-yl)benzamide (IX-19)

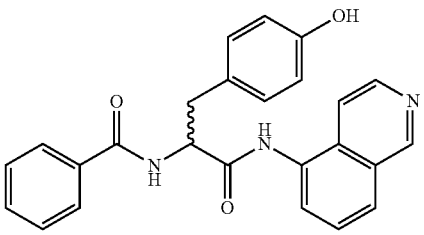

IX-19

IX-19 was prepared according to procedures in Example 22, but using 5-aminoisoquinoline (23 mg; 0.424 mmol; Aldrich) in place of 5,6,7,8-tetrahydro-1-naphthylamine.

Yield: 23 mg, 17%.

MS (MALDI): calculated: m/z 412.45 (MH$^+$); found: 412.24, 434.20 (M+Na$^+$).

Example 27. Preparation of N-(1-((2,3-dihydrobenzo[b][1,4]dioxin-5-yl)amino)-3-(4-hydroxyphenyl)-1-oxopropan-2-yl)benzamide (IX-21)

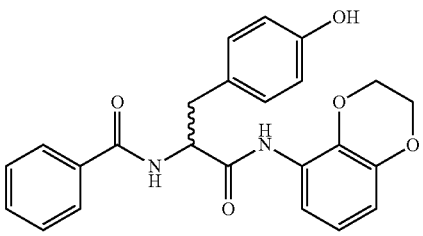

IX-21

IX-21 was prepared according to procedures in Example 22, but using 5-amino-1,4-benzodioxane (70.8 mg; 0.468 mmol; Aldrich) in place of 5,6,7,8-tetrahydro-1-naphthylamine.

Yield: 63.4 mg, 65%.

MS (MALDI): calculated: m/z 419.44 (MH$^+$); found: 441.20 (M+Na$^+$).

Example 28. Preparation of N-(3-(3,4-dihydroxyphenyl)-1-oxo-1-(o-tolylamino)propan-2-yl)benzamide (IX-25)

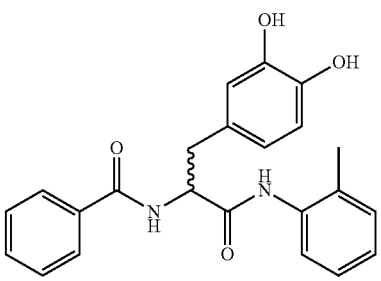

IX-25

Example 28.1. Preparation of 2-benzamido-3-(3,4-dihydroxyphenyl)propanoic acid 3,4-Dihydroxy-DL-phenylalanine (1.23 g; 6.22 mmol; Aldrich) was dissolved in 6.5 mL 2 M sodium carbonate solution. Benzoyl chloride (0.8 mL; 6.89 mmol; Aldrich) in 6.5 ml acetonitrile was slowly added to the mixture which was allowed to stir overnight. It was then poured into 10 ml 1 N HCl. The solid that precipitated was collected via vacuum filtration, washed with water and ether and dried under high vacuum to afford 2-benzamido-3-(3,4-dihydroxyphenyl)propanoic acid.

Example 28.2. Preparation of IX-25

2-Benzamido-3-(3,4-dihydroxyphenyl)propanoic acid (Example 28.2; 144.2 mg; 0.478 mmol), o-toluidine (57 dl; 0.536 mmol), pyridine (0.5 mL; 6.18 mmol; Aldrich) were dissolved in 1 mL ethyl acetate at 25° C. To the solution was added T3P solution (0.5 mL; 0.86 mmol; Aldrich) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to give the product IX-25.

MS (MALDI): calculated: m/z 391.43 (MH$^+$); found: 413.12 (M+Na$^+$).

Example 29. Preparation of N-(3-(4-hydroxyphenyl)-1-((2-methoxyphenyl)amino)-1-oxopropan-2-yl)benzamide (IX-26)

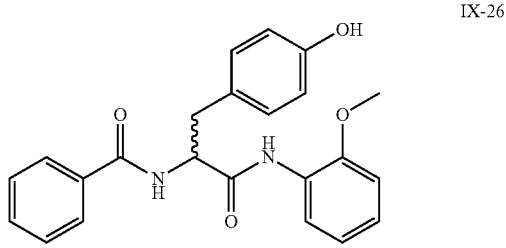 [SMILES: COc1ccccc1NC(=O)C(Cc1ccc(O)cc1)NC(=O)c1ccccc1]

IX-26

Example 29.1. Preparation of 2-amino-N-(2-methoxyphenyl)-3-phenylpropanamide

Boc-DL-tyrosine (243.1 mg; 0.864 mmol; Aldrich), o-anisidine (0.11 mL, 0.966 mmol), and pyridine (0.85 mL; 1.68 mmol; Aldrich) were dissolved in 1.7 mL ethyl acetate at 25° C. To the solution was added T3P solution (1 mL; 1.68 mmol; Aldrich) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford t-butyl (1-((2-methoxyphenyl)amino)-1-oxo-3-phenylpropan-2-yl)carbamate (190 mg; 0.492 mmol). The solid was dissolved in 5 mL dichloromethane, trifluoroacetic acid (0.38 mL; 4.96 mmol; Aldrich) was added and the mixture allowed to stir overnight. The mixture was evaporated, the residue was suspended in 5 mL saturated aqueous sodium bicarbonate and extracted with dichloromethane. The dichloromethane extract was evaporated to yield 2-amino-N-(2-methoxyphenyl)-3-phenylpropanamide (47.9 mg; 0.167 mmol; 34% yield).

Example 29.2. Preparation of IX-26

2-amino-N-(2-methoxyphenyl)-3-phenylpropanamide (47.9 mg, 0.167 mmol), benzoic acid (23 mg; 0.188 mmol; Aldrich) and pyridine (0.33 mL) were dissolved in 0.67 mL ethyl acetate at 25° C. To the solution was added T3P solution (0.2 mL; 0.336 mmol; Aldrich) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford IX-26.

MS (MALDI): calculated: m/z 391.43 (MH$^+$); found: 391.22, 413.18 (M+Na$^+$).

Example 30. Preparation of N-(1-((2-(fluoromethoxy)phenyl)amino)-1-oxo-3-phenylpropan-2-yl)benzamide (IX-27)

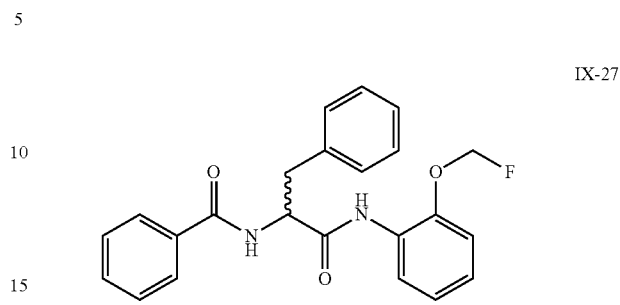

IX-27

Example 30.1. Preparation of N-(1-((2-hydroxyphenyl)amino)-1-oxo-3-phenylpropan-2-yl)benzamide DL-Benzoyl-phenylalanine (416.8 mg; 1.548 mmol; Chem-Impex), 2-amino-phenol (190.7 mg; 1.747 mmol; Aldrich), pyridine (1.5 mL) were dissolved in 3 mL dimethylformamide at 25° C. To the solution was added T3P solution (1.8 mL; 3.09 mmol; Aldrich) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford N-(1-((2-hydroxyphenyl)amino)-1-oxo-3-phenylpropan-2-yl)benzamide.

Example 30.2. Preparation of fluoromethyl 4-toluene-sulfonate

Methylene bis(toluene-4-sulfonate) (2.12 g; 5.96 mmol; Matrix Scientific) and tetrabutylammonium fluoride (6 mL; 1 M solution in THF; Aldrich) were refluxed in 6 mL acetonitrile overnight. Upon cooling, the reaction mixture was evaporated and purified by silica chromatography (ethyl acetate gradient in hexanes) to afford fluoromethyl 4-toluene-sulfonate.

Example 30.3. Preparation of IX-27

Fluoromethyl 4-toluene-sulfonate (Example 30.2; 91.4 mg, 0.448 mmol), N-(1-((2-hydroxyphenyl)amino)-1-oxo-3-phenylpropan-2-yl)benzamide (Example 30.1; 122.8 mg; 0.355 mmol) and potassium carbonate (72.7 mg; 0.526 mmol) were mixed and refluxed in 1 mL acetone for 48 hours. Upon cooling, the reaction mixture was evaporated and purified by silica chromatography (ethyl acetate gradient in hexanes) to give IX-27.

MS (MALDI): calculated: m/z 393.42 (MH$^+$); found: 393.24, 415.42 (M+Na$^+$).

Example 31. Preparation of N-(3-(4-hydroxyphenyl)-1-oxo-1-(o-tolylamino)propan-2-yl)thiophene-2-carboxamide (IX-28)

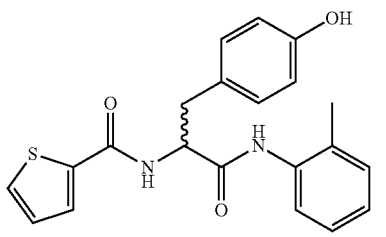

IX-28

Example 31.1. Preparation of 4-(3-methoxy-3-oxo-2-(thiophene-2-carboxamido)propyl)phenyl thiophene-2-carboxylate To DL-tyrosine methyl ester (1 g; 4.35 mmol; Aldrich) in 10 mL THF and triethylamine (2 mL; 14.3 mmol) was added 2-thiophenecarbonyl chloride (1 mL; 9.07 mmol; Aldrich) drop-wise. The resulting mixture was stirred overnight, then poured into 40 mL water and extracted with 40 mL ethyl acetate. The ethyl acetate extract was washed with brine, dried over anhydrous magnesium sulfate and evaporated to a solid. The solid was triturated with ether and dried under high vacuum to give 4-(3-methoxy-3-oxo-2-(thiophene-2-carboxamido)propyl)phenyl thiophene-2-carboxylate.

Example 31.2. Preparation of 3-(4-hydroxyphenyl)-2-(thiophene-2-carboxamido)propanoic acid 4-(3-Methoxy-3-oxo-2-(thiophene-2-carboxamido)propyl)phenyl thiophene-2-carboxylate (Example 31.1; 1 g; 2.41 mmol) was heated at 50° C. in 10 mL of 3:3:1 THF-MeOH-water containing lithium hydroxide hydrate (0.72 g; 17.04 mmol) for 12 hours, then cooled and evaporated to about 50% of the volume. The mixture was acidified with 1 N HCl to pH2 and extracted with ethyl acetate to give 3-(4-hydroxyphenyl)-2-(thiophene-2-carboxamido)propanoic acid.

Example 31.3. Preparation of IX-28

3-(4-Hydroxyphenyl)-2-(thiophene-2-carboxamido)propanoic acid (Example 31.2; 69.5 mg; 0.239 mmol), o-toluidine (28 µl, 0.263 mmol; Aldrich), pyridine (0.3 ml) were dissolved in 0.7 ml ethyl acetate at 25° C. To the solution was added T3P solution (0.29 mL, 0.49 mmol) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford the product IX-28.

MS (MALDI): calculated: m/z 381.46 (MH$^+$); found: 381.35, 403.34 (M+Na$^+$).

Example 32. Preparation of N-(1-((2-methoxyphenyl)amino)-1-oxo-3-phenylpropan-2-yl)thiophene-2-carboxamide (IX-29)

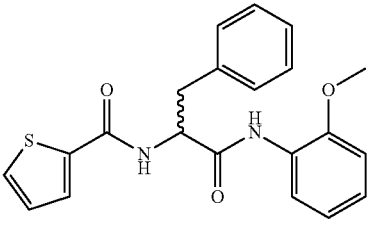

IX-29

Example 32.1. Preparation of 3-phenyl-2-(thiophene-2-carboxamido)propanoic acid To DL-tyrosine (9.35 g; 56.6 mmol; Aldrich) in 30 mL acetonitrile and 30 mL 2 M potassium carbonate was added 2-thiophenecarbonyl chloride (8 ml; 72.6 mmol; Aldrich) drop-wise. The resulting mixture was stirred overnight, then poured into 1N HCl and extracted with 250 mL ethyl acetate. The ethyl acetate extract was washed with brine, dried over anhydrous magnesium sulfate and evaporated to a solid. The solid was triturated with ether and dried under high vacuum to give 3-phenyl-2-(thiophene-2-carboxamido)propanoic acid.

Example 32.2. Preparation of IX-29

3-Phenyl-2-(thiophene-2-carboxamido)propanoic acid (Example 32.1; 125.2 mg; 0.455 mmol), o-anisidine (57 µl; 0.50 mmol; Aldrich), pyridine (0.5 mL) were dissolved in 1 mL ethyl acetate at 25° C. To the solution was added T3P solution (0.54 mL, 0.91 mmol) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to afford the product IX-29.

MS (MALDI): calculated: m/z 381.46 (MH$^+$); found: 381.35, 403.34 (M+Na$^+$).

Example 33. Preparation of N-(1-(isoquinolin-5-ylamino)-1-oxo-3-phenylpropan-2-yl)thiophene-2-carboxamide (IX-30)

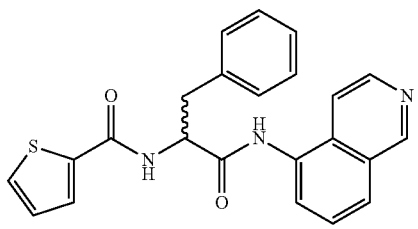

IX-30

IX-30 was prepared according to procedures in Example 32, but using 5-aminoisoquinoline in place of o-anisidine.

Example 34. Preparation of N-(1-((2,3-dihydrobenzo[b][1,4]dioxin-5-yl)amino)-1-oxo-3-phenylpropan-2-yl)thiophene-2-carboxamide (IX-31)

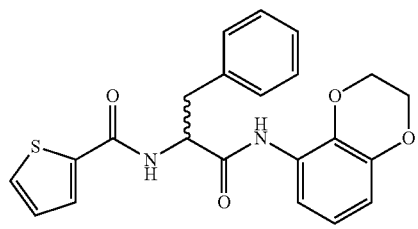

IX-31

IX-31 was prepared according to procedures in Example 32, but using 5-amino-1,4-benzodioxane in place of o-anisidine.
MS (MALDI): calculated: m/z 409.47 (MH⁺); found: 409.18, 431.14 (M+Na⁺).

Example 35. Preparation of N-(3-(4-hydroxyphenyl)-1-((2-methoxyphenyl)amino)-1-oxopropan-2-yl)thiophene-2-carboxamide (IX-32)

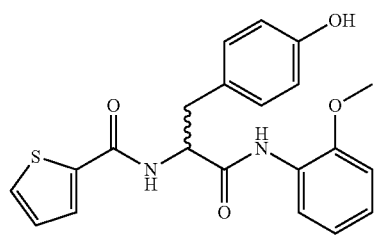

IX-32

IX-32 was prepared as according to procedures Example 31, but using o-anisidine in place of o-toluidine.
MS (MALDI): calculated: m/z 397.46 (MH⁺); found: 397.37, 419.43 (M+Na⁺).

Example 36. Preparation of N-(3-(4-hydroxyphenyl)-1-(isoquinolin-5-ylamino)-1-oxopropan-2-yl)thiophene-2-carboxamide (IX-33)

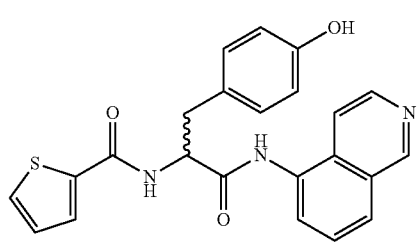

IX-33

IX-33 was prepared according to procedures in Example 31, but using 5-aminoisoquinoline in place of o-toluidine.

MS (MALDI): calculated: m/z 402.48 (MH⁺); found: 402.54, 424.22 (M+Na⁺).

MS (MALDI): calculated: m/z 418.48 (MH⁺); found: 418.40, 440.39 (M+Na⁺).

Example 37. Preparation of N-(1-((2,3-dihydrobenzo[b][1,4]dioxin-5-yl)amino)-3-(4-hydroxyphenyl)-1-oxopropan-2-yl)thiophene-2-carboxamide (IX-34)

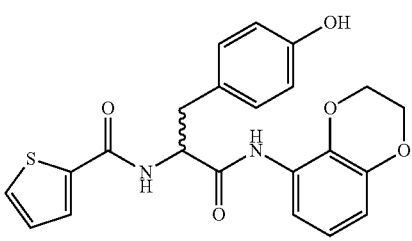

IX-34

IX-34 was prepared according to procedures in Example 31, but using 5-amino-1,4-benzodioxane in place of o-toluidine.
MS (MALDI): calculated: m/z 425.47 (MH⁺); found: 425.42, 447.62 (M+Na⁺).

Example 38. Preparation of N-(1-oxo-3-phenyl-1-(phthalazin-5-ylamino)propan-2-yl)benzamide (IX-35)

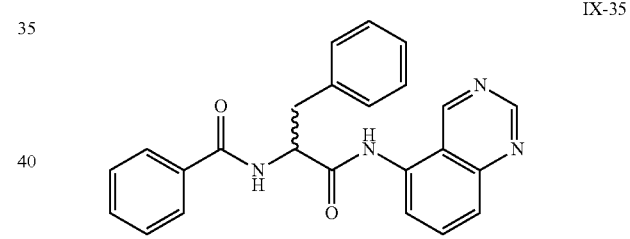

IX-35

IX-35 was prepared according to procedures in Example 18, but using 5-aminophthalazine (Ark Pharm) in place of 8-aminoquinoline.
MS (MALDI): calculated: m/z 397.44 (MH⁺); found: 397.34, 419.23 (M+Na⁺).

Example 39. Preparation of N-(1-((1H-indazol-4-yl)amino)-1-oxo-3-phenylpropan-2-yl)benzamide (IX-37)

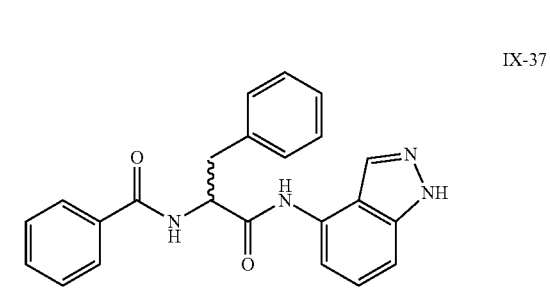 [SMILES: O=C(NC(Cc1ccccc1)C(=O)Nc1cccc2[nH]ncc12)c1ccccc1]

IX-37

IX-38 was prepared according to procedures in Example 18, but using 1H-indazol-4-amine (Aldrich) in place of 8-aminoquinoline.

MS (MALDI): calculated: m/z 385.15 (MH⁺); found: 385.14, 407.13 (M+Na⁺).

Example 40. Preparation of N-(1-((2-methoxypyridin-3-yl)amino)-1-oxo-3-phenylpropan-2-yl)benzamide (IX-38)

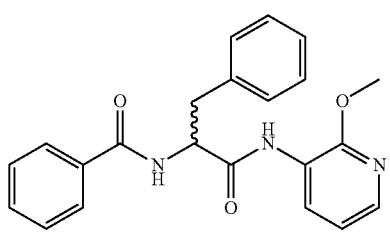

IX-38

IX-38 was prepared according to procedures in Example 18, but using 2-methoxy-3-pyridinamine (Aldrich) in place of 8-aminoquinoline.

MS (MALDI): calculated: m/z 376.42 (MH⁺); found: 376.34, 398.41 (M+Na⁺).

Example 41. Preparation of N-(1-((1H-indazol-7-yl)amino)-1-oxo-3-phenylpropan-2-yl)benzamide (IX-39)

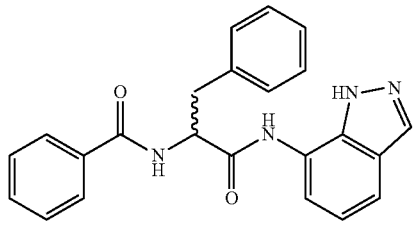

IX-39

IX-39 was prepared according to procedures in Example 18, but using 7-amino-1H-indazole (Aldrich) in place of 8-aminoquinoline.

MS (MALDI): calculated: m/z 385.43 (MH⁺); found: 385.20, 407.23 (M+Na⁺).

Example 42. Preparation of N-(1-((1H-indol-7-yl)amino)-3-(4-hydroxyphenyl)-1-oxopropan-2-yl)benzamide (IX-40)

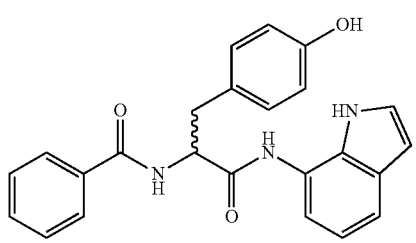

IX-40

IX-40 was prepared according to procedures in Example 22, but using 7-aminoindole (Aldrich) in place of 5,6,7,8-tetrahydro-1-naphthylamine.

MS (MALDI): calculated: m/z 399.44 (MH⁺); found: 399.89, 422.29 (M+Na⁺).

Example 43. Preparation of N-(1-((1H-indol-7-yl)amino)-1-oxo-3-phenylpropan-2-yl)thiophene-2-carboxamide (IX-41)

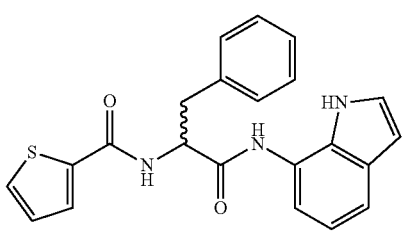

IX-41

IX-41 was prepared according to procedures in Example 32, but using 7-aminoindole (Aldrich) in place of o-anisidine.

MS (MALDI): calculated: m/z 390.47 (MH⁺); found: 390.14, 412.17 (M+Na⁺).

Example 44. Preparation of N-(1-((2-methoxyphenyl)amino)-1-oxo-3-phenylpropan-2-yl)-1H-indole-4-carboxamide (IX-43)

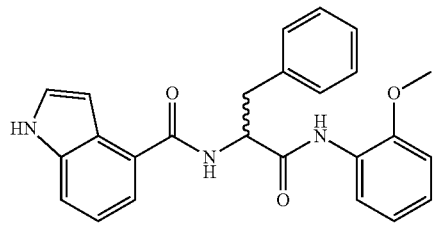

IX-43

Example 44.1. Preparation of (1H-indole-4-carbonyl)phenylalanine

DL-Methyl phenylalaninate hydrochloride (1.38 g; 6.4 mmol; Chem-Impex), 1H-indone-4-carboxylic acid (0.97 g; 6 mmol; Chem-Impex) and N,N-diisopropylethylamine (3.3 mL, 18.9 mmol; Aldrich) were dissolved in DMF (7.5 mL; Aldrich). To the solution was added T3P solution (7.35 mL, 12.3 mmol) drop-wise. The brown clear solution was stirred at 25° C. for 18 hours. 0.5N HCl (20 mL) was added followed by ethyl acetate (80 mL), separated, and the organic layer was washed with 1N HCl (2×20 mL) followed by saturated aqueous sodium bicarbonate (2×30 mL), and dried over anhydrous sodium sulfate to give methyl (1H-indole-4-carbonyl)phenylalaninate (0.79 g, yield 41%). It was treated with lithium hydroxide (0.31 g; 7.35 mmol; Alfa Aesar) in 14 mL of 3:3:1 MeOH-THF—H₂O at room temperature for 14 hours. The volatiles were removed under reduced pressure and the residue was treated by 1N HCl (10 mL), washed with water, ether and dried under vacuum to give 1H-indole-4-carbonyl)phenylalanine (0.75 g, yield 99%).

MS (MALDI): calculated: m/z 309.34 (MH⁺); found: 309.05, 331.03 (M+Na⁺).

Example 44.2. Preparation of IX-43

(1H-Indole-4-carbonyl)phenylalanine (Example 44.1; 100 mg; 0.324 mmol), o-methoxyaniline (37 mg; 0.30 mmol; Aldrich), and pyridine (0.28 mL; Aldrich) were dissolved into ethyl acetate (0.56 mL; Aldrich) at room temperature. Into the stirring solution, was added T3P solution (0.4 mL; Aldrich) drop-wise. The deep yellow clear solution was stirred at room temperature for 18 hours. An equal volume of 0.5N HCl (1 mL) was added and stirred at room temperature. The white solid precipitate was collected, was washed with water, ether and dried in vacuum to give IX-43.

Yield: 100 mg, 80%.

MS (MALDI): calculated: m/z 414.48 (MH⁺); found: 414.14, 436.13 (M+Na⁺).

Example 45. Preparation of N-(1-(isoquinolin-5-ylamino)-1-oxo-3-phenylpropan-2-yl)-1H-indole-4-carboxamide (IX-44)

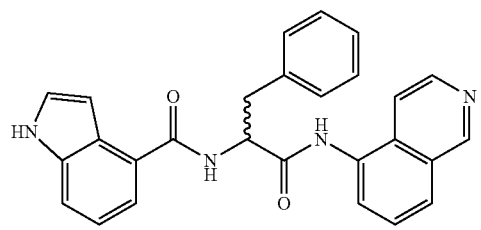

IX-44

IX-44 (yellow solid) was prepared according to procedures in Example 44.2, but using isoquinolin-5-amine (43 mg; 0.30 mmol; Acros Organics) in place of o-methoxyaniline.

Yield: 83 mg, 64%.

MS (MALDI): calculated: m/z 435.40 (MH⁺); found: 435.23, 457.27 (M+Na⁺).

Example 46. Preparation of N-(1-((2,3-dihydrobenzo[b][1,4]dioxin-5-yl)amino)-1-oxo-3-phenylpropan-2-yl)-1H-indole-4-carboxamide (IX-45)

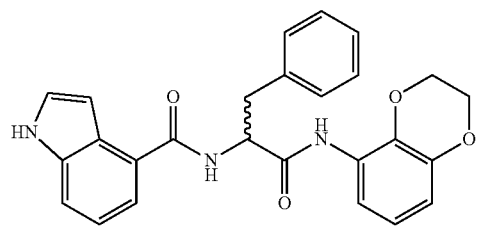

IX-45

IX-45 was prepared according to procedures in Example 44.2, but using 2,3-dihydrobenzo[b][1,4]dioxin-5-amine (92 mg; 0.61 mmol; Aldrich) in place of o-methoxyaniline.

Yield: 44 mg, 16%.

MS (MALDI): calculated: m/z 464.48 (MNa⁺); found: 464.28.

Example 47. Preparation of N-(1-((5-chloro-2-methylphenyl)amino)-3-(4-hydroxyphenyl)-1-oxo-propan-2-yl)benzamide (IX-51)

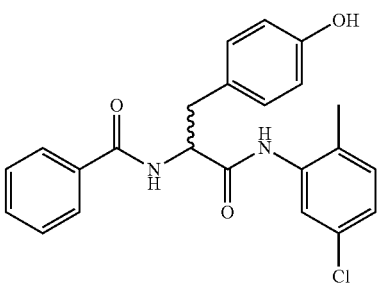

IX-51

IX-51 was prepared according to procedures in Example 22, but using 5-chloro-2-methylaniline in place of 5,6,7,8-tetrahydro-1-naphthylamine.

MS (MALDI): calculated: m/z 408.88 (MH⁺); found: 409.35, 431.37 (M+Na⁺).

Example 48. Preparation of N-(1-((5-chloro-2-methylphenyl)amino)-1-oxo-3-phenylpropan-2-yl)-1H-indole-4-carboxamide (IX-53)

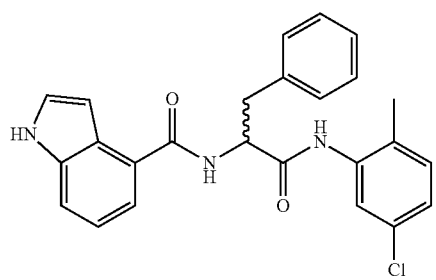

IX-53

IX-53 was prepared according to procedures in Example 44.2, but using 5-chloro-2-methylaniline (47 mg; 0.30 mmol; Aldrich) in place of o-methoxyaniline.

Yield: 87 mg, 67%.

MS (MALDI): calculated: m/z 432.92 (MH⁺); found: 432.18, 454.20 (M+Na⁺).

Example 49. Preparation of 2-fluoro-N-(3-(4-hydroxyphenyl)-1-oxo-1-(o-tolylamino)propan-2-yl)benzamide (IX-54)

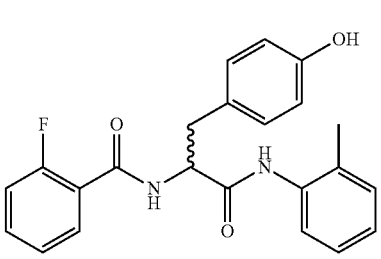

IX-54

Example 49.1. Preparation of 2-amino-3-(4-hydroxyphenyl)-N-phenylpropanamide Boc-DL-tyrosine (1.01 g, 3.61 mmol; Aldrich, Inc), o-toluidine (0.44 mL, 4.14 mmol; Aldrich, Inc.), pyridine (3.6 ml) were dissolved in 7.2 mL ethyl acetate at 25° C. To the solution was added T3P solution (4.4 mL, 7.39 mmol) drop-wise. The reaction mixture was stirred for 16 hours, an equal volume of 0.5N HC was added, stirring was continued for 10 minutes followed by addition of water. The resulting precipitate was collected by vacuum filtration, washed with water and ether and dried under vacuum to afford t-butyl (3-(4-hydroxyphenyl)-1-oxo-1-(o-tolylamino)propan-2-yl) carbamate. The solid (3.6 mmole) was dissolved in 20 mL dichloromethane containing 2.5 mL trifluoroacetic acid (32.7 mmol). The solution was stirred overnight and washed with saturated sodium bicarbonate. The dichloromethane layer was dried over anhydrous sodium sulfate and evaporated to give 2-amino-3-(4-hydroxyphenyl)-N-phenylpropanamide.

Example 49.2. Preparation of IX-54

2-Amino-3-(4-hydroxyphenyl)-N-phenylpropanamide (Example 49.1; 120.6 mg; 0.446 mmol), 2-fluorobenzoic acid (69.9 mg; 0.499 mmol; Aldrich), and pyridine (0.5 mL) were dissolved in 1 mL ethyl acetate at 25° C. To the solution was added T3P solution (0.53 mL; 0.89 mmol) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to give IX-54.

MS (MALDI): calculated: m/z 393.42 (MH$^+$); found: 393.23.

Example 50. Preparation of N-(1-((5-chloro-2-methylphenyl)amino)-1-oxo-3-phenylpropan-2-yl)-2-fluorobenzamide (IX-55)

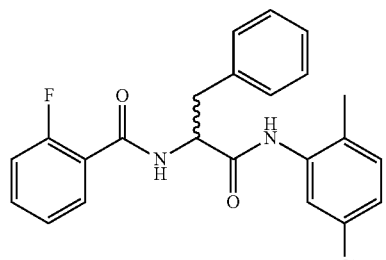

IX-55

Example 50.1. Preparation of 2-(2-fluorobenzamido)-3-phenylpropanoic acid

DL-Tyrosine (5 g; 30.3 mmol; Aldrich) was dissolved in 30 mL 2 M sodium carbonate. To this solution was added 2-fluorobenzoyl chloride (4.75 mL in 30 mL acetonitrile; 39.4 mmol; Aldrich) drop-wise with stirring. The mixture was allowed to stir overnight and then poured into 1 N HCl. The solid obtained was collected by vacuum filtration, washed with water and ether and dried under vacuum to give 2-(2-fluorobenzamido)-3-phenylpropanoic acid.

Example 50.2. Preparation of IX-55

2-(2-Fluorobenzamido)-3-phenylpropanoic acid (Example 50.1; 147.5 mg; 0.513 mmol), 4-chloro-2-methylaniline (92 mg; 0.649 mmol; Aldrich) and pyridine (0.5 mL) were dissolved in 1 mL ethyl acetate at 25° C. To the solution was added T3P solution (0.61 mL; 1.02 mmol) drop-wise. The reaction mixture was stirred for 16 hours, an equal volume of 0.5N HCl was added, stirring was continued for 10 minutes followed by addition of water. The resulting precipitate was collected by vacuum filtration, washed with water and ether and dried under vacuum to give IX-55.

MS (MALDI): calculated: m/z 411.87 (MH$^+$); found: 411.11, 433.13 (M+Na$^+$).

Example 51. Preparation of 2-fluoro-N-(1-((2-methoxyphenyl)amino)-1-oxo-3-phenylpropan-2-yl)benzamide (IX-56)

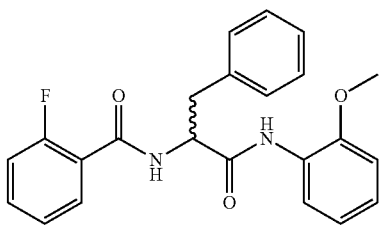

IX-56

IX-56 was prepared according to procedures in Example 50, but using o-anisidine in place of 4-chloro-2-methylaniline MS (MALDI): calculated: m/z 393.42 (MH$^+$); found: 393.22, 415.25 (M+Na$^+$).

Example 52. Preparation of 2-fluoro-N-(1-(isoquinolin-5-ylamino)-1-oxo-3-phenylpropan-2-yl)benzamide (IX-57)

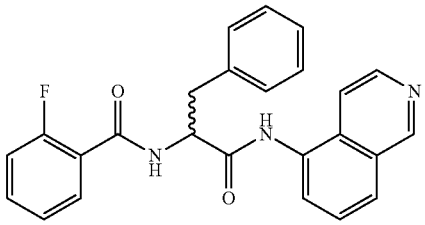

IX-57

IX-57 was prepared according to procedures in Example 50, but using 5-aminoisoquinoline in place of 4-chloro-2-methylaniline.

MS (MALDI): calculated: m/z 414.44 (MH$^+$); found: 414.18, 436.23 (M+Na$^+$).

Example 53. Preparation of 2-fluoro-N-(1-oxo-3-phenyl-1-(quinolin-5-ylamino)propan-2-yl)benzamide (IX-58)

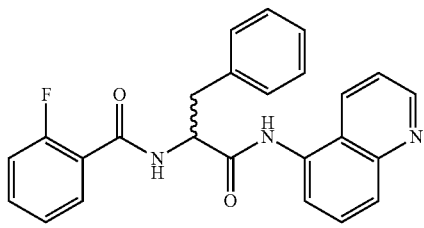

IX-58

IX-58 was prepared according to procedures in Example 50, but using 5-aminoquinoline in place of 4-chloro-2-methylaniline.

MS (MALDI): calculated: m/z 414.44 (MH$^+$); found: 414.48, 436.47 (M+Na$^+$).

Example 54. Preparation of N-(1-((2,3-dihydrobenzo[b][1,4]dioxin-5-yl)amino)-1-oxo-3-phenylpropan-2-yl)-2-fluorobenzamide (IX-59)

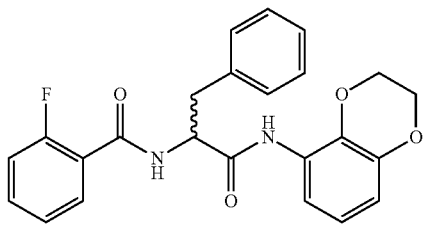

IX-59

IX-59 was prepared according to procedures in Example 50, but using 5-amino-1,4-benzodioxane in place of 4-chloro-2-methylaniline.

MS (MALDI): calculated: m/z 421.43 (MH$^+$); found: 421.18, 443.23 (M+Na$^+$).

Example 55. Preparation of 2-chloro-N-(3-(4-hydroxyphenyl)-1-oxo-1-(o-tolylamino)propan-2-yl)benzamide (IX-60)

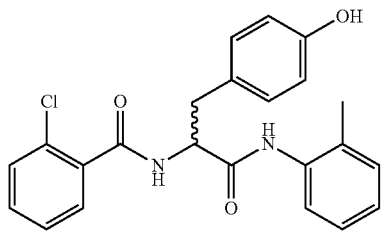

IX-60

IX-60 was prepared according to procedures in Example 49, but using 2-chlorobenzoic acid in place of 2-fluorobenzoic acid.

MS (MALDI): calculated: m/z 408.88 (MH$^+$); found: 409.25.

Example 56. Preparation of 2-chloro-N-(1-((5-chloro-2-methylphenyl)amino)-1-oxo-3-phenylpropan-2-yl)benzamide (IX-61)

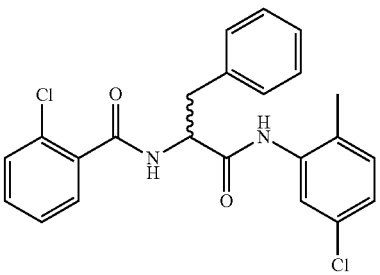

IX-61

IX-61 was prepared according to procedures in Example 50, but using 2-chlorobenzoic acid in place of 2-fluorobenzoic acid.

MS (MALDI): calculated: m/z 427.32 (MH$^+$); found: 427.29, 449.20 (M+Na$^+$).

Example 57. Preparation of 2-chloro-N-(1-((2-methoxyphenyl)amino)-1-oxo-3-phenylpropan-2-yl)benzamide (IX-62)

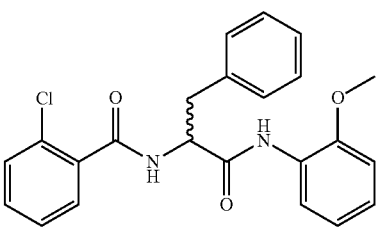

IX-62

IX-62 was prepared according to procedures in Example 50, but using 2-chlorobenzoyl chloride in place of 2-fluorobenzoyl chloride and o-anisidine in place of 4-chloro-2-methylaniline.

MS (MALDI): calculated: m/z 408.88 (MH$^+$); found: 431.25 (M+Na$^+$).

Example 58. Preparation 2-chloro-N-(1-(isoquinolin-5-ylamino)-1-oxo-3-phenylpropan-2-yl)benzamide (IX-63)

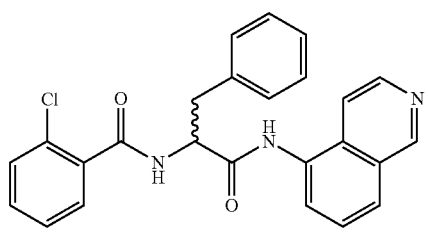

IX-63

IX-63 was prepared according to procedures in Example 50, but using 2-chlorobenzoyl chloride in place of 2-fluorobenzoyl chloride and 5-aminoisoquinoline in place of 4-chloro-2-methylaniline.

MS (MALDI): calculated: m/z 430.90 (MH$^+$); found: 430.16, 452.11 (M+Na$^+$).

Example 59. Preparation of 2-chloro-N-(1-oxo-3-phenyl-1-(quinolin-5-ylamino)propan-2-yl)benzamide (IX-64)

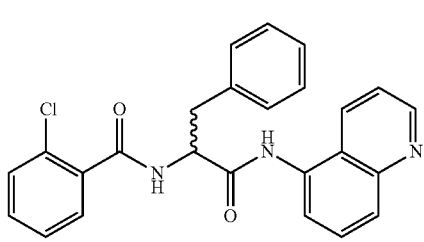

IX-64

IX-64 was prepared according to procedures in Example 50, but using 2-chlorobenzoyl chloride in place of 2-fluorobenzoyl chloride and 5-aminoquinoline in place of 4-chloro-2-methylaniline.

MS (MALDI): calculated: m/z 430.90 (MH$^+$); found: 430.14, 452.11 (M+Na$^+$).

Example 60. Preparation of 2-chloro-N-(1-((2,3-dihydrobenzo[b][1,4]dioxin-5-yl)amino)-1-oxo-3-phenylpropan-2-yl)benzamide (IX-65)

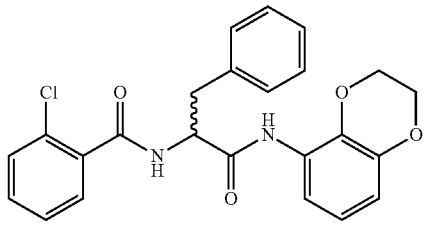

IX-65

IX-65 was prepared according to procedures in Example 50, but using 2-chlorobenzoyl chloride in place of 2-fluorobenzoyl chloride and 5-amino-1,4-benzodioxane in place of 4-chloro-2-methylaniline.

MS (MALDI): calculated: m/z 437.89 (MH$^+$); found: 437.27, 460.13 (M+Na$^+$).

Example 61. Preparation of N-(3-(4-hydroxyphenyl)-1-oxo-1-(o-tolylamino)propan-2-yl)-2-methylbenzamide (IX-66)

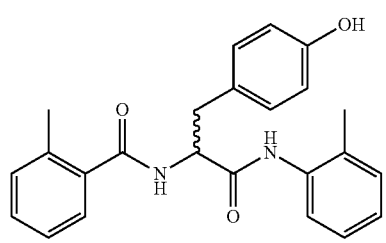

IX-66

IX-66 was prepared according to procedures in Example 49, but using 2-toluic acid in place of 2-fluorobenzoic acid.

MS (MALDI): calculated: m/z 389.46 (MH$^+$); found: 411.23 (M+Na$^+$).

Example 62. Preparation of N-(1-((5-chloro-2-methylphenyl)amino)-1-oxo-3-phenylpropan-2-yl)-2-methylbenzamide (IX-67)

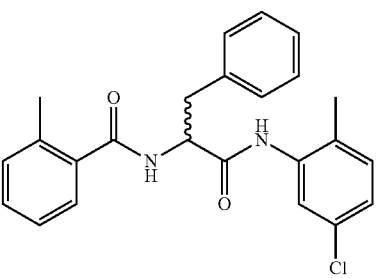

IX-67

Example 62.1. Preparation of 2-(2-methybenzamido)-3-phenylpropanoic acid

DL-Phenylalanine (5 g; 30.3 mmol; Aldrich) was dissolved in 30 mL 2M sodium carbonate. To this solution was added o-toluoyl chloride (5.2 mL in 30 mL acetonitrile; 39.5 mmol; Aldrich) drop-wise with stirring. The mixture was allowed to stir overnight and then poured into 1N HCl. The solid obtained was collected by vacuum filtration, washed with water and ether and dried under vacuum to give 2-(2-methybenzamido)-3-phenylpropanoic acid.

Example 62.2. Preparation of IX-67

2-(2-Methylbenzamido)-3-phenylpropanoic acid (Example 62.1; 138.5 mg; 0.489 mmol), 5-chloro-2-methylaniline (90 mg; 0.635 mmol) and pyridine (0.5 mL) were dissolved in 1 mL ethyl acetate at 25° C. To the solution was added T3P solution (0.61 mL; 1.02 mmol) drop-wise. The reaction mixture was stirred for 16 hours, an equal volume of 0.5N HCl was added, stirring was continued for 10 minutes followed by addition of water. The resulting precipitate was collected by vacuum filtration, washed with water and ether and dried under vacuum to give IX-67.

MS (MALDI): calculated: m/z 407.90 (MH$^+$); found: 429.11 (M+Na$^+$).

Example 63. Preparation of N-(1-((2-methoxyphenyl)amino)-1-oxo-3-phenylpropan-2-yl)-2-methylbenzamide (IX-68)

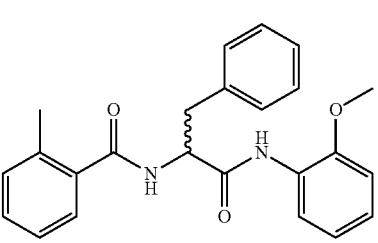

IX-68

IX-68 was prepared according to procedures in Example 62, but using o-anisidine in place of 5-chloro-2-methylaniline.

MS (MALDI): calculated: m/z 389.46 (MH$^+$); found: 389.23, 411.29 (M+Na$^+$).

Example 64. Preparation of N-(1-(isoquinolin-5-ylamino)-1-oxo-3-phenylpropan-2-yl)-2-methylbenzamide (IX-69)

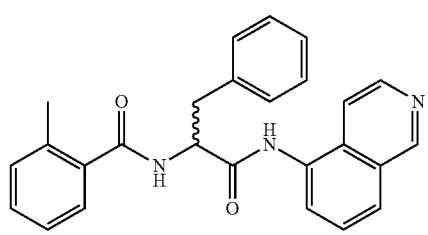

IX-69 was prepared according to procedures in Example 62, but using 5-aminoisoquinoline in place of 4-chloro-2-methylaniline.

MS (MALDI): calculated: m/z 410.48 (MH$^+$); found: 410.19, 432.12 (M+Na$^+$).

Example 65. Preparation of 2-methyl-N-(1-oxo-3-phenyl-1-(quinolin-5-ylamino)propan-2-yl)benzamide (IX-70)

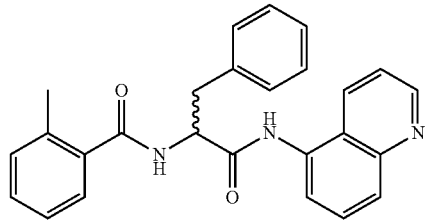

IX-70 was prepared according to procedures in Example 62, but using 5-aminoquinoline in place of 4-chloro-2-methylaniline.

MS (MALDI): calculated: m/z 410.48 (MH$^+$); found: 410.47, 432.09 (M+Na$^+$).

Example 66. Preparation of N-(1-((2,3-dihydrobenzo[b][1,4]dioxin-5-yl)amino)-1-oxo-3-phenylpropan-2-yl)-2-methylbenzamide (IX-71)

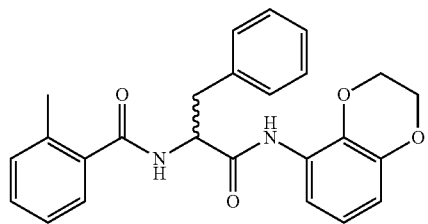

IX-71 was prepared according to procedures in Example 62, but using 5-amino-1,4-benzodioxane in place of 4-chloro-2-methylaniline.

MS (MALDI): calculated: m/z 417.47 (MH$^+$); found: 439.11 (M+Na$^+$).

Example 67. Preparation of N-(1-(benzo[d][1,3]dioxol-4-ylamino)-1-oxo-3-phenylpropan-2-yl)benzamide (IX-72)

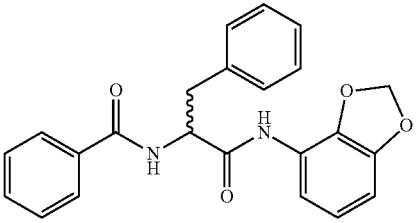

IX-72 was prepared according to procedures in Example 18, but using 4-amino-1,3-benzodioxole (Ark Pharm) in place of 8-aminoquinoline.

MS (MALDI): calculated: m/z 389.42 (MH$^+$); found: 389.28, 411.21 (M+Na$^+$).

Example 68. Preparation of N-(1-((5-fluoro-2-methoxyphenyl)amino)-1-oxo-3-phenylpropan-2-yl)benzamide (IX-73)

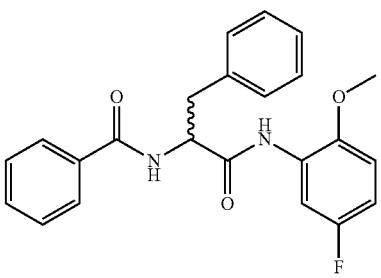

IX-73 was prepared according to procedures in Example 18, but using 5-fluoro-2-methoxyaniline (Aldrich) in place of 8-aminoquinoline.

Yield: 126 mg, 78%.

MS (MALDI): calculated: m/z 393.43 (MH$^+$); found: 393.13, 415.11 (M+Na$^+$).

Example 69. Preparation of N-(1-((7-fluoroquinolin-5-yl)amino)-1-oxo-3-phenylpropan-2-yl)benzamide (IX-75)

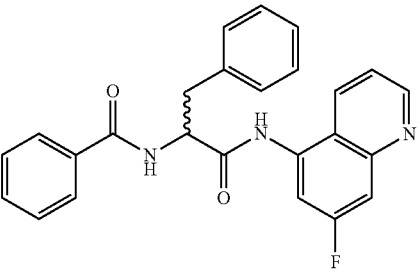

IX-75 (yellowish solid) was prepared according to procedures in Example 18, but using 7-fluoroquinolin-5-amine (Aces Pharm) in place of 8-aminoquinoline.

Yield: 104 mg, 61%.

MS (MALDI): calculated: m/z 414.45 (MH$^+$); found: 414.13, 436.11 (M+Na$^+$).

Example 70. Preparation of N-(1-((5-fluoro-2-methylphenyl)amino)-1-oxo-3-phenylpropan-2-yl)thiophene-2-carboxamide (IX-79)

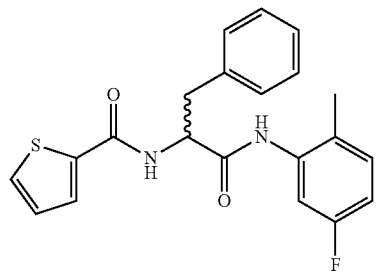

IX-79

IX-79 was prepared according to procedures in Example 32, but using 5-fluoro-2-methylaniline in place of o-anisidine.

MS (MALDI): calculated: m/z 383.45 (MH$^+$); found: 383.25, 405.23 (M+Na$^+$).

Example 71. Preparation of N-(1-((5-fluoro-2-methylphenyl)amino)-1-oxo-3-phenylpropan-2-yl)-1H-indole-4-carboxamide (IX-80)

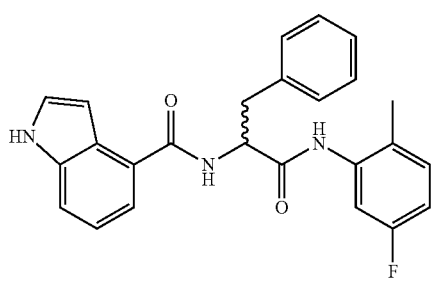

IX-80

IX-80 was prepared according to procedures in Example 44, but using 5-fluoro-2-methylaniline (38 mg; 0.30 mmol; Aldrich) in place of o-methoxyaniline.

Yield: 70 mg, 56%.

MS (MALDI): calculated: m/z 416.47 (MH$^+$); found: 416.13, 438.12 (M+Na$^+$).

Example 72. Preparation of 2-fluoro-N-(1-((5-fluoro-2-methylphenyl)amino)-1-oxo-3-phenylpropan-2-yl)benzamide (IX-81)

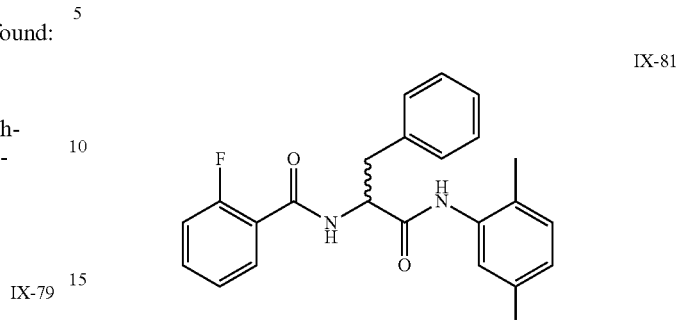

IX-81

IX-81 was prepared as in Example 50, but using 5-fluoro-2-methylaniline in place of 4-chloro-2-methylaniline.

MS (MALDI): calculated: m/z 395.41 (MH$^+$); found: 395.32, 417.18 (M+Na$^+$).

Example 73. Preparation of 2-chloro-N-(1-((5-fluoro-2-methylphenyl)amino)-1-oxo-3-phenylpropan-2-yl)benzamide (IX-82)

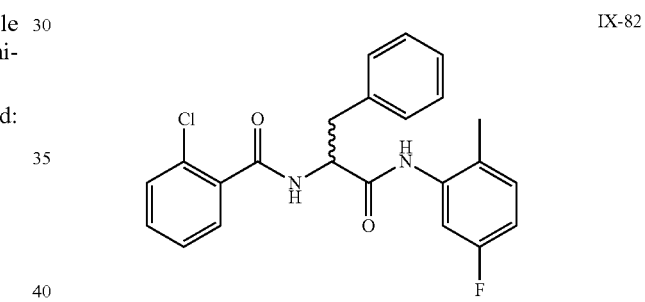

IX-82

IX-82 was prepared according to procedures in Example 50, but using 2-chlorobenzoyl chloride in place of 2-fluorobenzoyl chloride and 5-fluoro-2-methylaniline in place of 5-chloro-2-methylaniline.

MS (MALDI): calculated: m/z 411.87 (MH$^+$); found: 411.14, 433.18 (M+Na$^+$).

Example 74. Preparation of N-(1-((5-fluoro-2-methylphenyl)amino)-1-oxo-3-phenylpropan-2-yl)-2-methylbenzamide (IX-83)

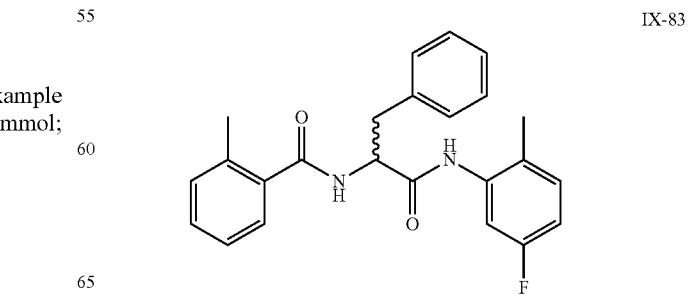

IX-83

IX-83 was prepared according to procedures in Example 62, but using 5-fluoro-2-methylaniline in place of 5-chloro-2-methylaniline.

MS (MALDI): calculated: m/z 391.45 (MH+); found: 391.28, 413.32 (M+Na+).

Example 75. Preparation of N-(1-oxo-3-phenyl-1-(quinolin-5-ylamino)propan-2-yl)thiophene-2-carboxamide (IX-85)

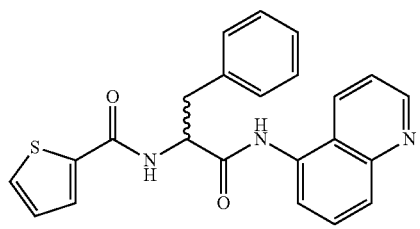

IX-85

IX-85 was prepared according to procedures in Example 32, but using 5-aminoquinoline in place of o-anisidine.

MS (MALDI): calculated: m/z 402.48 (MH+); found: 402.52, 424.26 (M+Na+).

Example 76. Preparation of N-(1-oxo-3-phenyl-1-((5,6,7,8-tetrahydronaphthalen-1-yl)amino)propan-2-yl)thiophene-2-carboxamide (IX-86)

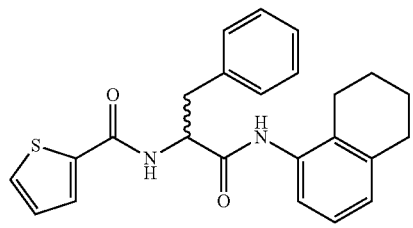

IX-86

IX-86 was prepared according to procedures in Example 32, but using 5,6,7,8-tetrahydro-1-naphthylamine (Aldrich) in place of o-anisidine.

MS (MALDI): calculated: m/z 405.52 (MH+); found: 405.26, 427.34 (M+Na+).

Example 77. Preparation of N-(1-((1H-indol-4-yl)amino)-1-oxo-3-phenylpropan-2-yl)-2-fluorobenzamide (IX-91)

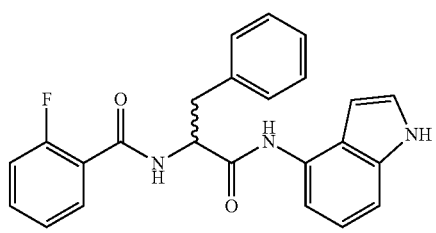

IX-91

IX-91 was prepared according to procedures in Example 50, but using 5-aminoindole in place of 5-chloro-2-methylaniline.

MS (MALDI): calculated: m/z 402.43 (MH+); found: 402.12, 424.12 (M+Na+).

Example 78. Preparation of N-(1-((5-chloro-2-methylphenyl)amino)-3-(4-hydroxyphenyl)-1-oxopropan-2-yl)thiophene-2-carboxamide (IX-94)

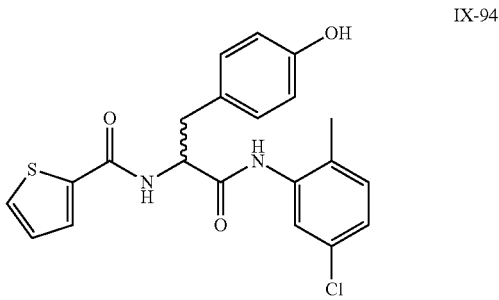 [SMILES: Cc1ccc(Cl)cc1NC(=O)C(Cc1ccc(O)cc1)NC(=O)c1cccs1]

IX-94

IX-94 was prepared according to procedures in Example 31, but using 5-chloro-2-methylaniline in place of o-toluidine.

MS (MALDI): calculated: m/z 415.91 (MH+); found: 415.46, 437.44 (M+Na+).

Example 79. Preparation of N-(1-((1H-indol-7-yl)amino)-1-oxo-3-phenylpropan-2-yl)-2-chlorobenzamide (IX-95)

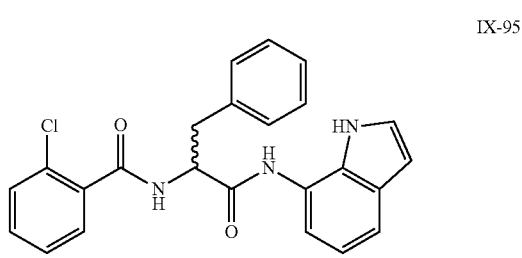 [SMILES: O=C(NC(Cc1ccccc1)C(=O)Nc1cccc2cc[nH]c12)c1ccccc1F]

IX-95

IX-95 was prepared according to procedures in Example 50, but using 2-chlorobenzoyl chloride in place of 2-fluorobenzoyl chloride and 7-aminoindole (Aldrich) in place of 5-chloro-2-methylaniline.

MS (MALDI): calculated: m/z 418.8 (MH+); found: 418.07, 440.14 (M+Na+).

Example 80. Preparation of N-(1-((1H-indol-7-yl)amino)-1-oxo-3-phenylpropan-2-yl)-2-fluorobenzamide (IX-96)

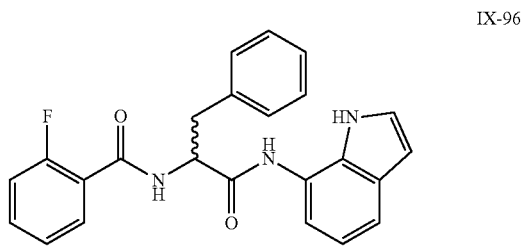 [SMILES: Cc1ccccc1C(=O)NC(Cc1ccccc1)C(=O)Nc1cccc2cc[nH]c12]

IX-96

IX-96 was prepared according to procedures in Example 50, but using and 7-aminoindole in place of 5-chloro-2-methylaniline.

MS (MALDI): calculated: m/z 402.43 (MH+); found: 402.21, 424.24 (M+Na+).

Example 81. Preparation of N-(1-((1H-indol-7-yl)amino)-1-oxo-3-phenylpropan-2-yl)-2-methylbenzamide (IX-97)

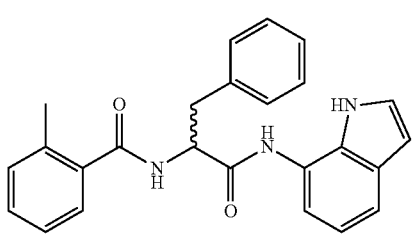

IX-97 was prepared according to procedures in Example 62, but using 7-aminoindole in place of 5-chloro-2-methylaniline.

MS (MALDI): calculated: m/z 398.47 (MH+); found: 398.34, 420.24 (M+Na+).

Example 82. Preparation N-(1-(benzo[d][1,3]dioxol-4-ylamino)-1-oxo-3-phenylpropan-2-yl)thiophene-2-carboxamide (IX-98)

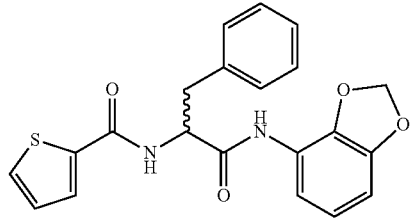

IX-98 was prepared according to procedures in Example 32, but using 4-amino-1,3-benzodioxole (Ark Pharm) in place of o-anisidine.

MS (MALDI): calculated: m/z 395.44 (MH+); found: 395.12, 417.18 (M+Na+).

Example 83. Preparation of N-(1-(benzo[d][1,3]dioxol-4-ylamino)-1-oxo-3-phenylpropan-2-yl)-2-fluorobenzamide (IX-99)

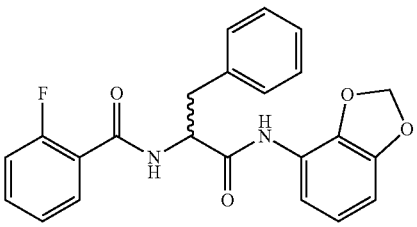

IX-99 was prepared according to procedures in Example 50, but using 4-amino-1,3-benzodioxole in place of 5-chloro-2-methylaniline.

MS (MALDI): calculated: m/z 407.41 (MH+); found: 407.21, 429.04 (M+Na+).

Example 84. Preparation of N-(1-((2-(difluoromethoxy)phenyl)amino)-1-oxo-3-phenylpropan-2-yl)thiophene-2-carboxamide (IX-100)

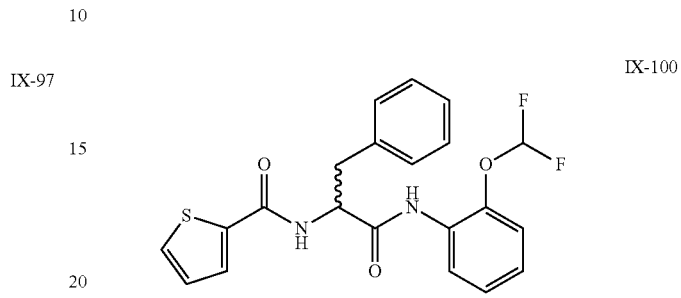

IX-100 was prepared according to procedures in Example 32, but using 2-(difluoromethoxy)aniline (Aldrich) in place of o-anisidine.

MS (MALDI): calculated: m/z 417.44 (MH+); found: 439.09 (M+Na+).

Example 85. Preparation of N-(1-((2-(difluoromethoxy)phenyl)amino)-1-oxo-3-phenylpropan-2-yl)-2-fluorobenzamide (IX-101)

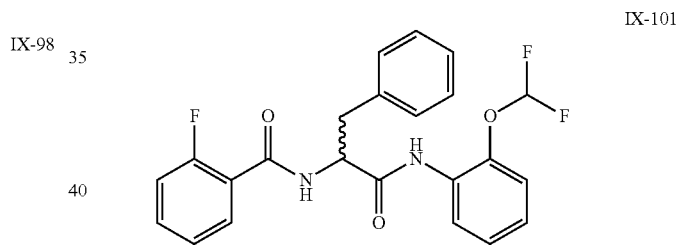

IX-101 was prepared according to procedures in Example 50, but using 2-(difluoromethoxy)aniline (Aldrich) in place of 5-chloro-2-methylaniline.

MS (MALDI): calculated: m/z 429.40 (MH+); found: 429.04, 451.24 (M+Na+).

Example 86. Preparation of N-(1-((5-bromo-2-methylphenyl)amino)-3-(4-hydroxyphenyl)-1-oxopropan-2-yl)benzamide (IX-103)

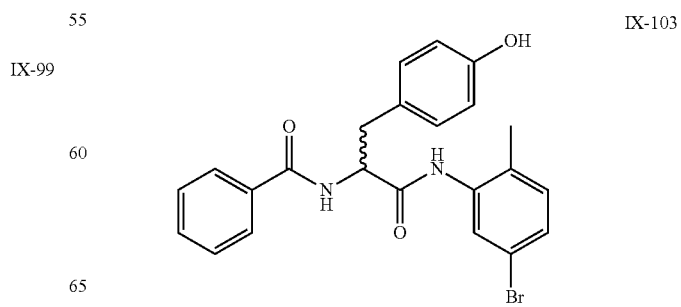

Example 86.1. Preparation of DL-2-benzamido-3-(4-(benzoyloxy)phenyl)propanoic acid DL-Tyrosine (1.25 g; 6.9 mmol; Aldrich) was dissolved in 15 mL 2 M sodium carbonate. Benzoyl chloride (2 mL; 17.2 mmol; Aldrich) in 15 mL acetonitrile was slowly added and stirring was allowed to continue for 18 hours. The mixture was poured into 30 mL 1 N HCl. The solid precipitate was collected via vacuum filtration, washed with water and ether and dried under vacuum to afford 2-benzamido-3-(4-(benzoyloxy)phenyl)propanoic acid.

Yield: 2.5 g, 93%.

MS (MALDI): calculated: m/z 390.12 (MH$^+$); found: 390.12, 412.09 (M+Na$^+$).

Example 86.2. Preparation of O-benzoyl-IX-103

O-Benzoyl-IX-103 was prepared according to procedures in Example 44.2, but using DL-2-benzamido-3-(4-(benzoyloxy)phenyl)propanoic acid (Example 86.1; 160 mg; 0.41 mmol) and 5-bromo-2-methylaniline (76 mg; 0.41 mmol; Aldrich) in place of (1H-indole-4-carbonyl)phenylalanine and o-methoxyaniline.

Yield: 62 mg, 27%.

MS (MALDI): calculated: m/z 557.44 (M); found: 557.17 (M), 581.16 (M+Na$^+$).

Example 86.3. Preparation of IX-103

O-Benzoyl-IX-103 (62 mg, 0.11 mmol) was stirred with 1.0 M LiOH (0.3 mL) in MeOH (0.6 mL) and THF (0.6 mL) at room temperature for 18 hours. Most volatiles were removed under reduced pressure. The residue was treated with 1.0N HCl (1.0 mL) at room temperature. White solid was collected by filtration, washed with water, ether and dried in vacuum.

Yield: 35 mg, 69%.

MS (MALDI): calculated: m/z 476.33 (MNa$^+$); found: 476.99 (M+Na$^+$).

Example 87. Preparation of N-(1-((1H-indol-4-yl)amino)-1-oxo-3-phenylpropan-2-yl)thiophene-2-carboxamide (IX-104)

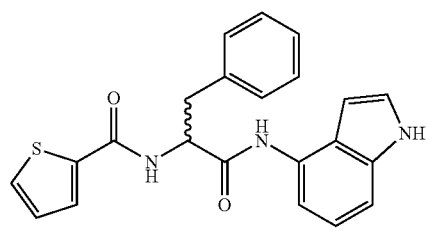

IX-104

IX-104 was prepared according to procedures in Example 32, but using 5-aminoindole (Aldrich) in place of o-anisidine.

MS (MALDI): calculated: m/z 390.12 (MH$^+$); found: 390.12, 412.09 (M+Na$^+$).

Example 88. Preparation of N-(1-oxo-3-phenyl-1-((2-(pyrrolidin-1-yl)phenyl)amino)propan-2-yl)thiophene-2-carboxamide (IX-105)

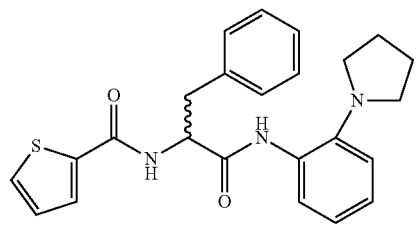

IX-105

IX-105 was prepared according to procedures in Example 32, but using (2-pyrrolidin-1-ylphenyl)amine (Aldrich) in place of o-anisidine.

MS (MALDI): calculated: m/z 420.54 (MH$^+$); found: 420.18, 442.14 (M+Na$^+$).

Example 89. Preparation of N-(1-((3-methoxy-2-methylphenyl)amino)-1-oxo-3-phenylpropan-2-yl)thiophene-2-carboxamide (IX-107)

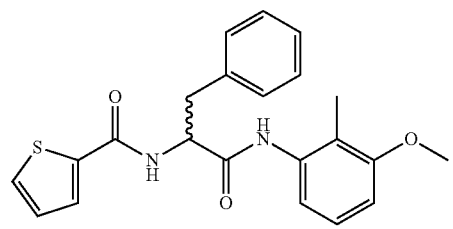

IX-107

IX-107 was prepared according to procedures in Example 32, but using 3-methoxy-2-methylaniline (Aldrich) in place of o-anisidine.

MS (MALDI): calculated: m/z 395.49 (MH$^+$); found: 395.19, 417.16 (M+Na$^+$).

Example 90. Preparation of 2-fluoro-N-(1-((3-methoxy-2-methylphenyl)amino)-1-oxo-3-phenylpropan-2-yl)benzamide (IX-108)

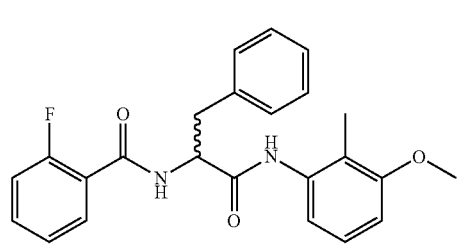

IX-108

IX-108 was prepared according to procedures in Example 50, but using 3-methoxy-2-methylaniline in place of 5-chloro-2-methylaniline.

MS (MALDI): calculated: m/z 407.46 (MH$^+$); found: 407.14, 429.25 (M+Na$^+$).

Example 91. Preparation of N-(1-((5-fluoro-2-(fluoromethoxy)phenyl)amino)-1-oxo-3-phenyl-propan-2-yl)-2-methylbenzamide (IX-111)

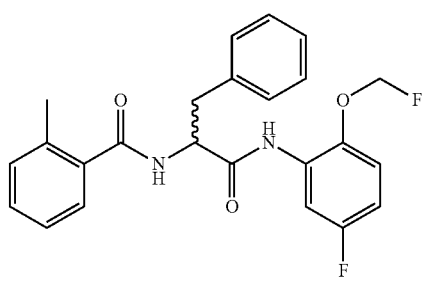

IX-111

Example 91.1. Preparation of N-(2-methylbenzoyl)-DL-phenylalanine

DL-phenylalanine (5.0 g; 30 mmol; Chem-Impex) was dissolved in 2 M sodium carbonate solution (30 mL), and an acetonitrile (ACN) solution (30 mL) of 2-methylbenzoyl chloride (5.2 mL; 38.9 mmol; Aldrich) was slowly added into the stirring solution at room temperature. The resulting mixture was stirred at the same temperature for 18 hrs, then added into an equal volume of 1 N HCl (60 mL). The product was collected by vacuum filtration, washed with water and ether, and dried under vacuum to give N-(2-methylbenzoyl)-DL-phenylalanine was obtained as white solid.

Yield: 6.7 g, 79%.
MS (MALDI): calculated: m/z 284.33 (MH$^+$); found: 284.17, 306.15 (M+Na$^+$).

Example 91.2. Preparation of N-(1-((5-fluoro-2-hydroxyphenyl)amino)-1-oxo-3-phenylpropan-2-yl)-2-methylbenzamide N-(2-Methylbenzoyl)-DL-phenylalanine (Example 91.1; 113 mg; 0.40 mmol), 2-amino-4-fluorophenol (58 mg; 0.46 mmol; Aldrich) and pyridine (0.5 mL) were dissolved in 1 mL ethyl acetate at 25° C. To the solution was added T3P solution (0.61 mL; 1.02 mmol) drop-wise. The reaction mixture was stirred for 16 hours, an equal volume of 0.5 N HCl was added, stirring was continued for 10 minutes followed by addition of water. The resulting precipitate was collected by vacuum filtration, washed with water and ether and dried under vacuum to give N-(1-((5-fluoro-2-hydroxyphenyl)amino)-1-oxo-3-phenylpropan-2-yl)-2-methylbenzamide.

Example 91.2. Preparation of IX-111

N-(1-((5-Fluoro-2-hydroxyphenyl)amino)-1-oxo-3-phenylpropan-2-yl)-2-methylbenzamide (Example 91.2; 80 mg; 0.2 mmol) was mixed with fluoromethyl 4-toluene-sulfonate (Example 30.2; 61 mg; 0.3 mmol) and cesium carbonate (130 mg, 0.4 mmol) in 2 mL of dry DMF, stirred and heated at 60° C. for 18 hours. The mixture was evaporated to dryness, re-dissolved in 50 mL ethyl acetate and extracted with water. The ethyl acetate layer was dried and purified by silica gel chromatography (20% ethyl acetate/hexane) to give IX-111.

Yield: 49 mg, 58%.
MS (MALDI): calculated: m/z 425.45 (MH$^+$); found: 425.06, 447.02 (M+Na$^+$).

Example 92. Preparation of 2-chloro-N-(1-((2-(difluoromethoxy)phenyl)amino)-1-oxo-3-phenylpropan-2-yl)benzamide (IX-119)

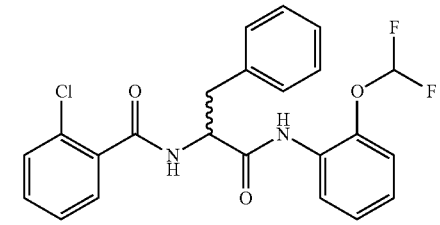

IX-119

Example 92.1. Preparation of N-(2-chlorobenzoyl)-DL-phenylalanine

N-(2-Chlorobenzoyl)-DL-phenylalanine (white solid) was prepared as in Example 91.1 but using 2-chlorobenzoyl chloride in place of 2-methylbenzoyl chloride.

MS (MALDI): calculated: m/z 304.74 (MH$^+$); found: 304.43 (M+H$^+$), 326.41 (M+Na$^+$).

Example 92.2. Preparation of IX-119

N-(2-Chlorobenzoyl)-DL-phenylalanine (Example 92.1; 201 mg, 0.66 mmol) and 2-(difluoromethoxy)aniline (100 µL; 0.78 mmol; Aldrich) and pyridine (0.5 mL, Aldrich) were dissolved into ethyl acetate (2 mL; Aldrich) at room temperature. Into the stirring solution, was added T3P solution (0.8 mL; Aldrich) drop-wise. The solution was stirred at room temperature for 18 hours. An equal volume of 0.5N HCl was added and stirred at room temperature. The white solid precipitate was collected, was washed with water, ether and dried in vacuum to give IX-119.

Yield: 40 mg, 14%.
MS (MALDI): calculated: m/z 445.86 (MH$^+$); found: 445.27, 467.27 (M+Na$^+$).

Example 93. Preparation of N-(1-((2-(difluoromethoxy)phenyl)amino)-1-oxo-3-phenylpropan-2-yl)-2-methylbenzamide (IX-120)

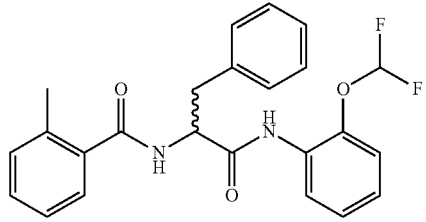

IX-120

IX-120 was according to procedures in Example 44, but using 2-methylbenzoyl)-DL-phenylalanine (154 mg; 0.54 mmol) and 2-(difluoromethoxy)aniline (77 μL; 0.6 mmol; Aldrich) in place of (1H-indole-4-carbonyl)phenylalanine and o-methoxyaniline.

Yield: 69 mg, 30%.

MS (MALDI): calculated: m/z 425.45 (MH+); found: 425.18, 447.17 (M+Na+).

Example 94. Preparation of N-(1-((2,2-difluorobenzo[d][1,3]dioxol-4-yl)amino)-1-oxo-3-phenyl-propan-2-yl)-2-fluorobenzamide (IX-122)

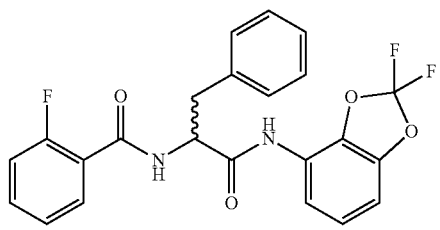

IX-122

Example 94.1. Preparation of 2-amino-N-(2,2-difluorobenzo[d][1,3]dioxol-4-yl)-3-phenylpropanamide t-Butyl-(1-((2,2-difluorobenzo[d][1,3]dioxol-4-yl)amino)-1-oxo-3-phenyl-propan-2-yl)carbamate (white solid; 370 mg; 0.88 mmol), was prepared according to procedures in Example 44, but using N-Boc-DL-phenylalanine (448 mg; 1.69 mmol) and 2,2-difluorobenzo[d][1,3]dioxol-4-amine (329 mg; 1.9 mmol, Aldrich) in place of (1H-indole-4-carbonyl)phenylalanine and o-methoxyaniline. It was treated with TFA (0.8 mL; Aldrich) in DCM (6 mL) at room temperature until no starting material was observed by TLC (1:1 ethyl acetate:hexanes). Most volatiles were removed under reduced pressure. The residue was treated with NaHCO₃ (sat. aqueous solution, 10 mL), extracted with DCM (25 mL×3) and dried over Na₂SO₄ to give 2-amino-N-(2,2-difluorobenzo[d][1,3]dioxol-4-yl)-3-phenylpropanamide.

Example 94.2. Preparation of IX-122

IX-122 was prepared according to Example 44 but using 2-fluorobenzoic acid (34 mg; 0.24 mmol; Aldrich) and 2-amino-N-(2,2-difluorobenzo[d][1,3]dioxol-4-yl)-3-phenylpropanamide (63 mg; 0.2 mmol) in place of (1H-indole-4-carbonyl)phenylalanine and o-methoxyaniline.

Yield: 28 mg, 32%.

MS (MALDI): calculated: m/z 443.39 (MH+); found: 443.06, 465.07 (M+Na+).

Example 95. Preparation of N-(1-((2,2-difluorobenzo[d][1,3]dioxol-4-yl)amino)-1-oxo-3-phenyl-propan-2-yl)thiophene-2-carboxamide (IX-124)

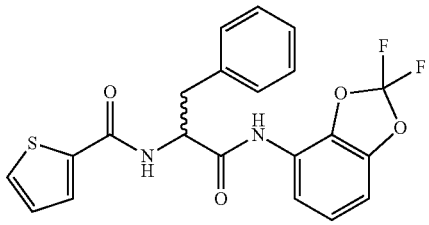

IX-124

2-Amino-N-(2,2-difluorobenzo[d][1,3]dioxol-4-yl)-3-phenylpropanamide (Example 94.1; 63 mg; 0.2 mmol) was dissolved in 10 mL THF, mixed with thiophene-2-carbonyl chloride (35 mg; 240 μL), and treated with TEA (61 μL, Aldrich) at room temperature for 2 hours. The mixture was poured into water (4 mL), extracted with ethyl acetate (4 mL), washed with NaHCO₃ (sat. aqueous solution, 2 mL), and dried over Na₂SO₄ to give IX-124.

Yield: 58 mg, 67%.

MS (MALDI): calculated: m/z 431.43 (MH+); found: 431.05, 453.03 (M+Na+).

Example 96. Preparation of N-(1-(benzo[d][1,3]dioxol-4-ylamino)-3-(4-hydroxyphenyl)-1-oxopropan-2-yl)-2-bromobenzamide (IX-125)

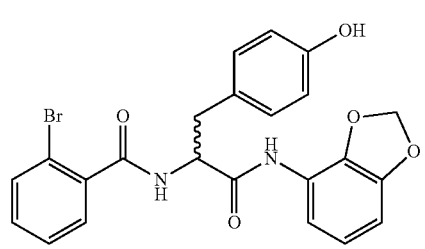

IX-125

IX-125 was prepared according to procedures in Example 15, but using 2-bromobenzoyl chloride in place of benzoyl chloride and 4-amino-1,3-benzodioxole in place of o-toluidine.

MS (MALDI): calculated: m/z 483.05 (MH+); found: 483.27, 505.13 (M+Na+).

Example 97. Preparation of N-(1-((1H-indazol-4-yl)amino)-1-oxo-3-phenylpropan-2-yl)-2-fluorobenzamide (IX-128)

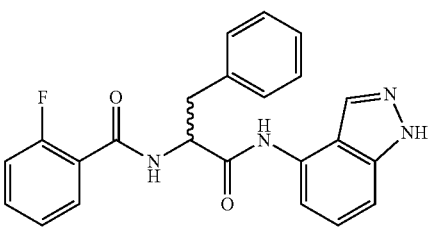

IX-128

Example 97.1. Preparation of N-(2-fluorobenzoyl)-DL-phenylalanine

N-(2-Fluorobenzoyl)-DL-phenylalanine was prepared as in Example 91.1 but using 2-fluorobenzoyl chloride in place of 2-methylbenzoyl chloride.

MS (MALDI): calculated: m/z 288.29 (MH$^+$); found: 288.03 (M+H$^+$), 310.01 (M+Na$^+$).

Example 97.2. Preparation of IX-128

IX-128 was prepared according to procedures in Example 44.2, but using N-(2-fluorobenzoyl)-DL-phenylalanine (Example 97.1; 144 mg; 0.5 mmol) and 1H-indazol-4-amine (73 mg; 0.55 mmol; Chem-Impex) in place of (1H-indole-4-carbonyl)phenylalanine and o-methoxyaniline.

Yield: 66 mg, 33%.

MS (MALDI): calculated: m/z 403.43 (MH$^+$); found: 403.17, 425.16 (M+Na$^+$).

Example 98. Preparation of N-(1-oxo-3-phenyl-1-((2-thiomorpholinophenyl)amino)propan-2-yl)-benzamide (IX-149)

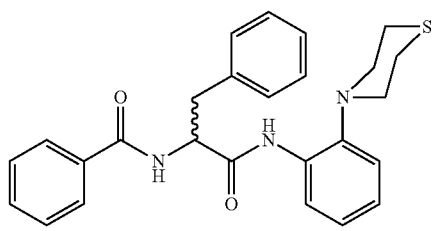

IX-149

Example 98.1. Preparation of 2-thiomorpholinoaniline

1-Fluoro-2-nitrobenzene (2.82 g; 20 mmol; Aldrich), thiomorpholine (2.16 g; 21 mmol, Aldrich) and sodium hydride (1.0 g; 25 mmol, 60% dispersion, Aldrich) were refluxed in THF (30 mL) for 18 hours. The dark brown mixture was cooled to room temperature, diluted with ethyl acetate (100 mL), washed with NaHCO$_3$ (sat. aqueous solution; 50 mL×3), and dried over Na$_2$SO$_4$ to give 4-(2-Nitrophenyl)thiomorpholine (brown oil; 2.8 g), which was purified by flash chromatography (Si-gel column; 20% EA/hexanes). The solid was then dissolved in ethanol (20 mL), 10% Pd/C (200 mg) was added, heated to 50° C., hydrazine hydrate (1.9 g; 1.84 mL. 38 mmol. Aldrich) was added slowly, and the black mixture was stirred and refluxed (90° C.) for 0.5 hour. It was filtered through celite. The solvent was evaporated to give the crude amine product which was purified by flash chromatography (Si-gel column, 10%-50% EA/hexanes) to give 2-thiomorpholinoaniline.

Yield: 1.32 g, 54%.

MS: calculated: m/z 195.30 (MH$^+$); found: 195.13.

Example 98.2. Preparation of IX-149

IX-149 (yellowish solid) was prepared according to procedures in Example 44.2, but using benzoyl-DL-phenylalanine (110 mg; 0.41 mmol) and 2-thiomorpholinoaniline (89 mg; 0.46 mmol) in place of (1H-indole-4-carbonyl)-phenylalanine and o-methoxyaniline.

Yield: 160 mg, 87%.

MS (MALDI): calculated: m/z 446.58 (MH$^+$); found: 446.18, 468.13 (M+Na$^+$).

Example 99. Preparation of N-(1-oxo-3-phenyl-1-((2-(piperazin-1-yl)phenyl)amino)propan-2-yl)-benzamide (IX-150)

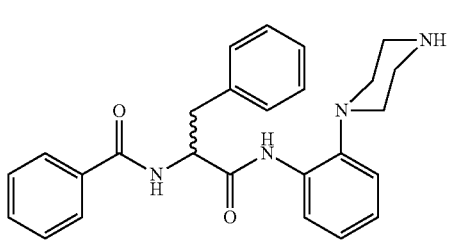

IX-150

Example 99.1. Preparation of Boc-IX-150

Boc-IX-150 (colorless oil) was prepared according to procedures in Example 44.2, but using benzoyl-DL-phenylalanine (110 mg; 0.41 mmol; Chem-Impex) and t-butyl 4-(2-aminophenyl)piperazine-1-carboxylate (127 mg; 0.46 mmol, Combi-Block) in place of (1H-indole-4-carbonyl)phenylalanine and o-methoxyaniline.

Yield: 150 mg, 69%.

MS (MALDI): calculated: m/z 529.65 (MH$^+$); found: 429.37, 551.23 (M+Na$^+$).

Example 99.2. Preparation of IX-150

Boc-IX-150 (Example 99.1; 150 mg; 0.28 mmol) was dissolved in DCM (1 mL) and treated with TFA (0.5 mL) at room temperature for 1 hour. The volatiles were removed under reduced pressure and the residue was mixed with DCM (10 mL), treated with NaHCO$_3$ (sat. aqueous solution, 5 mL×3), and dried over Na$_2$SO$_4$. The mixture was evaporated to give the crude amine product which was purified by flash chromatography (silica column, 50% ethyl acetate-hexanes followed by 10% MeOH-DCM) to give IX-50.

Yield: 87 mg, 73%.

MS (MALDI): calculated: m/z 429.54 (MH$^+$); found: 429.22, 451.20 (M+Na$^+$).

Example 100. Preparation of N-(1-((2-(4-methylpiperazin-1-yl)phenyl)amino)-1-oxo-3-phenyl-propan-2-yl)benzamide (IX-151)

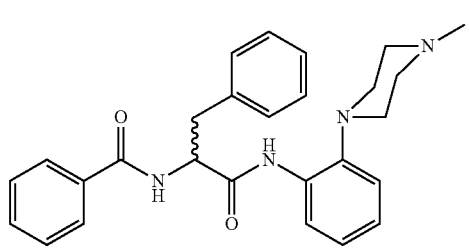

IX-151

IX-151 was prepared according to procedures in Example 44.2, but using benzoyl-DL-phenylalanine (110 mg; 0.41 mmol) and 2-(4-methylpiperazin-1-yl)aniline (99.5 mg; 0.52 mmol; Combi-Block) in place of (1H-indole-4-carbonyl)phenylalanine and o-methoxyaniline.

Yield: 123 mg, 56%.

MS (MALDI): calculated: m/z 443.56 (MH$^+$); found: 443.36, 465.29 (M+Na$^+$).

Example 101. Preparation of 2-fluoro-N-(1-((2-morpholinophenyl)amino)-1-oxo-3-phenylpropan-2-yl)benzamide (IX-152)

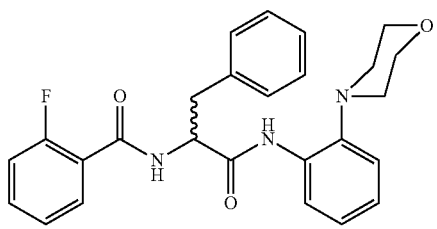
IX-152

Example 101.1. Preparation of 2-amino-N-(2-morpholinophenyl)-3-phenylpropanamide Boc-(1-((2-morpholinophenyl)amino)-1-oxo-3-phenyl-propan-2-yl)carbamate (570 mg; 1.33 mmol) was prepared according to procedures in Example 44.2, but using Boc-DL-phenylalanine (448 mg; 1.69 mmol) and 2-morpholinoaniline (338 mg; 1.9 mmol; Aldrich) in place of (1H-indole-4-carbonyl)phenylalanine and o-methoxyaniline, was treated with TFA (1.5 mL; Aldrich) in DCM (10 mL) at room temperature until no starting material was observed by TLC (50% ethyl acetate/hexanes). The mixture was suspended in NaHCO$_3$ (sat. aqueous solution, 10 mL), extracted with DCM (25 mL×3) and dried over Na$_2$SO$_4$ to give 2-amino-N-(2-morpholinophenyl)-3-phenylpropanamide.

Example 101.2. Preparation of IX-152

IX-152 was prepared according to procedures in Example 95, but using 2-fluorobenzoyl chloride (63 mg; 0.4 mmol; Aldrich) and 2-amino-N-(2-morpholinophenyl)-3-phenylpropanamide (Example 101.1; 110 mg; 0.31 mmol) in place of 2-amino-N-(2,2-difluorobenzo[d][1,3]dioxol-4-yl)-3-phenylpropanamide and thiophene-2-carbonyl chloride.

Yield: 125 mg, 90%.

MS (MALDI): calculated: m/z 448.51 (MH$^+$); found: 448.27, 470.24 (M+Na$^+$).

Example 102. Preparation of 2-methyl-N-(1-((2-morpholinophenyl)amino)-1-oxo-3-phenylpropan-2-yl)benzamide (IX-153)

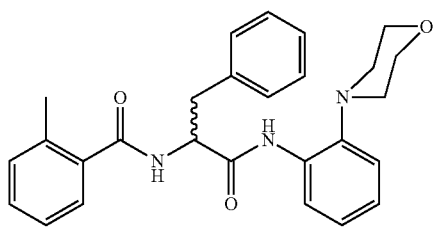
IX-153

IX-153 was prepared according to Example 101.2, but using 2-methylbenzoyl chloride (62 mg; 0.4 mmol; Aldrich) in place of 2-fluorobenzoyl chloride.

Yield: 125 mg, 91%.

MS (MALDI): calculated: m/z 444.55 (MH$^+$); found: 444.29, 466.21 (M+Na$^+$).

Example 103. Preparation of N-(3-(4-hydroxyphenyl)-1-((2-morpholinophenyl)amino)-1-oxo-propan-2-yl)benzamide (IX-154)

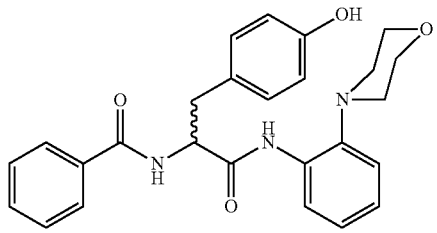
IX-154

IX-154 was prepared according to procedures in Example 86.2, but using 2-morpholinoaniline in place of 5-bromo-2-methylaniline.

Yield: 48 mg, 85%.

MS (MALDI): calculated: m/z 446.52 (MH$^+$); found: 446.16, 468.15 (M+Na$^+$).

Example 104. Preparation of 2-fluoro-N-(3-(4-hydroxyphenyl)-1-((2-morpholinophenyl)amino)-1-oxopropan-2-yl)benzamide (IX-155)

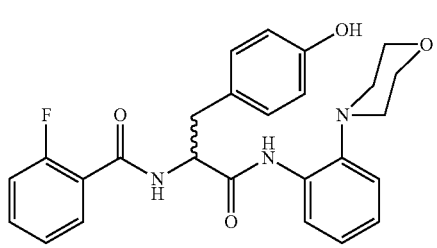
IX-155

Example 104.1. Preparation of 3-(4-acetoxyphenyl)-2-((t-butoxycarbonyl)amino)propanoic acid 3-(4-Acetoxyphenyl)-2-((t-butoxycarbonyl)amino)propanoic acid (white solid; 1.68 g; yield 97%) was prepared from N-Boc-tyrosine (1.51 g; 5.36 mmol; Chem-Impex) as in Example 86.1, but using acetic anhydride (1.08 g; 10.6 mmol; Aldrich) in place of benzoyl chloride.

Example 104.2. Preparation of 4-(2-amino-3-((2-morpholinophenyl)amino)-3-oxopropyl)phenyl acetate 4-(2-((t-butoxycarbonyl)amino)-3-((2-morpholinophenyl)amino)-3-oxopropyl)-phenyl acetate (off-white solid; 350 mg; 0.72 mmol) was prepared according to procedures in Example 44.2, but using 3-(4-acetoxyphenyl)-2-((t-butoxycarbonyl)amino)propanoic acid (Example 104.1; 549 mg; 1.7 mmol) and 2-morpholinoaniline (338 mg; 1.9 mmol; Aldrich) in place of (1H-indole-4-carbonyl)phenylalanine and o-methoxyaniline, was treated with TFA (1.2 mL; Aldrich) in DCM (5 mL) at room temperature until no starting material was observed by TLC (50% EA/hexane). Most volatiles were removed under reduced pressure. The residue was treated with $NaHCO_3$ (sat. aqueous solution, 10 mL), extracted with DCM (25 mL×3) and dried over $Na_2SO_4$ to give 4-(2-amino-3-((2-morpholinophenyl)amino)-3-oxopropyl)phenyl acetate (yield: 250 mg, 91%).

Example 104.3. Preparation of AcO-IX-155

AcO-IX-155 (yellowish oil) was prepared as in Example 101, but using 4-(2-amino-3-((2-morpholinophenyl)amino)-3-oxopropyl)phenyl acetate (100 mg, 0.26 mmol) in place of 2-amino-N-(2-morpholinophenyl)-3-phenylpropanamide.

Yield: 54 mg, 41%.

MS (MALDI): calculated: m/z 506.55 ($MH^+$); found: 506.43, 528.37 ($M+Na^+$).

Example 104.4. Preparation of IX-155

IX-155 (yellow solid) was prepared according to procedures in Example 86.3, but using AcO-IX-155 (47 mg; 0.09 mmol) in place of benzoyl-IX-103.

Yield: 43 mg, 99%.

MS (MALDI): calculated: m/z 464.51 ($MH^+$); found: 464.23, 486.17 ($M+Na^+$).

Example 105. Preparation of N-(3-(4-hydroxyphenyl)-1-((2-morpholinophenyl)amino)-1-oxopropan-2-yl)-2-methylbenzamide (IX-156)

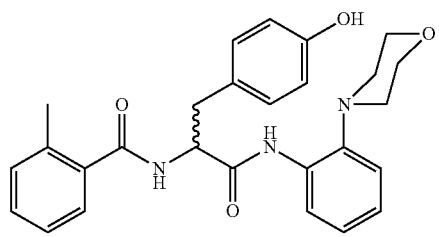

IX-156

IX-156 was prepared as in Example 104, but using 2-methylbenzoyl chloride in place of 2-fluorobenzoyl chloride.

Yield: 43 mg, 84%.

MS (MALDI): calculated: m/z 460.55 ($MH^+$); found: 460.28, 482.25 ($M+Na^+$).

Example 106. Preparation of N-(1-((5-fluoro-2-morpholinophenyl)amino)-1-oxo-3-phenylpropan-2-yl)benzamide (IX-157)

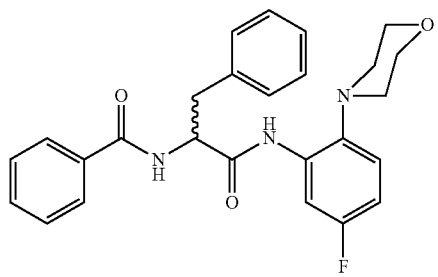

IX-157

Example 106.1. Preparation of 5-fluoro-2-morpholinoaniline 5-fluoro-2-morpholinoaniline was prepared as in Example 98.1, but using 4-(4-fluoro-2-nitrophenyl)morpholine (2.3 g; 10 mmol; Combi-Block) in place of 4-(2-nitrophenyl)morpholine.

Yield: 1.9 g, 97%.

MS: calculated: m/z 197.23 ($MH^+$); found: 197.07 ($M+H^+$).

Example 106.2. Preparation of 2-amino-N-(5-fluoro-2-morpholinophenyl)-3-phenylpropanamide 2-Amino-N-(5-fluoro-2-morpholinophenyl)-3-phenylpropanamide was prepared according to procedures in Example 101.1, but using 5-fluoro-2-morpholinoaniline (380 mg; 1.93 mmol) in place of 2-morpholinoaniline.

Example 106.3. Preparation of IX-157

IX-157 was prepared according to procedures in Example 95, but using benzoyl chloride (30 μL; 0.26 mmol; Aldrich) and 2-amino-N-(5-fluoro-2-morpholinophenyl)-3-phenylpropanamide (60 mg; 0.17 mmol) in place of 2-amino-N-(2,2-difluorobenzo[d][1,3]dioxol-4-yl)-3-phenylpropanamide and thiophene-2-carbonyl chloride.

Yield: 55 mg, 72%.

MS (MALDI): calculated: m/z 448.51 ($MH^+$); found: 448.16, 470.13 ($M+Na^+$).

Example 107. Preparation of 2-fluoro-N-(1-((5-fluoro-2-morpholinophenyl)amino)-1-oxo-3-phenyl-propan-2-yl)benzamide (IX-158)

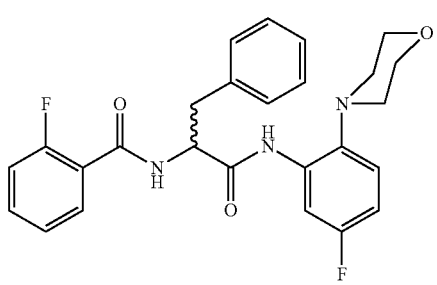

IX-158

IX-158 (yellowish oil) was prepared as in Example 106, but using 2-fluorobenzoyl chloride (30 μL; 0.26 mmol; Aldrich) in place of benzoyl chloride.
Yield: 98 mg, 95%.
MS (MALDI): calculated: m/z 466.50 (MH$^+$); found: 466.16, 488.22 (M+Na$^+$).

Example 108. Preparation of N-(1-((5-fluoro-2-morpholinophenyl)amino)-1-oxo-3-phenylpropan-2-yl)-2-methylbenzamide (IX-159)

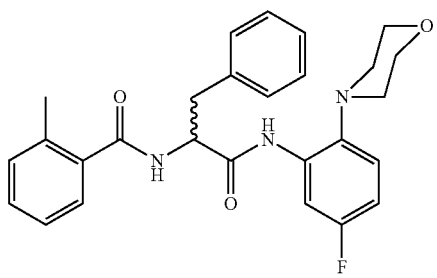

IX-159

IX-159 was prepared according to procedures in Example 106, but using 2-methylbenzoyl chloride (33 μL; 0.26 mmol; Aldrich) in place of benzoyl chloride.
Yield: 72 mg, 92%.
MS (MALDI): calculated: m/z 462.54 (MH$^+$); found: 462.29, 484.23 (M+Na$^+$).

Example 109. Preparation of N-(1-((5-fluoro-2-morpholinophenyl)amino)-1-oxo-3-phenylpropan-2-yl)thiophene-2-carboxamide (IX-160)

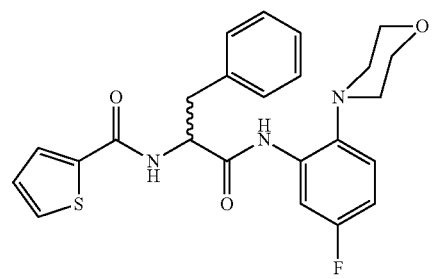

IX-160

IX-160 (white oil) was prepared according to procedures in Example 106, but using thiophene-2-carbonyl chloride (27 μL; 0.26 mmol; Aldrich) in place of benzoyl chloride.
Yield: 22 mg, 29%.
MS (MALDI): calculated: m/z 454.53 (MH$^+$); found: 454.27, 476.17 (M+Na$^+$).

Example 110. Preparation of 2-bromo-N-(1-((2,3-dihydrobenzo[b][1,4]dioxin-5-yl)amino)-3-(4-hydroxyphenyl)-1-oxopropan-2-yl)benzamide (IX-176)

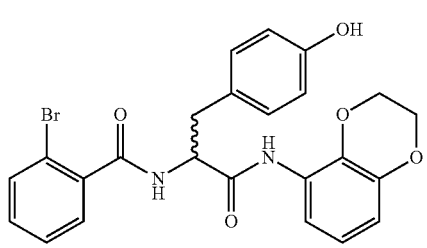

IX-176

IX-176 was prepared as in Example 15, but using 2-bromobenzoyl chloride in place of benzoyl chloride and 5-amino-1,4-benzodioxane in place of o-toluidine.
MS (MALDI): calculated: m/z 497.06 (MH$^+$); found: 497.27, 519.13 (M+Na$^+$).

Example 111. Preparation of 2-fluoro-N-(1-((5-fluoro-2-(fluoromethoxy)phenyl)amino)-1-oxo-3-phenylpropan-2-yl)benzamide (IX-177)

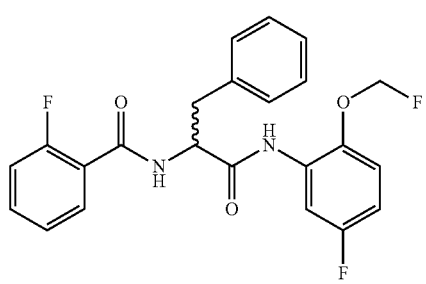

IX-177

IX-177 was prepared as in Example 91, but using 2-fluorobenzoyl chloride in place of 2-methylbenzoyl chloride.
Yield: 13 mg, 32%.
MS (MALDI): calculated: m/z 429.41 (MH$^+$); found: 429.07, 451.03 (M+Na$^+$).

Example 112. Preparation of 4-(2-(2-fluorobenzamido)-3-((2-morpholinophenyl)amino)-3-oxopropyl)phenyl acetate (IX-180)

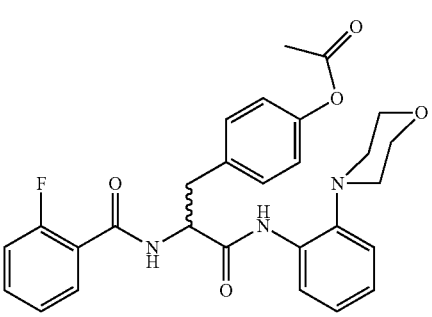

IX-180

IX-180 was prepared as in Example 104.3.

Yield: 54 mg, 41%.

MS (MALDI): calculated: m/z 506.55 (MH$^+$); found: 506.17, 528.13 (M+Na$^+$).

Example 113. Preparation of 4-(2-(2-methylbenzamido)-3-((2-morpholinophenyl)amino)-3-oxopropyl)phenyl acetate (IX-181)

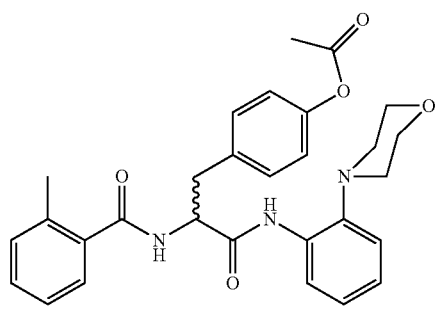

IX-181

IX-181 was made according to procedures in Example 104, but using 2-methylbenzoyl chloride in place of 2-fluorobenzoyl chloride.

Yield: 88 mg, 68%.

MS (MALDI): calculated: m/z 502.58 (MH$^+$); found: 502.21, 524.17 (M+Na$^+$).

Example 114. Preparation of 4-(3-((2-morpholinophenyl)amino)-3-oxo-2-(thiophene-2-carbox-amido)propyl)phenyl acetate (IX-182)

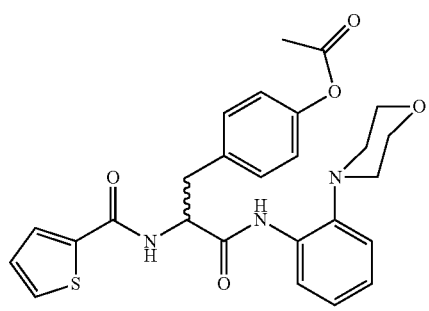

IX-182

IX-182 was made according to procedures in Example 104, but using thiophene-2-carbonyl chloride in place of 2-fluorobenzoyl chloride.

Yield: 89 mg, 69%.

MS (MALDI): calculated: m/z 494.58 (MH$^+$); found: 494.15, 516.13 (M+Na$^+$).

Example 115. Preparation of N-(3-(4-hydroxyphenyl)-1-((2-morpholinophenyl)amino)-1-oxopropan-2-yl)thiophene-2-carboxamide (IX-183)

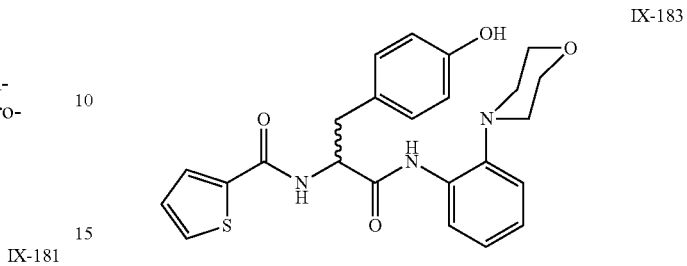

IX-183

IX-183 (white solid) was prepared according to procedures in Example 86.3, but using IX-182 (67 mg; 0.14 mmol) in place of benzoyl-IX-103.

Yield: 56 mg, 89%.

MS (MALDI): calculated: m/z 452.54 (MH$^+$); found: 452.28, 474.22 (M+Na$^+$).

Example 116. Preparation of 2-fluoro-N-(1-((5-fluoro-2-methylphenyl)amino)-3-(4-hydroxy-phenyl)-1-oxopropan-2-yl)benzamide (IX-184)

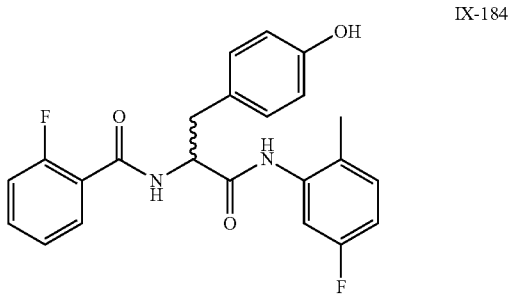 [SMILES: Cc1ccc(F)cc1NC(=O)C(Cc1ccc(O)cc1)NC(=O)c1ccccc1F]

IX-184

IX-184 was prepared according to procedures in Example 104, but using 5-fluoro-2-methylaniline in place of 2-morphinoaniline.

Yield: 33 mg, 89%.

MS (MALDI): calculated: m/z 411.42 (MH$^+$); found: 411.12, 433.12 (M+Na$^+$).

Example 117. Preparation of N-(1-((5-fluoro-2-methylphenyl)amino)-3-(4-hydroxyphenyl)-1-oxopropan-2-yl)-2-methylbenzamide (IX-186)

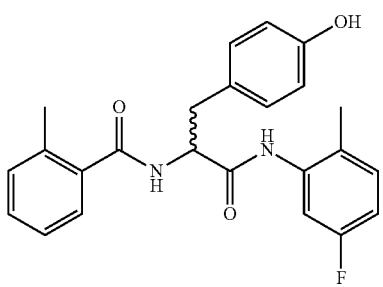

IX-186

IX-186 was prepared according to procedures in Examples 104 and 116, but using 2-methylbenzoyl chloride in place of 2-flurorobenzoyl chloride.

Yield: 36 mg, 98%.

MS (MALDI): calculated: m/z 407.46 (MH$^+$); found: 407.16, 429.16 (M+Na$^+$).

Example 118. Preparation of N-(1-((5-fluoro-2-methylphenyl)amino)-3-(4-hydroxyphenyl)-1-oxo-propan-2-yl)thiophene-2-carboxamide (IX-188)

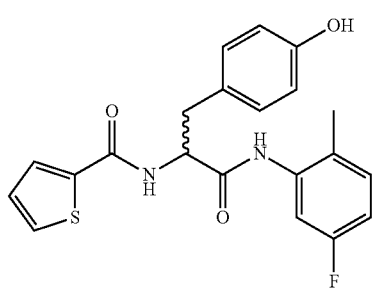

IX-188

IX-188 was prepared as in Examples 104 and 116, but using 2-thiophene carbonyl chloride in place of 2-flurorobenzoyl chloride.

Yield: 34 mg, 94%.

MS (MALDI): calculated: m/z 399.45 (MH$^+$); found: 399.14, 421.12 (M+Na$^+$).

Example 119. Preparation of N-(1-((1H-indazol-4-yl)amino)-1-oxo-3-phenylpropan-2-yl)-2-methyl-benzamide (IX-191)

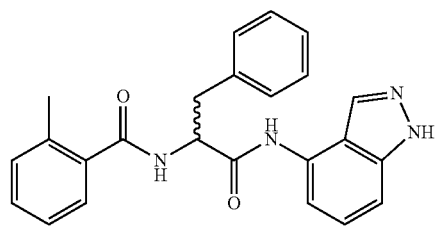

IX-191

IX-191 (yellow solid) was prepared according to procedures in example 44.2, but using N-(2-methylbenzoyl)-DL-phenylalanine (142 mg; 0.5 mmol; Example 91.1) and 1H-indazol-4-amine (73 mg; 0.55 mmol; Chem-Impex) in place of (1H-indole-4-carbonyl)phenylalanine and o-methoxyaniline.

Yield: 66 mg, 33%.

MS (MALDI): calculated: m/z 399.47 (MH$^+$); found: 399.19, 421.20 (M+Na$^+$).

Example 120. Preparation of N-(1-((1H-indazol-4-yl)amino)-1-oxo-3-phenylpropan-2-yl)thiophene-2-carboxamide (IX-201)

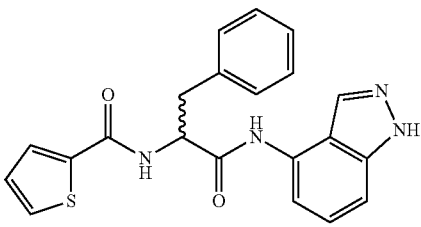

IX-201

Example 120.1. Preparation of N-(thiophene-2-carbonyl)-DL-phenylalanine

N-(thiophene-2-carbonyl)-DL-phenylalanine was prepared as in Example 91.1, but using thiophene-2-carbonyl chloride in place of 2-methylbenzoyl chloride.

Example 120.2. Preparation of IX-201

IX-201 was prepared according to procedures in example 44.2, but using N-(thiophene-2-carbonyl)-DL-phenylalanine (Example 120.1; 138 mg; 0.5 mmol) and 1H-indazol-4-amine (73 mg; 0.55 mmol; Chem-Impex) in place of (1H-indole-4-carbonyl)phenylalanine and o-methoxyaniline.

Yield: 140 mg, 72%.

MS (MALDI): calculated: m/z 391.46 (MH$^+$); found: 391.07, 413.05 (M+Na$^+$).

Example 121. Preparation of N-(1-((5-fluoro-2-methoxyphenyl)amino)-3-(4-hydroxyphenyl)-1-oxo-propan-2-yl)benzamide (IX-203)

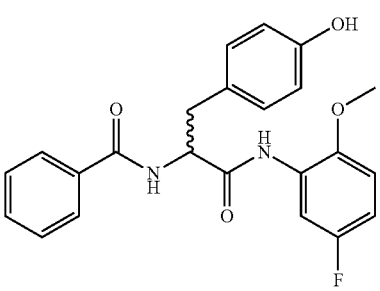

IX-203

IX-203 was prepared according to procedures in Examples 104 and 116, but using benzoyl chloride in place of 2-flurorobenzoyl chloride; and 5-fluoro-2-methoxyaniline in place of 5-fluoro-2-methylaniline.

Yield: 25 mg, 27%.

MS (MALDI): calculated: m/z 409.43 (MH$^+$); found: 409.06, 431.04 (M+Na$^+$).

Example 122. Preparation of 2-fluoro-N-(1-((5-fluoro-2-methoxyphenyl)amino)-3-(4-hydroxy-phenyl)-1-oxopropan-2-yl)benzamide (IX-204)

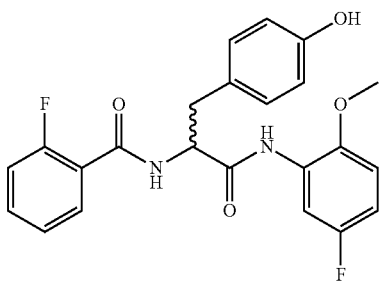

IX-204

IX-204 was prepared as in Example 104, but using 5-fluoro-2-methoxyaniline in place of 5-fluoro-2-methylaniline.
Yield: 36 mg, 99%.
MS (MALDI): calculated: m/z 427.42 (MH$^+$); found: 427.00, 449.00 (M+Na$^+$).

Example 123. Preparation of N-(1-((5-fluoro-2-methoxyphenyl)amino)-3-(4-hydroxyphenyl)-1-oxopropan-2-yl)-2-methylbenzamide (IX-205)

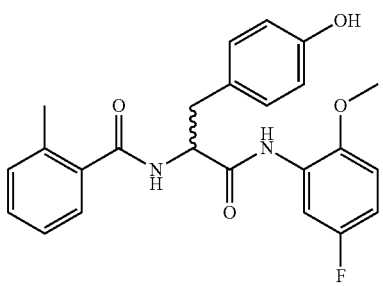

IX-205

IX-205 (white solid) was prepared according to procedures in Example 104 and Example 116, but using 2-methylbenzoyl chloride in place of 2-flurorobenzoyl chloride; and 5-fluoro-2-methoxyaniline in place of 5-fluoro-2-methylaniline.
Yield: 52 mg, 53%.
MS (MALDI): calculated: m/z 423.46 (MH$^+$); found: 423.09, 445.07 (M+Na$^+$).

Example 124. Preparation of N-(1-((5-fluoro-2-methoxyphenyl)amino)-3-(4-hydroxyphenyl)-1-oxopropan-2-yl)thiophene-2-carboxamide (IX-206)

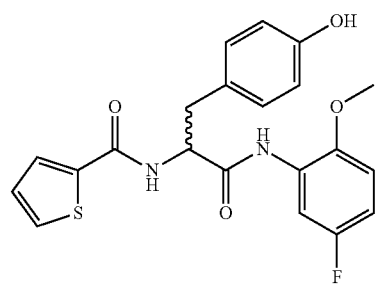

IX-206

IX-206 (white solid) was prepared according to procedures in Examples 104 and 116, but using thiophene-2-carbonyl chloride in place of 2-flurorobenzoyl chloride; and 5-fluoro-2-methoxyaniline in place of 5-fluoro-2-methylaniline.
Yield: 70 mg, 73%.
MS (MALDI): calculated: m/z 415.45 (MH$^+$); found: 415.00, 437.00 (M+Na$^+$).

Example 125. Preparation of 2-fluoro-N-(1-oxo-3-phenyl-1-((2-(piperazin-1-yl)phenyl)amino)-propan-2-yl)benzamide (IX-211)

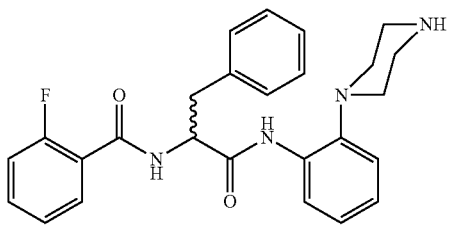

IX-211

IX-211 (colorless oil) was prepared according to procedures in Example 99, but using (2-fluorobenzoyl)phenylalanine (115 mg; 0.4 mmol) in place of benzoyl-DL-phenylalanine.
Yield: 55 mg, 30%.
MS (MALDI): calculated: m/z 447.53 (MH$^+$); found: 447.19, 469.14 (M+Na$^+$).

Example 126. Preparation of 2-methyl-N-(1-oxo-3-phenyl-1-((2-(piperazin-1-yl)phenyl)amino)-propan-2-yl)benzamide (IX-212)

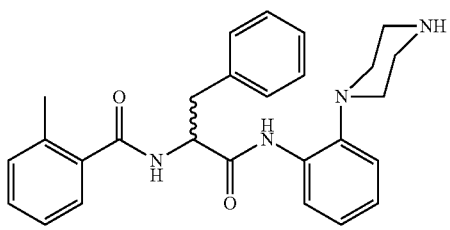

IX-212

IX-212 (yellowish oil) was prepared according to procedures in Example 99, but using (2-methylbenzoyl)phenylalanine (113 mg; 0.4 mmol) in place of benzoyl-DL-phenylalanine.
Yield: 62 mg, 35%.
MS (MALDI): calculated: m/z 443.56 (MH$^+$); found: 443.26, 465.22 (M+Na$^+$).

Example 127. Preparation of N-(1-oxo-3-phenyl-1-((2-(piperazin-1-yl)phenyl)amino)propan-2-yl)thiophene-2-carboxamide (IX-213)

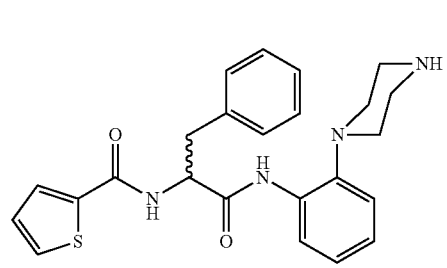

IX-213

IX-213 (yellowish oil) was prepared according to procedures in Example 99, but using (thiophene-2-carbonyl)phenylalanine (110 mg; 0.4 mmol) in place of benzoyl-DL-phenylalanine.

Yield: 130 mg, 77%.

MS (MALDI): calculated: m/z 435.56 (MH⁺); found: 435.24, 457.19 (M+Na⁺).

Example 128. Preparation of 2-fluoro-N-(1-((5-fluoro-2-(piperazin-1-yl)phenyl)amino)-1-oxo-3-phenylpropan-2-yl)benzamide (IX-214)

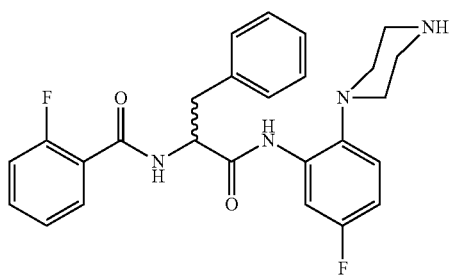

IX-214

IX-214 was prepared according to procedures in Example 99, but using (2-fluorobenzoyl)phenylalanine (115 mg; 0.4 mmol) in place of benzoyl-DL-phenylalanine; and t-butyl 4-(2-amino-4-fluorophenyl)piperazine-1-carboxylate (136 mg; 0.46 mmol; Oakwood Chemical) in place of t-butyl 4-(2-aminophenyl)piperazine-1-carboxylate.

Yield: 70 mg, 38%.

MS (MALDI): calculated: m/z 466.52 (MH⁺); found: 466.08, 488.07 (M+Na⁺).

Example 129. Preparation of N-(1-((5-fluoro-2-(piperazin-1-yl)phenyl)amino)-1-oxo-3-phenylpropan-2-yl)-2-methylbenzamide (IX-215)

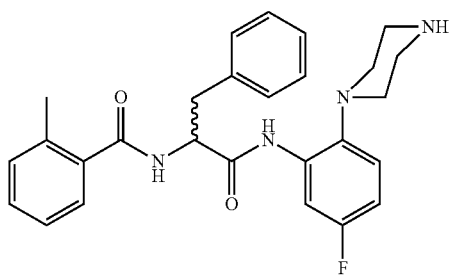

IX-215

IX-215 was prepared according to procedures in Example 99, but using (2-methylbenzoyl)-phenylalanine (113 mg; 0.4 mmol) in place of benzoyl-DL-phenylalanine; and t-butyl 4-(2-amino-4-fluorophenyl)piperazine-1-carboxylate (136 mg; 0.46 mmol; Oakwood Chemical) in place of t-butyl 4-(2-aminophenyl)piperazine-1-carboxylate.

Yield: 56 mg, 30%.

MS (MALDI): calculated: m/z 461.55 (MH⁺); found: 461.19, 483.17 (M+Na⁺).

Example 130. Preparation of N-(1-((5-fluoro-2-(piperazin-1-yl)phenyl)amino)-1-oxo-3-phenylpropan-2-yl)thiophene-2-carboxamide (IX-216)

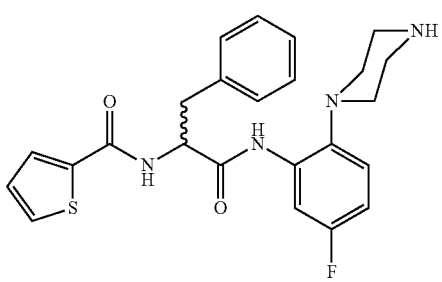

IX-216

IX-216 (colorless oil) was prepared according to procedures in Example 99, but using (thiophene-2-carbonyl)phenylalanine (110 mg; 0.4 mmol) in place of benzoyl-DL-phenylalanine; and t-butyl 4-(2-amino-4-fluorophenyl)piperazine-1-carboxylate (136 mg; 0.46 mmol; Oakwood Chemical) in place of t-butyl 4-(2-aminophenyl)piperazine-1-carboxylate.

Yield: 170 mg, 94%.

MS (MALDI): calculated: m/z 453.55 (MH⁺); found: 453.06, 475.05 (M+Na⁺).

Example 131. Preparation of N-(3-(4-hydroxyphenyl)-1-oxo-1-((2-(piperazin-1-yl)phenyl)amino)-propan-2-yl)thiophene-2-carboxamide (IX-219)

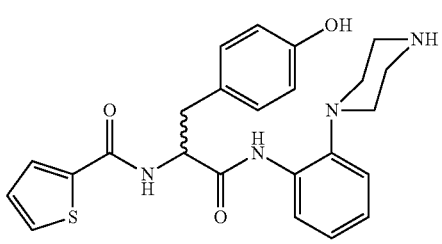

IX-219

Example 131.1. Preparation of methyl 3-(4-acetoxyphenyl)-2-((t-butoxycarbonyl)amino)propanoate Methyl 3-(4-acetoxyphenyl)-2-((t-butoxycarbonyl)amino)propanoate (colorless oil, yield: 3.3 g, 98%) was prepared according to procedures in Example 86.1, but using acetic anhydride (1.53 g; 115 mmol; Aldrich) in place of benzoyl chloride, and methyl N-Boc-tyrosinate (2.95 g; 10 mmol; Chem-Impex) in place of DL-tyrosine.

MS (MALDI): calculated: m/z 238.37 (M-Boc+H⁺); found: 238.43 (M-Boc+H⁺), 360.37 (M+Na⁺).

Example 131.2. Preparation of methyl 3-(4-acetoxyphenyl)-2-aminopropanoate

Methyl 3-(4-Acetoxyphenyl)-2-((t-butoxycarbonyl)amino)propanoate (Example 131.1; 3.3 g; 9.8 mmol) was treated with TFA (5 mL; Aldrich) in DCM (30 mL) at room temperature until no starting material was observed by TLC (40% ethyl acetate/hexanes). Most volatiles were removed under reduced pressure. The residue was treated with NaHCO₃ (sat. aqueous solution, 30 mL), extracted with DCM (40 mL×3) and dried over Na₂SO₄ to give methyl 3-(4-acetoxyphenyl)-2-aminopropanoate.

Yield: 1.74 g, 73% until.

Example 131.3. Preparation of methyl 3-(4-acetoxyphenyl)-2-(thiophene-2-carboxamido)propanoate Methyl 3-(4-acetoxyphenyl)-2-aminopropanoate (Example 131.2; 237 mg, 1.0 mmol) was treated with thiophene-2-carbonyl chloride (130 μL; 1.2 mmol) and TEA (170 μL; 1.2 mmol) in THF (2 mL) at room temperature for 1 hour. Methyl 3-(4-acetoxyphenyl)-2-(thiophene-2-carboxamido)propanoate (colorless oil; 312 mg; yield 90%) was obtained from silica flash chromatography (20% EA/hexanes) of the crude product.

Example 131.4. Preparation of (thiophene-2-carbonyl)tyrosine

Methyl 3-(4-acetoxyphenyl)-2-(thiophene-2-carboxamido)propanoate (Example 131.3; 312 mg, 0.93 mmol) was treated with LiOH (1.0 M; 2 mL) in THF (6 mL) and MeOH (6 mL) at room temperature for 18 hours. The volatiles were removed under reduced pressure and the residue was treated with 1N HCl to pH 1, extracted with DCM (7 mL×3) and dried over sodium sulfate to give thiophene-2-carbonyl)tyrosine. Yield: 240 mg, 89%.

MS: calculated: m/z 291.32 (MH⁺); found: 291.43.

Example 131.5. Preparation of IX-219

IX-219 (yellowish oil) was prepared according to procedures in Example 99, but using (thiophene-2-carbonyl)tyrosine (60 mg; 0.21 mmol) instead of benzoyl-DL-phenylalanine.

Yield: 20 mg, 21%.

MS (MALDI): calculated: m/z 451.56 (MH⁺); found: 451.06, 473.03 (M+Na⁺).

Example 132. Preparation of N-(1-((5-fluoro-2-(piperazin-1-yl)phenyl)amino)-3-(4-hydroxyphenyl)-1-oxopropan-2-yl)thiophene-2-carboxamide (IX-222)

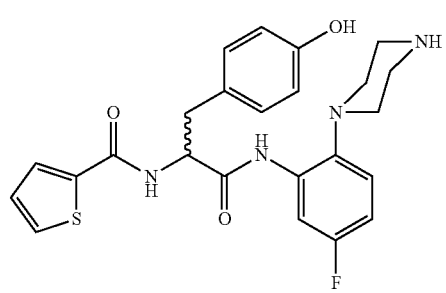

IX-222

IX-222 was prepared according to procedures in Examples 99 and 131, but using (thiophene-2-carbonyl)tyrosine (60 mg; 0.21 mmol) in place of benzoyl-DL-phenylalanine; and t-butyl 4-(2-amino-4-fluorophenyl)piperazine-1-carboxylate (68 mg; 0.23 mmol; Oakwood Chemical) in place of t-butyl 4-(2-aminophenyl)piperazine-1-carboxylate.

Yield: 33 mg, 34%.

MS (MALDI): calculated: m/z 469.55 (MH⁺); found: 469.16, 491.05 (M+Na⁺).

Example 133. Preparation of N-(1-((1H-benzo[d][1,2,3]triazol-4-yl)amino)-1-oxo-3-phenylpropan-2-yl)benzamide (IX-223)

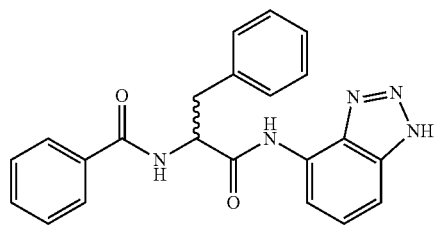

IX-223

IX-223 (off white solid) was prepared according to procedures in Example 44.2, but using DL-benzoyl phenylalanine (110 mg, 0.41 mmol) and 1H-benzo[d][1,2,3]triazol-4-amine (129 mg; 0.46 mmol; ChemBridge) in place of (1H-indole-4-carbonyl)phenylalanine and o-methoxyaniline.

Yield: 140 mg, 89%.

MS (MALDI): calculated: m/z 386.43 (MH⁺); found: 386.24, 408.23 (M+Na⁺).

Example 134. Preparation of N-(1-((1-methyl-1H-benzo[d][1,2,3]triazol-7-yl)amino)-1-oxo-3-phenylpropan-2-yl)benzamide (IX-224)

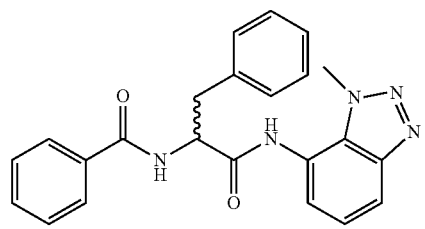

IX-224

IX-224 (white solid) was prepared as in Example 44.2, but using DL-benzoyl phenylalanine (110 mg' 0.41 mmol) and 1-methyl-1H-benzo[d][1,2,3]triazol-7-amine (129 mg, 0.46 mmol, Princeton Biomolecular Research) in place of (1H-indole-4-carbonyl)phenylalanine and o-methoxyaniline.

Yield: 112 mg, 68%.

MS (MALDI): calculated: m/z 400.45 (MH⁺); found: 400.17, 422.13 (M+Na⁺).

Example 135. Preparation of N-(1-((1-methyl-1H-indazol-4-yl)amino)-1-oxo-3-phenylpropan-2-yl)benzamide (IX-225)

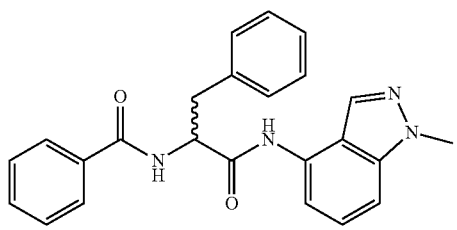

IX-225

IX-225 was prepared according to procedures in Example 44.2, but using DL-benzoyl phenylalanine (110 mg; 0.41 mmol) and 1-methyl-1H-indazol-4-amine (68 mg; 0.46 mmol; Chem-Impex) in place of (1H-indole-4-carbonyl)phenylalanine and o-methoxyaniline.

Yield: 110 mg, 67%.

MS (MALDI): calculated: m/z 399.47 (MH$^+$); found: 399.13, 431.10 (M+Na$^+$).

Example 136. Preparation of N-(1-((1H-benzo[d]imidazol-7-yl)amino)-1-oxo-3-phenylpropan-2-yl)benzamide (IX-230)

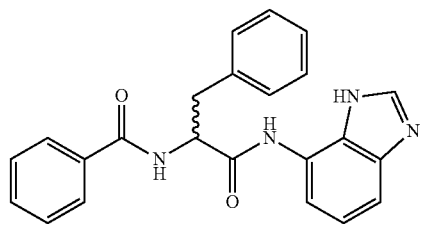

IX-230

IX-230 (yellow oil) was prepared as in Example 44.2, but using DL-benzoyl phenylalanine (110 mg; 0.41 mmol) and 1H-benzo[d]imidazol-7-amine (61 mg; 0.46 mmol; Combi-Block) in place of (1H-indole-4-carbonyl)phenylalanine and o-methoxyaniline.

Yield: 52 mg, 33%.

MS (MALDI): calculated: m/z 385.44 (MH$^+$); found: 385.12, 407.10 (M+Na$^+$).

Example 137. Preparation of N-(1-((1-methyl-1H-indol-7-yl)amino)-1-oxo-3-phenylpropan-2-yl)benzamide (IX-231)

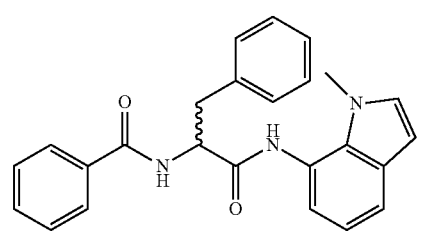

IX-231

IX-231 (yellowish solid) was prepared as in Example 44.2, but using DL-benzoyl phenylalanine (110 mg; 0.41 mmol) and 1-methyl-1H-indol-7-amine (67 mg; 0.46 mmol; FCH) in place of (1H-indole-4-carbonyl)phenylalanine and o-methoxyaniline.

Yield: 110 mg, 67%.

MS (MALDI): calculated: m/z 398.48 (MH$^+$); found: 398.20, 420.21 (M+Na$^+$).

Example 138. Preparation of N-(1-((1-methyl-1H-benzo[d]imidazol-7-yl)amino)-1-oxo-3-phenyl-propan-2-yl)benzamide (IX-232)

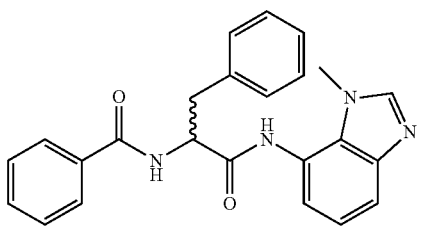

IX-232

IX-232 (white solid) was prepared as in Example 44.2, but using DL-benzoyl phenylalanine (55 mg; 0.21 mmol) and 1-methyl-1H-benzo[d]imidazol-7-amine (34 mg; 0.25 mmol; Accela) in place of (1H-indole-4-carbonyl)phenylalanine and o-methoxyaniline.

Yield: 55 mg, 66%.

MS (MALDI): calculated: m/z 399.47 (MH$^+$); found: 399.00, 421.00 (M+Na$^+$).

Example 139. Preparation of N-(1-(benzo[d]thiazol-7-ylamino)-1-oxo-3-phenylpropan-2-yl)benz-amide (IX-234)

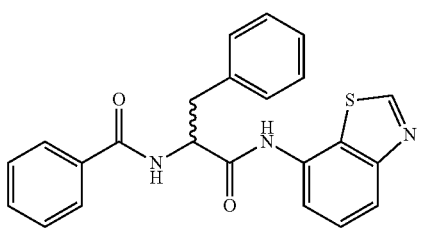

IX-234

IX-234 (white solid) was prepared as in Example 44.2, but using DL-benzoyl phenylalanine (110 mg; 0.41 mmol) and benzo[d]thiazol-7-amine (69 mg; 0.46 mmol; Ark Pharm) in place of (1H-indole-4-carbonyl)phenylalanine and o-methoxyaniline.

Yield: 120 mg, 73%.

MS (MALDI): calculated: m/z 402.48 (MH$^+$); found: 402.14, 424.13 (M+Na$^+$).

Example 140. Preparation of N-(1-(benzo[d]thiazol-4-ylamino)-1-oxo-3-phenylpropan-2-yl)benz-amide (IX-235)

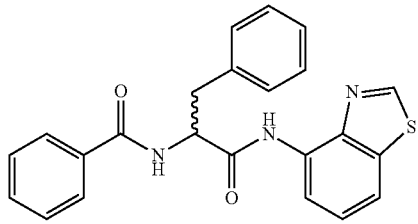

IX-235

IX-235 (yellow solid) was prepared as in Example 44.2, but using DL-benzoyl phenylalanine (110 mg; 0.41 mmol) and benzo[d]thiazol-4-amine (69 mg; 0.46 mmol; Matrix Scientific) in place of (1H-indole-4-carbonyl)phenylalanine and o-methoxyaniline.

Yield: 140 mg, 85%.

MS (MALDI): calculated: m/z 402.48 (MH$^+$); found: 402.10, 424.08 (M+Na$^+$).

Example 141. Preparation of N-(1-((2-(4-acetylpiperazin-1-yl)phenyl)amino)-1-oxo-3-phenyl-propan-2-yl)benzamide (IX-236)

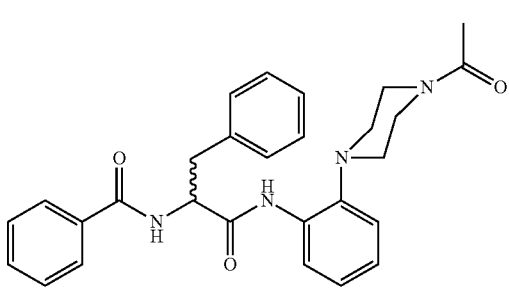

IX-236

IX-150 (20 mg, 0.05 mmol) was treated with acetyl chloride (5.3 µL; 0.075 mmol; Aldrich) and TEA (10 µL; 0.14 mmol; Aldrich) in DCM (1 mL) at room temperature for 0.5 hour, and IX-236 was obtained as yellowish oil.

Yield: 12 mg, 51%.

MS (MALDI): calculated: m/z 471.57 (MH$^+$); found: 471.17, 493.15 (M+Na$^+$).

Example 142. Preparation of 4-(2-(2-benzamido-3-phenylpropanamido)phenyl)-N-methyl-piperazine-1-carboxamide (IX-238)

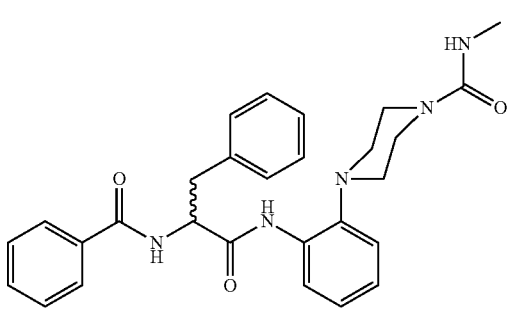

IX-238

IX-150 (20 mg, 0.05 mmol) was treated with N-methyl-1H-imidazole-1-carboxamide (6.3 mg, 0.05 mmol, Matrix Scientific) and TEA (10 µL, 0.14 mmol, Aldrich) in DCM (1 mL) at room temperature for 0.5 hour, and IX-238 was obtained.

Yield: 13 mg, 54%.

MS (MALDI): calculated: m/z 486.59 (MH$^+$); found: 486.15, 508.14 (M+Na$^+$).

Example 143. Preparation of N-(1-((1H-indazol-4-yl)amino)-1-oxo-3-phenylpropan-2-yl)-1H-indole-4-carboxamide (IX-241)

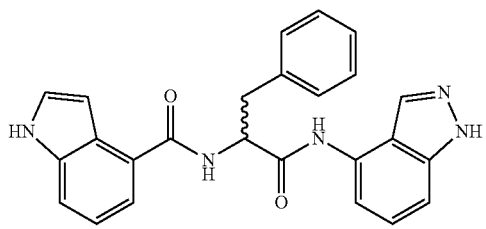

IX-241

IX-241 was prepared according to procedures in Example 44, using (1H-indole-4-carbonyl)phenylalanine (78 mg; 0.25 mmol), but using 1H-indazol-4-amine (43 mg; 0.33 mmol' Chem-Impex) in place of o-methoxyaniline.

Yield: 82 mg, 77%.

MS (MALDI): calculated: m/z 424.48 (MH$^+$); found: 424.08, 446.06 (M+Na$^+$).

Example 144. Preparation of N-(1-oxo-3-phenyl-1-((2-(piperazin-1-yl)phenyl)amino)propan-2-yl)-1H-indole-4-carboxamide (IX-242)

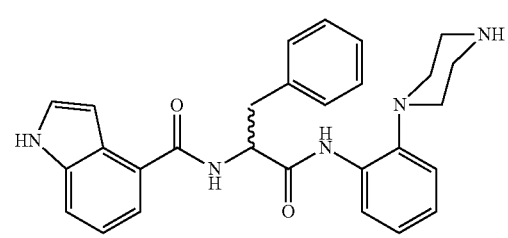

IX-242

Boc-IX-242 (yellowish oil) was prepared according to procedures in Example 44, using (1H-indole-4-carbonyl)phenylalanine (78 mg; 0.25 mmol), but using t-butyl 4-(2-aminophenyl)piperazine-1-carboxylate (91 mg; 0.33 mmol; Combi-Block) in place of o-methoxyaniline. The Boc group of Boc-IX-242 was removed according to procedures in Example 99, providing IX-242 as a yellowish oil.

Yield: 53 mg, 45%.

MS (MALDI): calculated: m/z 468.57 (MH$^+$); found: 468.05, 490.02 (M+Na$^+$).

Example 145. Preparation of N-(1-oxo-3-phenyl-1-((2-(piperazin-1-yl)phenyl)amino)propan-2-yl)-1H-indole-4-carboxamide (IX-243)

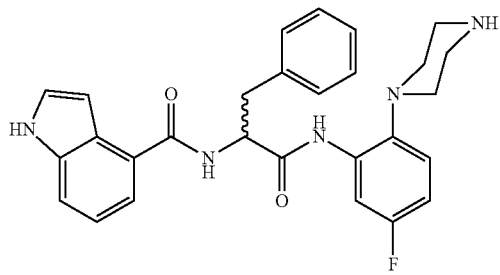

IX-243

Boc-IX-243 (yellowish oil) was prepared according to procedures in Example 44, using (1H-indole-4-carbonyl)phenylalanine (78 mg; 0.25 mmol), but using t-butyl 4-(2-amino-4-fluorophenyl)piperazine-1-carboxylate (97 mg; 0.33 mmol; Oakwood Chemical) in place of o-methoxyaniline. The Boc group of Boc-IX-243 was removed as in Example 99, providing IX-243 as yellowish oil.

Yield: 58 mg, 48%.
MS (MALDI): calculated: m/z 486.56 (MH⁺); found: 486.07, 508.05 (M+Na⁺).

Example 146. Preparation of N-(1-((5-fluoro-2-methoxyphenyl)amino)-1-oxo-3-phenylpropan-2-yl)-1H-indole-4-carboxamide (IX-244)

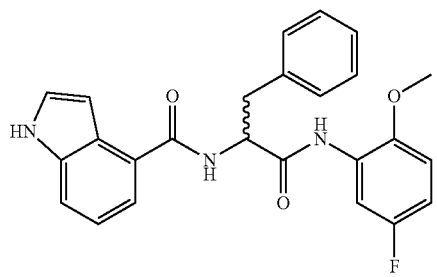

IX-244

IX-244 was prepared according to procedures in Example 44, using (1H-indole-4-carbonyl)phenylalanine (78 mg; 0.25 mmol), but using 5-fluoro-2-methoxyaniline (39 µL; 0.33 mmol; Aldrich) in place of o-methoxy-aniline.

Yield: 80 mg, 74%.
MS (MALDI): calculated: m/z 432.47 (MH⁺); found: 432.06, 454.06 (M+Na⁺).

Example 147. Preparation of N-(1-((5-fluoro-2-(piperazin-1-yl)phenyl)amino)-1-oxo-3-phenyl-propan-2-yl)benzamide (IX-245)

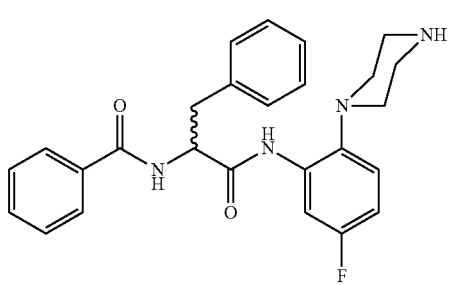

IX-245

IX-245 (yellowish solid) was prepared according to procedures in Example 99, using DL-benzoyl phenylalanine (110 mg; 0.41 mmol), but using t-butyl 4-(2-amino-4-fluorophenyl)piperazine-1-carboxylate (136 mg; 0.46 mmol; Oakwood Chemical) in place of o-methoxyaniline.

Yield: 133 mg, 73%.
MS (MALDI): calculated: m/z 447.53 (MH⁺); found: 447.13, 469.11 (M+Na⁺).

Example 148. Preparation of N-(1-((5-fluoro-2-(piperazin-1-yl)phenyl)amino)-3-(4-hydroxy-phenyl)-1-oxopropan-2-yl)benzamide (IX-246)

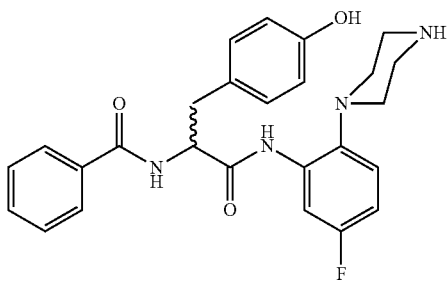

IX-246

DL-2-benzamido-3-(4-(benzoyloxy)phenyl)propanoic acid (Example 86.1; 160 mg; 0.41 mmol) and t-butyl 4-(2-amino-4-fluorophenyl)piperazine-1-carboxylate (136 mg; 0.46 mmol, Oakwood Chemical) were coupled to form the intermediate benzoyl-Boc-IX-246 (colorless oil; 65 mg) under the conditions as described in Example 44.2. The benzoyl group was removed under the conditions described in Example 86.3, and the Boc group was removed under the conditions described in Example 99.2, providing IX-246 as a yellowish oil.

Yield: 32 mg, 17%.
MS (MALDI): calculated: m/z 463.53 (MH⁺); found: 463.14, 485.11 (M+Na⁺).

Example 149. Preparation of N-(1-((5-fluoro-2-(4-(2-hydroxyethyl)piperazin-1-yl)phenyl)amino)-1-oxo-3-phenylpropan-2-yl)thiophene-2-carboxamide (IX-247)

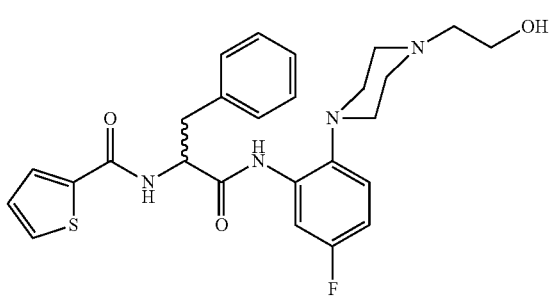

IX-247

IX-216 (75 mg; 0.17 mmol; Example 130) was dissolved into ACN (2 ml), 2-bromoethanol (12 µL; 0.17 mmol; Aldrich) and cesium carbonate (85 mg; 0.26 mmol; Aldrich) were added. The mixture was heated at 75° C. until no IX-216 was observed on TLC (10% MeOH/DCM, 18 hours). Most volatiles were removed under reduced pressure. The residue was mixed with ethyl acetate (50 mL), washed with brine and dried over $Na_2SO_4$. IX-247 (yellowish oil) was isolated from the crude product by flash chromatography (Si-gel, 10% MeOH/DCM).

Yield: 67 mg, 79%.

MS (MALDI): calculated: m/z 497.60 ($MH^+$); found: 497.07, 519.05 ($M+Na^+$).

Example 150. Preparation of N-(1-((2-(2,6-dimethylmorpholino)phenyl)amino)-1-oxo-3-phenyl-propan-2-yl)benzamide (IX-265)

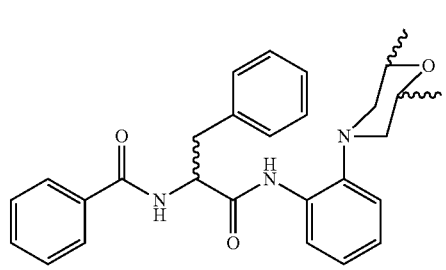

Example 150.1. Preparation of 2-(2,6-dimethylmorpholino)aniline 2-(2,6-Dimethylmorpholino)aniline (off-white solid; 4.1 g; yield 99%) was prepared according to procedures in Example 98.1, using 1-fluoro-2-nitrobenzene (2.82 g; 20 mmol; Aldrich), but using 2,6-dimethylmorpholine (2.73 mL; 22 mmol; Acros Organic) in place of thiomorpholine.

Example 150.2. Preparation of 2-amino-N-(2-(2,6-dimethylmorpholino)phenyl)-3-phenylpropanamide 2-Amino-N-(2-(2,6-dimethylmorpholino)phenyl)-3-phenylpropanamide (yellowish oil; 1.07 g; yield 98%) was prepared as in Example 101.1, but using Boc-DL-phenylalanine (900 mg; 3.4 mmol; Chem-Impex) and 2-(2,6-dimethylmorpholino)aniline (800 mg; 3.9 mmol) in place of 2-morpholinoaniline.

Example 150.3. Preparation of IX-265

IX-265 (colorless oil) was prepared as in Example 95, but using benzoyl chloride (49 µL; 0.42 mmol; Aldrich) and 2-amino-N-(2-(2,6-dimethylmorpholino)phenyl)-3-phenylpropanamide (Example 150.2; 100 mg; 0.28 mmol) in place of 2-amino-N-(2,2-difluorobenzo[d][1,3]dioxol-4-yl)-3-phenylpropanamide and thiophene-2-carbonyl chloride.

Yield: 65 mg, 51%.

MS (MALDI): calculated: m/z 458.57 ($MH^+$); found: 458.18, 480.16 ($M+Na^+$).

Example 151. Preparation of N-(1-((2-(2,6-dimethylmorpholino)phenyl)amino)-3-(4-hydroxy-phenyl)-1-oxopropan-2-yl)benzamide (IX-266)

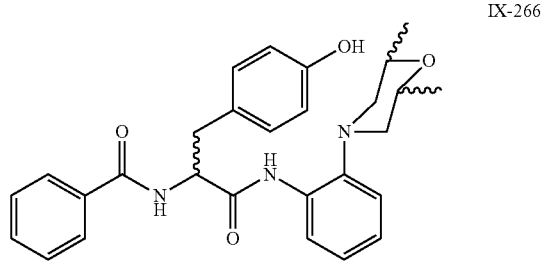

Example 151.1. Preparation of 4-(2-amino-3-((2-(2,6-dimethylmorpholino)phenyl)amino)-3-oxopropyl)-phenyl acetate 4-(2-Amino-3-((2-(2,6-dimethylmorpholino)phenyl)amino)-3-oxopropyl)-phenyl acetate (yellow oil; 680 mg; yield 80%) was prepared according to procedures in Example 104.2, using 3-(4-acetoxyphenyl)-2-((t-butoxycarbonyl)amino)propanoic acid in place of (2-((t-butoxycarbonyl)amino)-3-((2-morpholinophenyl)amino)-3-oxopropyl)-phenyl acetate and 2-(2,6-dimethylmorpholino)aniline (Example 150.1) in place of 2-morpholinoaniline.

Example 151.2. Preparation of IX-266

4-(2-Amino-3-((2-(2,6-dimethylmorpholino)phenyl)amino)-3-oxopropyl)-phenyl acetate (Example 151.1; 110 mg; 0.27 mmol) was coupled with benzoyl chloride to form O-benzoyl-IX-266 (white solid; 54 mg). The acetyl group was removed under the conditions described in Example 86.3, providing IX-266 as a colorless oil.

Yield: 41 mg, 32%.

MS (MALDI): calculated: m/z 474.57 ($MH^+$); found: 474.06, 496.05 ($M+Na^+$).

Example 152. Preparation of N-(1-((5-chloro-2-(piperazin-1-yl)phenyl)amino)-1-oxo-3-phenylpropan-2-yl)-2-fluorobenzamide (IX-274)

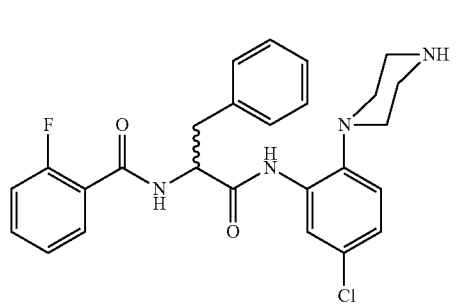

Example 152.1. Preparation of t-butyl 4-(2-amino-4-chlorophenyl)piperazine-1-carboxylate t-Butyl piperazine-1-carboxylate (3.73 g; 20 mmol, Acros Organics) and 2-fluoro-5-chloronitrobenzene (3.5 g; 20 mmol; Matrix Scientific) were treated with TEA (2.78 mL; 20 mmol; Aldrich) in ethanol (40 mL) at ambient temperature for 48 hours. Volatiles were removed under reduced pressure, and the residue was taken up in ethyl acetate (300 mL), neutralized with $Na_2CO_3$ (sat. aq.), washed with water, brine, and dried over $MgSO_4$ to give 6.8 g of t-butyl 4-(2-nitro-4-chlorophenyl)piperazine-1-carboxylate (purified by silica gel column chromatography; 20% ethyl acetate/hexane). The product was dissolved in ethanol (50 mL), stirred with 10% Pd/C (0.5 g) with heating at 50° C., and hydrazine hydrate (3 mL, Aldrich) was added slowly. The resulting black mixture was refluxed for 0.5 hour, filtered through celite, and volatiles were removed under reduced pressure. t-Butyl 4-(2-amino-4-chlorophenyl)piperazine-1-carboxylate was obtained by silica gel column chromatography (20% ethyl acetate/hexanes).

Yield: 4.5 g, 72%.

MS (MALDI): calculated: m/z 311.81/312.81 (M/MH$^+$); found: 311.07 (M), 312.03 (M+H$^+$).

Example 152.2. Preparation of IX-274

IX-274 was prepared according to procedures in Example 99, but using (2-fluorobenzoyl)phenylalanine (115 mg; 0.4 mmol) in place of benzoyl-DL-phenylalanine; and t-butyl 4-(2-amino-4-chlorophenyl)piperazine-1-carboxylate (143 mg; 0.46 mmol) in place of t-butyl 4-(2-aminophenyl)piperazine-1-carboxylate.

Yield: 52 mg, 27%.

MS (MALDI): calculated: m/z 481.97 (M); found: 481.14, 503.12 (M+Na$^+$).

Example 153. Preparation of N-(1-((5-chloro-2-(piperazin-1-yl)phenyl)amino)-1-oxo-3-phenyl-propan-2-yl)-2-methylbenzamide (IX-275)

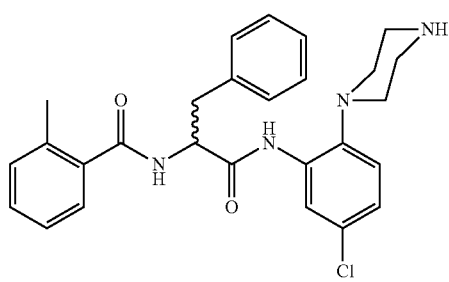

IX-275

IX-275 (yellow oil) was prepared according to procedures in Example 99, but using (2-methylbenzoyl)phenylalanine (113 mg; 0.4 mmol) in place of benzoyl-DL-phenylalanine and t-butyl 4-(2-amino-4-chlorophenyl)piperazine-1-carboxylate (143 mg; 0.46 mmol) in place of t-butyl 4-(2-aminophenyl)piperazine-1-carboxylate.

Yield: 48 mg, 25%. MS (MALDI): calculated: m/z 477.01 (M H$^+$); found: 477.10.

Example 154. Preparation of 2-fluoro-N-(1-((5-fluoro-2-methoxyphenyl)amino)-1-oxo-3-phenyl-propan-2-yl)benzamide (IX-276)

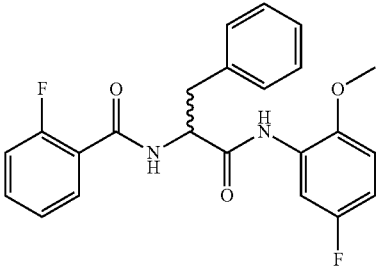

IX-276

IX-276 (white solid) was prepared according to procedures in Example 44.2, but using (2-fluorobenzoyl)phenylalanine (115 mg; 0.4 mmol) and 5-fluoro-2-methoxyaniline (54 μL; 0.46 mmol; Chem-Impex) in place of (1H-indole-4-carbonyl)phenylalanine and o-methoxyaniline.

Yield: 73 mg, 43%.

MS (MALDI): calculated: m/z 411.42 (MH$^+$); found: 411.09, 433.08 (M+Na$^+$).

Example 155. Preparation of N-(1-((5-fluoro-2-methoxyphenyl)amino)-1-oxo-3-phenylpropan-2-yl)-2-methylbenzamide (IX-277)

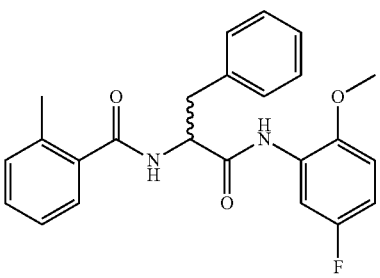

IX-277

IX-277 (white solid) was prepared according to procedures in Example 44.2, but using (2-methylbenzoyl)phenylalanine (113 mg; 0.4 mmol) and 5-fluoro-2-methoxyaniline (54 μL; 0.46 mmol; Chem-Impex) in place of (1H-indole-4-carbonyl)phenylalanine and o-methoxyaniline.

Yield: 85 mg, 52%.

MS (MALDI): calculated: m/z 407.46 (MH$^+$); found: 407.11, 429.09 (M+Na$^+$).

Example 156. Preparation of N-(1-((5-chloro-2-methoxyphenyl)amino)-1-oxo-3-phenylpropan-2-yl)-2-fluorobenzamide (IX-278)

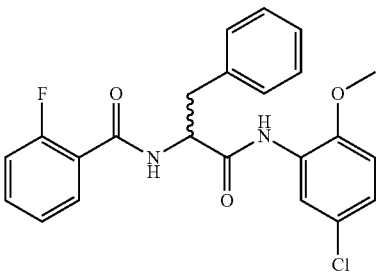

IX-278

IX-278 (white solid) was prepared as in Example 44.2, but using (2-fluorobenzoyl)phenylalanine (115 mg; 0.4 mmol) and 5-chloro-2-methoxyaniline (73 mg; 0.46 mmol; TCI) in place of (1H-indole-4-carbonyl)phenylalanine and o-methoxyaniline.

Yield: 113 mg, 65%.

MS (MALDI): calculated: m/z 427.87 (MH⁺); found: 427.06, 449.04 (M+Na⁺).

Example 157. Preparation of N-(1-((5-chloro-2-methoxyphenyl)amino)-1-oxo-3-phenylpropan-2-yl)-2-methylbenzamide (IX-279)

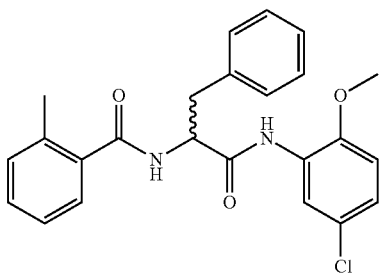

IX-279

IX-279 (white solid) was prepared as in Example 44.2, but using (2-methylbenzoyl)phenylalanine (113 mg; 0.4 mmol) and 5-chloro-2-methoxyaniline (73 mg; 0.46 mmol; TCI) in place of (1H-indole-4-carbonyl)phenylalanine and o-methoxyaniline.

Yield: 106 mg, 61%.

MS (MALDI): calculated: m/z 423.91 (MH⁺); found: 423.08, 445.06 (M+Na⁺).

Example 158. Preparation of N-(1-((1H-benzo[d]imidazol-7-yl)amino)-1-oxo-3-phenylpropan-2-yl)-2-fluorobenzamide (IX-280)

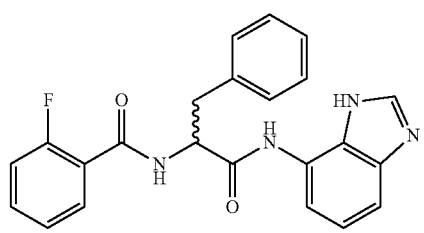

IX-280

IX-280 was prepared according to procedures in Example 44.2, but using (2-fluorobenzoyl)phenylalanine (115 mg; 0.4 mmol) and 1H-benzo[d]imidazol-7-amine (73 mg; 0.55 mmol; Combi-Block) in place of (1H-indole-4-carbonyl)phenylalanine and o-methoxyaniline.

Yield: 64 mg, 39%.

MS (MALDI): calculated: m/z 403.43 (MH⁺); found: 403.04 (M+H⁺), 425.01 (M+Na⁺).

Example 159. Preparation of N-(1-((1H-benzo[d]imidazol-7-yl)amino)-1-oxo-3-phenylpropan-2-yl)-2-methylbenzamide (IX-281)

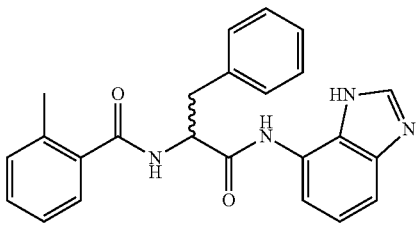

IX-281

IX-281 was prepared according to procedures in Example 44.2, but using (2-methylbenzoyl)phenylalanine (113 mg; 0.4 mmol) and 1H-benzo[d]imidazol-7-amine (61 mg; 0.46 mmol, Combi-Block) in place of (1H-indole-4-carbonyl)phenylalanine and o-methoxyaniline.

Yield: 82 mg, 50%.

MS (MALDI): calculated: m/z 399.47 (MH⁺); found: 399.08, 421.06 (M+Na⁺).

Example 160. Preparation of 2-fluoro-N-(1-((1-methyl-1H-indazol-4-yl)amino)-1-oxo-3-phenyl-propan-2-yl)benzamide (IX-296)

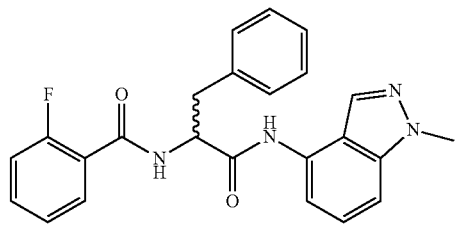

IX-296

IX-296 was prepared according to procedures in Example 44.2, but using (2-fluorobenzoyl)phenylalanine (58 mg; 0.2 mmol) and 1-methyl-1H-indazol-4-amine (32 mg; 0.22 mmol; Chem-Impex) in place of (1H-indole-4-carbonyl)phenylalanine and o-methoxyaniline.

Yield: 60 mg, 65%.

MS (MALDI): calculated: m/z 417.46 (MH⁺); found: 417.04, 439.2 (M+Na⁺).

Example 161. Preparation of 2-methyl-N-(1-((1-methyl-1H-indazol-4-yl)amino)-1-oxo-3-phenyl-propan-2-yl)benzamide (IX-297)

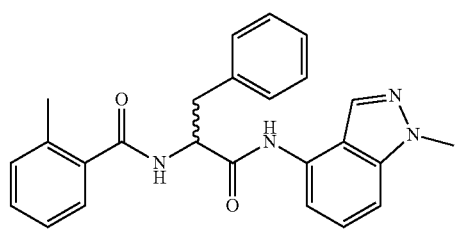

IX-297

IX-297 was prepared according to procedures in Example 44.2, but using (2-methylbenzoyl)phenylalanine (113 mg; 0.4 mmol) and 1-methyl-1H-indazol-4-amine (68 mg; 0.46 mmol; Chem-Impex) in place of (1H-indole-4-carbonyl)phenylalanine and o-methoxyaniline.

Yield: 75 mg, 44%.

MS (MALDI): calculated: m/z 413.49 (MH⁺); found: 413.19 (M+H⁺), 435.17 (M+Na⁺).

Example 162. Preparation of 2-fluoro-N-(1-((1-methyl-1H-benzo[d][1,2,3]triazol-7-yl)amino)-1-oxo-3-phenylpropan-2-yl)benzamide (IX-300)

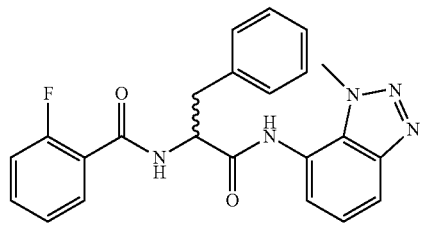

IX-300

IX-300 was prepared according to procedures in Example 44.2, but using (2-fluorobenzoyl)phenylalanine (115 mg; 0.4 mmol) and 1-methyl-1H-benzo[d][1,2,3]triazol-7-amine (67 mg; 0.46 mmol; Princeton Biomolecular Research) in place of (1H-indole-4-carbonyl)phenylalanine and o-methoxyaniline.

Yield: 123 mg, 73%.

MS (MALDI): calculated: m/z 418.44 (MH⁺); found: 418.07, 440.05 (M+Na⁺).

Example 163. Preparation of 2-methyl-N-(1-((1-methyl-1H-benzo[d][1,2,3]triazol-7-yl)amino)-1-oxo-3-phenylpropan-2-yl)benzamide (IX-301)

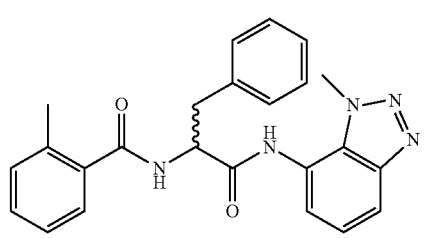

IX-301

IX-301 was prepared according to procedures in Example 44.2, but using (2-methylbenzoyl)phenylalanine (113 mg; 0.4 mmol) and 1-methyl-1H-benzo[d][1,2,3]triazol-7-amine (67 mg; 0.46 mmol; Princeton Biomolecular Research) in place of (1H-indole-4-carbonyl)phenylalanine and o-methoxyaniline.

Yield: 95 mg, 56%.

MS (MALDI): calculated: m/z 414.48 (MH⁺); found: 414.20, 436.18 (M+Na⁺).

Example 164. Preparation of 2-fluoro-N-(1-((5-fluoro-2-(3-methylpiperazin-1-yl)phenyl)amino)-1-oxo-3-phenylpropan-2-yl)benzamide (IX-305)

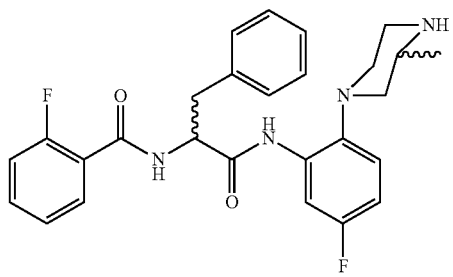

IX-305

Example 164.1. Preparation of t-butyl 4-(2-amino-4-fluorophenyl)-2-methylpiperazine-1-carboxylate t-Butyl 4-(2-amino-4-fluorophenyl)-2-methylpiperazine-1-carboxylate (colorless oil; 0.58 g; yield 19%) was prepared as in Example 98.1, but using 1,4-di-fluoro-2-nitrobenzene (1.08 mL; 10 mmol; Acros Organics) in place of 1-fluoro-2-nitrobenzene and t-butyl 2-methylpiperazine-1-carboxylate (2.1 g; 10.5 mmol; Ark Pharm) in place of thiomorpholine.

Example 164.2. Preparation of IX-305

IX-305 was prepared according to procedures in Example 99, but using (2-fluorobenzoyl)phenylalanine (115 mg; 0.4 mmol) in place of benzoyl-DL-phenylalanine; and t-Butyl 4-(2-amino-4-fluorophenyl)-2-methylpiperazine-1-carboxylate (142 mg; 0.46 mmol) in place of t-butyl 4-(2-aminophenyl)piperazine-1-carboxylate.

Yield: 90 mg, 46%.

MS (MALDI): calculated: m/z 479.54 (MH⁺); found: 479.08, 501.08 (M+Na⁺).

Example 165. Preparation of N-(1-((2-(3-aminopyrrolidin-1-yl)-5-fluorophenyl)amino)-1-oxo-3-phenylpropan-2-yl)-2-fluorobenzamide (IX-306)

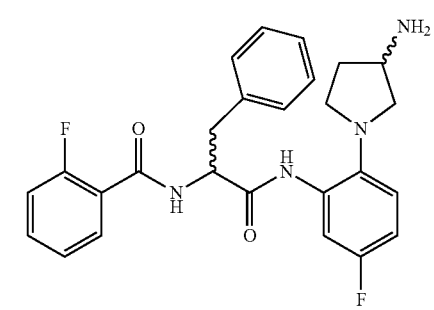

IX-306

Example 165.1. Preparation of t-butyl (1-(2-amino-4-fluorophenyl)pyrrolidin-3-yl)carbamate t-Butyl (1-(2-amino-4-fluorophenyl)pyrrolidin-3-yl)carbamate (colorless oil; 570 mg; yield 77%) was prepared according to procedures in Example 152.1, but using butyl pyrrolidin-3-ylcarbamate (975 mg; 3 mmol; Alfa Aesar) in place of t-butyl piperazine-1-carboxylate and 1,4-di-fluoro-2-nitrobenzene (270 µL; 10 mmol; Acros Organic) in place of 2-fluoro-5-chloronitrobenzene.

Example 164.2. Preparation of IX-306

IX-306 was prepared according to procedures in Example 99, but using (2-fluorobenzoyl)phenylalanine (115 mg; 0.4 mmol) in place of benzoyl-DL-phenylalanine and t-butyl (1-(2-amino-4-fluorophenyl)pyrrolidin-3-yl)carbamate (136 mg; 0.46 mmol) in place of t-butyl 4-(2-aminophenyl)piperazine-1-carboxylate.

Yield: 24 mg, 13%.

MS (MALDI): calculated: m/z 465.52 (MH$^+$); found: 465.19, 487.17 (M+Na$^+$).

Example 166. Preparation of 2-fluoro-N-(1-((5-fluoro-2-(octahydro-6H-pyrrolo[3,4-b]pyridin-6-yl)-phenyl)amino)-1-oxo-3-phenylpropan-2-yl)benzamide (IX-307)

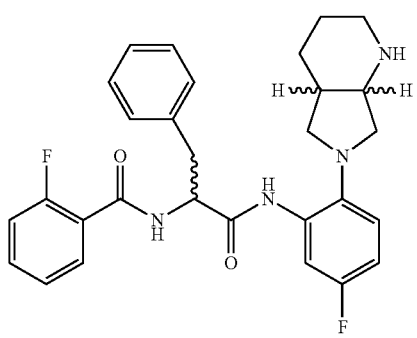

IX-307

Example 166.1. Preparation of t-butyl 6-(2-amino-4-fluorophenyl)octahydro-1H-pyrrolo[3,4-b]-pyridine-1-carboxylate t-Butyl 6-(2-amino-4-fluorophenyl)octahydro-1H-pyrrolo[3,4-b]pyridine-1-carboxylate was prepared according to procedures in Example 98.1, but using t-butyl octahydro-1H-pyrrolo[3,4-b]pyridine-1-carboxylate (500 mg; 2.2 mmol, Combi-block) in place of thiomorpholine and 1,4-di-fluoro-2-nitrobenzene (0.23 mL; 2.1 mmol; Acros Organic) in place of 1-fluoro-2-nitrobenzene.

Example 166.2. Preparation of IX-307

IX-307 was prepared according to procedures in Example 99, but using (2-fluorobenzoyl)phenylalanine (115 mg; 0.4 mmol) in place of benzoyl-DL-phenylalanine and t-butyl 6-(2-amino-4-fluorophenyl)octahydro-1H-pyrrolo[3,4-b]pyridine-1-carboxylate (Example 166.1; 154 mg, 0.46 mmol) in place of t-butyl 4-(2-aminophenyl)piperazine-1-carboxylate.

Yield: 50 mg, 24%.

MS (MALDI): calculated: m/z 505.58 (MH$^+$); found: 505.15, 527.13 (M+Na$^+$).

Example 167. Preparation of N-(1-((2-(3,5-dimethylpiperazin-1-yl)-5-fluorophenyl)amino)-1-oxo-3-phenylpropan-2-yl)-2-fluorobenzamide (IX-308)

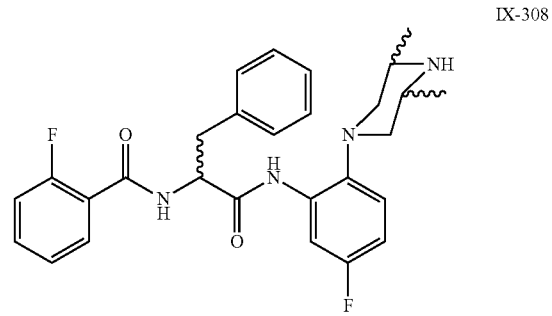

IX-308

Example 167.1. Preparation of 2-(3,5-dimethylpiperazin-1-yl)-5-fluoroaniline 2-(3,5-dimethylpiperazin-1-yl)-5-fluoroaniline was prepared according to procedures in Example 98.1, but using 3,5-dimethylpiperazin (1.2 g; 10.5 mmol; Ark Pharm) in place of thiomorpholine and 1,4-di-fluoro-2-nitrobenzene (1.08 mL; 10 mmol; Acros Organic) in place of 1-fluoro-2-nitrobenzene.

Example 167.2. Preparation of IX-308

IX-308 was prepared according to procedures in Example 99, but using (2-fluorobenzoyl)phenylalanine (115 mg; 0.4 mmol) in place of benzoyl-DL-phenylalanine and 2-(3,5-dimethylpiperazin-1-yl)-5-fluoroaniline (103 mg; 0.46 mmol) in place of t-butyl 4-(2-aminophenyl)piperazine-1-carboxylate.

Yield: 110 mg, 54%.

MS (MALDI): calculated: m/z 493.57 (MH$^+$); found: 493.16, 515.14 (M+Na$^+$).

Example 168. Preparation of N-(1-((2-(4-aminopiperidin-1-yl)-5-fluorophenyl)amino)-1-oxo-3-phenylpropan-2-yl)-2-fluorobenzamide (IX-312)

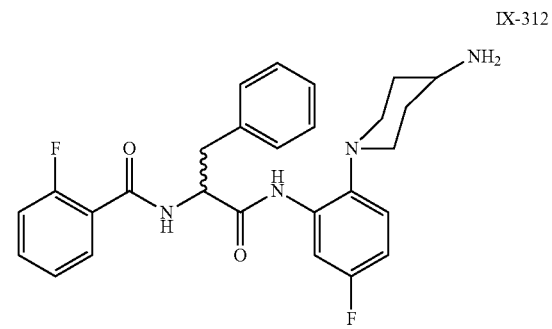 [SMILES: NC1CCN(c2ccc(F)cc2NC(=O)C(Cc2ccccc2)NC(=O)c2ccccc2F)CC1]

IX-312

IX-312 (yellowish oil) was prepared according to procedures in Example 99, but using (2-fluorobenzoyl)phenylalanine (115 mg; 0.4 mmol) in place of benzoyl-DL-phenylalanine and t-butyl (1-(2-amino-4-fluorophenyl)piperidin-4- yl)carbamate (142 mg; 0.46 mmol, Combi-Block) in place of t-butyl 4-(2-aminophenyl)piperazine-1-carboxylate.

Yield: 66 mg, 34%.

MS (MALDI): calculated: m/z 479.54 (MH⁺); found: 479.14, 501.12 (M+Na⁺).

Example 169. Preparation of 2-fluoro-N-(1-((5-fluoro-2-(hexahydropyrrolo[3,4-c]pyrrol-2(1H)-yl)phenyl)amino)-1-oxo-3-phenylpropan-2-yl)benzamide (IX-313)

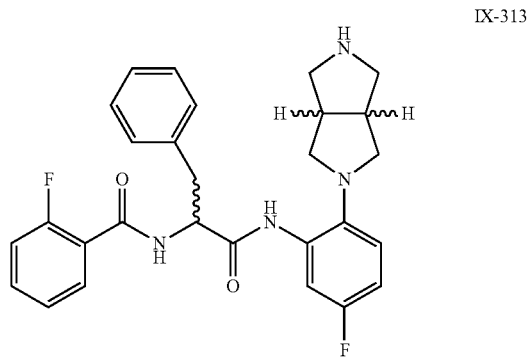 [SMILES: O=C(NC(Cc1ccccc1)C(=O)Nc1cc(F)ccc1N1CC2CNCC2C1)c1ccccc1F]

IX-313

Example 169.1. Preparation of t-butyl 5-(2-amino-4-fluorophenyl)hexahydropyrrolo[3,4-c]pyrrole-2(1H)-carboxylate t-Butyl 5-(2-amino-4-fluorophenyl)hexahydropyrrolo[3,4-c]pyrrole-2(1H)-carboxylate was prepared according to procedures in Example 98.1, but using t-butyl hexahydropyrrolo[3,4-c]pyrrole-2(1H)-carboxylate (500 mg; 2.4 mmol; Ark Pharm) in place of thiomorpholine, and 1,4-difluoro-2-nitrobenzene (238 µL; 2.2 mmol; Acros Organic) in place of 1-fluoro-2-nitrobenzene.

MS (MALDI): calculated: m/z 322.28 (MH⁺); found: 322.02 (M+H⁺), 344.01 (M+Na⁺).

Example 169.2. Preparation of IX-313

IX-313 was prepared according to procedures in Example 99, but using (2-fluorobenzoyl)phenylalanine (115 mg; 0.4 mmol) in place of benzoyl-DL-phenylalanine and t-butyl 5-(2-amino-4-fluorophenyl)-hexahydropyrrolo[3,4-c]pyrrole-2(1H)-carboxylate (Example 169.1; 148 mg, 0.46 mmol) in place of t-butyl 4-(2-aminophenyl)piperazine-1-carboxylate.

Yield: 40 mg, 20%.

MS (MALDI): calculated: m/z 491.55 (MH⁺); found: 491.07, 513.05 (M+Na⁺).

Example 170. Preparation of 2-bromo-N-(1-((5-fluoro-2-(piperazin-1-yl)phenyl)amino)-1-oxo-3-phenylpropan-2-yl)benzamide (IX-315)

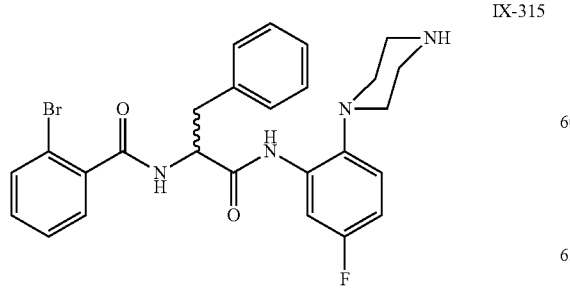

IX-315

IX-315 was prepared according to procedures in Example 99, but using (2-bromobenzoyl)phenylalanine (139 mg; 0.4 mmol) in place of benzoyl-DL-phenylalanine, and t-butyl 4-(2-amino-4-fluorophenyl)piperazine-1-carboxylate (148 mg; 0.5 mmol; Oakwood Chemical) in place of t-butyl 4-(2-aminophenyl)piperazine-1-carboxylate.

Yield: 160 mg, 74%.

MS (MALDI): calculated: m/z 526.42 (MH⁺); found: 526.06, 548.05 (M+Na⁺).

Example 171. Preparation of 2-bromo-N-(1-((5-fluoro-2-(piperazin-1-yl)phenyl)amino)-1-oxo-3-phenylpropan-2-yl)benzamide (IX-316)

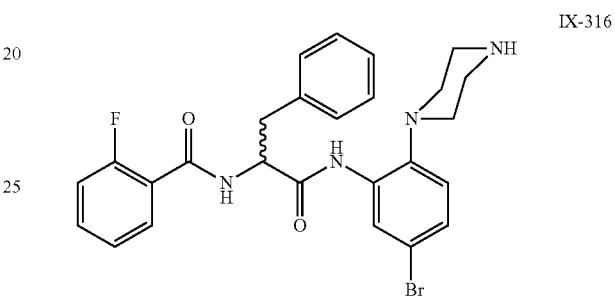

IX-316

IX-316 was prepared according to procedures in Example 99, but using (2-fluorobenzoyl)phenylalanine (115 mg; 0.4 mmol) in place of benzoyl-DL-phenylalanine; and t-butyl 4-(2-amino-4-bromophenyl)piperazine-1-carboxylate (164 mg; 0.46 mmol; Oakwood Chemical) in place of t-butyl 4-(2-aminophenyl)piperazine-1-carboxylate.

Yield: 36 mg, 17%.

MS (MALDI): calculated: m/z 525.42 (M); found: 525.06, 548.05 (M+Na⁺).

Example 172. Preparation of N-(1-((2-(4-acetyl-1,4-diazepan-1-yl)-5-fluorophenyl)amino)-1-oxo-3-phenylpropan-2-yl)-2-fluorobenzamide (IX-319)

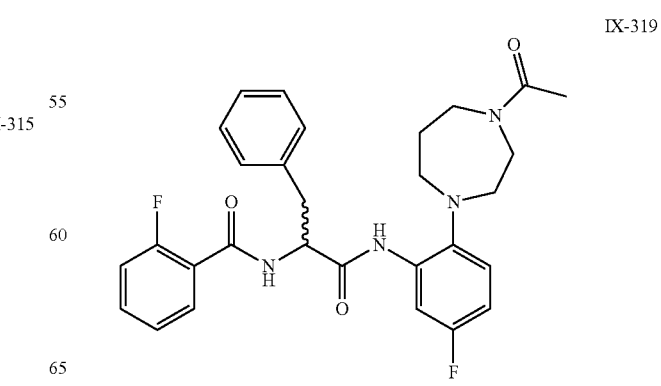

IX-319

IX-319 was prepared according to procedures in Example 99, but using (2-fluorobenzoyl)phenylalanine (115 mg; 0.4 mmol) in place of benzoyl-DL-phenylalanine, and 1-(4-(2-amino-4-fluorophenyl)-1,4-diazepan-1-yl)ethan-1-one (116 mg; 0.46 mmol; FCH) in place of t-butyl 4-(2-aminophenyl)piperazine-1-carboxylate.

Yield: 70 mg, 33%.

MS (MALDI): calculated: m/z 521.58 (MH$^+$); found: 521.25, 543.23 (M+Na$^+$).

TABLE 1

Inhibition of mycobacterial RNA polymerase (IC50s)

| | |
|---|---|
| AAP1 (DL) | 0.68 μM |
| AAP1a (D) | 0.13 μM |
| AAP1b (L) | 12 μM |
| AAP2 | 5.3 μM |

(radiochemical transcription assays; *M. tuberculosis* RNA polymerase)

TABLE 2

Inhibition of mycobacterial growth in culture (MICs)

| | |
|---|---|
| AAP1 (DL) | 6.25 μg/ml |
| AAP1a (D) | 3.13 μg/ml |
| AAP1b (L) | >50 μg/ml |
| AAP2 | 50 μg/ml |

(MABA-MIC assays; *M. tuberculosis* H37Rv)

TABLE 3

Inhibition of mycobacterial growth in culture (MICs)

| | |
|---|---|
| AAP1 (DL) | 0.39 μg/ml |
| AAP1a (D) | 0.20 μg/ml |
| AAP1b (L) | 1.56 μg/ml |
| AAP3 | 1.56 μg/ml |
| AAP4 | 0.78 μg/ml |
| AAP5 | 12.5 μg/ml |
| AAP6 | 1.56 μg/ml |

(broth microdilution assays; *M. smegmatis* ATCC19420)

TABLE 4

AAP1 spontaneous resistance rate

| | |
|---|---|
| spontaneous resistance rate at 2xMIC | $5 \times 10^{-9}$/generation |
| spontaneous resistance rate at 4xMIC | $4 \times 10^{-9}$/generation |
| spontaneous resistance rate at 8xMIC | $5 \times 10^{-9}$/generation |

(96 h fluctuation assays; *M. smegmatis* ATCC19420)

TABLE 5

Spontaneous AAP1-resistant mutants: summary statistics

| | |
|---|---|
| number of independent AAP1-resistant isolates | 19 |
| number of independent AAP1-resistant isolates containing mutations in rpoB | 17 |
| number of independent AAP1-resistant isolates containing mutations in rpoC | 2 |

TABLE 5-continued

Spontaneous AAP1-resistant mutants: summary statistics

| | |
|---|---|
| percent of independent AAP1-resistant isolates containing mutations in rpoB or rpoC | 100 |

(2xMIC AAP1; *M. smegmatis* ATCC19420)

TABLE 6

AAP1-resistant mutants: sequences and properties

| amino acid substitution | number of independent isolates | resistance level (MIC/MIC$_{wild-type}$)$^a$ |
|---|---|---|
| rpoB (RNA polymerase β subunit) | | |
| 468 Pro→Ser | 1 | >60 |
| 470 His→Arg | 2 | >60 |
| 477 Ile→Phe | 1 | >60 |
| 553 Arg→Cys | 2 | >60 |
| 553 Arg→Gly | 1 | |
| 553 Arg→Pro | 1 | >60 |
| 557 Gly→Ser | 3 | >60 |
| 557 Val→Gly | 2 | |
| 571 Asp→Gly | 2 | >60 |
| 576 Gln→Arg | 2 | |
| rpoC (RNA polymerase β' subunit) | | |
| 833 Arg→Gly | 1 | |
| 850 Ile→Ser | 1 | >60 |

$^a$Data are for derivatives of *M. smegmatis* ATCC19420.
$^b$MIC with wild-type rpoB and wild-type rpoC is 0.78 μg/ml.

TABLE 7

AAP1-resistant mutants: absence of cross-resistance to rifampin

| amino acid substitution | cross-resistance level (MIC/MIC$_{wild-type}$)$^{a,b}$ |
|---|---|
| rpoB (RNA polymerase β subunit) | |
| 468 Pro→Ser | 0.5 |
| 470 His→Arg | 0.5 |
| 477 Ile→Phe | 1 |
| 553 Arg→Cys | 0.5 |
| 553 Arg→Pro | 1 |
| 557 Gly→Ser | 1 |
| 571 Asp→Gly | 0.5 |
| rpoC (RNA polymerase β' subunit) | |
| 850 Ile→Ser | 0.5 |

$^a$Data are for derivatives of *M. smegmatis* ATCC19420.
$^b$MIC with wild-type rpoB and wild-type rpoC is 3.13 μg/ml for rifampin.

TABLE 8

Rifampin-resistant mutants: absence of cross-resistance to AAP1

| amino acid substitution | cross-resistance level (MIC/MIC$_{wild-type}$)$^{a,b}$ |
|---|---|
| rpoB (RNA polymerase β subunit) | |
| 442 His→Tyr | 1 |
| 447 Ser→Leu | 0.5 |

$^a$Data are for derivatives of *M. smegmatis* ATCC19420.
$^b$MIC with wild-type rpoB is 0.39 μg/ml for AAP-1.

TABLE 9

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 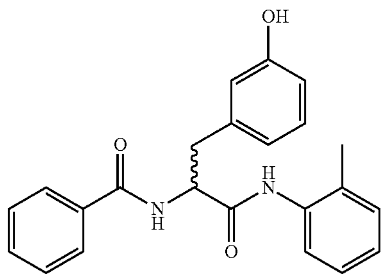 [SMILES: Cc1ccccc1NC(=O)C(Cc1cccc(O)c1)NC(=O)c1ccccc1] | I-12 | 374.44 | 375.12 (M + H+)<br>397.11 (M + Na+) |
| 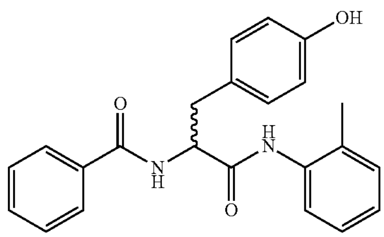 [SMILES: Cc1ccccc1NC(=O)C(Cc1ccc(O)cc1)NC(=O)c1ccccc1] | I-13 | 374.44 | 375.19 (M + H+)<br>397.25 (M + Na+) |
| 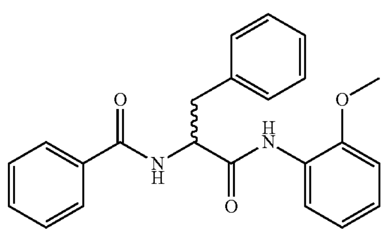 [SMILES: COc1ccccc1NC(=O)C(Cc1ccccc1)NC(=O)c1ccccc1] | I-17 | 374.44 | 375.11 (M + H+)<br>397.12 (M + Na+) |
| 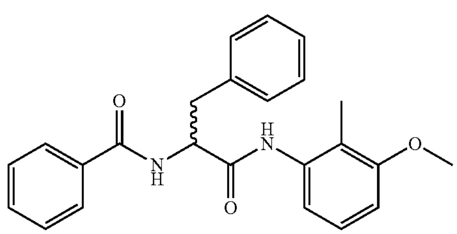 [SMILES: COc1cccc(NC(=O)C(Cc2ccccc2)NC(=O)c2ccccc2)c1C] | I-18 | 388.47 | 389.16 (M + H+)<br>411.15 (M + Na+) |
| 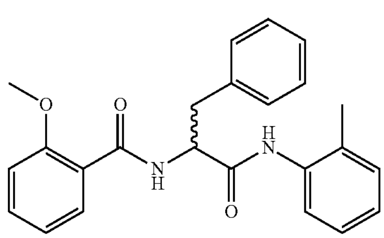 [SMILES: COc1ccccc1C(=O)NC(Cc1ccccc1)C(=O)Nc1ccccc1C] | I-25 | 388.47 | 389.14 (M + H+)<br>411.09 (M + Na+) |
| 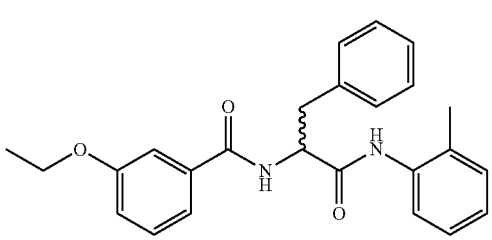 [SMILES: CCOc1cccc(C(=O)NC(Cc2ccccc2)C(=O)Nc2ccccc2C)c1] | I-37 | 402.49 | 403.16 (M + H+)<br>425.15 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 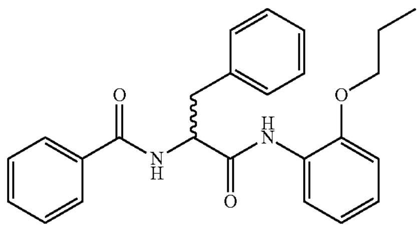 [SMILES: CCCOc1ccccc1NC(=O)C(Cc1ccccc1)NC(=O)c1ccccc1] | I-39 | 402.49 | 403.17 (M + H+)<br>425.17 (M + Na+) |
| 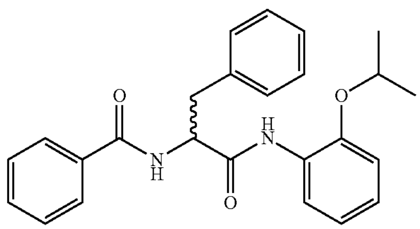 [SMILES: CC(C)Oc1ccccc1NC(=O)C(Cc1ccccc1)NC(=O)c1ccccc1] | I-50 | 402.49 | 403.17 (M + H+)<br>425.16 (M + Na+) |
| 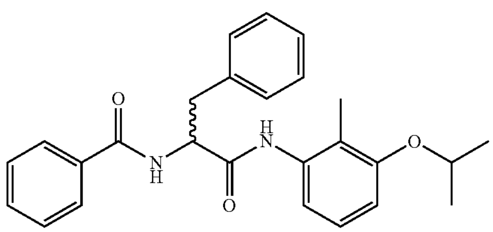 [SMILES: Cc1c(NC(=O)C(Cc2ccccc2)NC(=O)c2ccccc2)cccc1OC(C)C] | I-51 | 416.52 | 417.23 (M + H+)<br>439.16 (M + Na+) |
| 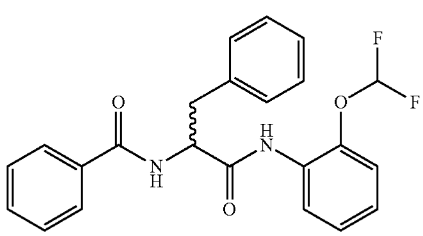 [SMILES: O=C(NC(Cc1ccccc1)C(=O)Nc1ccccc1OC(F)F)c1ccccc1] | I-61 | 410.42 | 411.13 (M + H+)<br>433.12 (M + Na+) |
| 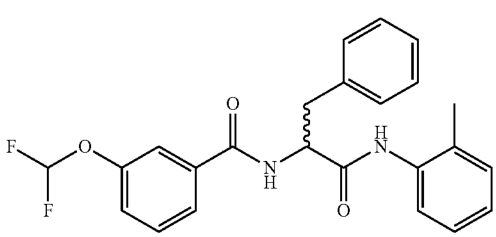 [SMILES: Cc1ccccc1NC(=O)C(Cc1ccccc1)NC(=O)c1cccc(OC(F)F)c1] | I-70 | 424.44 | 425.15 (M + H+)<br>447.14 (M + Na+) |
| 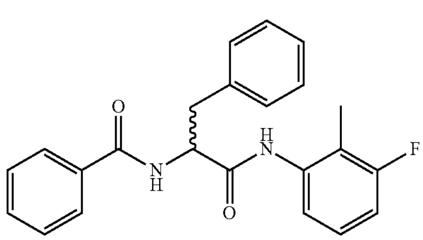 [SMILES: Cc1c(F)cccc1NC(=O)C(Cc1ccccc1)NC(=O)c1ccccc1] | I-73 | 376.42 | 377.16 (M + H+)<br>399.15 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 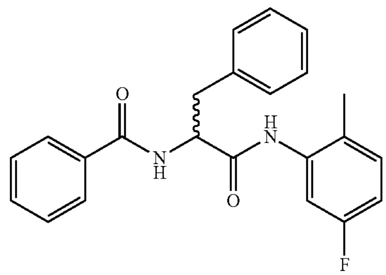 [SMILES: Cc1ccc(F)cc1NC(=O)C(Cc1ccccc1)NC(=O)c1ccccc1] | I-75 | 376.42 | 377.14 (M + H+) 399.13 (M + Na+) |
| 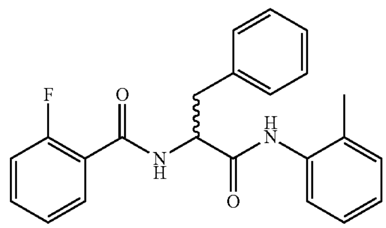 [SMILES: Cc1ccccc1NC(=O)C(Cc1ccccc1)NC(=O)c1ccccc1F] | I-80 | 376.42 | 377.20 (M + H+) 399.21 (M + Na+) |
| 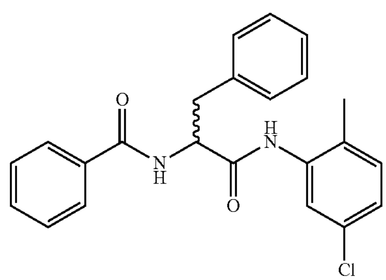 [SMILES: Cc1ccc(Cl)cc1NC(=O)C(Cc1ccccc1)NC(=O)c1ccccc1] | I-86 | 392.88 | 393.46 (M + H+) 415.15 (M + Na+) |
| 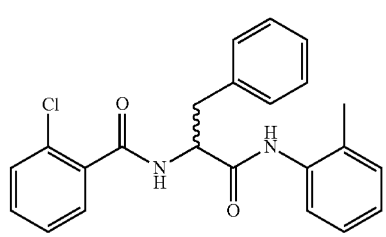 [SMILES: Cc1ccccc1NC(=O)C(Cc1ccccc1)NC(=O)c1ccccc1Cl] | I-91 | 392.88 | 393.11 (M + H+) 415.12 (M + Na+) |
| 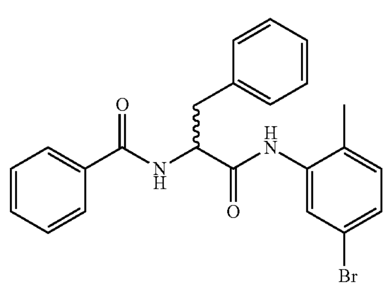 | I-97 | 437.33 | 437.04 (M + H+) 459.03 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 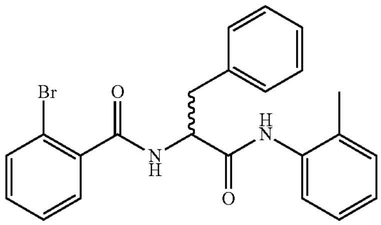 [SMILES: Cc1ccccc1NC(=O)C(Cc1ccccc1)NC(=O)c1ccccc1Br] | I-102 | 437.33 | 437.15 (M + H+) 459.09 (M + Na+) |
| 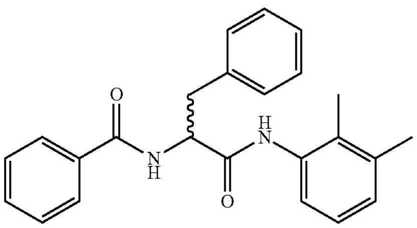 [SMILES: Cc1cccc(NC(=O)C(Cc2ccccc2)NC(=O)c2ccccc2)c1C] | I-105 | 372.46 | 373.18 (M + H+) 395.18 (M + Na+) |
| 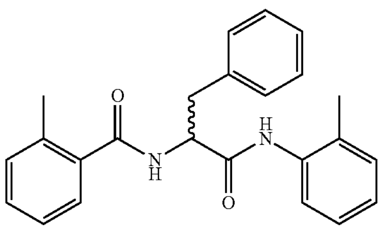 [SMILES: Cc1ccccc1NC(=O)C(Cc1ccccc1)NC(=O)c1ccccc1C] | I-112 | 372.46 | 373.16 (M + H+) 396.17 (M + Na+) |
| 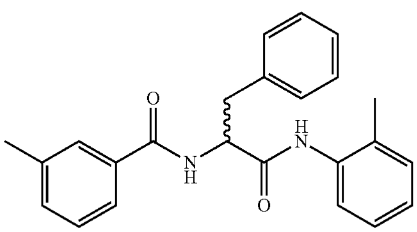 [SMILES: Cc1cccc(C(=O)NC(Cc2ccccc2)C(=O)Nc2ccccc2C)c1] | I-113 | 372.46 | 373.18 (M + H+) 395.19 (M + Na+) |
| 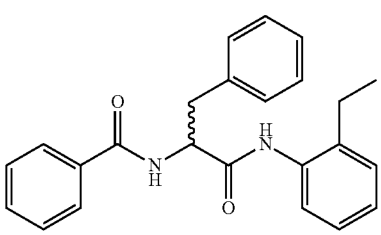 [SMILES: CCc1ccccc1NC(=O)C(Cc1ccccc1)NC(=O)c1ccccc1] | I-115 | 372.46 | 373.18 (M + H+) 395.18 (M + Na+) |
| 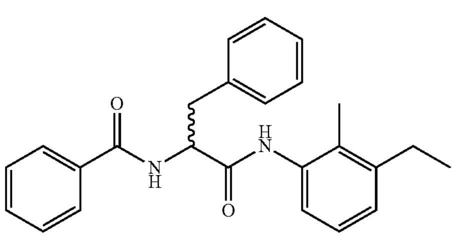 [SMILES: CCc1cccc(NC(=O)C(Cc2ccccc2)NC(=O)c2ccccc2)c1C] | I-116 | 386.49 | 409.19 (M + Na+) 425.31 (M + K+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 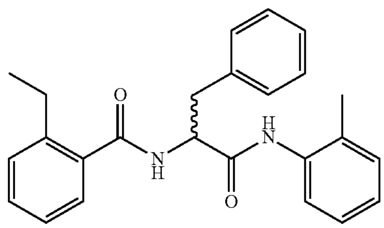 [SMILES: CCc1ccccc1C(=O)NC(Cc1ccccc1)C(=O)Nc1ccccc1C] | I-123 | 386.49 | 409.21 (M + Na+)<br>425.16 (M + K+) |
| 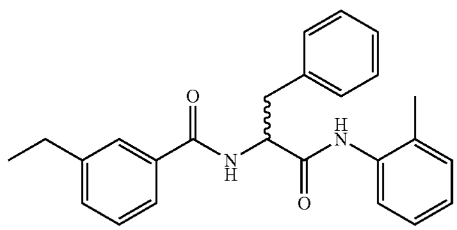 [SMILES: CCc1cccc(C(=O)NC(Cc2ccccc2)C(=O)Nc2ccccc2C)c1] | I-124 | 386.49 | 409.28 (M + Na+)<br>425.14 (M + K)+ |
| 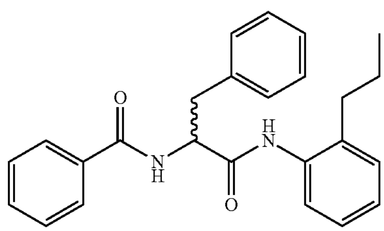 [SMILES: CCCc1ccccc1NC(=O)C(Cc1ccccc1)NC(=O)c1ccccc1] | I-126 | 386.49 | 409.21 (M + Na+)<br>425.16 (M + K+) |
| 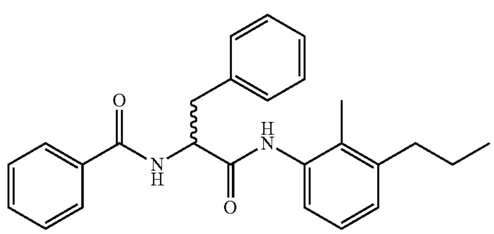 [SMILES: CCCc1cccc(NC(=O)C(Cc2ccccc2)NC(=O)c2ccccc2)c1C] | I-127 | 400.51 | 401.23 (M + H+)<br>423.23 (M + Na+) |
| 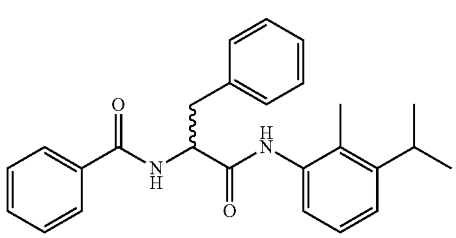 [SMILES: Cc1c(NC(=O)C(Cc2ccccc2)NC(=O)c2ccccc2)cccc1C(C)C] | I-138 | 400.51 | 401.23 (M + H+)<br>423.23 (M + Na+) |
| 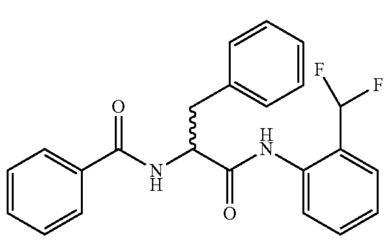 [SMILES: O=C(NC(Cc1ccccc1)C(=O)Nc1ccccc1C(F)F)c1ccccc1] | I-148 | 394.41 | 417.13 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 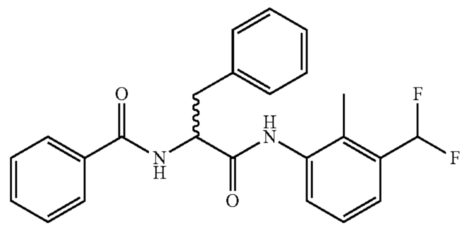 [SMILES: Cc1c(NC(=O)C(Cc2ccccc2)NC(=O)c2ccccc2)cccc1C(F)F] | I-149 | 408.44 | 408.18 (M + H+)<br>431.15 (M + Na+) |
| 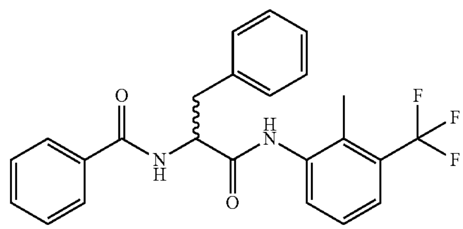 [SMILES: Cc1c(NC(=O)C(Cc2ccccc2)NC(=O)c2ccccc2)cccc1C(F)(F)F] | I-160 | 426.43 | 449.15 (M + Na+) |
| 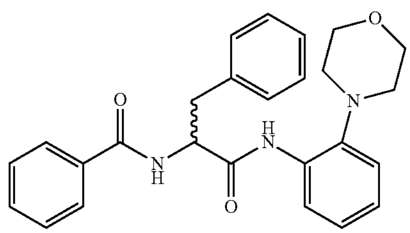 [SMILES: O=C(NC(Cc1ccccc1)C(=O)Nc1ccccc1N1CCOCC1)c1ccccc1] | I-181 | 429.51 | 430.22 (M + H+)<br>452.19 (M + Na+) |
| 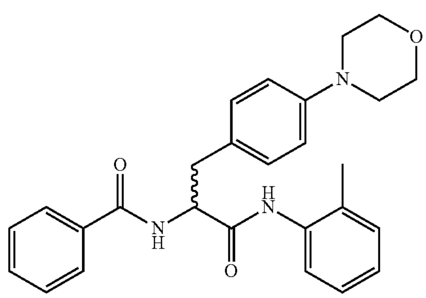 [SMILES: Cc1ccccc1NC(=O)C(Cc1ccc(N2CCOCC2)cc1)NC(=O)c1ccccc1] | I-188 | 443.54 | 444.23 (M + H+)<br>466.21 (M + Na+) |
| 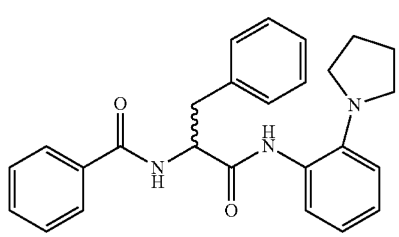 [SMILES: O=C(NC(Cc1ccccc1)C(=O)Nc1ccccc1N1CCCC1)c1ccccc1] | I-192 | 413.51 | 414.25 (M + H+)<br>437.25 (M + Na+) |
| 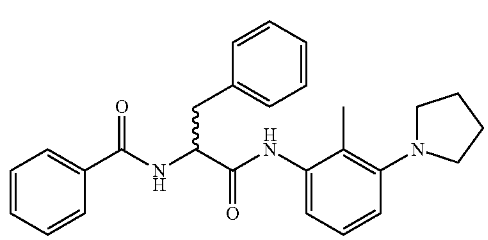 [SMILES: Cc1c(NC(=O)C(Cc2ccccc2)NC(=O)c2ccccc2)cccc1N1CCCC1] | I-193 | 427.54 | 428.25 (M + H+)<br>450.22 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 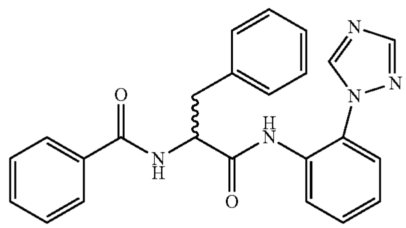 [SMILES: O=C(NC(Cc1ccccc1)C(=O)Nc1ccccc1-n1cncn1)c1ccccc1] | I-203 | 411.26 | 412.19 (M + H+) 434.16 (M + Na+) |
| 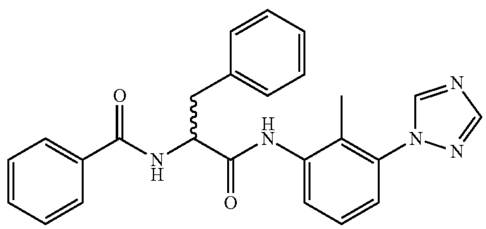 [SMILES: Cc1c(NC(=O)C(Cc2ccccc2)NC(=O)c2ccccc2)cccc1-n1cncn1] | I-204 | 425.48 | 426.23 (M + H+) 448.18 (M + Na+) |
| 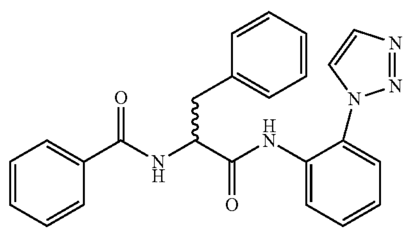 [SMILES: O=C(NC(Cc1ccccc1)C(=O)Nc1ccccc1-n1ccnn1)c1ccccc1] | I-214 | 411.46 | 411.18 (M + H+) 434.17 (M + Na+) |
| 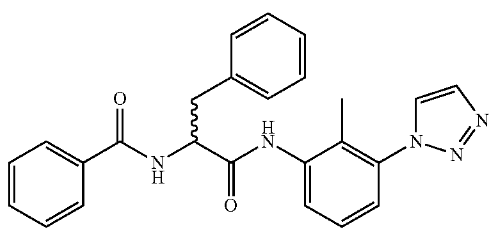 [SMILES: Cc1c(NC(=O)C(Cc2ccccc2)NC(=O)c2ccccc2)cccc1-n1ccnn1] | I-215 | 425.48 | 426.22 (M + H+) 448.19 (M + Na+) |
| 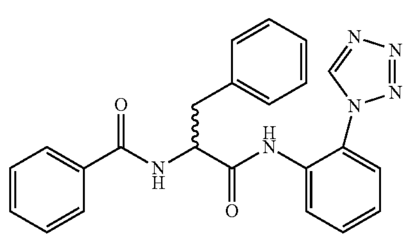 [SMILES: O=C(NC(Cc1ccccc1)C(=O)Nc1ccccc1-n1cnnn1)c1ccccc1] | I-225 | 412.44 | 435.16 (M + Na+) |
| 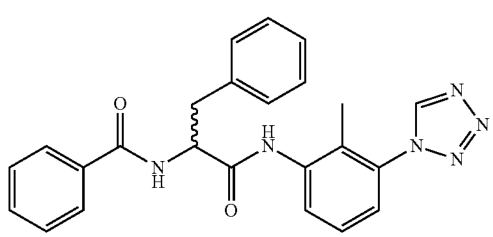 [SMILES: Cc1c(NC(=O)C(Cc2ccccc2)NC(=O)c2ccccc2)cccc1-n1cnnn1] | I-226 | 426.47 | 449.12 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 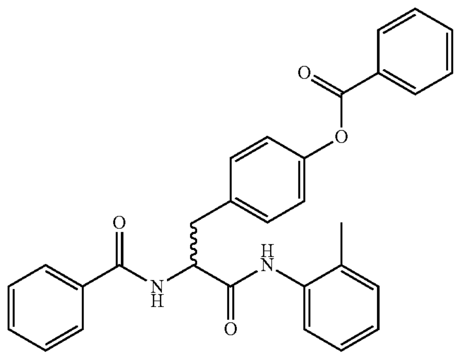 [SMILES: Cc1ccccc1NC(=O)C(Cc1ccc(OC(=O)c2ccccc2)cc1)NC(=O)c1ccccc1] | I-236 | 478.54 | 501.20 (M + Na+) |
| 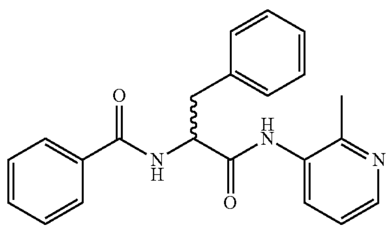 [SMILES: Cc1ncccc1NC(=O)C(Cc1ccccc1)NC(=O)c1ccccc1] | II-5 | 359.42 | 360.17 (M + H+) <br> 383.15 (M + Na+) |
| 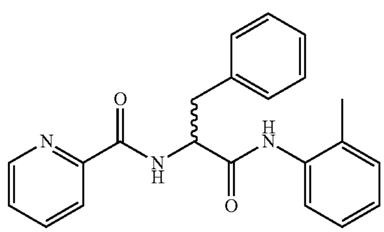 [SMILES: Cc1ccccc1NC(=O)C(Cc1ccccc1)NC(=O)c1ccccn1] | II-12 | 359.42 | 360.19 (M + H+) <br> 381.17 (M + Na+) |
| 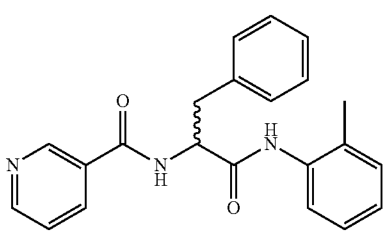 [SMILES: Cc1ccccc1NC(=O)C(Cc1ccccc1)NC(=O)c1cccnc1] | II-13 | 359.42 | 360.17 (M + H+) <br> 382.15 (M + Na+) |
| 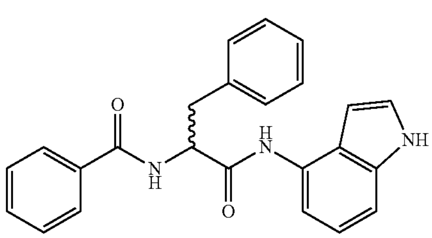 [SMILES: O=C(NC(Cc1ccccc1)C(=O)Nc1cccc2[nH]ccc12)c1ccccc1] | II-27 | 383.44 | 384.20 (M + H+) <br> 406.19 (M + Na+) |
| 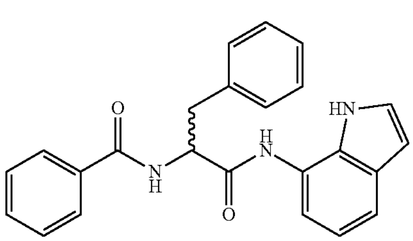 [SMILES: O=C(NC(Cc1ccccc1)C(=O)Nc1cccc2cc[nH]c12)c1ccccc1] | II-28 | 383.44 | 384.18 (M + H+) <br> 406.16 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 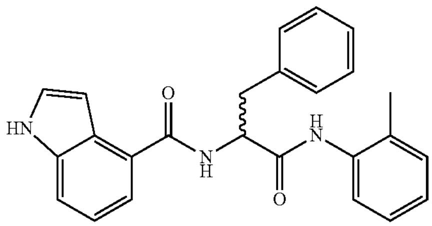 [SMILES: Cc1ccccc1NC(=O)C(Cc1ccccc1)NC(=O)c1cccc2[nH]ccc12] | II-39 | 397.47 | 398.23 (M + H+)<br>420.23 (M + Na+) |
| 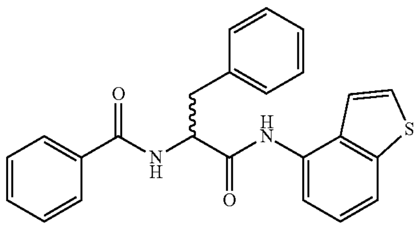 [SMILES: O=C(NC(Cc1ccccc1)C(=O)Nc1cccc2sccc12)c1ccccc1] | II-46 | 400.49 | 401.13 (M + H+)<br>423.12 (M + Na+) |
| 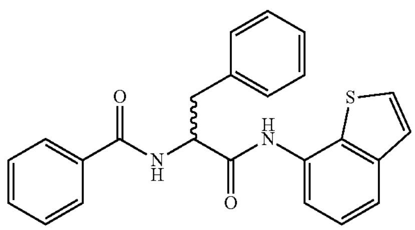 [SMILES: O=C(NC(Cc1ccccc1)C(=O)Nc1cccc2ccsc12)c1ccccc1] | II-47 | 400.49 | 401.14 (M + H+)<br>423.12 (M + Na+) |
| 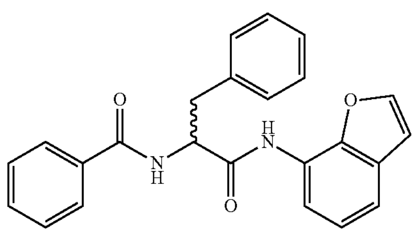 [SMILES: O=C(NC(Cc1ccccc1)C(=O)Nc1cccc2ccoc12)c1ccccc1] | II-65 | 384.43 | 385.15 (M + H+)<br>407.14 (M + Na+) |
| 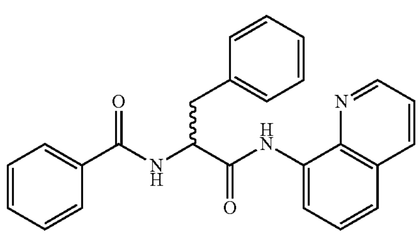 [SMILES: O=C(NC(Cc1ccccc1)C(=O)Nc1cccc2cccnc12)c1ccccc1] | IX-2 | 395.45 | 396.07 (M + H+)<br>418.04 (M + Na+) |
| 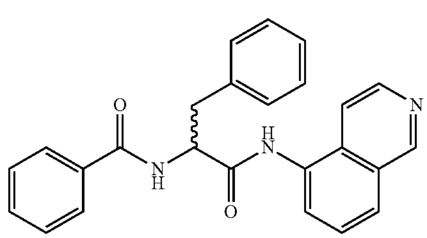 [SMILES: O=C(NC(Cc1ccccc1)C(=O)Nc1cccc2cnccc12)c1ccccc1] | IX-3 | 395.45 | 396.21 (M + H+)<br>418.08 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 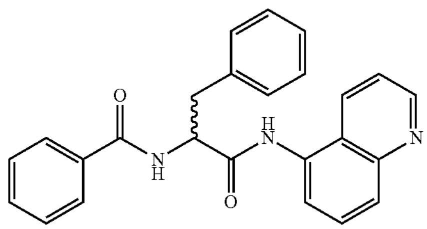 [SMILES: O=C(NC(Cc1ccccc1)C(=O)Nc1cccc2ncccc12)c1ccccc1] | IX-4 | 395.45 | 396.11 (M + H+)<br>418.06 (M + Na+) |
| 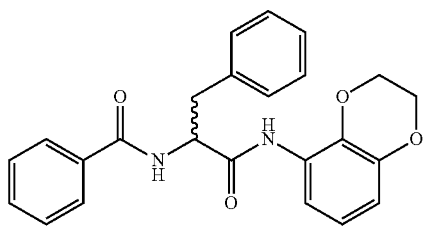 [SMILES: O=C(NC(Cc1ccccc1)C(=O)Nc1cccc2c1OCCO2)c1ccccc1] | IX-5 | 402.44 | 403.07 (M + H+)<br>425.07 (M + Na+) |
| 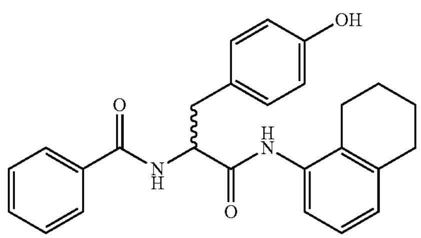 [SMILES: O=C(NC(Cc1ccc(O)cc1)C(=O)Nc1cccc2c1CCCC2)c1ccccc1] | IX-6 | 414.50 | 421.35 (M + Li+)<br>437.32 (M + Na+) |
| 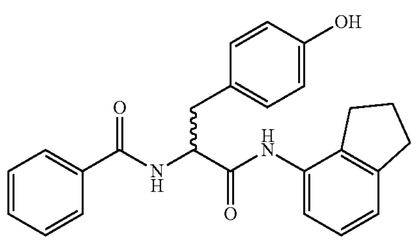 [SMILES: O=C(NC(Cc1ccc(O)cc1)C(=O)Nc1cccc2c1CCC2)c1ccccc1] | IX-14 | 400.47 | 401.21 (M + H+)<br>423.22 (M + Na+) |
| 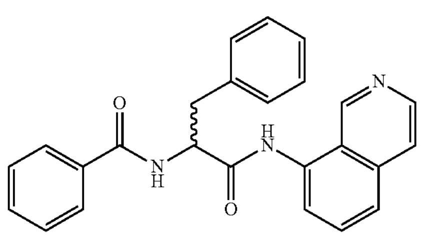 [SMILES: O=C(NC(Cc1ccccc1)C(=O)Nc1cccc2ccncc12)c1ccccc1] | IX-15 | 395.45 | 396.21 (M + H+)<br>418.18 (M + Na+) |
| 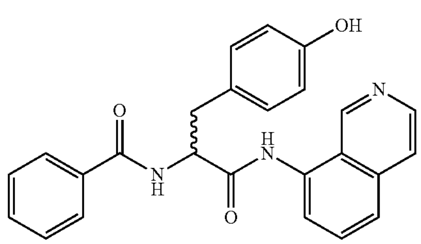 [SMILES: O=C(NC(Cc1ccc(O)cc1)C(=O)Nc1cccc2ccncc12)c1ccccc1] | IX-18 | 411.45 | 412.27 (M + H+)<br>434.27 (M + Na+) |

TABLE 9-continued
Structures, calculated m/z values, and experimental m/z values for compounds according to general structural formulae (V) and (VI)
(Examples 8, 9, 14, and 15-172)
| structure | name | MW | MALDI-MS m/z |
|---|---|---|---|
| 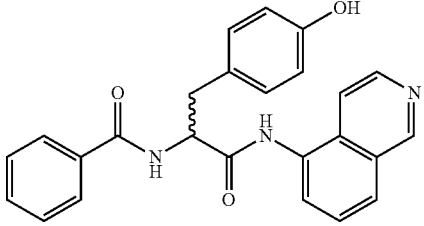 [SMILES: O=C(NC(Cc1ccc(O)cc1)C(=O)Nc1cccc2cnccc12)c1ccccc1] | IX-19 | 411.45 | 412.23 (M + H+) <br> 434.20 (M + Na+) |
| 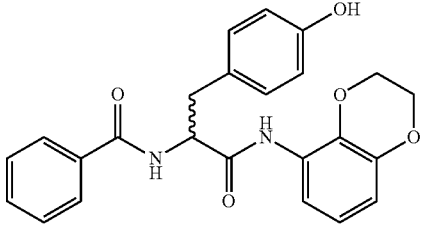 [SMILES: O=C(NC(Cc1ccc(O)cc1)C(=O)Nc1cccc2c1OCCO2)c1ccccc1] | IX-21 | 418.44 | 441.20 (M + Na+) |
| 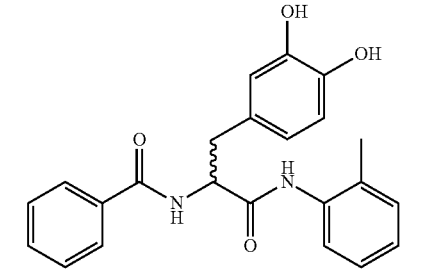 [SMILES: Cc1ccccc1NC(=O)C(Cc1ccc(O)c(O)c1)NC(=O)c1ccccc1] | IX-25 | 390.43 | 413.11 (M + Na+) |
| 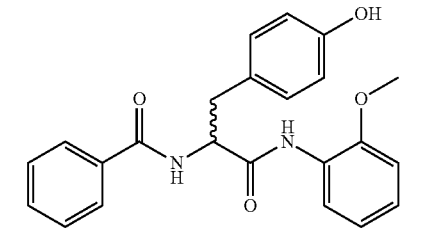 [SMILES: COc1ccccc1NC(=O)C(Cc1ccc(O)cc1)NC(=O)c1ccccc1] | IX-26 | 390.43 | 391.22 (M + H+) <br> 413.18 (M + Na+) |
| 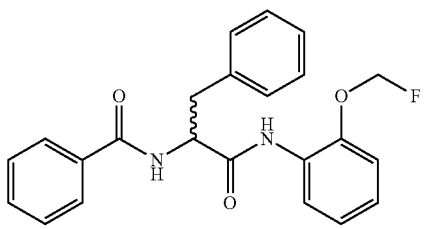 [SMILES: O=C(NC(Cc1ccccc1)C(=O)Nc1ccccc1OCF)c1ccccc1] | IX-27 | 392.42 | 393.24 (M + H+) <br> 415.42 (M + Na+) |
| 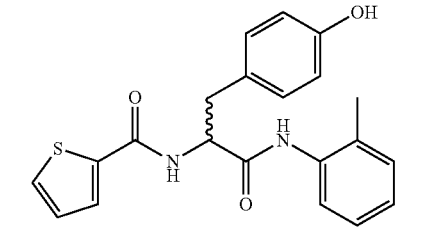 [SMILES: Cc1ccccc1NC(=O)C(Cc1ccc(O)cc1)NC(=O)c1cccs1] | IX-28 | 380.46 | 381.35 (M + H+) <br> 403.34 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 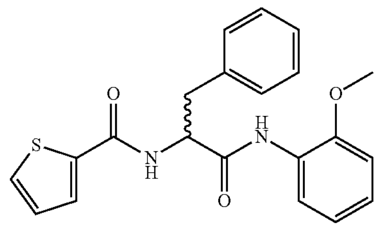 [SMILES: COc1ccccc1NC(=O)C(Cc1ccccc1)NC(=O)c1cccs1] | IX-29 | 380.46 | 381.11 (M + H+)<br>403.25 (M + Na+) |
| 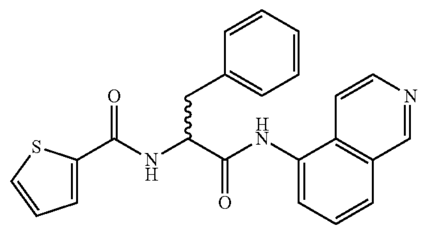 [SMILES: O=C(NC(Cc1ccccc1)C(=O)Nc1cccc2cnccc12)c1cccs1] | IX-30 | 401.48 | 402.54 (M + H+)<br>424.22 (M + Na+) |
| 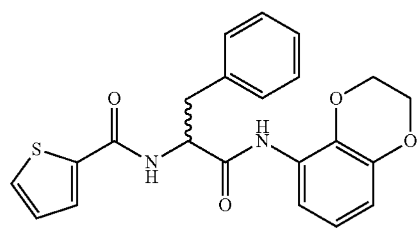 [SMILES: O=C(NC(Cc1ccccc1)C(=O)Nc1cccc2c1OCCO2)c1cccs1] | IX-31 | 408.47 | 409.18 (M + H+)<br>431.14 (M + Na+) |
| 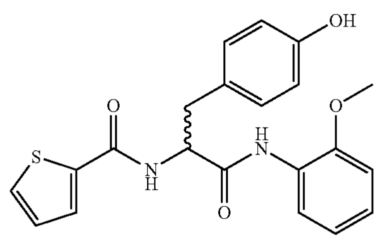 [SMILES: COc1ccccc1NC(=O)C(Cc1ccc(O)cc1)NC(=O)c1cccs1] | IX-32 | 396.46 | 397.37 (M + H+)<br>419.43 (M + Na+) |
| 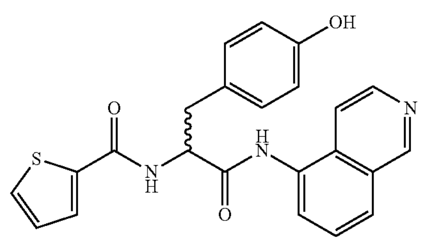 [SMILES: O=C(NC(Cc1ccc(O)cc1)C(=O)Nc1cccc2cnccc12)c1cccs1] | IX-33 | 417.48 | 418.40 (M + H+)<br>440.39 (M + Na+) |
| 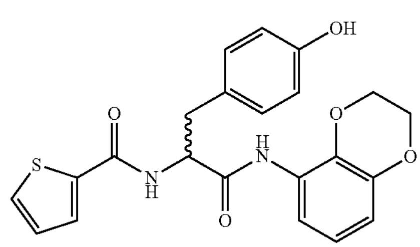 [SMILES: O=C(NC(Cc1ccc(O)cc1)C(=O)Nc1cccc2c1OCCO2)c1cccs1] | IX-34 | 424.47 | 425.41 (M + H+)<br>447.62 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 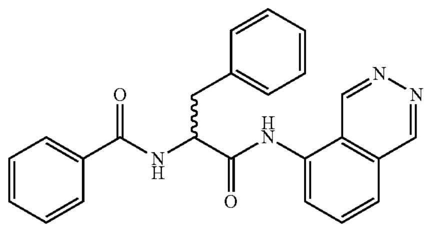 [SMILES: O=C(NC(Cc1ccccc1)C(=O)Nc1cccc2cnncc12)c1ccccc1] | IX-35 | 396.44 | 397.34 (M + H+)<br>419.23 (M + Na+) |
| 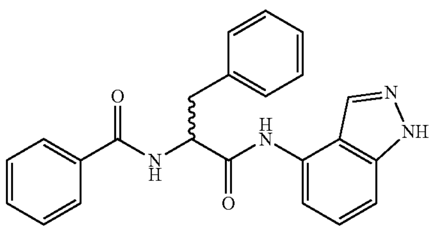 [SMILES: O=C(NC(Cc1ccccc1)C(=O)Nc1cccc2[nH]ncc12)c1ccccc1] | IX-37 | 384.40 | 385.13 (M + H+)<br>407.13 (M + Na+) |
| 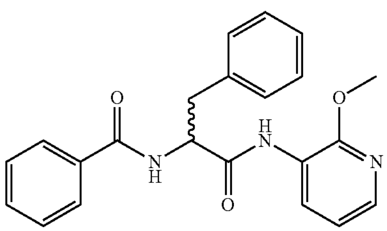 [SMILES: COc1ncccc1NC(=O)C(Cc1ccccc1)NC(=O)c1ccccc1] | IX-38 | 375.42 | 376.34 (M + H+)<br>398.40 (M + Na+) |
| 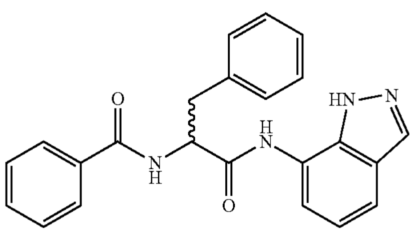 [SMILES: O=C(NC(Cc1ccccc1)C(=O)Nc1cccc2cn[nH]c12)c1ccccc1] | IX-39 | 384.43 | 385.20 (M + H+)<br>407.23 (M + Na+) |
| 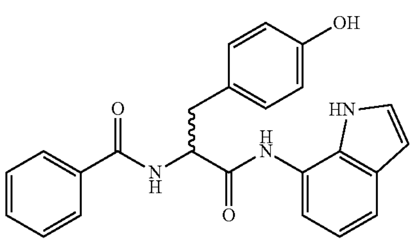 [SMILES: O=C(NC(Cc1ccc(O)cc1)C(=O)Nc1cccc2cc[nH]c12)c1ccccc1] | IX-40 | 399.44 | 399.89 (M + H+)<br>422.29 (M + Na+) |
| 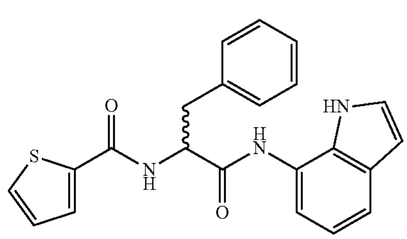 [SMILES: O=C(NC(Cc1ccccc1)C(=O)Nc1cccc2cc[nH]c12)c1cccs1] | IX-41 | 389.47 | 390.14 (M + H+)<br>412.17 (M + Na+) |

TABLE 9-continued
Structures, calculated m/z values, and experimental m/z values for compounds according to general structural formulae (V) and (VI) (Examples 8, 9, 14, and 15-172)
| structure | name | MW | MALDI-MS m/z |
|---|---|---|---|
| 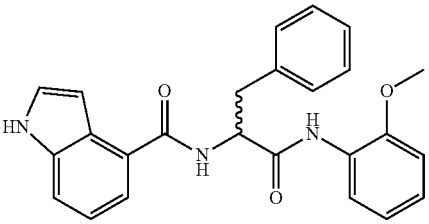 [SMILES: COc1ccccc1NC(=O)C(Cc1ccccc1)NC(=O)c1cccc2[nH]ccc12] | IX-43 | 413.48 | 414.14 (M + H+)<br>436.13 (M + Na+) |
| 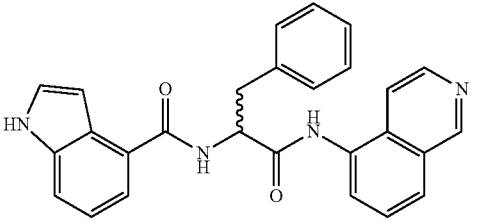 | IX-44 | 434.40 | 435.23 (M + H+)<br>457.20 (M + Na+) |
| 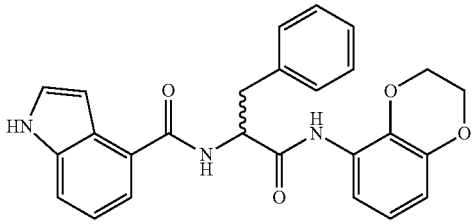 [SMILES: O=C(NC(Cc1ccccc1)C(=O)Nc1cccc2cnccc12)c1cccc2[nH]ccc12] | IX-45 | 441.49 | 442.48 (M + H+)<br>464.28 (M + Na+) |
| 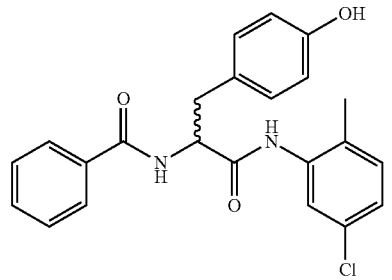 [SMILES: Cc1ccc(Cl)cc1NC(=O)C(Cc1ccc(O)cc1)NC(=O)c1ccccc1] | IX-51 | 408.88 | 409.35 (M + H+)<br>431.37 (M + Na+) |
| 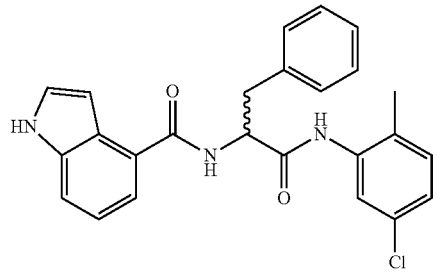 | IX-53 | 431.92 | 432.18 (M + H+)<br>454.20 (M + Na+) |
| 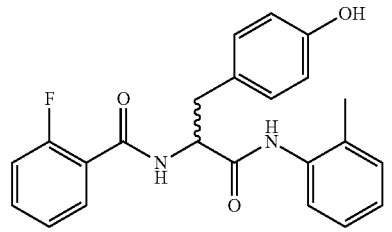 [SMILES: Cc1ccccc1NC(=O)C(Cc1ccc(O)cc1)NC(=O)c1ccccc1F] | IX-54 | 392.42 | 393.23 (M + H+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 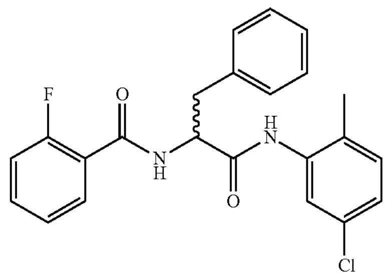 [SMILES: Cc1ccc(Cl)cc1NC(=O)C(Cc1ccccc1)NC(=O)c1ccccc1F] | IX-55 | 410.87 | 411.11 (M + H+) <br> 433.13 (M + Na+) |
| 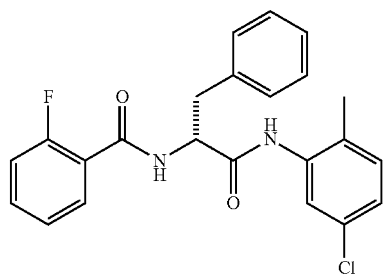 [SMILES: Cc1ccc(Cl)cc1NC(=O)[C@@H](Cc1ccccc1)NC(=O)c1ccccc1F] | IX-55a | 410.87 | 433.15 (M + Na+) |
| 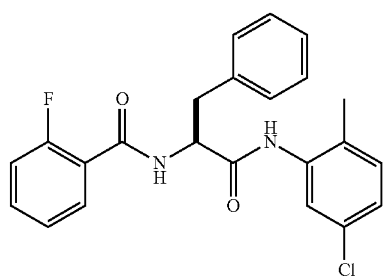 [SMILES: Cc1ccc(Cl)cc1NC(=O)[C@H](Cc1ccccc1)NC(=O)c1ccccc1F] | IX-55b | 410.87 | 411.14 (M + H+) <br> 433.16 (M + Na+) |
| 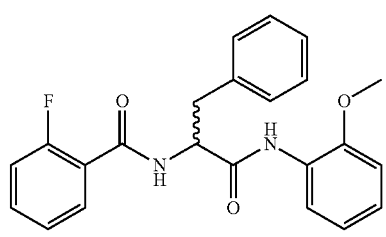 [SMILES: COc1ccccc1NC(=O)C(Cc1ccccc1)NC(=O)c1ccccc1F] | IX-56 | 392.42 | 393.21 (M + H+) <br> 415.25 (M + Na+) |
| 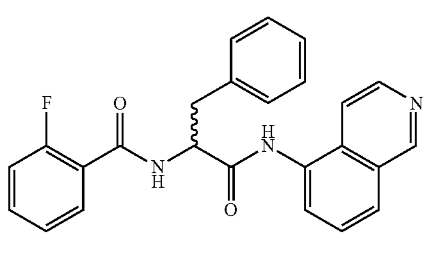 [SMILES: O=C(NC(Cc1ccccc1)C(=O)Nc1cccc2cnccc12)c1ccccc1F] | IX-57 | 413.44 | 414.18 (M + H+) <br> 436.23 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 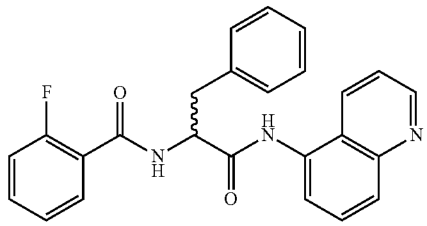 [SMILES: O=C(NC(Cc1ccccc1)C(=O)Nc1cccc2ncccc12)c1ccccc1F] | IX-58 | 413.44 | 414.48 (M + H+) 436.47 (M + Na+) |
| 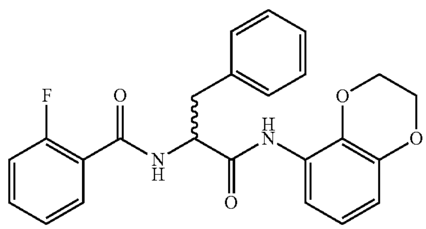 [SMILES: O=C(NC(Cc1ccccc1)C(=O)Nc1cccc2c1OCCO2)c1ccccc1F] | IX-59 | 420.43 | 421.18 (M + H+) 443.28 (M + Na+) |
| 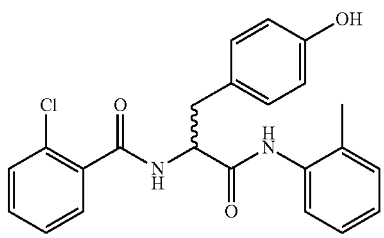 [SMILES: Cc1ccccc1NC(=O)C(Cc1ccc(O)cc1)NC(=O)c1ccccc1Cl] | IX-60 | 408.88 | 409.25 (M + H+) |
| 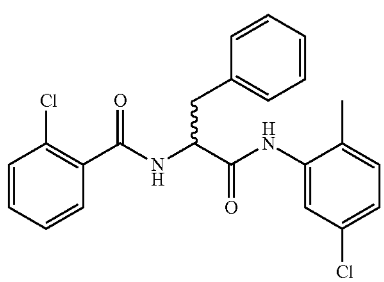 [SMILES: Cc1ccc(Cl)cc1NC(=O)C(Cc1ccccc1)NC(=O)c1ccccc1Cl] | IX-61 | 427.33 | 427.29 (M + H+) 449.20 (M + Na+) |
| 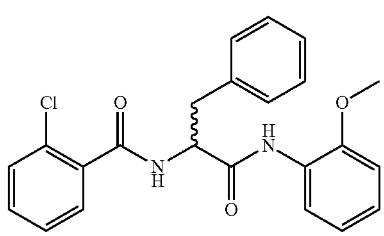 [SMILES: COc1ccccc1NC(=O)C(Cc1ccccc1)NC(=O)c1ccccc1Cl] | IX-62 | 408.88 | 431.25 (M + Na+) |
| 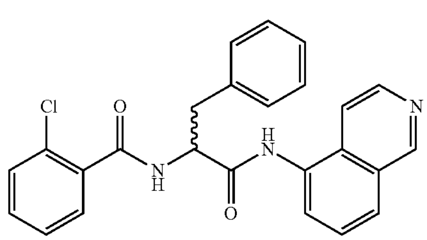 [SMILES: O=C(NC(Cc1ccccc1)C(=O)Nc1cccc2cnccc12)c1ccccc1Cl] | IX-63 | 429.90 | 430.16 (M + H+) 452.10 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 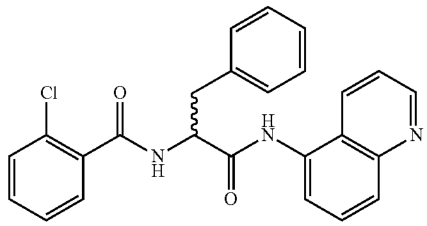 [SMILES: O=C(NC(Cc1ccccc1)C(=O)Nc1cccc2ncccc12)c1ccccc1Cl] | IX-64 | 429.90 | 430.14 (M + H+) 452.11 (M + Na+) |
| 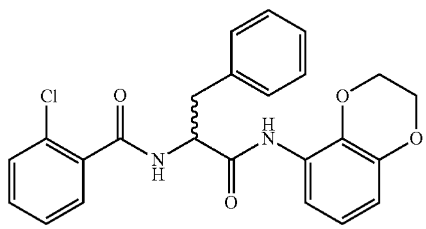 [SMILES: O=C(NC(Cc1ccccc1)C(=O)Nc1cccc2c1OCCO2)c1ccccc1Cl] | IX-65 | 436.89 | 437.26 (M + H+) 460.12 (M + Na+) |
| 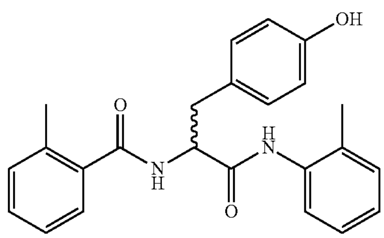 [SMILES: Cc1ccccc1NC(=O)C(Cc1ccc(O)cc1)NC(=O)c1ccccc1C] | IX-66 | 388.46 | 411.23 (M + Na+) |
| 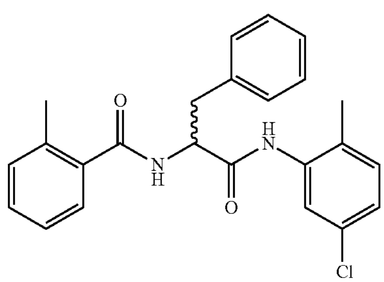 [SMILES: Cc1ccc(Cl)cc1NC(=O)C(Cc1ccccc1)NC(=O)c1ccccc1C] | IX-67 | 406.90 | 429.10 (M + Na+) |
| 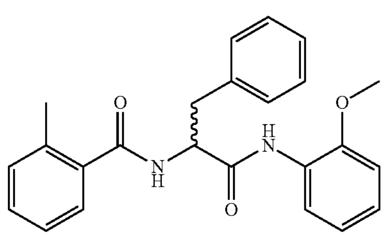 [SMILES: COc1ccccc1NC(=O)C(Cc1ccccc1)NC(=O)c1ccccc1C] | IX-68 | 388.46 | 389.23 (M + H+) 411.29 (M + Na+) |
| 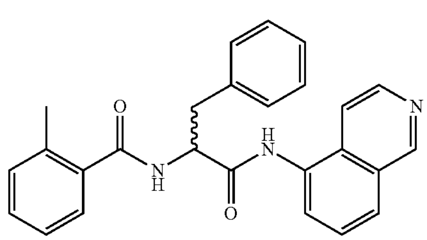 [SMILES: Cc1ccccc1C(=O)NC(Cc1ccccc1)C(=O)Nc1cccc2cnccc12] | IX-69 | 409.48 | 410.19 (M + H+) 432.11 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 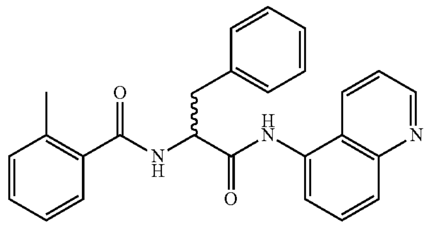 [SMILES: Cc1ccccc1C(=O)NC(Cc1ccccc1)C(=O)Nc1cccc2ncccc12] | IX-70 | 409.48 | 410.47 (M + H+) <br> 432.09 (M + Na+) |
| 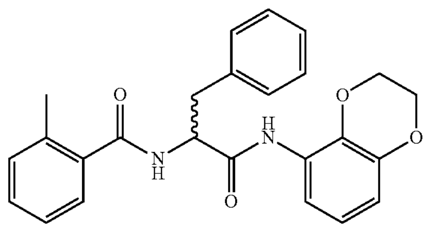 [SMILES: Cc1ccccc1C(=O)NC(Cc1ccccc1)C(=O)Nc1cccc2c1OCCO2] | IX-71 | 416.47 | 439.10 (M + Na+) |
| 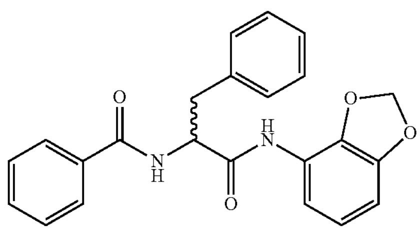 [SMILES: O=C(NC(Cc1ccccc1)C(=O)Nc1cccc2c1OCO2)c1ccccc1] | IX-72 | 388.42 | 389.28 (M + H+) <br> 411.20 (M + Na+) |
| 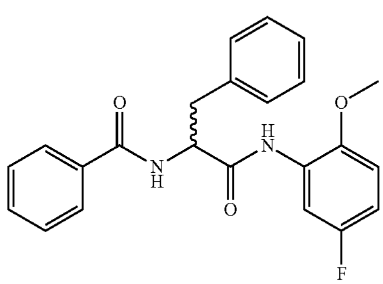 [SMILES: COc1ccc(F)cc1NC(=O)C(Cc1ccccc1)NC(=O)c1ccccc1] | IX-73 | 392.43 | 393.13 (M + H+) <br> 415.11 (M + Na+) |
| 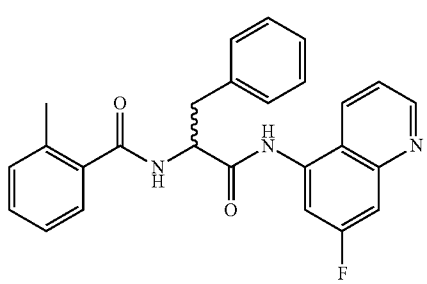 | IX-75 | 413.45 | 414.13 (M + H+) <br> 436.11 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 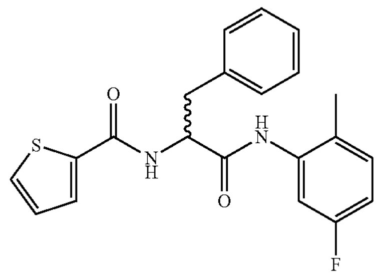 [SMILES: Cc1ccc(F)cc1NC(=O)C(Cc1ccccc1)NC(=O)c1cccs1] | IX-79 | 382.45 | 383.24 (M + H+)<br>405.23 (M + Na+) |
| 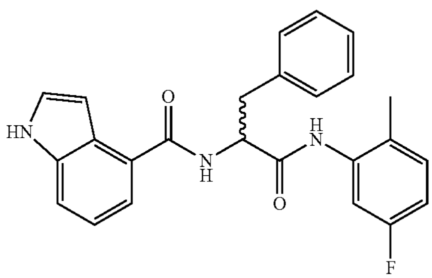 [SMILES: Cc1ccc(F)cc1NC(=O)C(Cc1ccccc1)NC(=O)c1cccc2[nH]ccc12] | IX-80 | 415.47 | 416.13 (M + H+)<br>438.12 (M + Na+) |
| 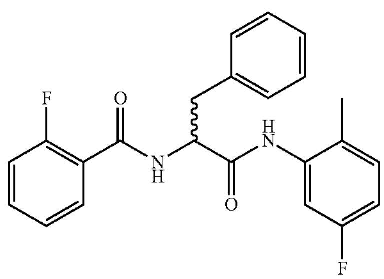 [SMILES: Cc1ccc(F)cc1NC(=O)C(Cc1ccccc1)NC(=O)c1ccccc1F] | IX-81 | 394.41 | 395.32 (M + H+)<br>417.18 (M + Na+) |
| 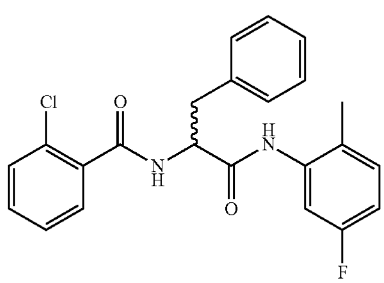 | IX-82 | 410.87 | 411.14 (M + H+)<br>433.17 (M + Na+) |
| 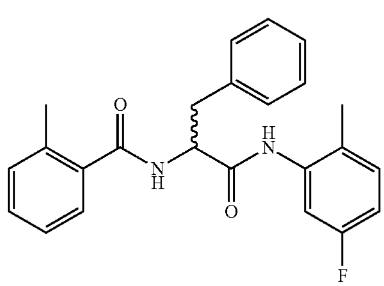 [SMILES: Cc1ccc(F)cc1NC(=O)C(Cc1ccccc1)NC(=O)c1ccccc1C] | IX-83 | 390.45 | 391.28 (M + H+)<br>413.32 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 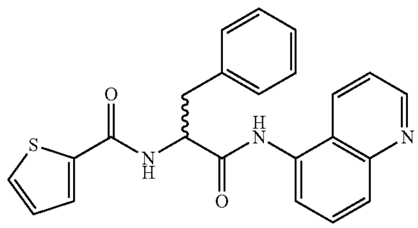 [SMILES: O=C(NC(Cc1ccccc1)C(=O)Nc1cccc2ncccc12)c1cccs1] | IX-85 | 401.48 | 402.52 (M + H+)<br>424.26 (M + Na+) |
| 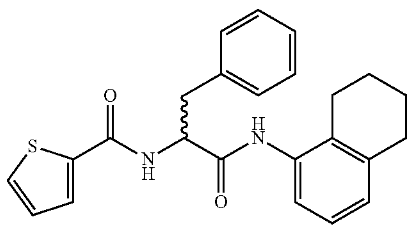 [SMILES: O=C(NC(Cc1ccccc1)C(=O)Nc1cccc2c1CCCC2)c1cccs1] | IX-86 | 404.52 | 405.26 (M + H+)<br>427.34 (M + Na+) |
| 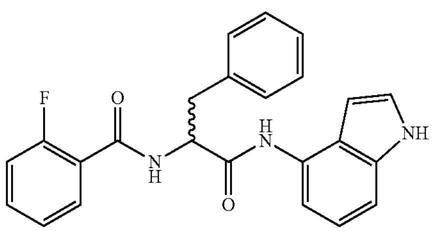 [SMILES: O=C(NC(Cc1ccccc1)C(=O)Nc1cccc2[nH]ccc12)c1ccccc1F] | IX-91 | 401.40 | 402.12 (M +H+)<br>424.12 (M + Na+) |
| 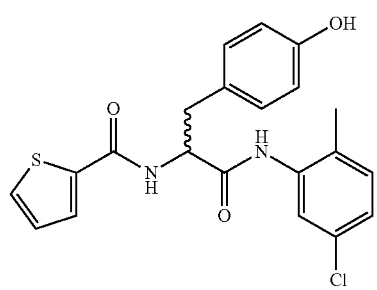 [SMILES: Cc1ccc(Cl)cc1NC(=O)C(Cc1ccc(O)cc1)NC(=O)c1cccs1] | IX-94 | 414.91 | 415.15 (M + H+)<br>437.43 (M + Na+) |
| 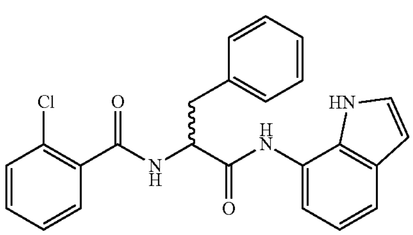 [SMILES: O=C(NC(Cc1ccccc1)C(=O)Nc1cccc2cc[nH]c12)c1ccccc1Cl] | IX-95 | 417.89 | 418.07 (M + H+)<br>440.13 (M + Na+) |
| 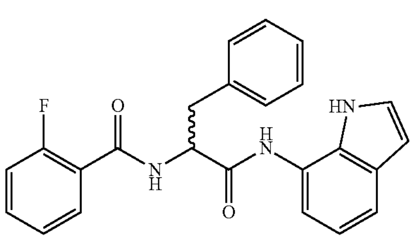 [SMILES: O=C(NC(Cc1ccccc1)C(=O)Nc1cccc2cc[nH]c12)c1ccccc1F] | IX-96 | 401.43 | 402.20 (M + H+)<br>424.23 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 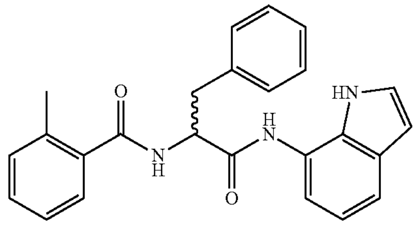 [SMILES: Cc1ccccc1C(=O)NC(Cc1ccccc1)C(=O)Nc1cccc2cc[nH]c12] | IX-97 | 397.47 | 398.33 (M + H+) 420.23 (M + Na+) |
| 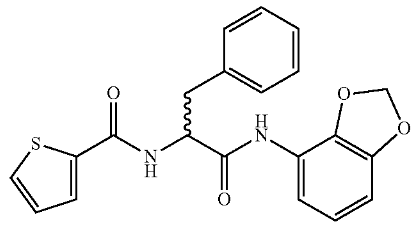 [SMILES: O=C(NC(Cc1ccccc1)C(=O)Nc1cccc2c1OCO2)c1cccs1] | IX-98 | 394.44 | 395.12 (M + H+) 417.17 (M + Na+) |
| 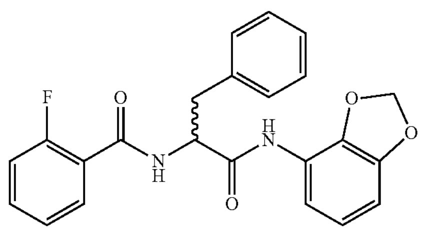 [SMILES: O=C(NC(Cc1ccccc1)C(=O)Nc1cccc2c1OCO2)c1ccccc1F] | IX-99 | 406.41 | 407.21 (M + H+) 429.03 (M + Na+) |
| 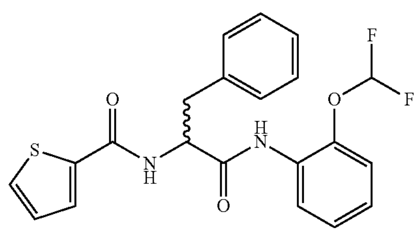 [SMILES: O=C(NC(Cc1ccccc1)C(=O)Nc1ccccc1OC(F)F)c1cccs1] | IX-100 | 416.44 | 439.08 (M + Na+) |
| 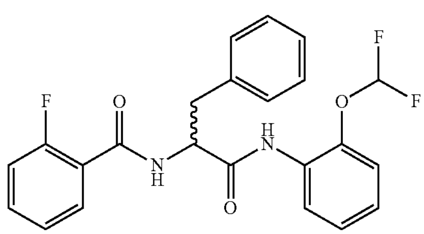 [SMILES: O=C(NC(Cc1ccccc1)C(=O)Nc1ccccc1OC(F)F)c1ccccc1F] | IX-101 | 428.40 | 429.04 (M + H+) 451.23 (M + Na+) |
| 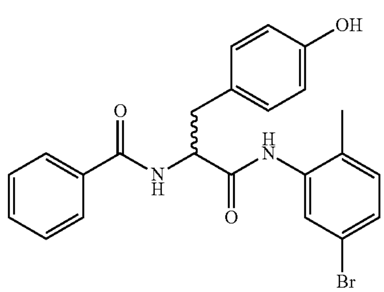 [SMILES: Cc1ccc(Br)cc1NC(=O)C(Cc1ccc(O)cc1)NC(=O)c1ccccc1] | IX-103 | 453.34 | 476.99 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 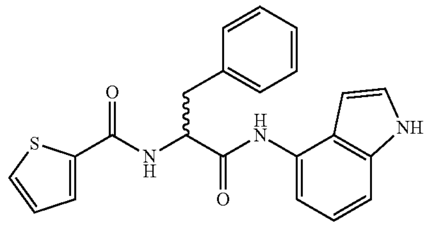 [SMILES: O=C(NC(Cc1ccccc1)C(=O)Nc1cccc2[nH]ccc12)c1cccs1] | IX-304 | 389.50 | 390.10 (M + H+) <br> 412.09 (M + Na+) |
| 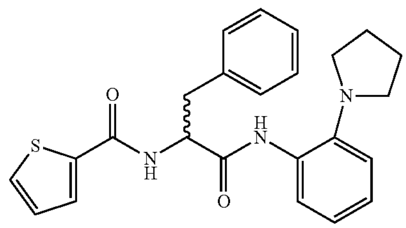 [SMILES: O=C(NC(Cc1ccccc1)C(=O)Nc1ccccc1N1CCCC1)c1cccs1] | IX-105 | 419.54 | 420.17 (M + H+) <br> 442.14 (M + Na+) |
| 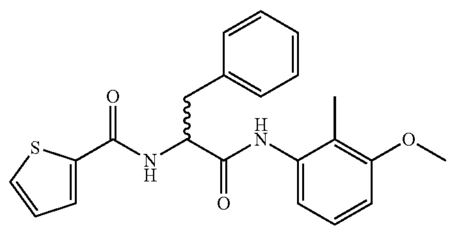 [SMILES: COc1cccc(NC(=O)C(Cc2ccccc2)NC(=O)c2cccs2)c1C] | IX 107 | 394.49 | 395.19 (M + H+) <br> 417.15 (M + Na+) |
| 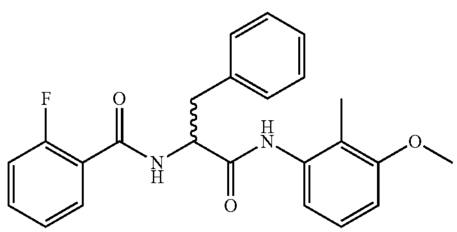 [SMILES: COc1cccc(NC(=O)C(Cc2ccccc2)NC(=O)c2ccccc2F)c1C] | IX-108 | 406.45 | 407.14 (M + H+) <br> 429.25 (M + Na+) |
| 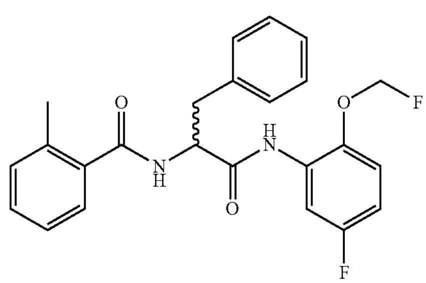 [SMILES: Cc1ccccc1C(=O)NC(Cc1ccccc1)C(=O)Nc1cc(F)ccc1OCF] | IX-111 | 424.45 | 425.06 (M + H+) <br> 447.02 (M + Na+) |
| 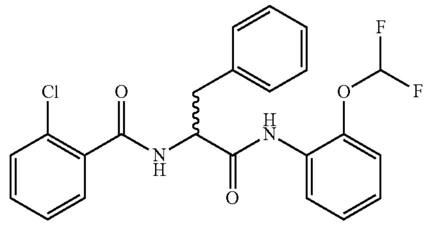 | IX-119 | 444.86 | 445.27 (M + H+) <br> 467.27 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 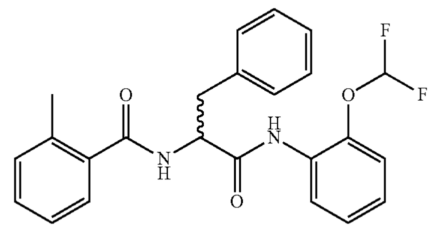 | IX-120 | 424.45 | 425.18 (M + H+) <br> 447.17 (M + Na+) |
| 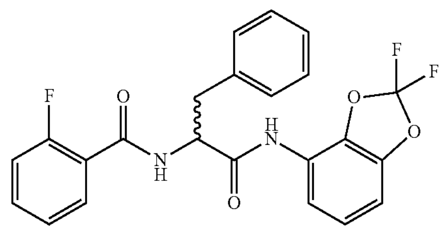 [SMILES: O=C(NC(Cc1ccccc1)C(=O)Nc1cccc2c1OC(F)(F)O2)c1ccccc1F] | IX-122 | 442.39 | 443.06 (M + H+) <br> 465.07 (M + Na+) |
| 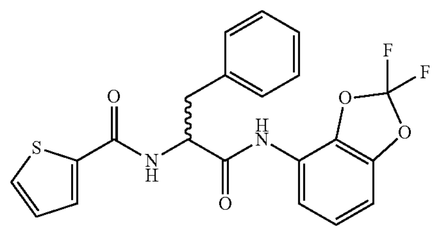 [SMILES: O=C(NC(Cc1ccccc1)C(=O)Nc1cccc2c1OC(F)(F)O2)c1cccs1] | IX-124 | 430.43 | 431.05 (M + H+) <br> 453.03 (M + Na+) |
| 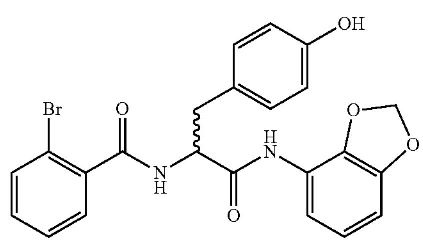 [SMILES: O=C(NC(Cc1ccc(O)cc1)C(=O)Nc1cccc2c1OCO2)c1ccccc1Br] | IX-125 | 383.30 | 482.05 (M + H+) |
| 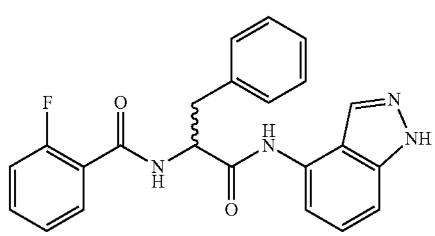 | IX-128 | 402.43 | 403.17 (M + H+) <br> 425.16 (M + Na+) |
| 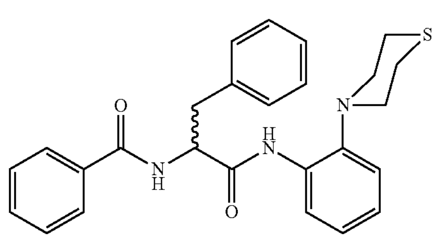 [SMILES: O=C(NC(Cc1ccccc1)C(=O)Nc1ccccc1N1CCSCC1)c1ccccc1] | IX-149 | 445.58 | 446.18 (M + H+) <br> 468.13 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 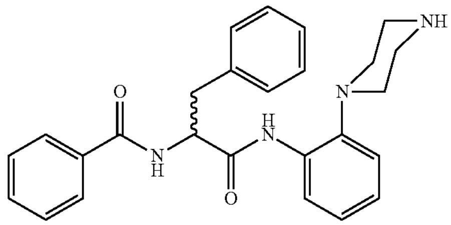 [SMILES: O=C(NC(Cc1ccccc1)C(=O)Nc1ccccc1N1CCNCC1)c1ccccc1] | IX-150 | 446.58 | 446.18 (M + H+)<br>468.13 (M + Na+) |
| 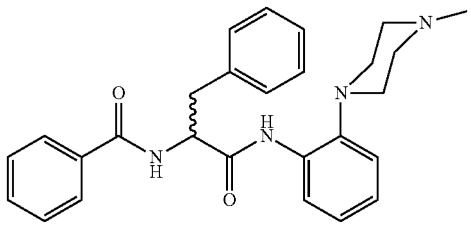 [SMILES: CN1CCN(c2ccccc2NC(=O)C(Cc2ccccc2)NC(=O)c2ccccc2)CC1] | IX-151 | 442.56 | 443.36 (M + H+)<br>465.29 (M + Na+) |
| 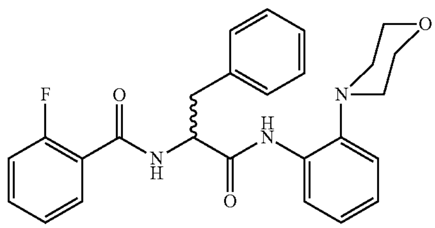 | IX-152 | 447.51 | 448.27 (M + H+)<br>470.24 (M + Na+) |
| 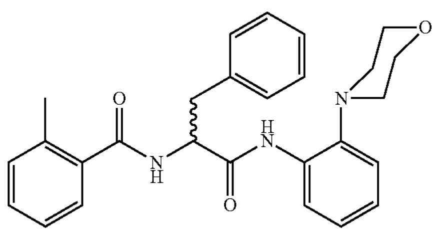 | IX-153 | 443.55 | 444.29 (M + H+)<br>466.21 (M + Na+) |
| 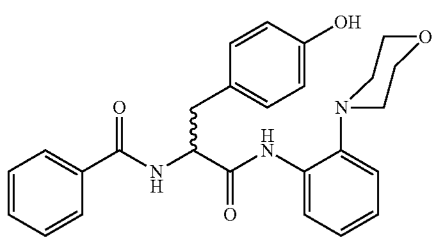 [SMILES: O=C(NC(Cc1ccc(O)cc1)C(=O)Nc1ccccc1N1CCOCC1)c1ccccc1] | IX-154 | 445.52 | 446.16 (M + H+)<br>468.15 (M + Na+) |
| 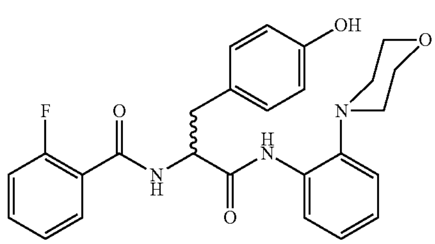 [SMILES: O=C(NC(Cc1ccc(O)cc1)C(=O)Nc1ccccc1N1CCOCC1)c1ccccc1F] | IX-155 | 463.51 | 464.23 (M + H+)<br>486.17 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 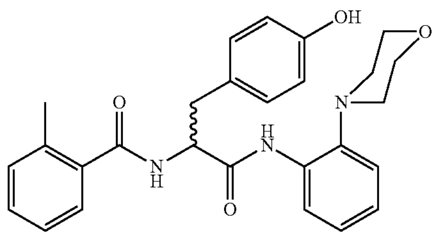 [SMILES: Cc1ccccc1C(=O)NC(Cc1ccc(O)cc1)C(=O)Nc1ccccc1N1CCOCC1] | IX-156 | 459.55 | 460.28 (M + H+) 482.25 (M + Na+) |
| 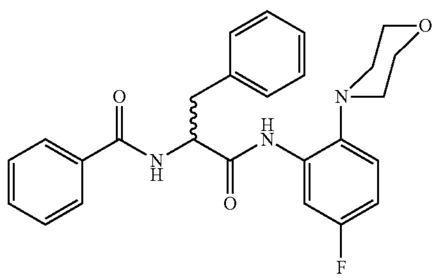 [SMILES: O=C(NC(Cc1ccccc1)C(=O)Nc1cc(F)ccc1N1CCOCC1)c1ccccc1] | IX-157 | 447.51 | 448.16 (M + H+) 470.13 (M + Na+) |
| 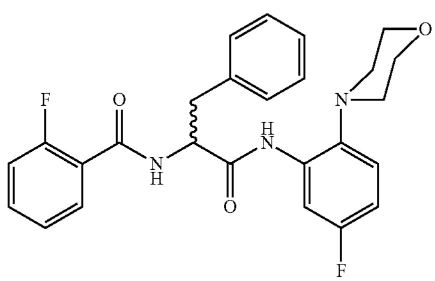 | IX-158 | 465.50 | 466.16 (M + H+) 488.22 (M + Na+) |
| 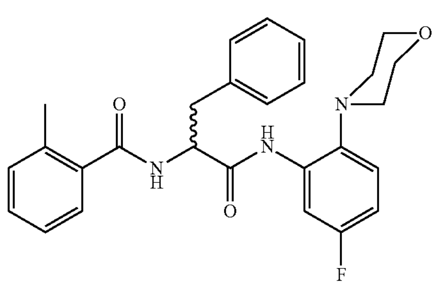 [SMILES: Cc1ccccc1C(=O)NC(Cc1ccccc1)C(=O)Nc1cc(F)ccc1N1CCOCC1] | IX-159 | 461.54 | 462.29 (M + H+) 484.23 (M + Na+) |
| 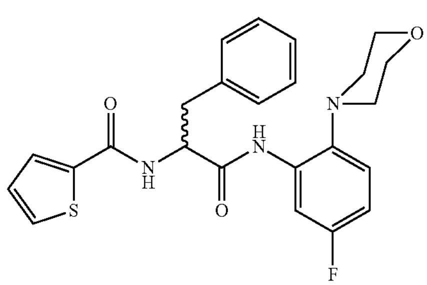 [SMILES: O=C(NC(Cc1ccccc1)C(=O)Nc1cc(F)ccc1N1CCOCC1)c1cccs1] | IX-160 | 453.53 | 454.27 (M + H+) 476.17 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 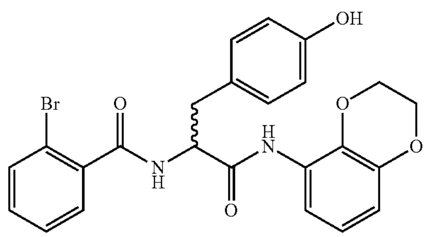 [SMILES: O=C(NC(Cc1ccc(O)cc1)C(=O)Nc1cccc2c1OCCO2)c1ccccc1Br] | IX-176 | 496.10 | 496.06 (M + H+) |
| 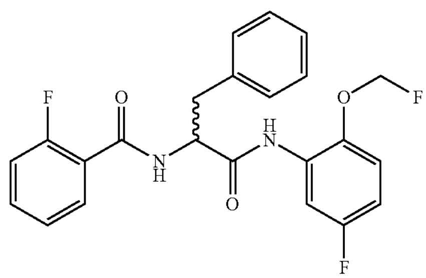 [SMILES: O=C(NC(Cc1ccccc1)C(=O)Nc1cc(F)ccc1OCF)c1ccccc1F] | IX-177 | 428.41 | 429.07 (M + H+)<br>451.03 (M + Na+) |
| 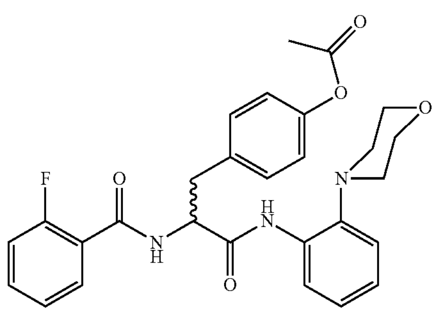 [SMILES: CC(=O)Oc1ccc(CC(NC(=O)c2ccccc2F)C(=O)Nc2ccccc2N2CCOCC2)cc1] | IX-180 | 505.55 | 506.17 (M + H+)<br>528.13 (M + Na+) |
| 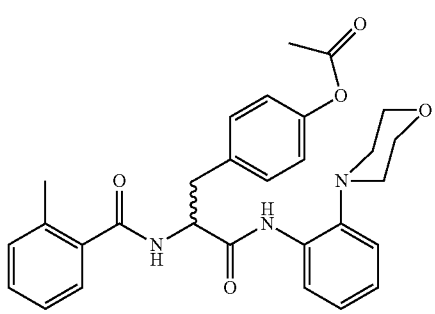 [SMILES: CC(=O)Oc1ccc(CC(NC(=O)c2ccccc2C)C(=O)Nc2ccccc2N2CCOCC2)cc1] | IX-181 | 501.58 | 502.21 (M + H+)<br>524.17 (M + Na+) |
| 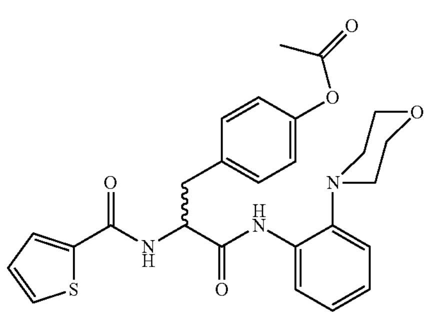 [SMILES: CC(=O)Oc1ccc(CC(NC(=O)c2cccs2)C(=O)Nc2ccccc2N2CCOCC2)cc1] | IX-182 | 493.58 | 494.15 (M + H+)<br>516.13 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 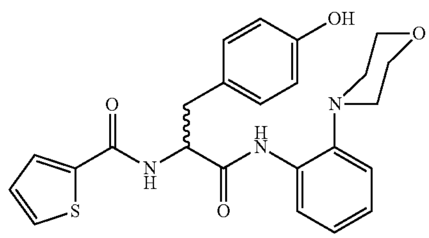 [SMILES: O=C(NC(Cc1ccc(O)cc1)C(=O)Nc1ccccc1N1CCOCC1)c1cccs1] | IX-183 | 451.54 | 452.28 (M + H+) 474.22 (M + Na+) |
| 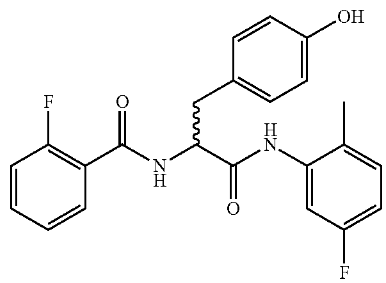 [SMILES: Cc1ccc(F)cc1NC(=O)C(Cc1ccc(O)cc1)NC(=O)c1ccccc1F] | IX-184 | 410.42 | 411.12 (M + H+) 433.12 (M + Na+) |
| 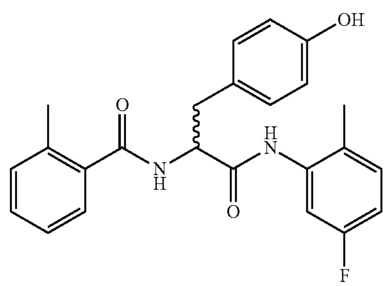 [SMILES: Cc1ccc(F)cc1NC(=O)C(Cc1ccc(O)cc1)NC(=O)c1ccccc1C] | IX-186 | 406.46 | 407.16 (M + H+) 429.16 (M + Na+) |
| 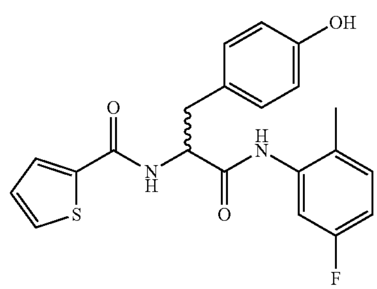 [SMILES: Cc1ccc(F)cc1NC(=O)C(Cc1ccc(O)cc1)NC(=O)c1cccs1] | IX-188 | 398.45 | 399.14 (M + H+) 421.12 (M + Na+) |
| 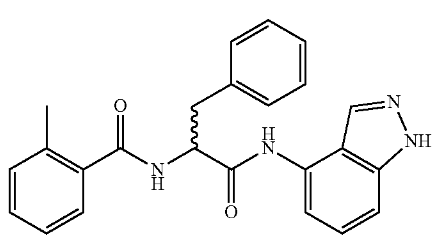 [SMILES: Cc1ccccc1C(=O)NC(Cc1ccccc1)C(=O)Nc1cccc2[nH]ncc12] | IX-191 | 398.47 | 399.19 (M + H+) 421.20 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 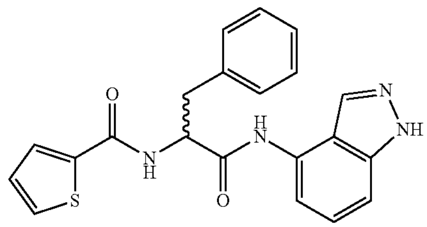 [SMILES: O=C(NC(Cc1ccccc1)C(=O)Nc1cccc2[nH]ncc12)c1cccs1] | IX-201 | 390.46 | 391.07 (M + H+) <br> 413.05 (M + Na+) |
| 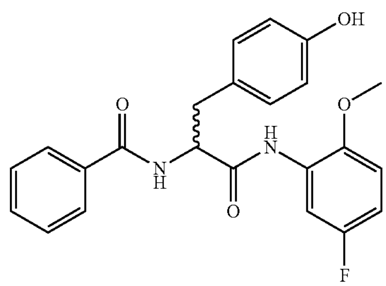 [SMILES: COc1ccc(F)cc1NC(=O)C(Cc1ccc(O)cc1)NC(=O)c1ccccc1] | IX-203 | 408.43 | 409.06 (M + H+) <br> 431.04 (M + Na+) |
| 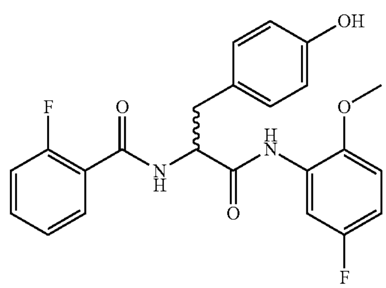 [SMILES: COc1ccc(F)cc1NC(=O)C(Cc1ccc(O)cc1)NC(=O)c1ccccc1F] | IX-204 | 426.42 | 427.00 (M + H+) <br> 449.00 (M + Na+) |
| 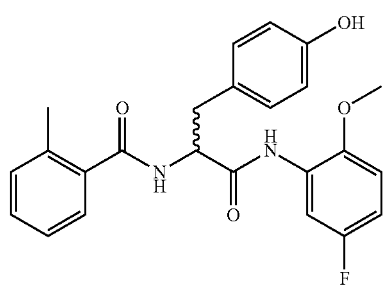 [SMILES: COc1ccc(F)cc1NC(=O)C(Cc1ccc(O)cc1)NC(=O)c1ccccc1C] | IX-205 | 422.46 | 423.09 (M + H+) <br> 445.07 (M + Na+) |
| 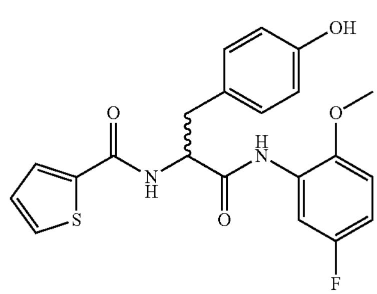 [SMILES: COc1ccc(F)cc1NC(=O)C(Cc1ccc(O)cc1)NC(=O)c1cccs1] | IX-206 | 414.45 | 415.00 (M + H+) <br> 437.00 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 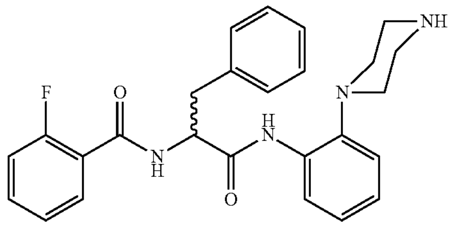 | IX-211 | 446.53 | 447.19 (M + H+)<br>469.14 (M + Na+) |
| 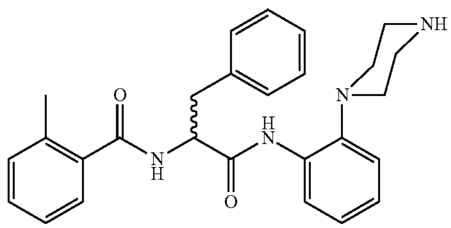 [SMILES: Cc1ccccc1C(=O)NC(Cc1ccccc1)C(=O)Nc1ccccc1N1CCNCC1] | IX-212 | 442.56 | 443.26 (M + H+)<br>465.22 (M + Na+) |
| 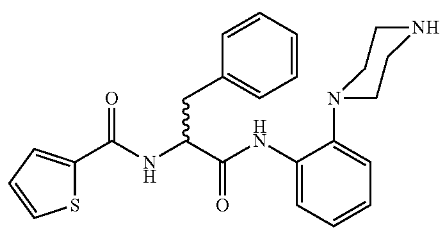 [SMILES: O=C(NC(Cc1ccccc1)C(=O)Nc1ccccc1N1CCNCC1)c1cccs1] | IX-213 | 434.56 | 435.24 (M + H+)<br>457.19 (M + Na+) |
| 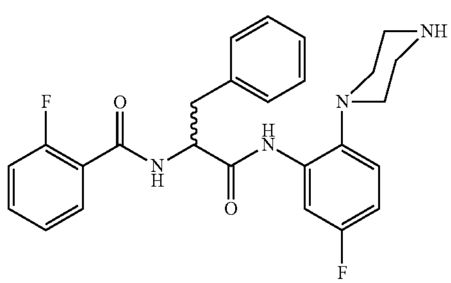 [SMILES: O=C(NC(Cc1ccccc1)C(=O)Nc1cc(F)ccc1N1CCNCC1)c1ccccc1F] | IX-214 | 464.52 | 465.08 (M + H+)<br>487.07 (M + Na+) |
| 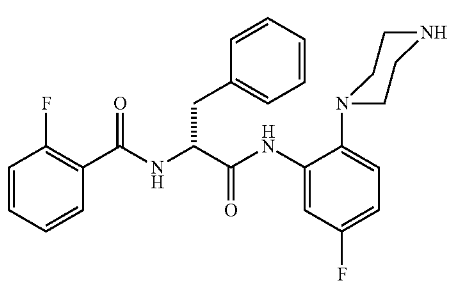 [SMILES: O=C(N[C@H](Cc1ccccc1)C(=O)Nc1cc(F)ccc1N1CCNCC1)c1ccccc1F] | IX-214a | 464.52 | 465.29 (M + H+)<br>487.19 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 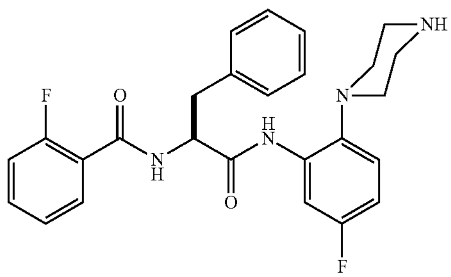 | IX-214b | 464.52 | 465.25 (M +H+) 487.20 (M +Na+) |
| 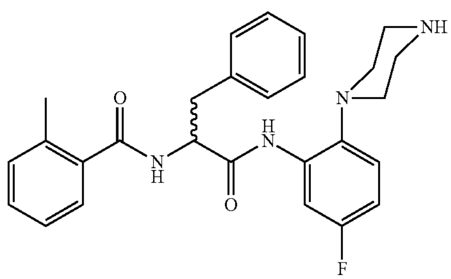 [SMILES: Cc1ccccc1C(=O)NC(Cc1ccccc1)C(=O)Nc1cc(F)ccc1N1CCNCC1] | IX-215 | 460.55 | 461.19 (M + H+) 483.17 (M + Na+) |
| 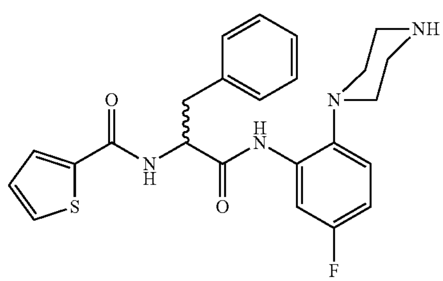 [SMILES: O=C(NC(Cc1ccccc1)C(=O)Nc1cc(F)ccc1N1CCNCC1)c1cccs1] | IX-216 | 452.55 | 453.06 (M + H+) 475.05 (M + Na+) |
| 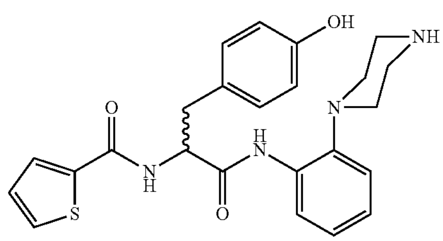 [SMILES: O=C(NC(Cc1ccc(O)cc1)C(=O)Nc1ccccc1N1CCNCC1)c1cccs1] | IX-219 | 450.56 | 451.06 (M + H+) 473.03 (M + Na+) |
| 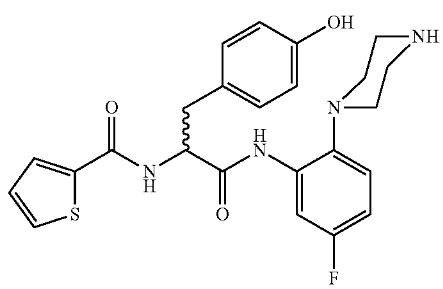 [SMILES: O=C(NC(Cc1ccc(O)cc1)C(=O)Nc1cc(F)ccc1N1CCNCC1)c1cccs1] | IX-222 | 468.55 | 469.16 (M + H+) 491.05 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 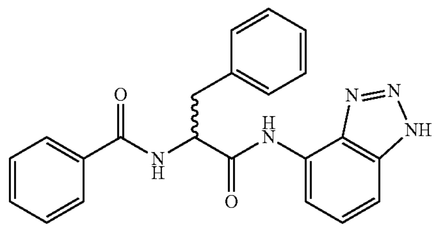 [SMILES: O=C(NC(Cc1ccccc1)C(=O)Nc1cccc2[nH]nnc12)c1ccccc1] | IX-223 | 385.43 | 386.24 (M + H+)<br>408.23 (M + Na+) |
| 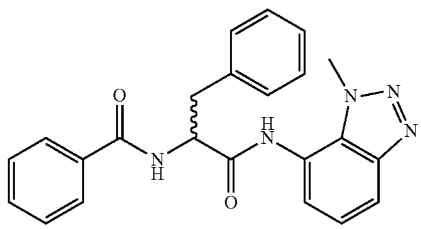 [SMILES: Cn1nnc2cccc(NC(=O)C(Cc3ccccc3)NC(=O)c3ccccc3)c21] | IX-224 | 399.45 | 400.17 (M + H+)<br>422.13 (M + Na+) |
| 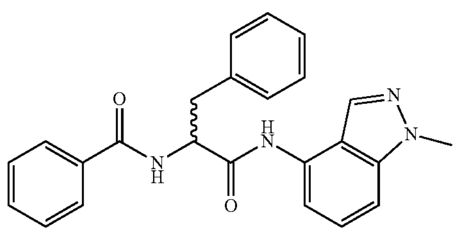 [SMILES: Cn1ncc2c(NC(=O)C(Cc3ccccc3)NC(=O)c3ccccc3)cccc21] | IX-225 | 398.47 | 399.13 (M + H+)<br>421.10 (M + Na+) |
| 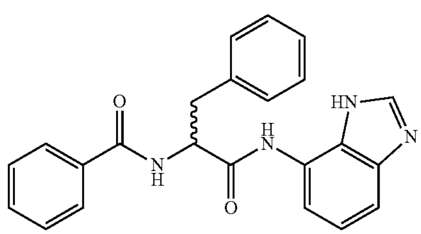 [SMILES: O=C(NC(Cc1ccccc1)C(=O)Nc1cccc2nc[nH]c12)c1ccccc1] | IX-230 | 384.44 | 385.12 (M + H+)<br>407.10 (M + Na+) |
| 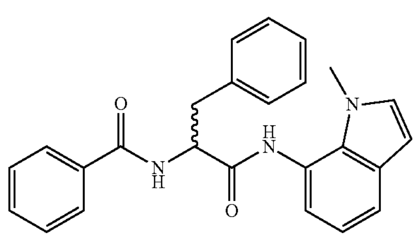 [SMILES: Cn1ccc2cccc(NC(=O)C(Cc3ccccc3)NC(=O)c3ccccc3)c21] | IX-231 | 397.48 | 398.20 (M + H+)<br>420.21 (M + Na+) |
| 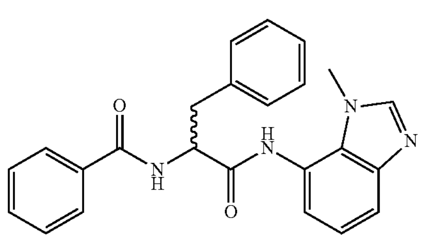 [SMILES: Cn1cnc2cccc(NC(=O)C(Cc3ccccc3)NC(=O)c3ccccc3)c21] | IX-232 | 398.47 | 399.00 (M + H+)<br>421.00 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 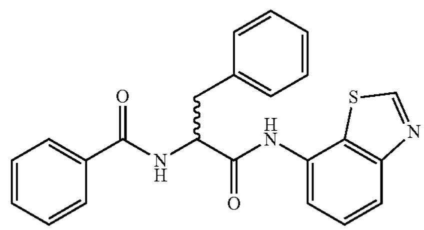 | IX-234 | 401.48 | 402.14 (M + H+) 424.13 (M + Na+) |
| 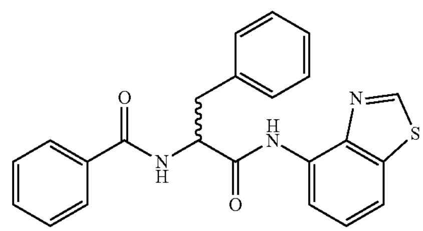 [SMILES: O=C(NC(Cc1ccccc1)C(=O)Nc1cccc2scnc12)c1ccccc1] | IX-235 | 401.48 | 402.10 (M + H+) 424.08 (M + Na+) |
| 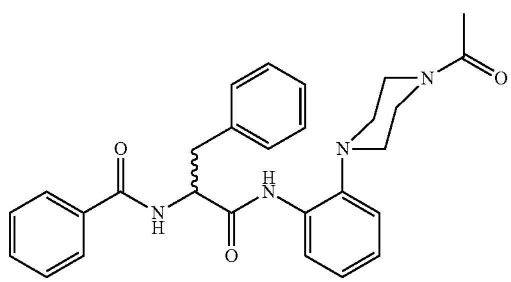 [SMILES: CC(=O)N1CCN(c2ccccc2NC(=O)C(Cc2ccccc2)NC(=O)c2ccccc2)CC1] | IX-236 | 470.57 | 471.17 (M + H+) 493.15 (M + Na+) |
| 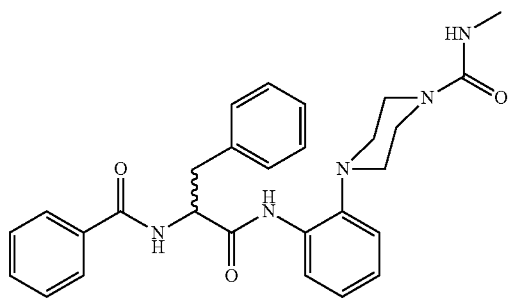 [SMILES: CNC(=O)N1CCN(c2ccccc2NC(=O)C(Cc2ccccc2)NC(=O)c2ccccc2)CC1] | IX-238 | 485.59 | 486.15 (M + H+) 508.14 (M + Na+) |
| 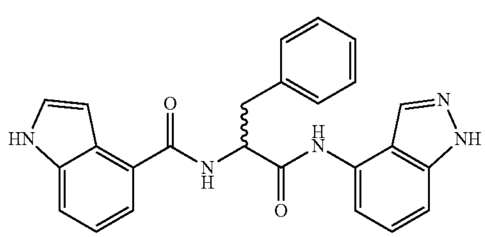 [SMILES: O=C(NC(Cc1ccccc1)C(=O)Nc1cccc2[nH]ncc12)c1cccc2[nH]ccc12] | IX-241 | 423.48 | 424.08 (M + H+) 446.06 (M + Na+) |
| 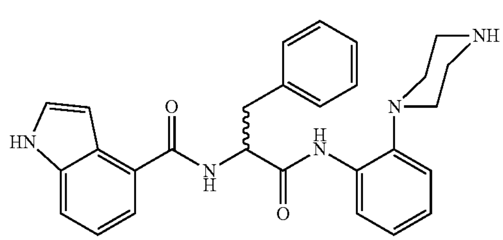 [SMILES: O=C(NC(Cc1ccccc1)C(=O)Nc1ccccc1N1CCNCC1)c1cccc2[nH]ccc12] | IX-242 | 467.57 | 468.05 (M + H+) 490.02 (M + Na+) |

TABLE 9-continued
Structures, calculated m/z values, and experimental m/z values for compounds according to general structural formulae (V) and (VI)
(Examples 8, 9, 14, and 15-172)
| structure | name | MW | MALDI-MS m/z |
|---|---|---|---|
| 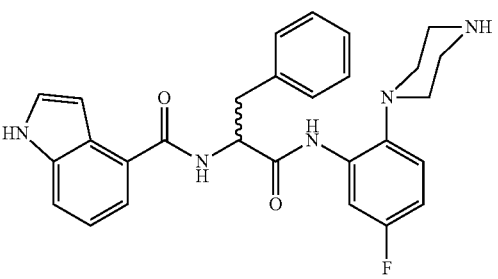 [SMILES: O=C(NC(Cc1ccccc1)C(=O)Nc1cc(F)ccc1N1CCNCC1)c1cccc2[nH]ccc12] | IX-243 | 485.56 | 486.07 (M + H+)<br>508.05 (M + Na+) |
| 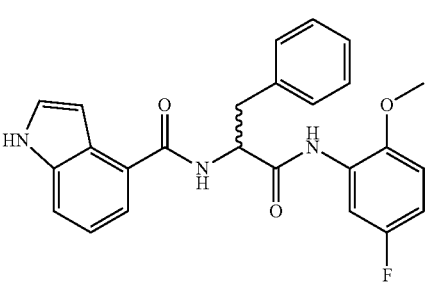 [SMILES: COc1ccc(F)cc1NC(=O)C(Cc1ccccc1)NC(=O)c1cccc2[nH]ccc12] | IX-244 | 431.47 | 432.06 (M + H+)<br>454.06 (M + Na+) |
| 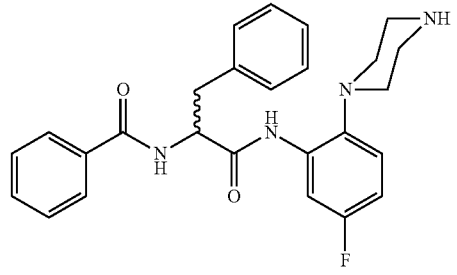 [SMILES: O=C(NC(Cc1ccccc1)C(=O)Nc1cc(F)ccc1N1CCNCC1)c1ccccc1] | IX-245 | 446.53 | 447.13 (M + H+)<br>469.11 (M + Na+) |
| 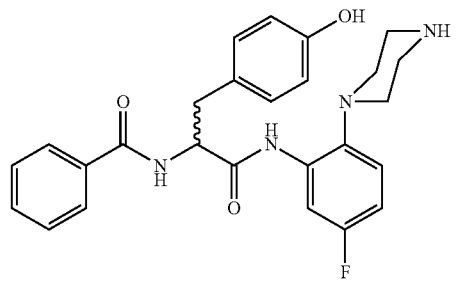 [SMILES: O=C(NC(Cc1ccc(O)cc1)C(=O)Nc1cc(F)ccc1N1CCNCC1)c1ccccc1] | IX-246 | 42.53 | 463.14 (M + H+)<br>485.11 (M + Na+) |
| 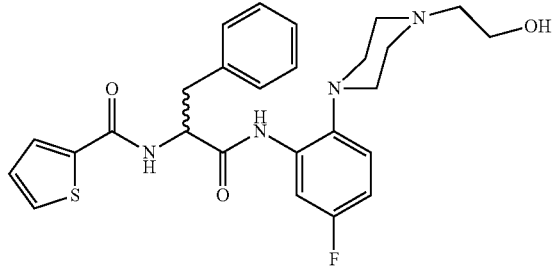 [SMILES: O=C(NC(Cc1ccccc1)C(=O)Nc1cc(F)ccc1N1CCN(CCO)CC1)c1cccs1] | IX-247 | 496.60 | 497.07 (M + H+)<br>519.05 (M + Na+) |

TABLE 9-continued

Structures, calculated m/z values, and experimental m/z values for compounds according to general structural formulae (V) and (VI)
(Examples 8, 9, 14, and 15-172)

| structure | name | MW | MALDI-MS m/z |
|---|---|---|---|
| 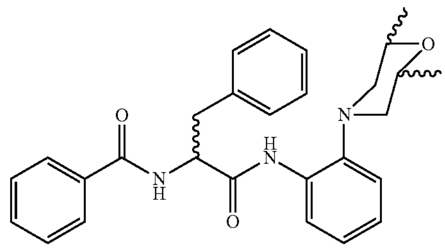 | IX-265 | 457.57 | 458.18 (M + H+)<br>480.16 (M + Na+) |
| 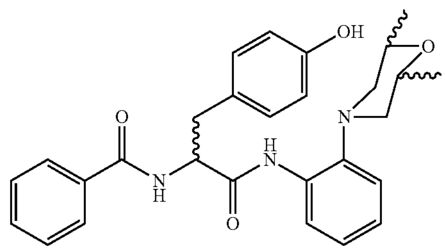 | IX-266 | 473.57 | 474.06 (M + H+)<br>496.05 (M + Na+) |
| 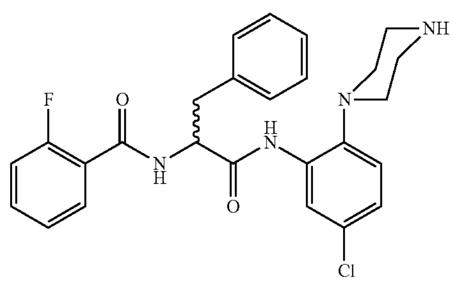 [SMILES: O=C(NC(Cc1ccccc1)C(=O)Nc1cc(Cl)ccc1N1CCNCC1)c1ccccc1F] | IX-274 | 480.97 | 481.14 (M + H+)<br>503.12 (M + Na+) |
| 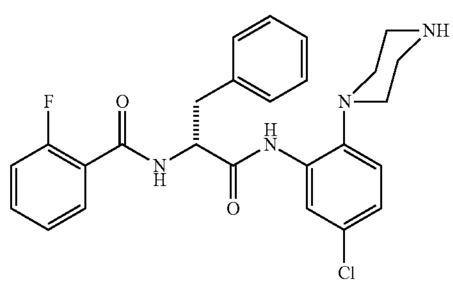 [SMILES: O=C(N[C@H](Cc1ccccc1)C(=O)Nc1cc(Cl)ccc1N1CCNCC1)c1ccccc1F] | IX-274a | 480.97 | 481.33 (M + H+)<br>503.22 (M + Na+) |
| 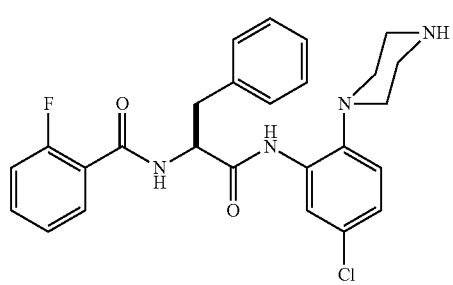 | IX-274b | 480.97 | 481.40 (M + H+)<br>503.23 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 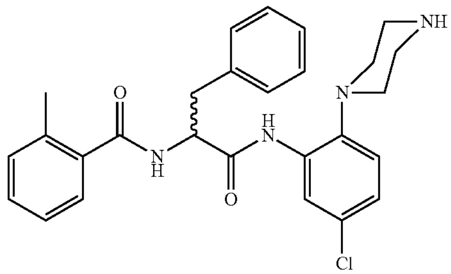 [SMILES: Cc1ccccc1C(=O)NC(Cc1ccccc1)C(=O)Nc1cc(Cl)ccc1N1CCNCC1] | IX-275 | 477.01 | 477.10 (M + H+) |
| 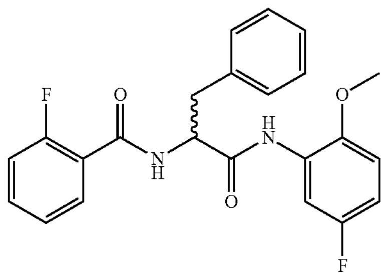 [SMILES: COc1ccc(F)cc1NC(=O)C(Cc1ccccc1)NC(=O)c1ccccc1F] | IX-276 | 410.42 | 411.09 (M + H+)<br>433.08 (M + Na+) |
| 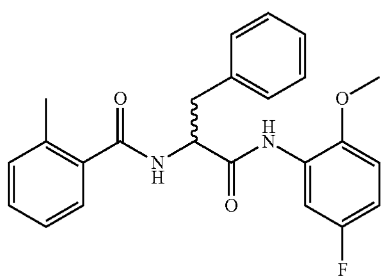 [SMILES: COc1ccc(F)cc1NC(=O)C(Cc1ccccc1)NC(=O)c1ccccc1C] | IX-277 | 406.46 | 407.11 (M + H+)<br>429.09 (M + Na+) |
| 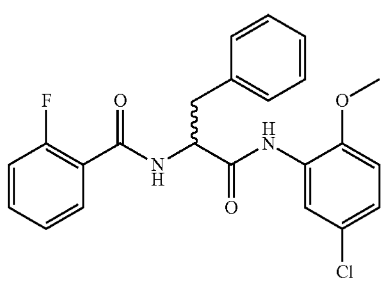 [SMILES: COc1ccc(Cl)cc1NC(=O)C(Cc1ccccc1)NC(=O)c1ccccc1F] | IX-278 | 426.87 | 427.06 (M + H+)<br>449.04 (M + Na+) |
| 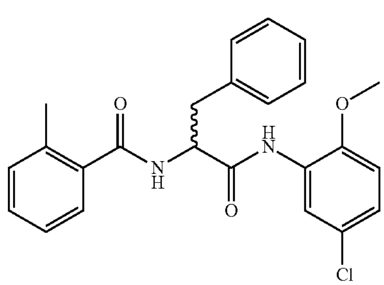 [SMILES: COc1ccc(Cl)cc1NC(=O)C(Cc1ccccc1)NC(=O)c1ccccc1C] | IX-279 | 422.91 | 423.08 (M + H+)<br>445.06 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 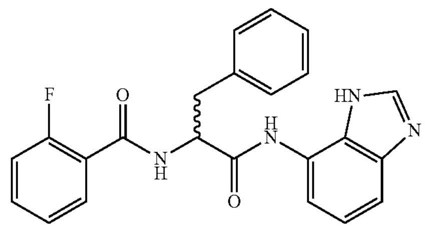 [SMILES: O=C(NC(Cc1ccccc1)C(=O)Nc1cccc2nc[nH]c12)c1ccccc1F] | IX-280 | 402.43 | 403.04 (M + H+)<br>425.01 (M + Na+) |
| 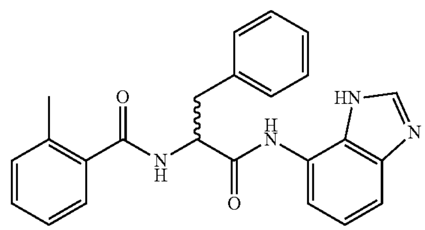 [SMILES: Cc1ccccc1C(=O)NC(Cc1ccccc1)C(=O)Nc1cccc2nc[nH]c12] | IX-281 | 398.47 | 399.08 (M + H+)<br>421.06 (M + Na+) |
| 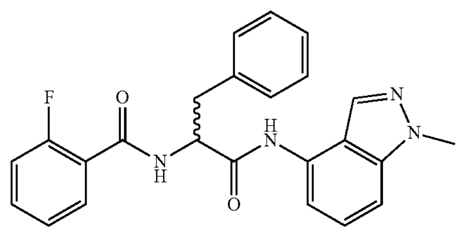 [SMILES: Cn1ncc2c(NC(=O)C(Cc3ccccc3)NC(=O)c3ccccc3F)cccc21] | IX-296 | 416.46 | 417.04 (M + H+)<br>439.02 (M + Na+) |
| 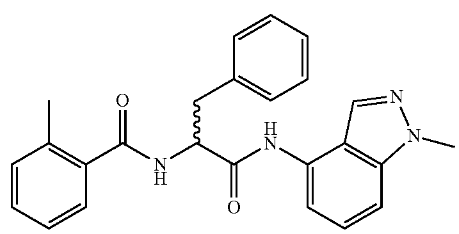 [SMILES: Cc1ccccc1C(=O)NC(Cc1ccccc1)C(=O)Nc1cccc2c1cnn2C] | IX-297 | 412.49 | 413.19 (M + H+)<br>435.17 (M + Na+) |
| 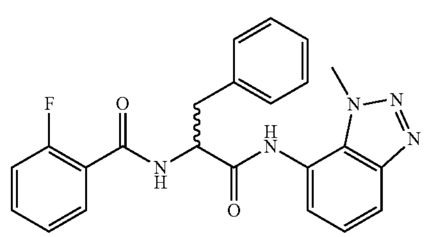 [SMILES: Cn1nnc2cccc(NC(=O)C(Cc3ccccc3)NC(=O)c3ccccc3F)c21] | IX-300 | 417.44 | 418.07 (M + H+)<br>440.05 (M + Na+) |
| 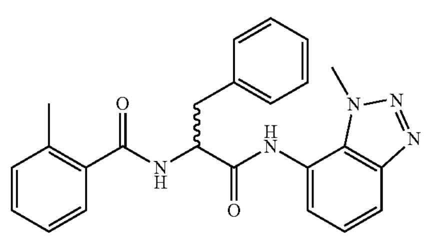 [SMILES: Cc1ccccc1C(=O)NC(Cc1ccccc1)C(=O)Nc1cccc2nnn(C)c12] | IX-301 | 413.48 | 414.20 (M + H+)<br>436.18 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 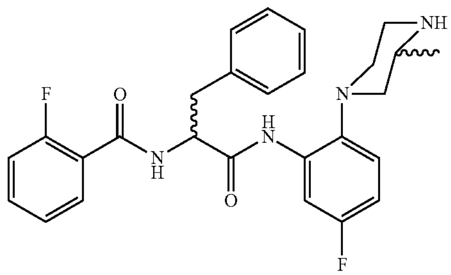 [SMILES: CC1CN(c2ccc(F)cc2NC(=O)C(Cc2ccccc2)NC(=O)c2ccccc2F)CCN1] | IX-305 | 478.54 | 479.08 (M + H+)<br>501.08 (M + Na+) |
| 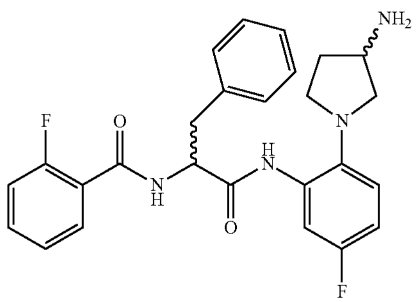 [SMILES: NC1CCN(c2ccc(F)cc2NC(=O)C(Cc2ccccc2)NC(=O)c2ccccc2F)C1] | IX-306 | 464.52 | 465.19 (M + H+)<br>487.17 (M + Na+) |
| 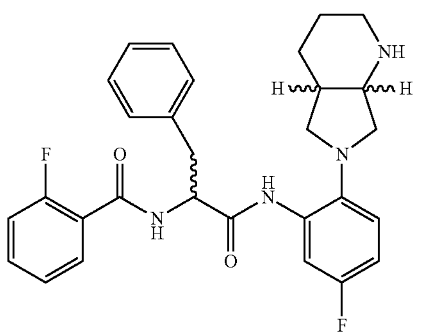 [SMILES: O=C(NC(Cc1ccccc1)C(=O)Nc1cc(F)ccc1N1CC2CCCNC2C1)c1ccccc1F] | IX-307 | 504.58 | 505.15 (M + H+)<br>527.13 (M + Na+) |
| 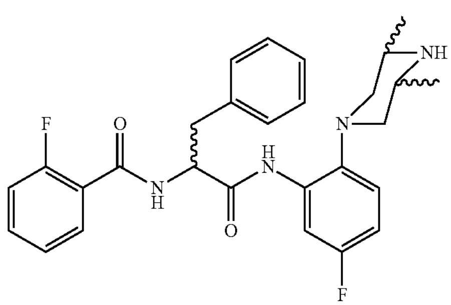 | IX-308 | 492.57 | 493.16 (M + H+)<br>515.14 (M + Na+) |
| 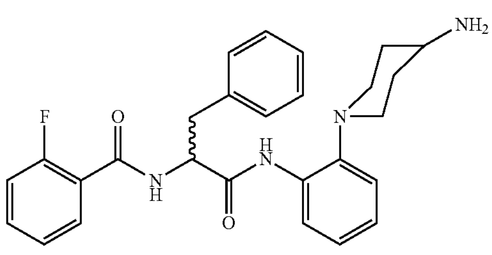 [SMILES: NC1CCN(c2ccccc2NC(=O)C(Cc2ccccc2)NC(=O)c2ccccc2F)CC1] | IX-312 | 478.54 | 479.14 (M + H+)<br>501.12 (M + Na+) |

TABLE 9-continued

Structures, calculated m/z values, and experimental m/z values for compounds according to general structural formulae (V) and (VI) (Examples 8, 9, 14, and 15-172)

| structure | name | MW | MALDI-MS m/z |
|---|---|---|---|
| 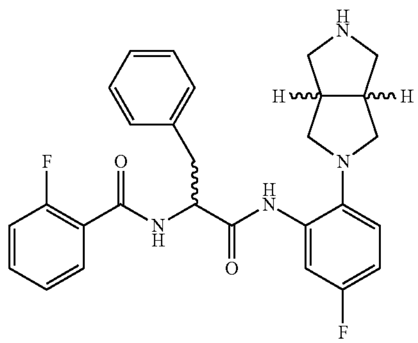 [SMILES: O=C(NC(Cc1ccccc1)C(=O)Nc1cc(F)ccc1N1CC2CNCC2C1)c1ccccc1F] | IX-313 | 490.55 | 491.07 (M + H+)<br>513.05 (M + Na+) |
| 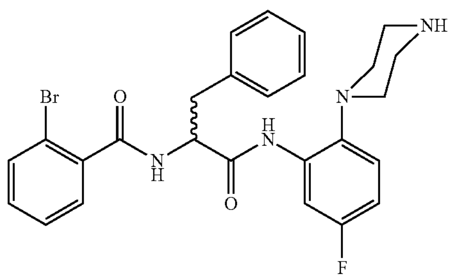 [SMILES: O=C(NC(Cc1ccccc1)C(=O)Nc1cc(F)ccc1N1CCNCC1)c1ccccc1Br] | IX-315 | 525.42 | 525.06 (M + H+)<br>548.05 (M + Na+) |
| 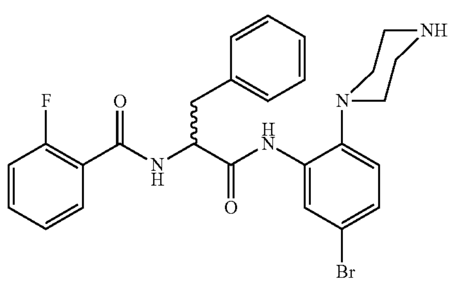 [SMILES: O=C(NC(Cc1ccccc1)C(=O)Nc1cc(Br)ccc1N1CCNCC1)c1ccccc1F] | IX-316 | 525.42 | 525.07 (M + H+)<br>548.09 (M + Na+) |
| 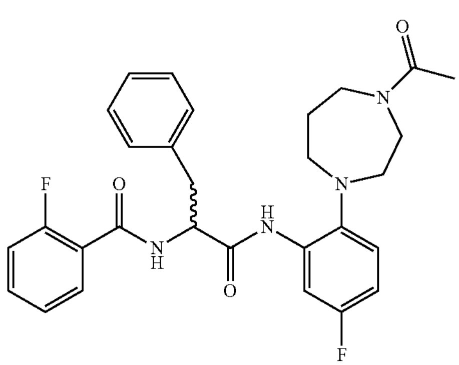 [SMILES: CC(=O)N1CCCN(c2ccc(F)cc2NC(=O)C(Cc2ccccc2)NC(=O)c2ccccc2F)CC1] | IX-319 | 520.58 | 521.25 (M + H+)<br>543.23 (M + Na+) |

TABLE 10

RNA polymerase inhibitory activities, antibacterial activities against *Mycobacterium smegmatis*, antibacterial activities against *Mycobacterium tuberculosis*, antibacterial activities against *Mycobacterium avium*, and mammalian-cell cytotoxicities of compounds according to general structural formulae (V) and (VI) (Examples 8, 9, 14, and 15-172)

| name | IC50 *Mycobacterium tuberculosis* RNA polymerase (µM) | MIC *Mycobacterium smegmatis* ATCC 19420 (µg/ml) | MIC *Mycobacterium tuberculosis* H37Rv (µg/ml) | MIC *Mycobacterium avium* ATCC 25291 (µg/ml) | MCC mammalian cells Vero E6 ATCC CRL1586 (µg/ml) |
|---|---|---|---|---|---|
| I-12 | 3.5 | 3.125 | >50 | | >100 |
| I-13 | | 0.195 | 12.5 | 25 | 37 |
| I-17 | | 0.39 | 3.13 | 6.25 | >37 |
| I-18 | | 0.78 | >50 | >50 | >100 |
| I-25 | | 6.25 | >50 | | 57 |
| I-37 | | 25 | >50 | | 5 |
| I-39 | | 0.78 | 6.25 | >50 | 20 |
| I-50 | | 0.78 | 12.5 | >50 | >100 |
| I-51 | | 1.56 | >50 | >50 | >100 |
| I-61 | | 0.39 | 6.25 | 6.25 | >100 |
| I-70 | | 50 | 6.25 | >50 | 90 |
| I-73 | | 0.78 | >50 | >50 | 19 |
| I-75 | 0.99 | 0.195 | 1.56 | 1.56 | 4 |
| I-80 | 2.8 | 0.39 | 3.12 | 6.25 | 43 |
| I-86 | 0.92 | 0.195 | 1.56 | 3.125 | 13 |
| I-91 | | 0.39 | >50 | >50 | 19 |
| I-97 | | 0.78 | 25 | >50 | |
| I-102 | | 3.125 | >50 | | 29 |
| I-105 | | 0.39 | 3.125 | 12.5 | 21 |
| I-112 | | 0.39 | >50 | >50 | 13 |
| I-113 | | 1.56 | >50 | | >100 |
| I-115 | | 0.39 | >50 | >50 | 37 |
| I-116 | | 0.78 | 6.25 | 6.25 | 90 |
| I-123 | | 1.56 | >50 | >50 | >100 |
| I-124 | | 25 | >50 | | >39 |
| I-126 | | 1.56 | >50 | >50 | 10 |
| I-127 | | 3.125 | >50 | >50 | 100 |
| I-138 | | 0.78 | 6.25 | >50 | >100 |
| I-148 | | 3.125 | 6.25 | >50 | 100 |
| I-149 | | 0.39 | >50 | >50 | 20 |
| I-160 | | 3.125 | >50 | >50 | 21 |
| I-181 | 0.4 | 0.073 | 0.78 | 6.25 | >100 |
| I-188 | | 6.25 | 25 | | 35 |
| I-192 | | 0.78 | 9.4 | 25 | >100 |
| I-193 | | 6.25 | 6.25 | 50 | >100 |
| I-203 | | 0.78 | 12.5 | 50 | >100 |
| I-204 | | 3.125 | 25 | | >100 |
| I-214 | | 3.125 | >50 | | >100 |
| I-215 | | 3.125 | >50 | | >100 |
| I-225 | | 6.25 | >50 | | >100 |
| I-226 | | 0.78 | >50 | | >100 |
| I-236 | | 0.39 | 25 | | >48 |
| II-5 | | 3.12 | 50 | >50 | >36 |
| II-12 | | 3.125 | 25 | 50 | >36 |
| II-13 | | 6.25 | >50 | | >36 |
| II-27 | | 0.39 | 12.5 | >50 | 41 |
| II-28 | | 0.78 | 12.5 | >50 | 13 |
| II-39 | | 0.39 | 12.5 | 12.5 | 36 |
| II-46 | | 0.195 | 3.125 | 3.125 | >100 |
| II-47 | | 1.56 | 1.56 | 3.125 | >100 |
| II-65 | | 0.39 | >50 | >50 | 78 |
| IX-2 | | 3.125 | >39 | >50 | >39 |
| IX-3 | | 0.195 | 3.13 | 6.25 | >40 |
| IX-4 | | 0.78 | 12.5 | >50 | >40 |
| IX-5 | | 0.39 | 6.25 | 6.25 | >40 |
| IX-6 | | 1.56 | 6.25 | 6.25 | 21 |
| IX-14 | | 0.39 | 6.25 | 12.5 | >40 |
| IX-15 | | 0.78 | 6.25 | 25 | 85 |
| IX-18 | | 0.39 | 6.25 | 12.5 | >100 |
| IX-19 | | 0.39 | 6.25 | | 42 |
| IX-21 | | 0.78 | 6.25 | 6.25 | >100 |
| IX-25 | | 1.56 | | | 21 |
| IX-26 | | 1.25 | 25 | 50 | >100 |
| IX-27 | 0.99 | 0.195 | 1.56 | 3.125 | >100 |
| IX-28 | | 0.39 | 12.5 | 12.5 | 80 |
| IX-29 | | 0.195 | 3.125 | 6.25 | >100 |

TABLE 10-continued

RNA polymerase inhibitory activities, antibacterial activities against *Mycobacterium smegmatis*, antibacterial activities against *Mycobacterium tuberculosis*, antibacterial activities against *Mycobacterium avium*, and mammalian-cell cytotoxicities of compounds according to general structural formulae (V) and (VI) (Examples 8, 9, 14, and 15-172)

| name | IC50 *Mycobacterium tuberculosis* RNA polymerase (µM) | MIC *Mycobacterium smegmatis* ATCC 19420 (µg/ml) | MIC *Mycobacterium tuberculosis* H37Rv (µg/ml) | MIC *Mycobacterium avium* ATCC 25291 (µg/ml) | MCC mammalian cells Vero E6 ATCC CRL1586 (µg/ml) |
|---|---|---|---|---|---|
| IX-30 | | 0.195 | 3.125 | 6.25 | 37 |
| IX-31 | | 0.195 | 3.125 | 3.125 | 30 |
| IX-32 | | 0.195 | 12.5 | 6.25 | 100 |
| IX-33 | | 0.195 | 12.5 | 6.25 | 80 |
| IX-34 | | 0.39 | 6.25 | 3.125 | 85 |
| IX-35 | | 12.5 | | | >100 |
| IX-37 | 3.3 | 0.195 | 12.5 | 12.5 | 55 |
| IX-38 | | 0.39 | 6.25 | 6.25 | 38 |
| IX-39 | | 1.56 | >50 | >50 | 20 |
| IX-40 | | 0.39 | 12.5 | 12.5 | 78 |
| IX-41 | | 0.39 | 12.5 | 12.5 | 48 |
| IX-43 | | 0.39 | 6.25 | 12.5 | 59 |
| IX-44 | | 0.195 | 1.56 | 3.125 | 70 |
| IX-45 | | 0.39 | 3.125 | 6.25 | 71 |
| IX-51 | | 0.78 | 3.125 | 6.25 | 60 |
| IX-53 | | 0.39 | 3.125 | 3.125 | 34 |
| IX-54 | | 1.56 | 25 | 50 | >100 |
| IX-55 | 0.47 | 0.39 | 1.56 | 3.125 | 10 |
| IX-55a | | 0.073 | 0.78 | 0.78 | |
| IX-55b | | 25 | >50 | >50 | |
| IX-56 | | 0.39 | 3.125 | 6.25 | 97 |
| IX-57 | | 0.39 | 6.25 | 12.5 | 79 |
| IX-58 | | 1.56 | | | 78 |
| IX-59 | | 0.095 | 3.125 | 6.25 | 49 |
| IX-60 | | 3.125 | 50 | >50 | >100 |
| IX-61 | | 0.39 | >50 | >50 | 9.2 |
| IX-62 | | 0.39 | 6.25 | 6.25 | 12 |
| IX-63 | | 0.78 | 6.25 | 12.5 | >100 |
| IX-64 | | 0.78 | 12.5 | 50 | 78 |
| IX-65 | | 0.78 | 3.125 | 6.25 | 18 |
| IX-66 | | 1.56 | 50 | | >100 |
| IX-67 | | 0.19 | 1.56 | 1.56 | 8 |
| IX-68 | | 0.39 | 3.125 | 6.25 | 17 |
| IX-69 | | 0.39 | 3.125 | 3.125 | >100 |
| IX-70 | | 0.39 | 12.5 | 25 | 63 |
| IX-71 | | 0.39 | 1.56 | 3.125 | 10 |
| IX-72 | | 0.095 | 6.25 | 3.125 | 33 |
| IX-73 | | 0.19 | 1.56 | 0.78 | >100 |
| IX-75 | | 0.39 | 0.78 | 0.78 | >100 |
| IX-79 | | 0.19 | 1.56 | 1.56 | 23 |
| IX-80 | | 0.195 | 1.56 | 3.125 | 33 |
| IX-81 | | 0.195 | 1.56 | 3.125 | 38 |
| IX-82 | | 0.39 | 1.56 | 3.125 | 20 |
| IX-83 | | 0.195 | 0.78 | 1.56 | 1.4 |
| IX-85 | | 0.39 | 12.5 | 25 | 40 |
| IX-86 | | 0.78 | >50 | >50 | 50 |
| IX-91 | | 1.56 | 50 | 50 | 65 |
| IX-94 | | 0.78 | 3.125 | 3.125 | 58 |
| IX-95 | | 0.39 | 12.5 | 25 | 20 |
| IX-96 | | 0.78 | 12.5 | 25 | 44 |
| IX-97 | | 0.39 | 6.25 | 12.5 | 15 |
| IX-98 | | 0.195 | 6.25 | 3.125 | 13 |
| IX-99 | | 0.195 | 3.125 | 6.25 | >100 |
| IX-100 | | 0.39 | 6.25 | 6.25 | 42 |
| IX-101 | | 0.39 | 6.25 | 6.25 | >100 |
| IX-103 | | 0.78 | 12.5 | 12.5 | 62 |
| IX-104 | | 0.39 | 25 | 50 | 33 |
| IX-105 | | 0.78 | 6.25 | 25 | >100 |
| IX-107 | | 0.78 | >50 | 50 | >100 |
| IX-108 | | 0.78 | 12.5 | 25 | 80 |
| IX-111 | | 0.39 | 0.39 | 0.78 | 100 |
| IX-119 | | 0.39 | 3.125 | 12.5 | 5.6 |
| IX-120 | | 0.19 | 3.125 | 3.125 | >100 |
| IX-122 | | 1.56 | >50 | >50 | 94 |
| IX-124 | | 0.78 | >50 | >50 | 38 |
| IX-125 | | 1.56 | 25 | 50 | |

TABLE 10-continued

RNA polymerase inhibitory activities, antibacterial activities against *Mycobacterium smegmatis*, antibacterial activities against *Mycobacterium tuberculosis*, antibacterial activities against *Mycobacterium avium*, and mammalian-cell cytotoxicities of compounds according to general structural formulae (V) and (VI) (Examples 8, 9, 14, and 15-172)

| name | IC50 *Mycobacterium tuberculosis* RNA polymerase (µM) | MIC *Mycobacterium smegmatis* ATCC 19420 (µg/ml) | MIC *Mycobacterium tuberculosis* H37Rv (µg/ml) | MIC *Mycobacterium avium* ATCC 25291 (µg/ml) | MCC mammalian cells Vero E6 ATCC CRL1586 (µg/ml) |
|---|---|---|---|---|---|
| IX-128 |  | 0.39 | 12.5 | 25 | 58 |
| IX-149 |  | 0.095 | 3.125 | >50 | >100 |
| IX-150 |  | 0.39 | 6.25 | 3.125 | 38 |
| IX-151 |  | 0.78 | 12.5 | 12.5 | 35 |
| IX-152 |  | 0.073 | 1.56 | 3.125 | 90 |
| IX-153 |  | 0.036 | 0.78 | 1.56 | 84 |
| IX-154 |  | 0.095 | 1.56 | 1.56 | >100 |
| IX-155 |  | 0.195 | 1.56 | 12.5 | 77 |
| IX-156 |  | 0.095 | 1.56 | 3.125 | 81 |
| IX-157 |  | 0.047 | 0.78 | 1.56 | 48 |
| IX-158 |  | 0.097 | 0.78 | 0.78 | >100 |
| IX-159 |  | 0.047 | 0.39 | 0.39 | 10 |
| IX-160 |  | 0.097 | 0.78 | 0.78 | 30 |
| IX-176 |  | 3.1 | 6.25 | 6.25 | 100.0 |
| IX-177 |  | 0.39 | 0.39 | 0.78 | >100 |
| IX-180 |  | 0.097 | 1.56 | 6.25 | 91 |
| IX-181 |  | 0.097 | 0.78 | 3.125 | 84 |
| IX-182 |  | 0.097 | 0.78 | 3.125 | 99 |
| IX-183 |  | 0.097 | 1.56 | 6.25 | >100 |
| IX-184 |  | 0.39 | 1.56 | 3.125 | 77 |
| IX-186 |  | 0.39 | 1.56 | 3.125 | 78 |
| IX-188 |  | 0.097 | 1.56 | 1.56 | 48 |
| IX-191 |  | 0.39 | 12.5 | 12.5 | >100 |
| IX-201 |  | 0.09 | 25 | 12.5 | 47 |
| IX-203 |  | 0.195 | 0.78 | 0.78 | >100 |
| IX-204 | 0.39 | 0.39 | 0.78 | 1.56 | 50 |
| IX-205 |  | 0.39 | 0.78 | 0.78 | 70 |
| IX-206 |  | 0.195 | 0.78 | 0.39 | 70 |
| IX-211 |  | 0.09 | 1.56 | 1.56 | 18 |
| IX-212 |  | 0.097 | 1.56 | 1.56 | 15 |
| IX-213 |  | 0.097 | 1.56 | 0.78 | 33 |
| IX-214 | 0.049 | 0.195 | 1.56 | 1.56 | 7 |
| IX-214a | 0.01 | 0.073 | 0.78 | <0.195 |  |
| IX-214b |  | 6.25 | 12.5 | 12.5 |  |
| IX-215 | 0.14 | 0.19 | 1.56 | 0.78 | 7 |
| IX-216 | 0.28 | 0.097 | 1.56 | 0.78 | 11 |
| IX-219 |  | 0.78 | 1.56 | 3.125 | 69 |
| IX-222 |  | 0.78 | 1.56 | 1.56 | 38 |
| IX-223 |  | 0.78 | 25 | 50 | 64 |
| IX-224 |  | 0.39 | 6.25 | 25 | >100 |
| IX-225 |  | 0.195 | 1.56 | 1.56 | 45 |
| IX-230 |  | 0.39 | 50 | 25 | 84 |
| IX-231 |  | 1.56 | 25 | >50 | >100 |
| IX-232 |  | 1.56 | 25 | 25 | 96 |
| IX-234 |  | 0.39 | 3.125 | 3.125 | 80 |
| IX-235 |  | 0.78 | 3.125 | 6.25 |  |
| IX-236 |  | 0.195 | 6.25 | 6.25 |  |
| IX-238 |  | 0.195 | 1.56 | 1.56 |  |
| IX-241 |  | 0.78 | 25 | 12.5 | 36 |
| IX-242 |  | 0.04 | 3.125 | 0.78 | 12 |
| IX-243 |  | 0.19 | 6.25 | 0.78 | 11 |
| IX-244 |  | 0.78 | 6.25 | 3.125 | 58 |
| IX-245 | 0.22 | 0.39 | 1.56 | 0.78 | 17 |
| IX-246 |  | 0.195 | 3.125 | 0.78 | 34 |
| IX-247 |  | 0.39 | 1.56 | 3.125 |  |
| IX-265 |  | 1.56 | 6.25 | 6.25 | >100 |
| IX-266 |  | 1.56 | 6.25 | 6.25 | 71 |
| IX-274 | 0.074 | 0.097 | 1.56 | 0.78 | 16 |
| IX-274a | 0.017 | 0.073 | 0.78 | 0.39 |  |
| IX-274b |  | 6.25 | 6.25 | 6.25 |  |
| IX-275 | 0.1 | 0.39 | 1.56 | 0.78 | 12.5 |
| IX-276 |  | 0.39 | 0.16 | 0.78 |  |
| IX-277 |  | 0.39 | 0.31 | 0.39 |  |
| IX-278 |  | 0.39 | 0.78 | 2.3 | 29 |
| IX-279 |  | 1.56 | 0.78 | 0.78 | 87 |
| IX-280 |  | 1.56 | 12.5 | 25 | 78 |

TABLE 10-continued

RNA polymerase inhibitory activities, antibacterial activities against *Mycobacterium smegmatis*, antibacterial activities against *Mycobacterium tuberculosis*, antibacterial activities against *Mycobacterium avium*, and mammalian-cell cytotoxicities of compounds according to general structural formulae (V) and (VI) (Examples 8, 9, 14, and 15-172)

| name | IC50 *Mycobacterium tuberculosis* RNA polymerase (μM) | MIC *Mycobacterium smegmatis* ATCC 19420 (μg/ml) | MIC *Mycobacterium tuberculosis* H37Rv (μg/ml) | MIC *Mycobacterium avium* ATCC 25291 (μg/ml) | MCC mammalian cells Vero E6 ATCC CRL1586 (μg/ml) |
|---|---|---|---|---|---|
| IX-281 |  | 0.78 | 12.5 | 12.5 | 92 |
| IX-296 |  | 0.78 | 1.56 | 1.56 |  |
| IX-297 |  | 0.78 | 12.5 | 12.5 | >100 |
| IX-300 |  | 1.56 | 6.25 | 6.25 |  |
| IX-301 |  | 0.39 | 6.25 | 3.13 |  |
| IX-305 |  | 0.78 | 1.56 | 12.5 |  |
| IX-306 |  | 0.78 |  |  |  |
| IX-307 |  | 6.125 | 12.5 | 25 |  |
| IX-308 |  | 0.39 | 3.13 | <0.39 |  |
| IX-312 |  | 0.195 | 3.13 | 3.13 |  |
| IX-313 |  | 0.39 | 1.56 | 1.56 |  |
| IX-315 | 0.21 | 0.39 | 3.125 | 1.56 | 12.5 |
| IX-316 | 0.43 | 0.39 | 3.125 | 1.56 |  |
| IX-319 |  | 0.39 | 3.125 | 6.25 | >100 |

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

What is claimed is:

1. A compound of formula (V), or a salt thereof:

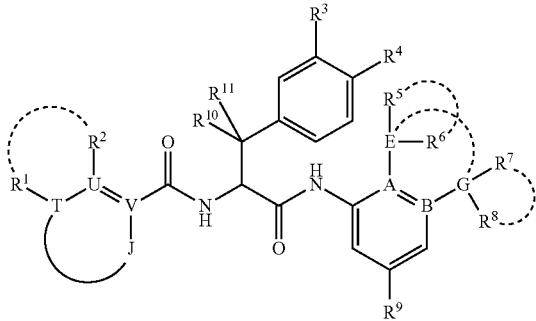
(V)

wherein T and U each is carbon;

V is carbon;

A and B each is carbon;

E is one of carbon (CH), nitrogen, oxygen, and sulfur;

G is one of hydrogen, halogen, carbon (CH), nitrogen, oxygen, and sulfur;

J is carbon, and J, together with T, U, V, and two additional carbon atoms, forms a phenyl;

$R^1$ and $R^2$ each independently is hydrogen, halogen, alkyl, alkoxy-substituted alkyl, or alkoxy, each optionally substituted by halogen;

$R^3$ and $R^4$ each independently is hydrogen, halogen, hydroxy; —O—C(=O)—$C_1$-$C_4$alkyl, —O—C(=O)-phenyl, or morpholino $R^5$, $R^6$, $R^7$, and $R^8$ each independently is absent, hydrogen, halogen, or alkyl which is optionally substituted by halogen; or $R^5$ and $R^6$, together with E, form a cycle containing 5 to 9 atoms selected from carbon, nitrogen, oxygen, and sulfur, said cycle optionally substituted with halogen, amine, alkyl, or acyl; or $R^7$ and $R^8$, together with G, form a cycle containing 5 atoms selected from carbon and nitrogen; and $R^9$, $R^{10}$, and $R^{11}$ each independently is hydrogen or halogen;

provided that when E is carbon, G is hydrogen or is the carbon atom of an unsubstituted methyl group, $R^1$, $R^2$, $R^3$, $R^4$, $R^9$, $R^{10}$, and $R^{11}$ are hydrogen; then E is bonded to no more than two hydrogen atoms and no more than two fluorine atoms;

provided that when E is oxygen, G is hydrogen, and $R^1$, $R^3$, $R^9$, $R^{10}$, and $R^{11}$ are hydrogen; then E is not bonded to hydrogen or unsubstituted ethyl; and provided that when E is oxygen, G is hydrogen, and $R^1$, $R^2$, $R^3$, $R^9$, $R^{10}$, and $R^{11}$ are hydrogen, and $R^9$ is chlorine; then E is not bonded to hydrogen or unsubstituted methyl.

2. The compound of claim 1 wherein the compound of formula (V) is a compound of formula (VI), or a salt thereof:
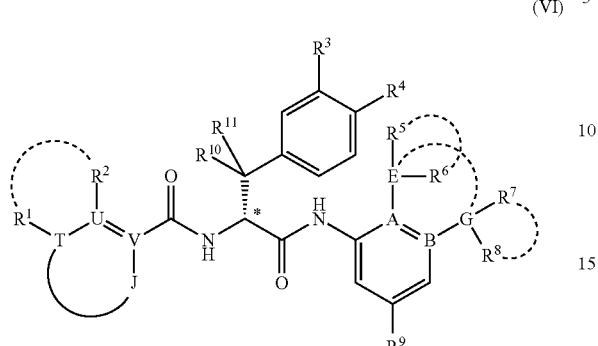
(VI)
wherein the configuration of the Cα atom of the central amino acid moiety, the carbon identified with the *, has the indicated, D, absolute configuration.
3. The compound of claim 1 which is selected from the group consisting of:
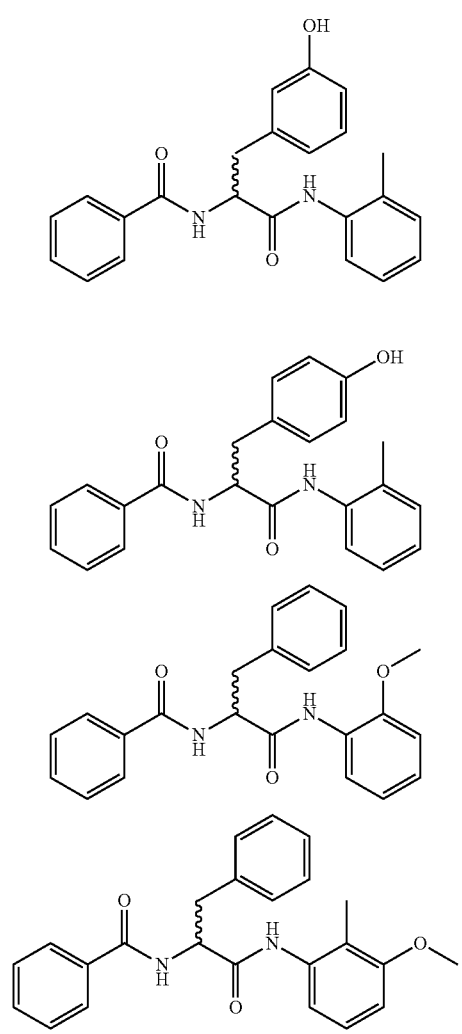
-continued
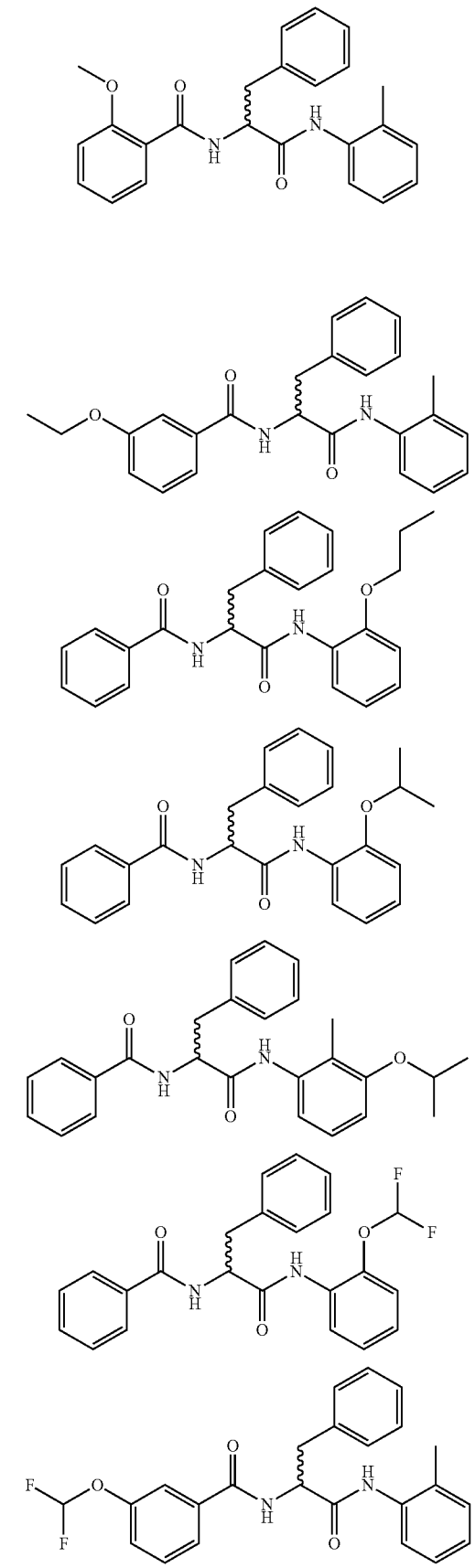

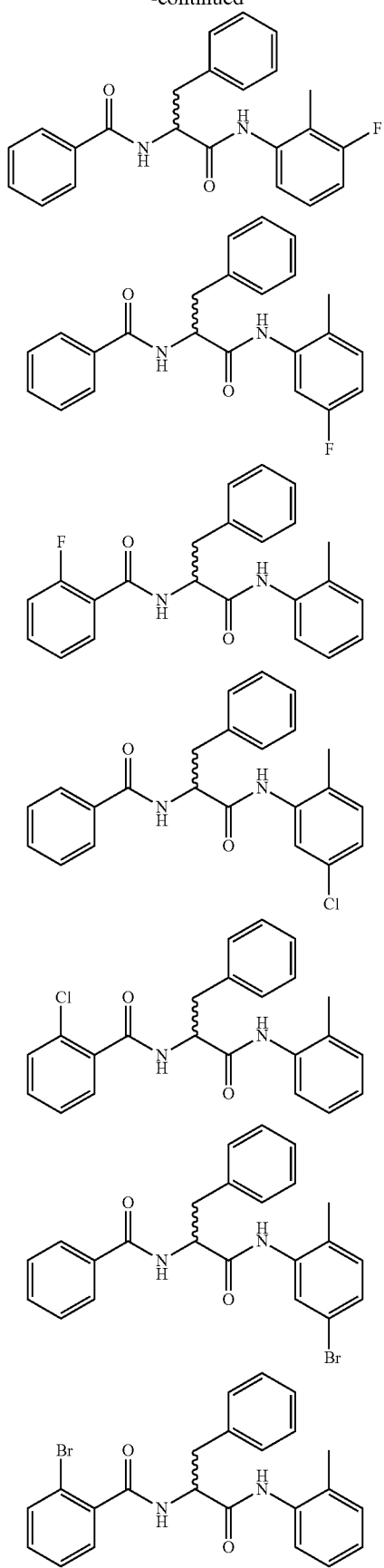
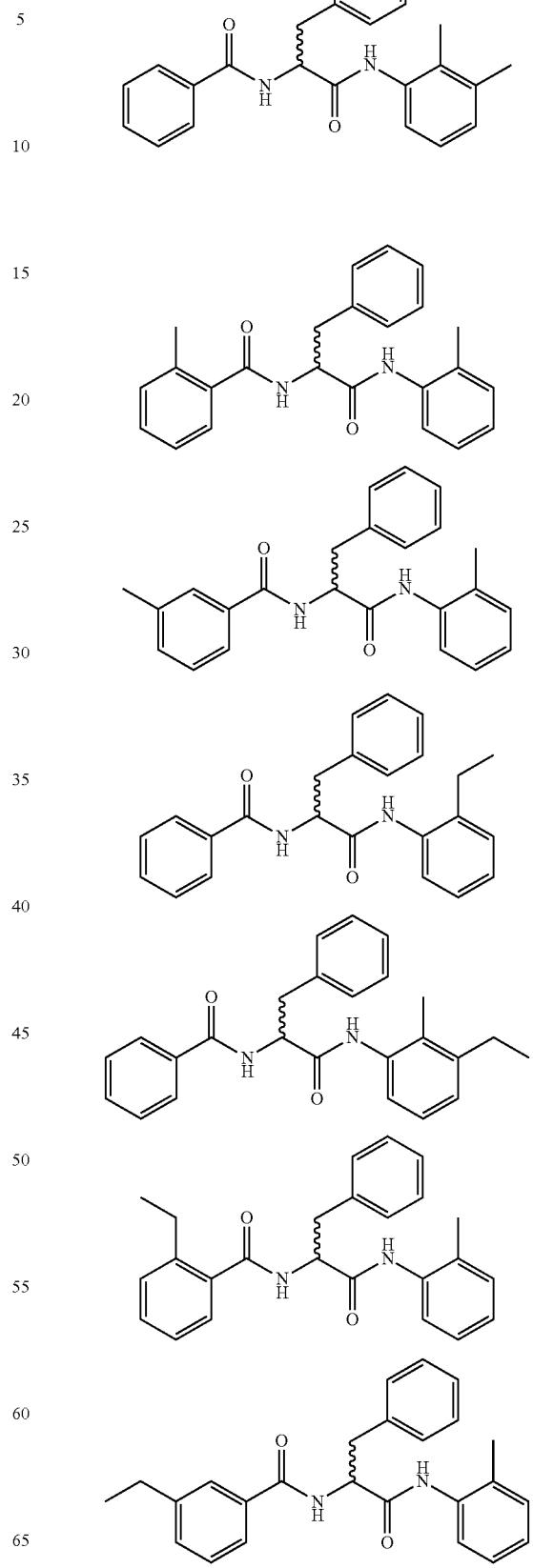

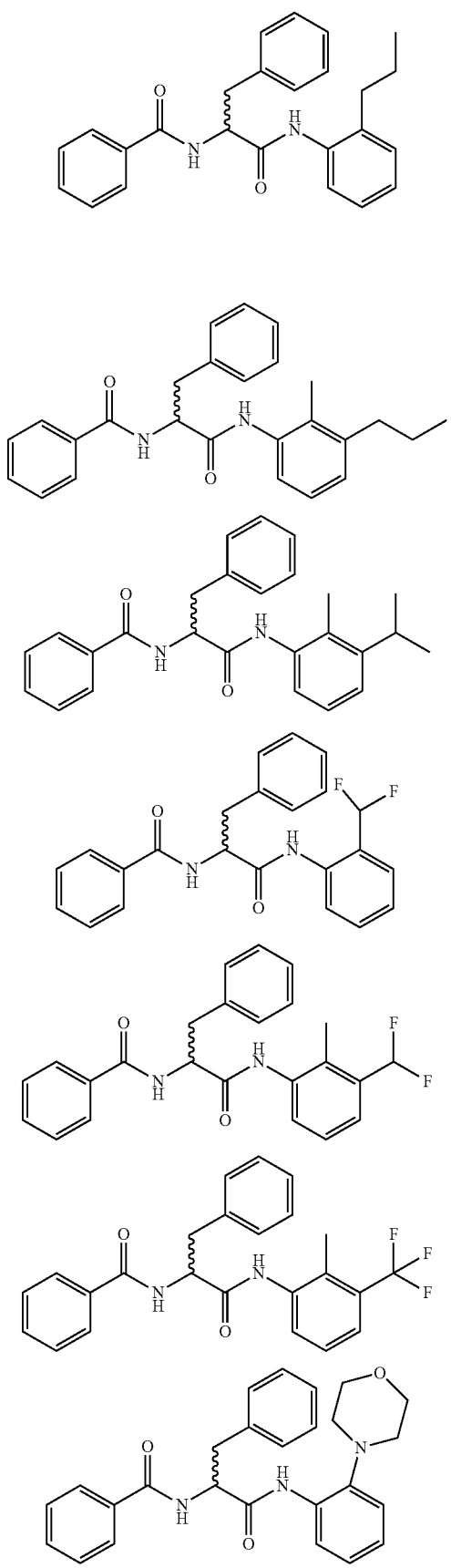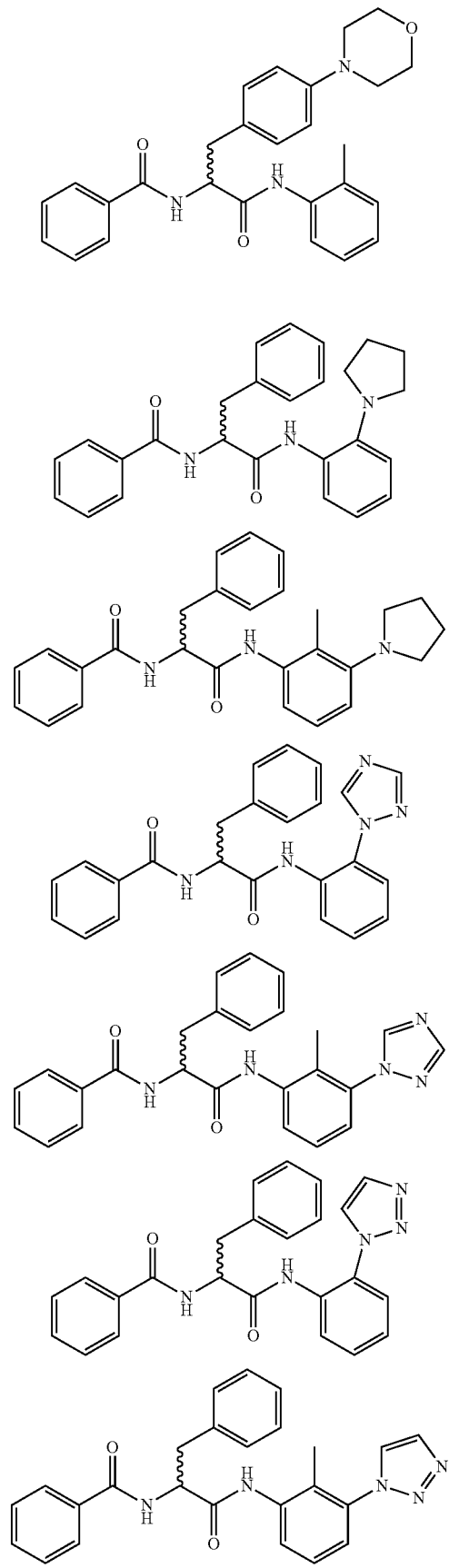

233
-continued
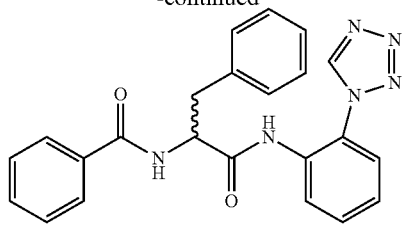
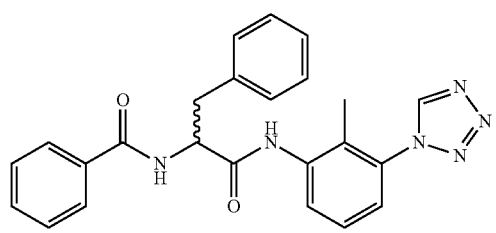
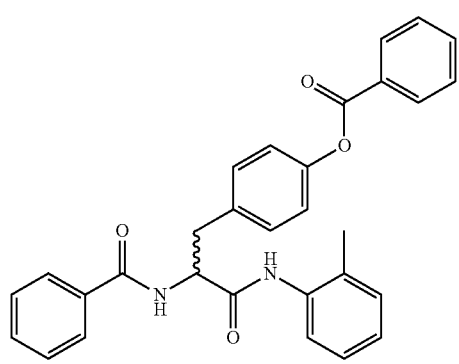
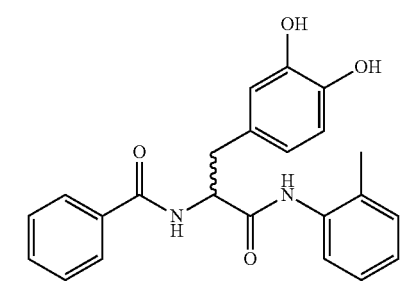
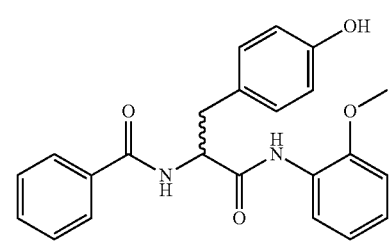
234
-continued
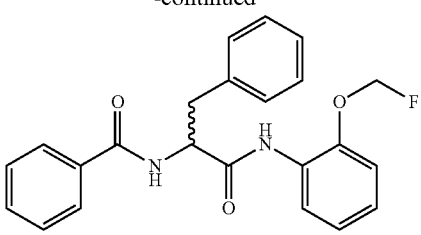
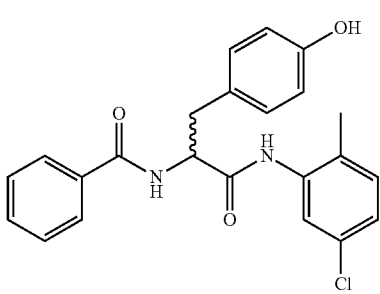
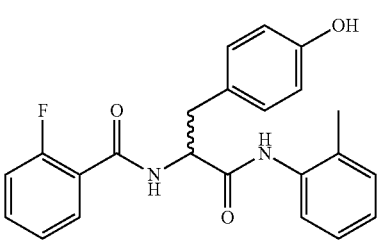
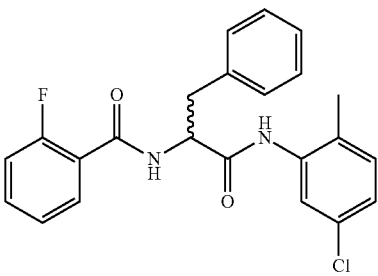
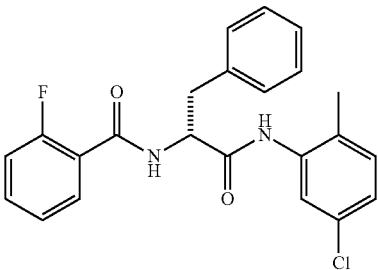
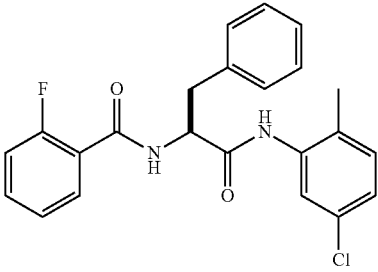

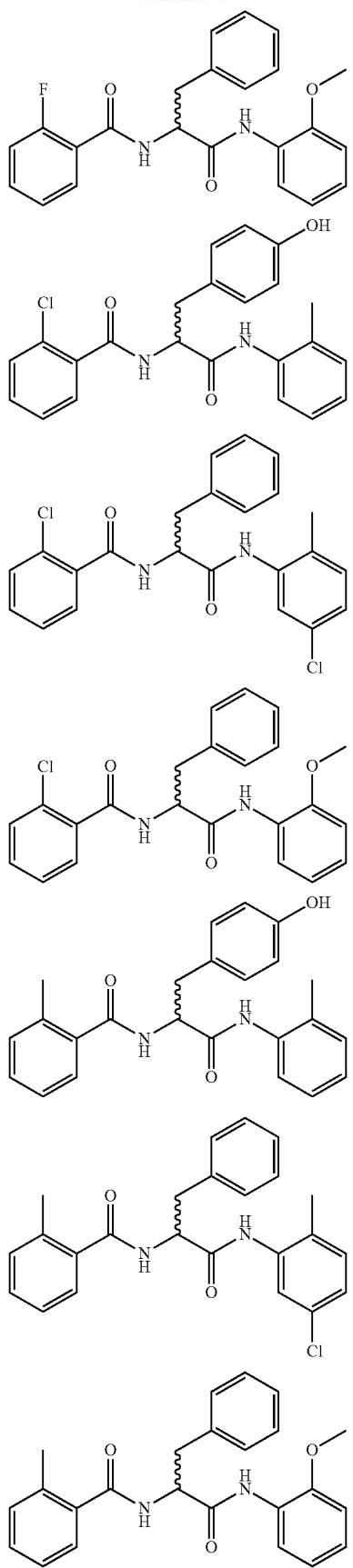
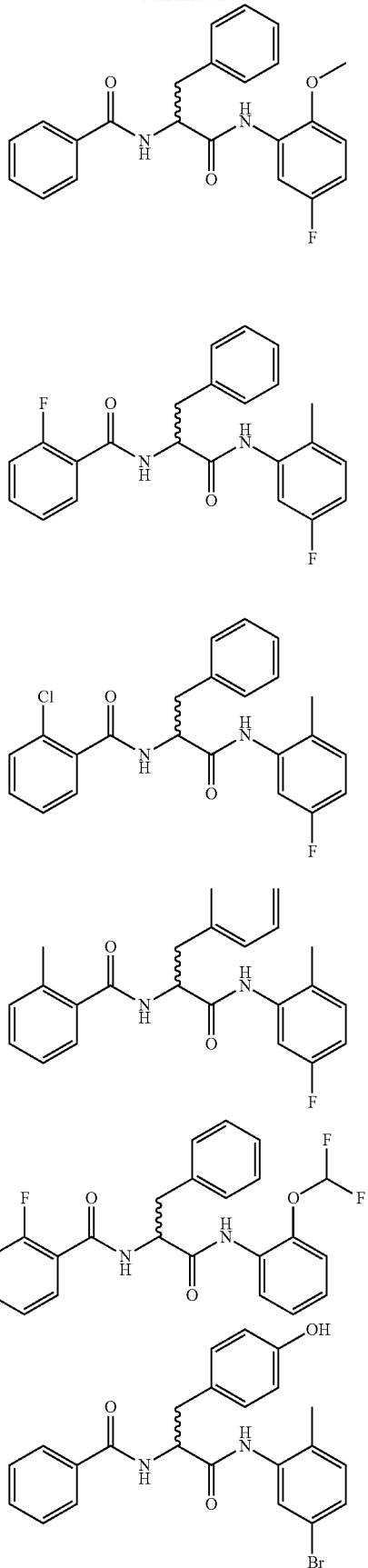

237
-continued
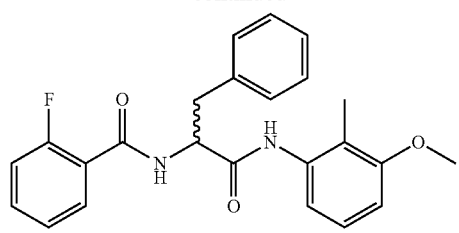
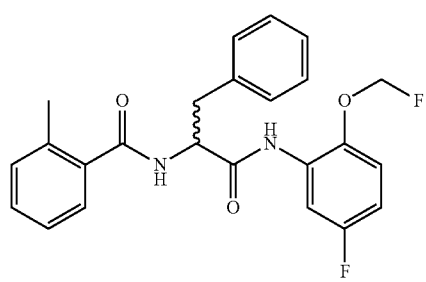
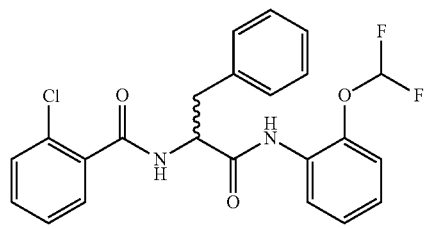
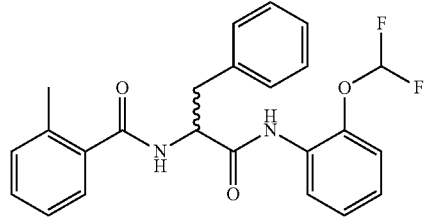
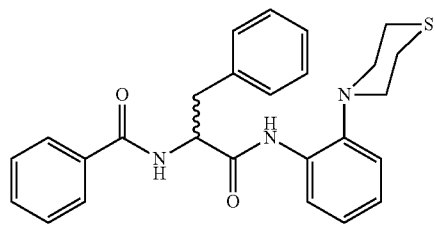
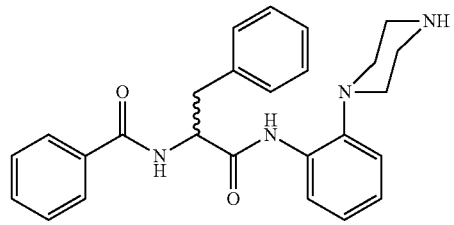
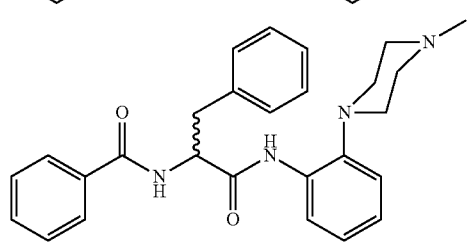
238
-continued
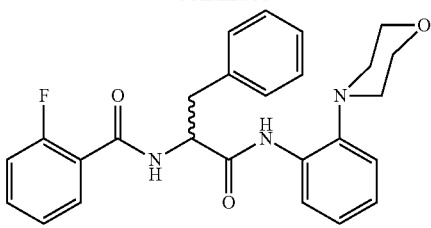
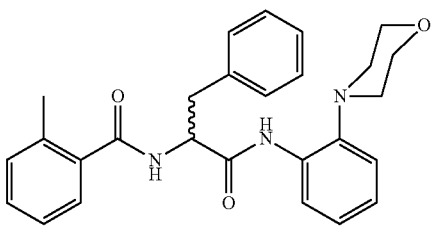
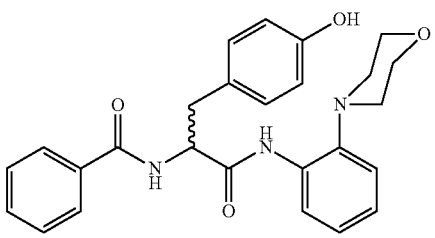
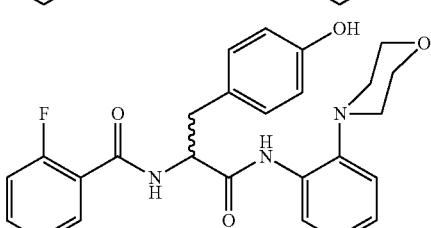
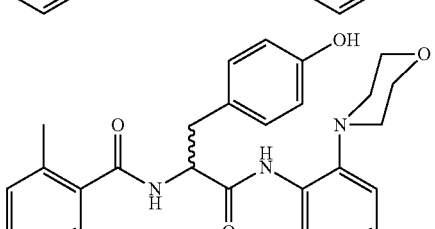
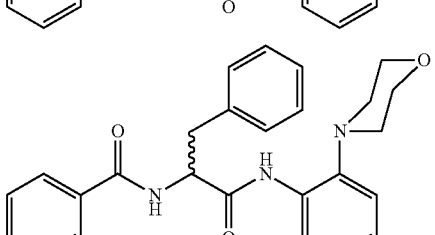
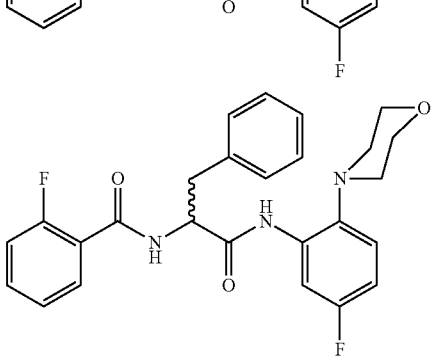

239
-continued
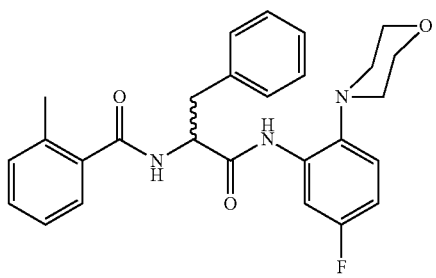
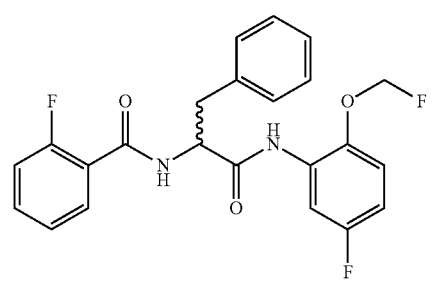
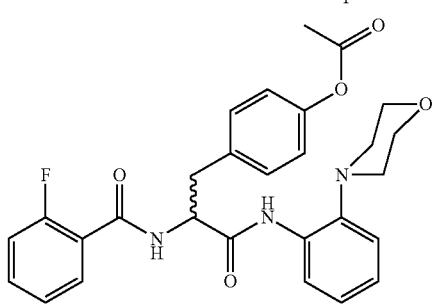
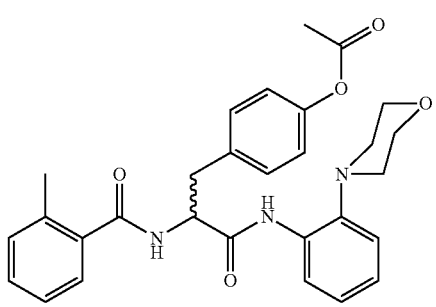
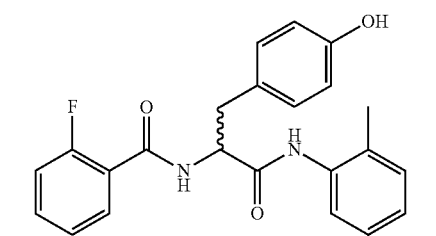
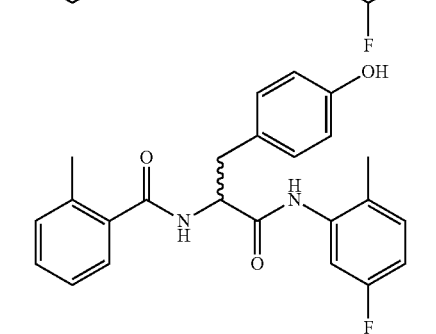
240
-continued
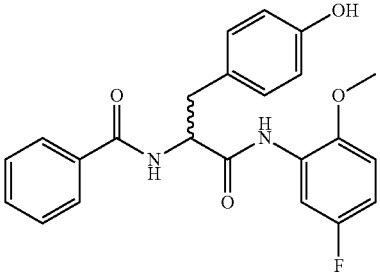
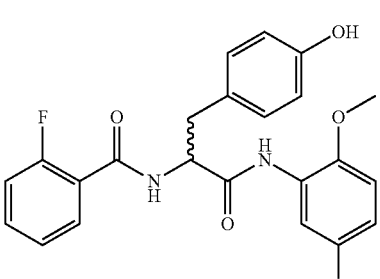
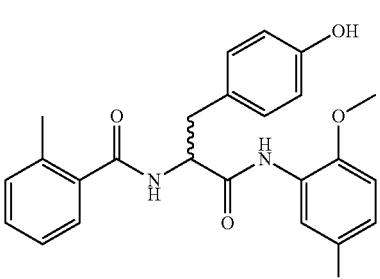
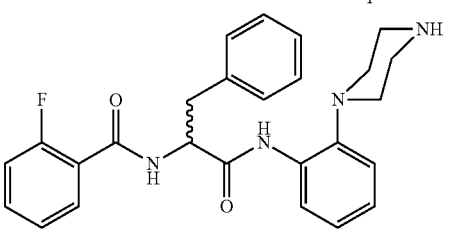
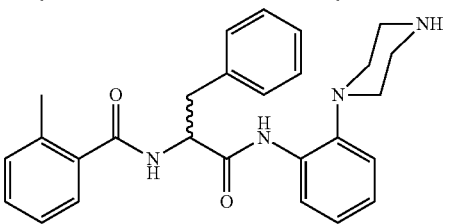
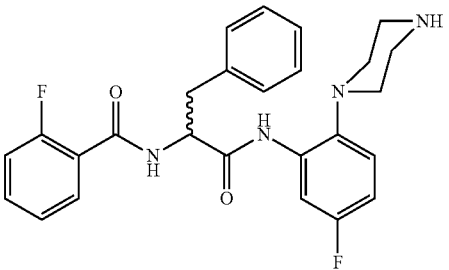

241
-continued
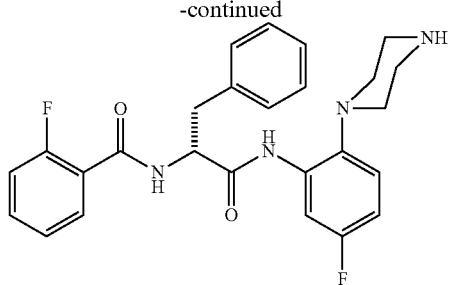
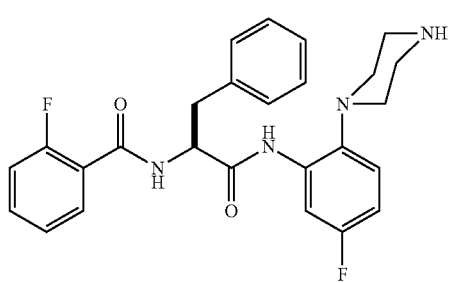
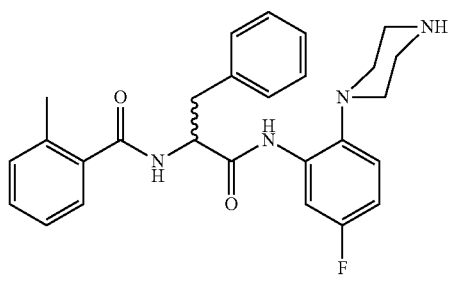
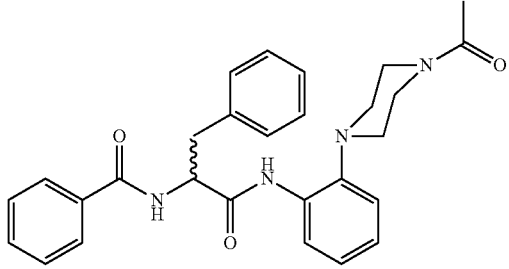
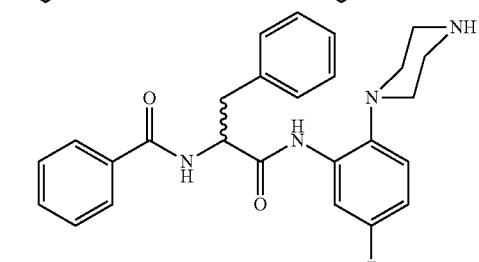
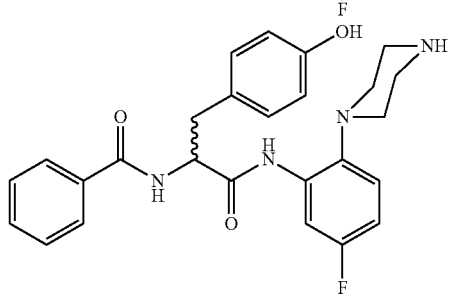
242
-continued
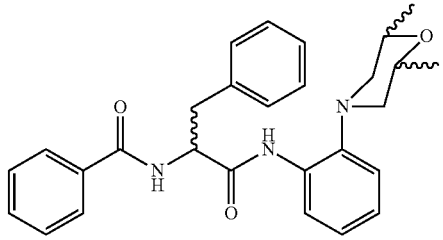
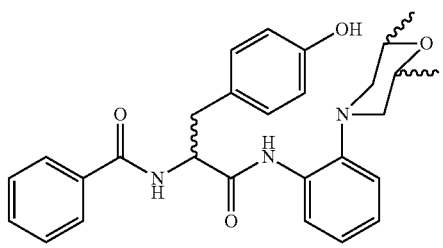
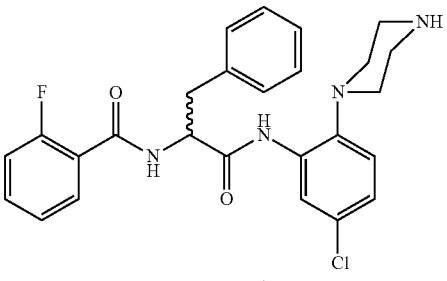
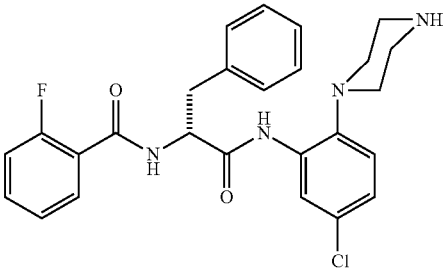
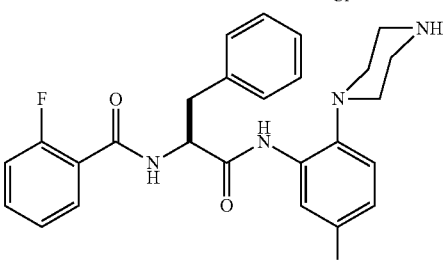
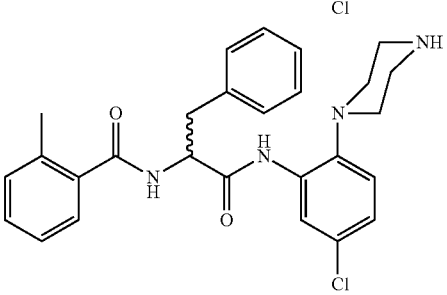

243
-continued
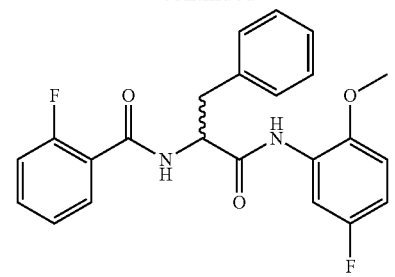
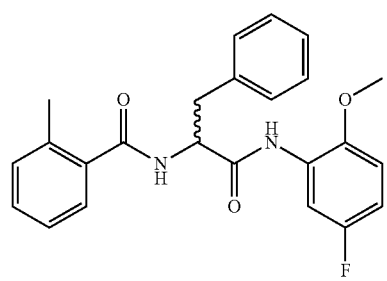
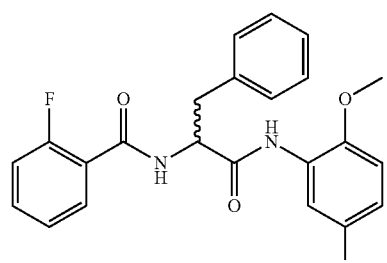
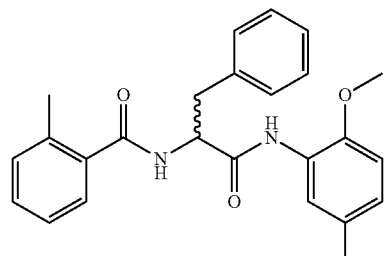
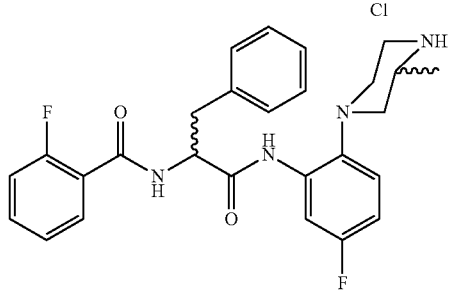
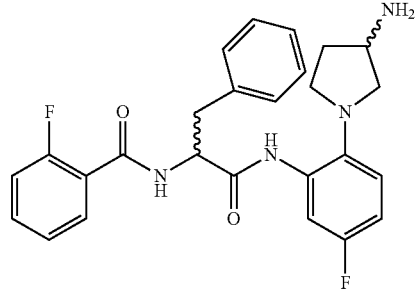
244
-continued
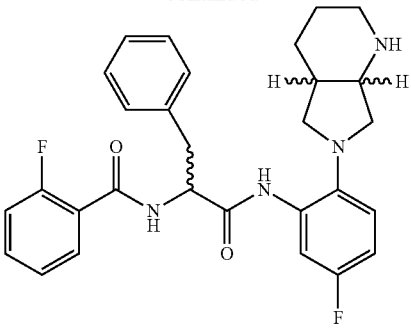
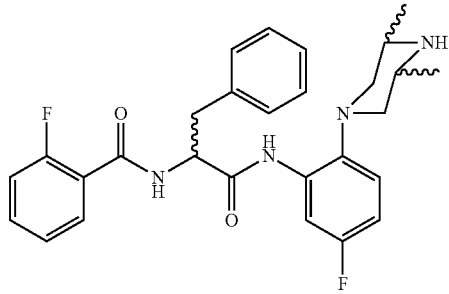
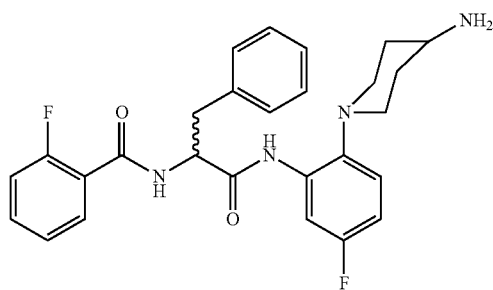
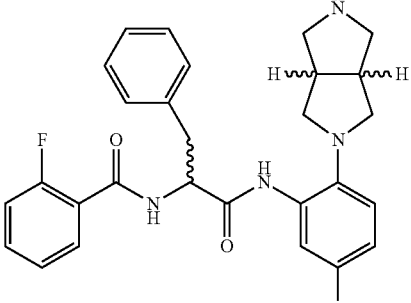
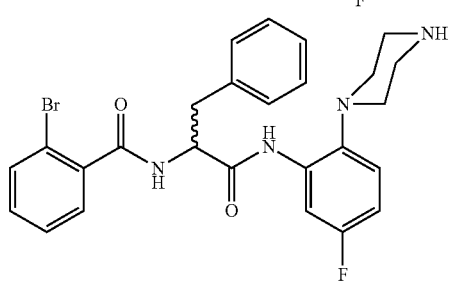

245

-continued

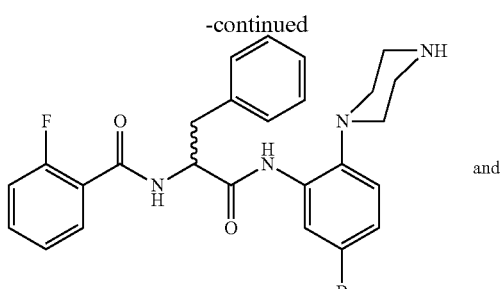

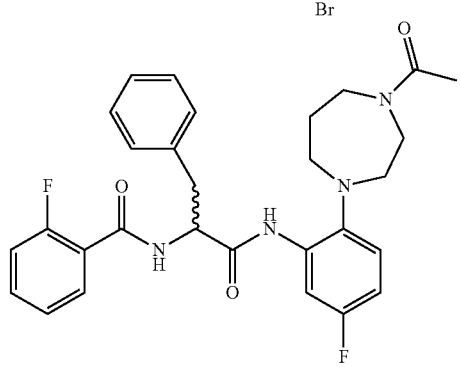

and salts thereof.

4. A pharmaceutical composition comprising a compound as described in claim 1 or a pharmaceutically acceptable salt thereof and a pharmaceutically acceptable diluent or carrier.

5. The compound of claim 1, wherein $R^3$ and $R^4$ each independently is hydrogen or hydroxy.

6. The compound of claim 1, wherein $R^5$ and $R^6$ each independently is absent, hydrogen, halogen, or alkyl which is optionally substituted by halogen.

7. The compound of claim 1, wherein $R^5$ and $R^6$, together with E, form a cycle containing 6 atoms selected from carbon, nitrogen, oxygen, and sulfur, said cycle optionally substituted with halogen, amine or acyl.

8. The compound of claim 1, wherein G is hydrogen; and $R^7$ and $R^8$ are absent.

9. A compound of formula (V), or a salt thereof:

(V)

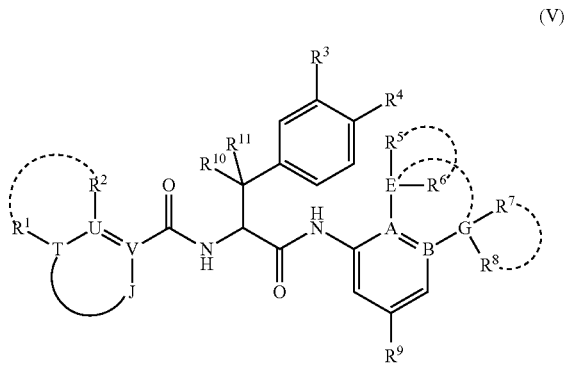

wherein T and U each is carbon;
V is carbon;
A and B each is carbon;
E is one of carbon (CH), nitrogen, oxygen, and sulfur;
G is one of carbon (CH), nitrogen, oxygen, and sulfur;
J is carbon, and J, together with T, U, V, and two additional atoms, forms a phenyl;
$R^1$ and $R^2$ each independently is hydrogen, halogen, or is alkyl which is optionally substituted by halogen;

246

$R^3$ and $R^4$ each independently is hydrogen, halogen, or hydroxy; and $R^6$ and $R^7$ are absent and E and G, together with A and B, form a cycle containing 5 to 6 atoms selected from carbon, nitrogen, oxygen, and sulfur, said cycle optionally substituted with halogen or alkyl;

$R^5$ and $R^8$ each independently is absent, hydrogen, halogen, or alkyl; and $R^9$, $R^{10}$, and $R^{11}$ each independently is hydrogen or halogen.

10. The compound of claim 9 wherein the compound of formula (V) is a compound of formula (VI), or a salt thereof:

(VI)

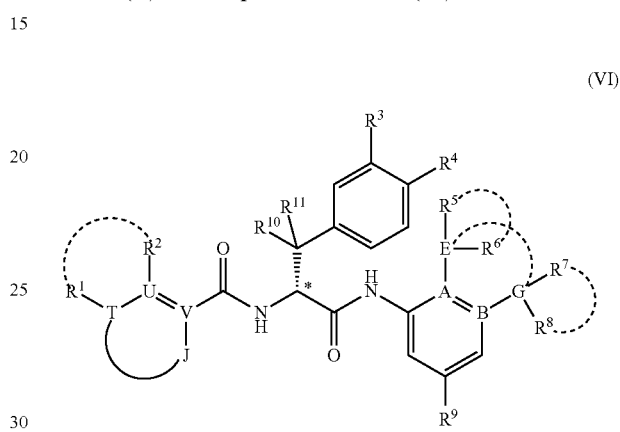

wherein the configuration of the Cα atom of the central amino acid moiety, the carbon identified with the *, has the indicated, D, absolute configuration.

11. The compound of claim 9 which is selected from the group consisting of:

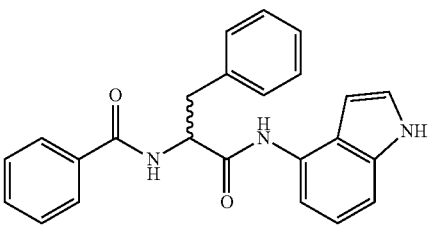

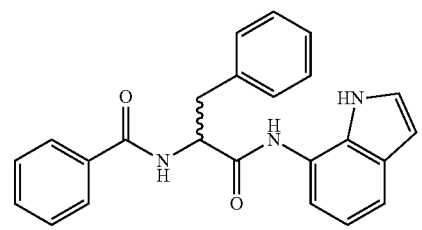

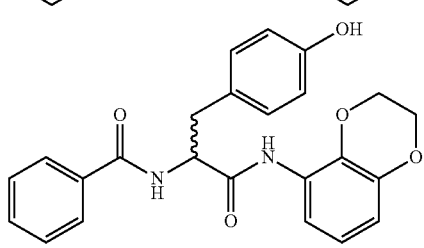

247
-continued
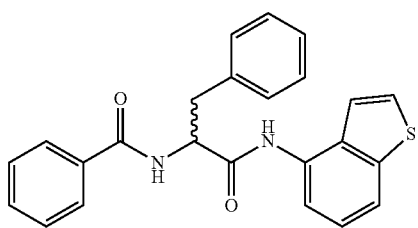
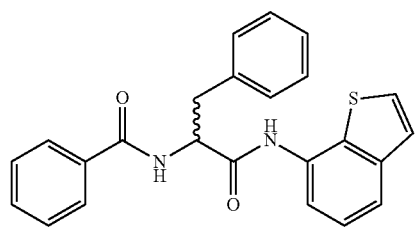
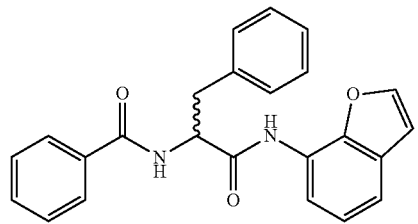
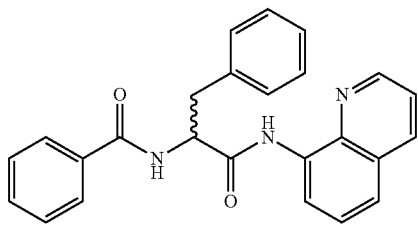
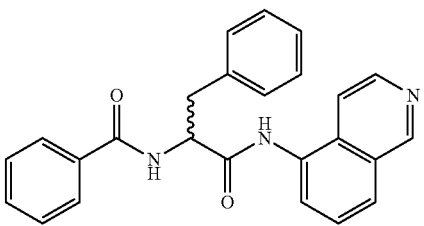
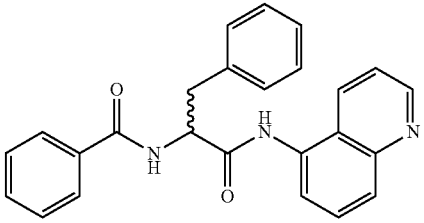
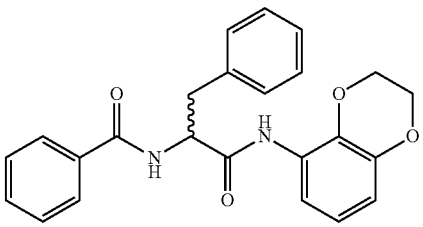
248
-continued
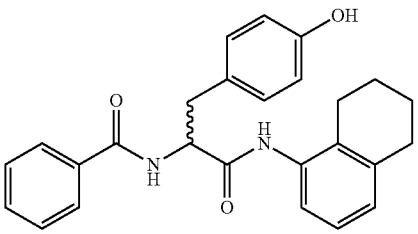
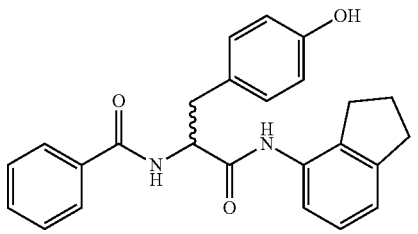
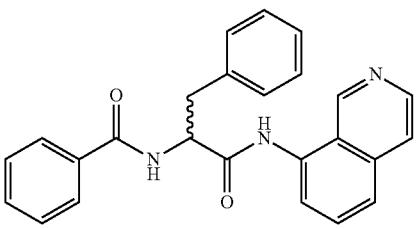
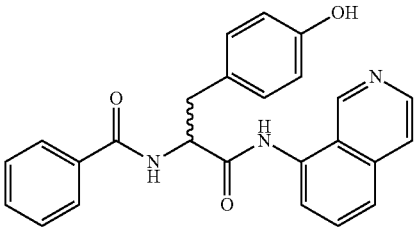
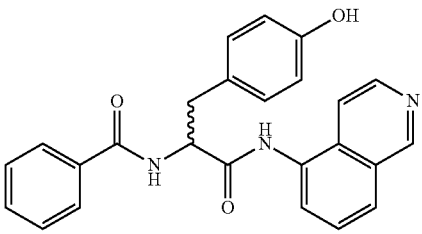
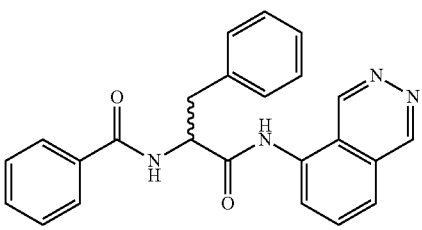
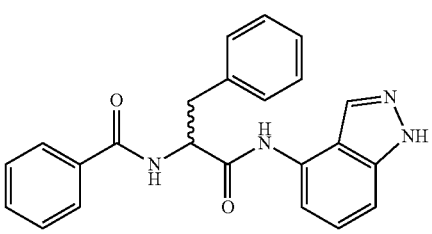

249
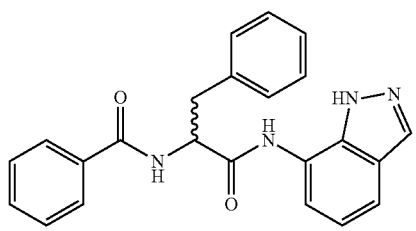
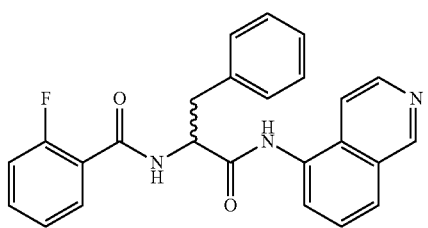
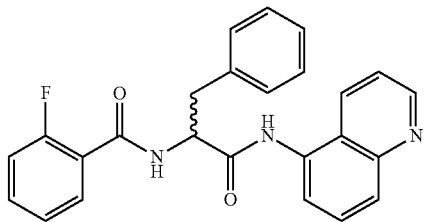
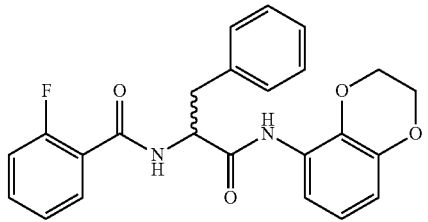
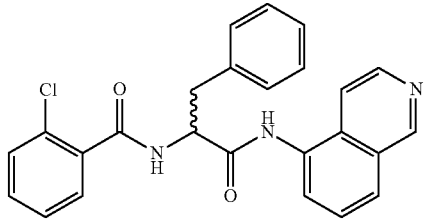
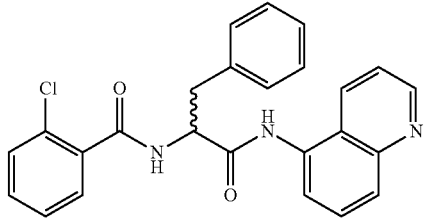
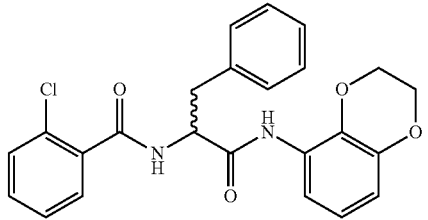
250
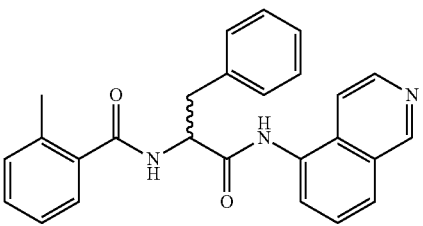
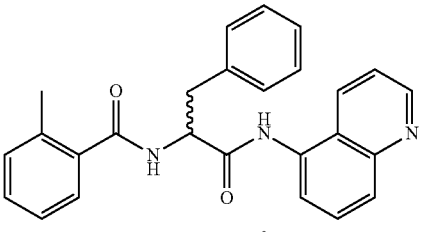
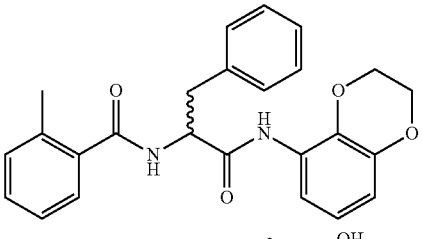
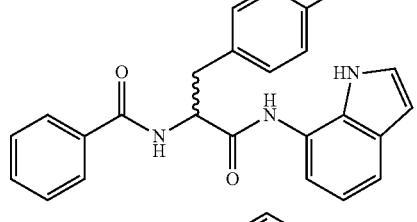
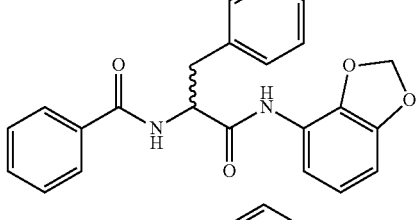
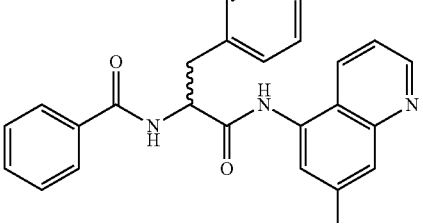
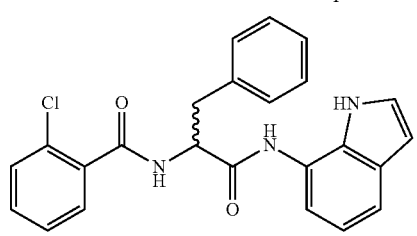

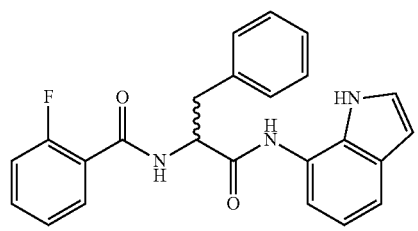
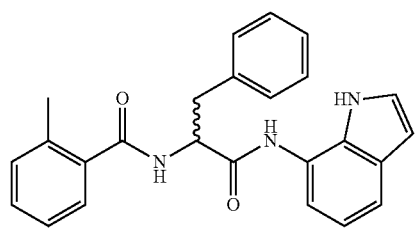
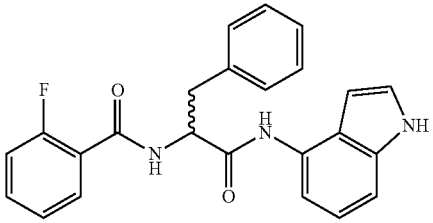
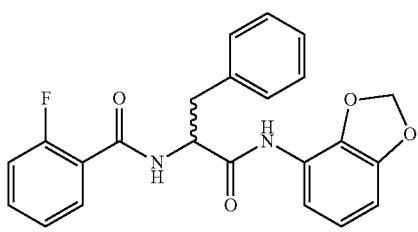
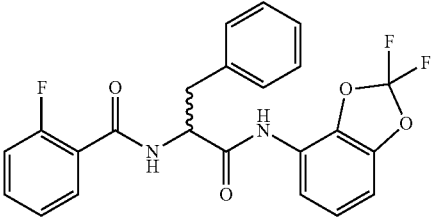
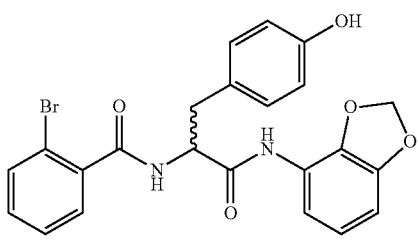
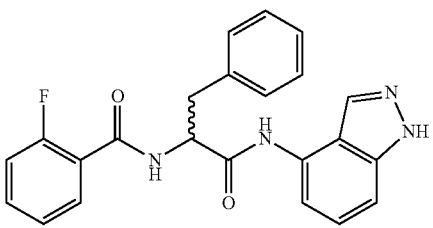
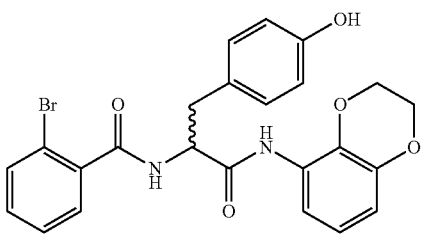
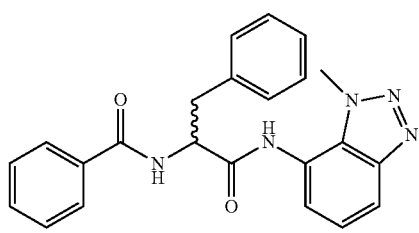
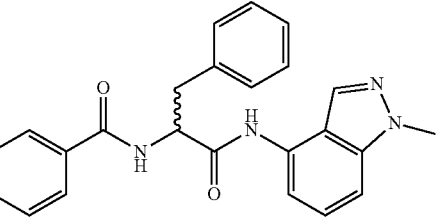
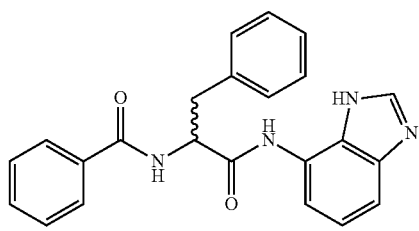
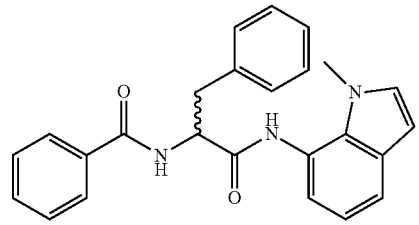
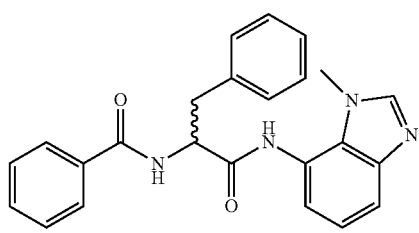
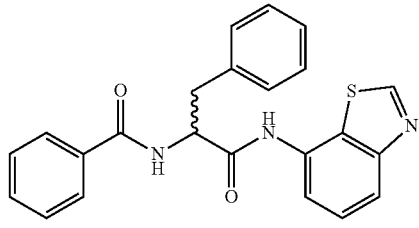

-continued

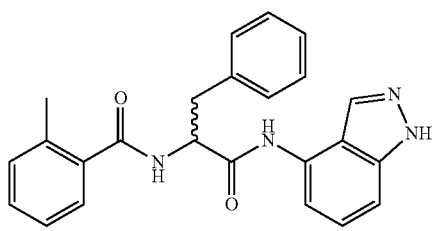

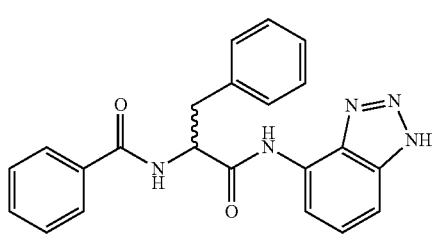

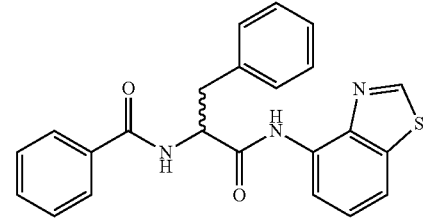

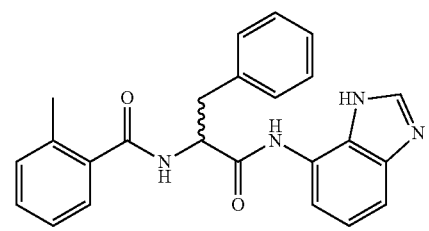

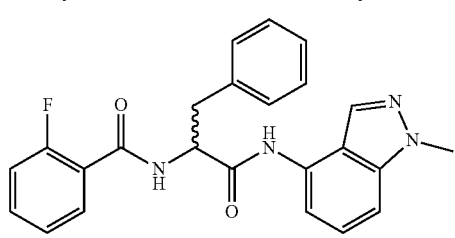

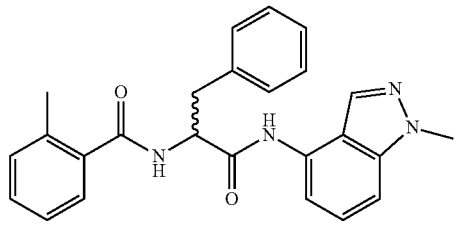

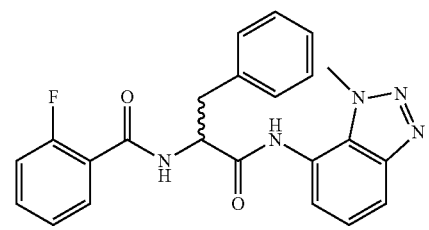

-continued

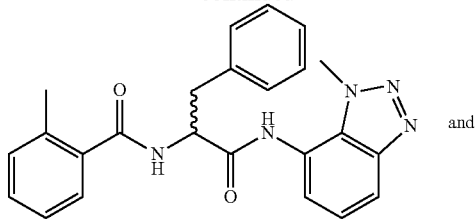 and

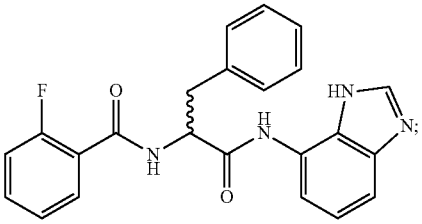

and salts thereof.

12. A compound of formula (V), or a salt thereof:

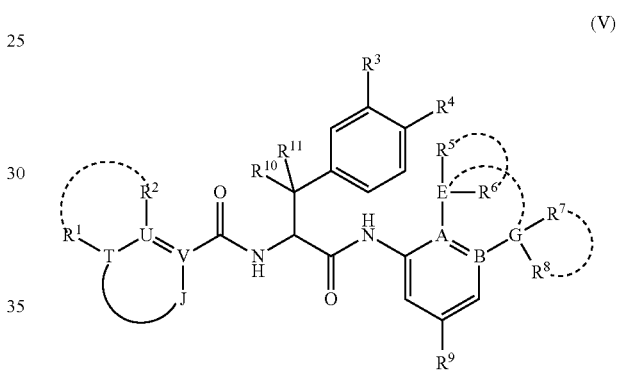

(V)

wherein T and U each is carbon;
V is carbon;
A and B each is carbon;
E is one of carbon (CH), nitrogen, oxygen, and sulfur;
G is one of hydrogen, halogen, carbon (CH), nitrogen, oxygen, and sulfur;
J is sulfur, and J, together with T, U, V, and one additional atom, forms a thiophenyl;
$R^1$ and $R^2$ each independently is hydrogen, halogen, or alkyl that is optionally substituted by halogen;
$R^3$ and $R^4$ each independently is hydrogen, halogen, hydroxy, or —O—C(=O)—$C_1$-$C_4$alkyl;
$R^5$, $R^6$, $R^7$, and $R^8$ each independently is absent, hydrogen, halogen, or alkyl which is optionally substituted by halogen; or $R^5$ and $R^6$, together with E, form a cycle containing 5 to 6 atoms selected from carbon, nitrogen, oxygen, and sulfur, said cycle optionally substituted with halogen, amine, alkyl, or hydroxy-substituted alkyl; or $R^6$ and $R^7$ are absent and E and G, together with A and B, form a cycle containing 5 to 6 atoms selected from carbon, nitrogen, oxygen, and sulfur, said cycle optionally substituted with halogen or alkyl which is optionally substituted by halogen; and
$R^9$, $R^{10}$, and $R^{11}$ each independently is hydrogen or halogen;
provided that when E is carbon, G is hydrogen or is the carbon atom of an unsubstituted methyl group, and $R^1$, $R^2$, $R^3$, $R^4$, $R^9$, $R^{10}$, and $R^{11}$ are hydrogen; then E is bonded to no more than two hydrogen atoms and no more than two fluorine atoms;

provided that when E, and G are carbon, $R^1$ is hydrogen, $R^2$ is hydrogen or methyl, and $R^3$, $R^4$, $R^9$, $R^{10}$, and $R^{11}$ are hydrogen; then A, B, E, and G are not part of a phenyl cycle;

provided that when E is nitrogen, G is hydrogen, and $R^1$, $R^2$, $R^3$, $R^4$, $R^9$, $R^{10}$, and $R^{11}$ are hydrogen; then E, $R^5$, and $R^6$ are not part of a morpholine cycle;

provided that when E is oxygen, G is hydrogen, and $R^1$, $R^3$, $R^9$, $R^{10}$, and $R^{11}$ are hydrogen; then E is not bonded to hydrogen or unsubstituted ethyl; and provided that when E is oxygen, G is hydrogen, and $R^1$, $R^2$, $R^3$, $R^9$, $R^{10}$, and $R^{11}$ are hydrogen, and $R^9$ is chlorine; then E is not bonded to hydrogen or unsubstituted methyl.

13. The compound of claim 12 wherein the compound of formula (V) is a compound of formula (VI), or a salt thereof:

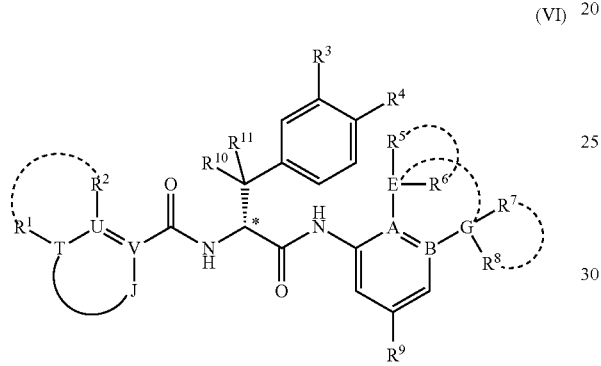

(VI)

wherein the configuration of the Cα atom of the central amino acid moiety, the carbon identified with the *, has the indicated, D, absolute configuration.

14. The compound of claim 12, wherein E is one of carbon (CH), nitrogen, and sulfur.

15. The compound of claim 12, wherein $R^5$, $R^6$, $R^7$, and $R^8$ each independently is absent, hydrogen, halogen, or alkyl which is optionally substituted by halogen; or $R^5$ and $R^6$, together with E, form a cycle containing 5 to 6 atoms selected from carbon, nitrogen, oxygen, and sulfur, said cycle optionally substituted with halogen, amine, alkyl, or hydroxy-substituted alkyl.

16. The compound of claim 12, wherein $R^5$ and $R^8$ each independently is absent, hydrogen, halogen, or alkyl which is optionally substituted by halogen; $R^6$ and $R^7$ are absent and E and G, together with A and B, form a cycle containing 5 to 6 atoms selected from carbon, nitrogen, oxygen, and sulfur, said cycle optionally substituted with halogen or alkyl which is optionally substituted by halogen.

17. The compound of claim 12 which is selected from the group consisting of:

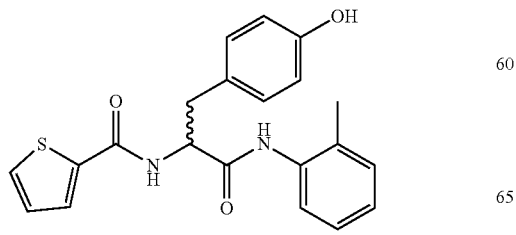

-continued

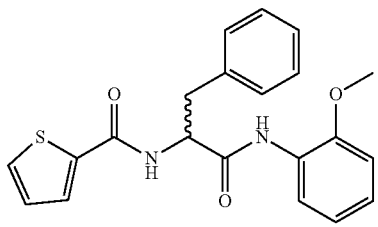

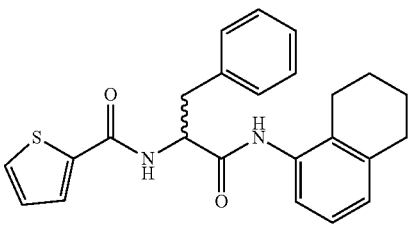

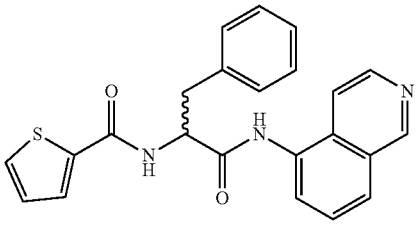

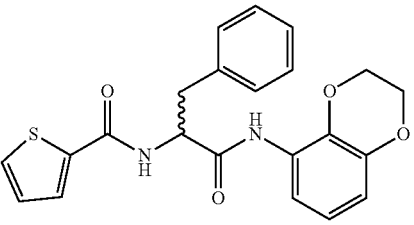

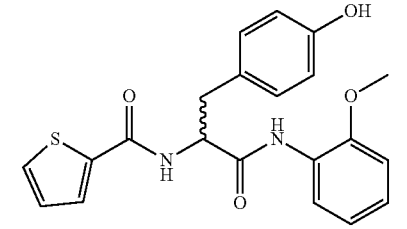

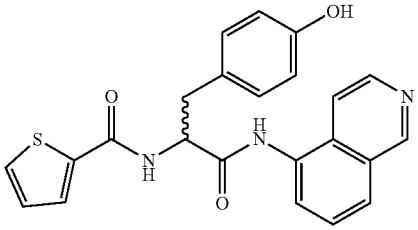

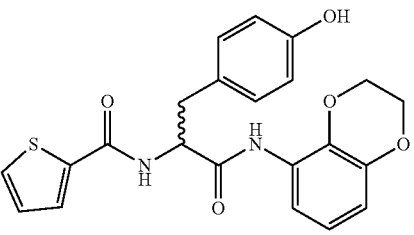

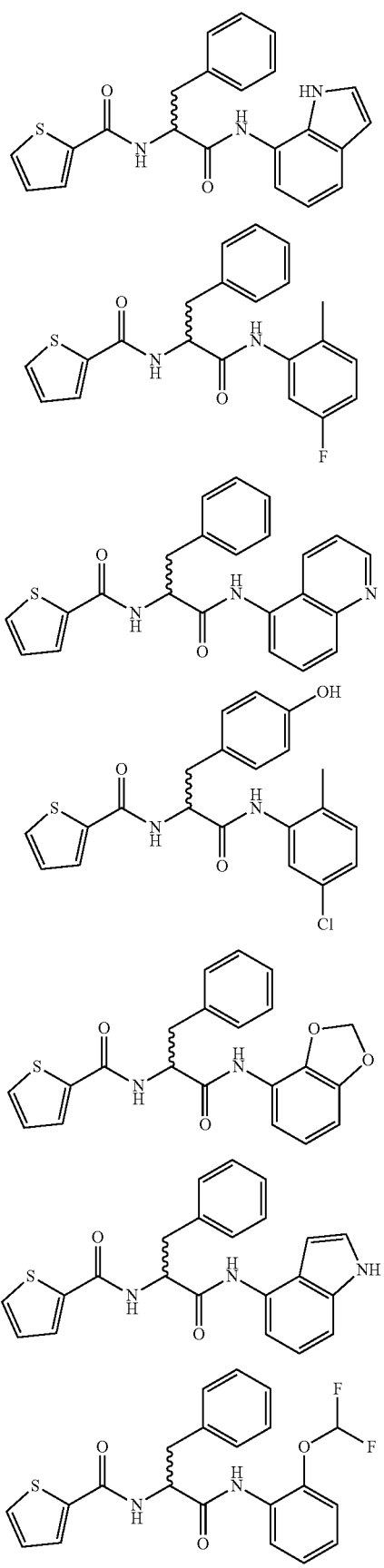
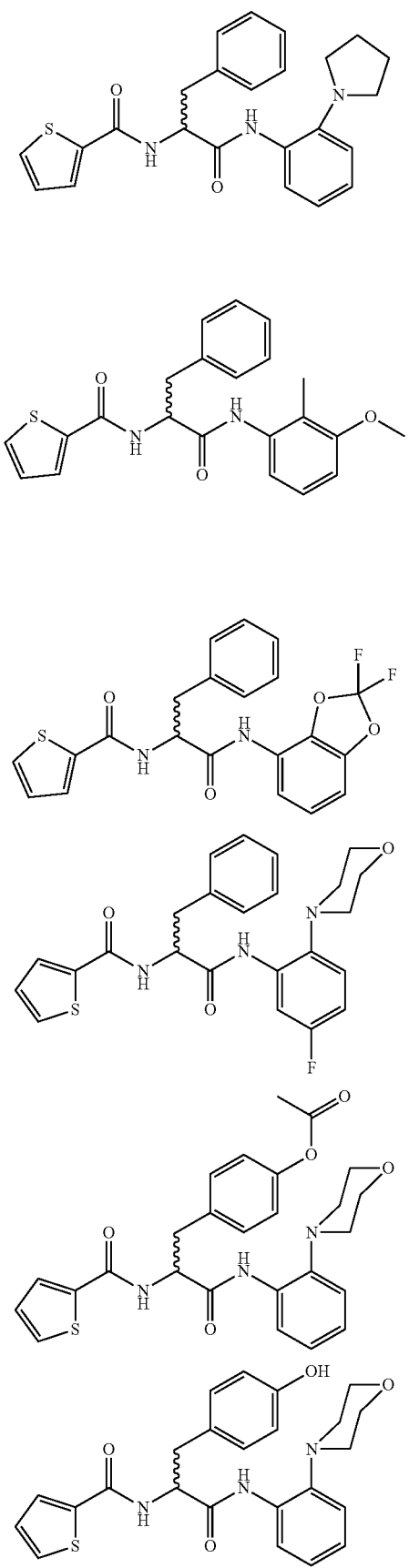

-continued

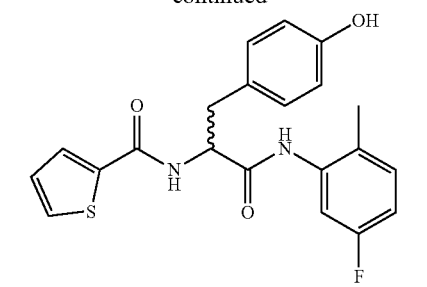

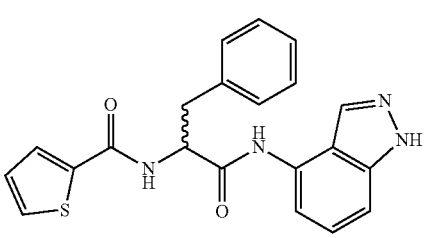

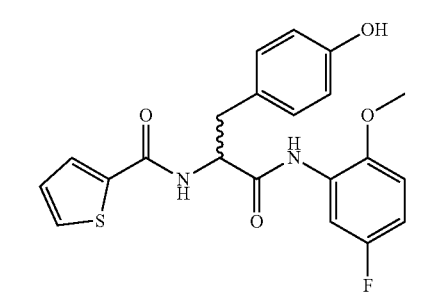

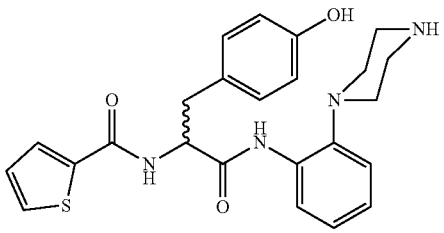

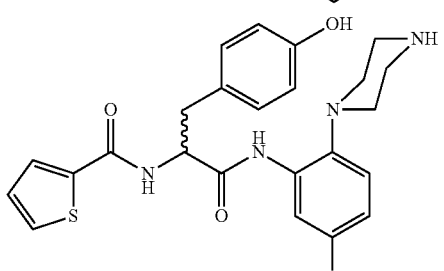

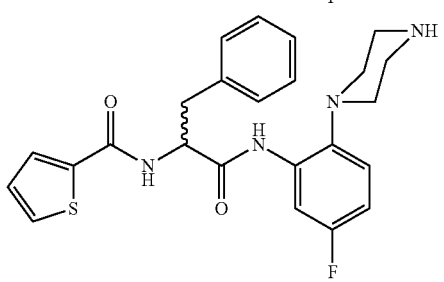

-continued

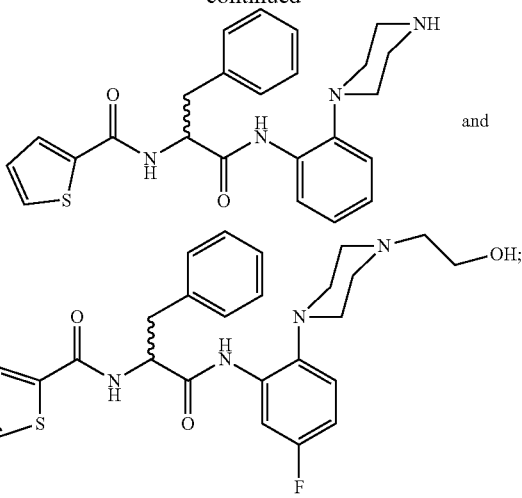

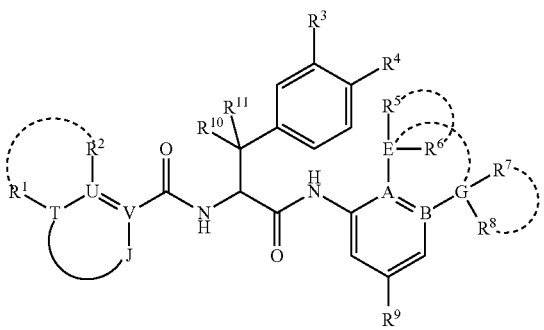

and salts thereof.

18. A compound of formula (V), or a salt thereof:

(V)

wherein T and U each is carbon;
V is carbon;
A and B each is carbon;
E is one of carbon (CH), nitrogen, oxygen, and sulfur;
G is one of hydrogen, halogen, carbon (CH), nitrogen, oxygen, and sulfur;
J is carbon, and J, together with T, U, V, and two additional atoms, forms a phenyl;
$R^1$ and $R^2$, together with T and U, form a cycle containing 5 to 6 atoms selected from carbon, and nitrogen;
$R^3$ and $R^4$ each independently is hydrogen, halogen, or hydroxy;
$R^5$, $R^6$, $R^7$, and $R^8$ each independently is absent, hydrogen, halogen, or alkyl which is optionally substituted by halogen; or $R^5$ and $R^6$, together with E, form a cycle containing 5 to 6 atoms selected from carbon, nitrogen, oxygen, and sulfur, said cycle optionally substituted with halogen, amine, or alkyl; or $R^6$ and $R^7$ are absent and E and G, together with A and B, form a cycle containing 5 to 6 atoms selected from carbon, nitrogen, oxygen, and sulfur, said cycle optionally substituted with halogen or alkyl which is optionally substituted by halogen; and
$R^9$, $R^{10}$, and $R^{11}$ each independently is hydrogen or halogen.

19. The compound of claim 18 wherein the compound of formula (V) is a compound of formula (VI), or a salt thereof:

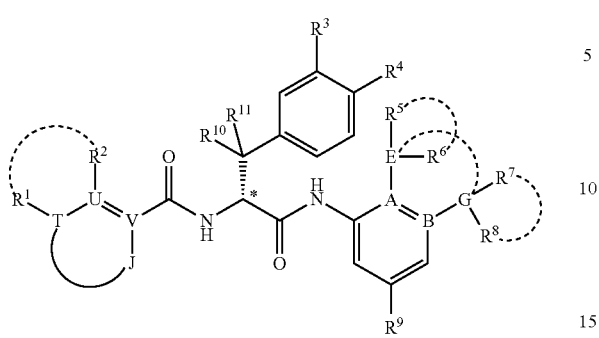

(VI)

wherein the configuration of the Cα atom of the central amino acid moiety, the carbon identified with the *, has the indicated, D, absolute configuration.

20. The compound of claim 18, wherein $R^5$, $R^6$, $R^7$, and $R^8$ each independently is absent, hydrogen, halogen, or alkyl which is optionally substituted by halogen; or $R^5$ and $R^6$, together with E, form a cycle containing 5 to 6 atoms selected from carbon, nitrogen, oxygen, and sulfur, said cycle optionally substituted with halogen, amine, or alkyl.

21. The compound of claim 18, wherein $R^5$ and $R^8$ each independently is absent, hydrogen, halogen, or alkyl which is optionally substituted by halogen; $R^6$ and $R^7$ are absent and E and G, together with A and B, form a cycle containing 5 to 6 atoms selected from carbon, nitrogen, oxygen, and sulfur, said cycle optionally substituted with halogen or alkyl which is optionally substituted by halogen.

22. The compound of claim 18 which is selected from the group consisting of:

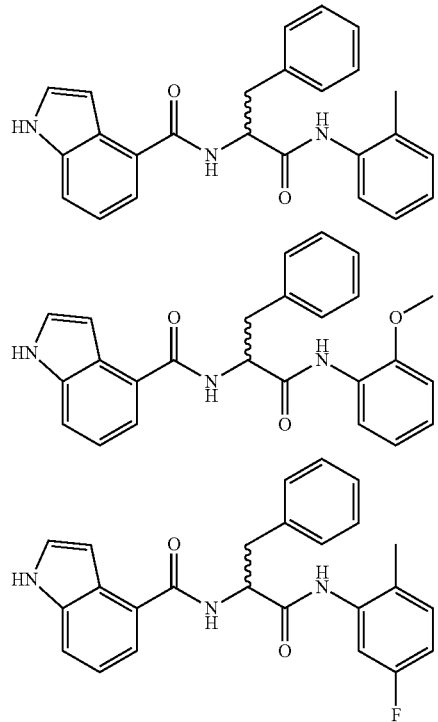

-continued

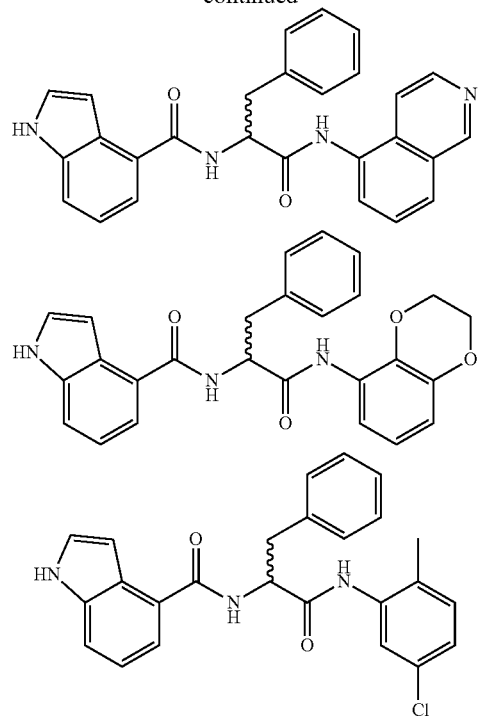

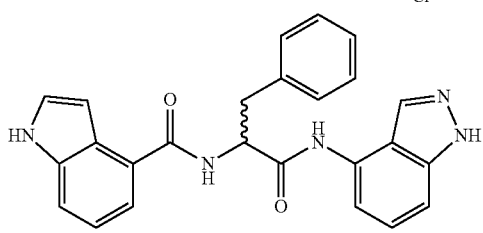

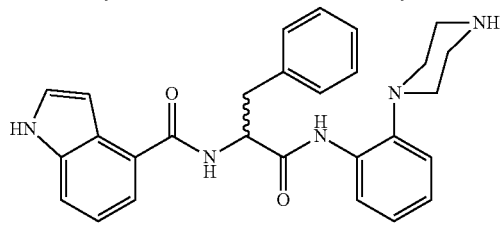

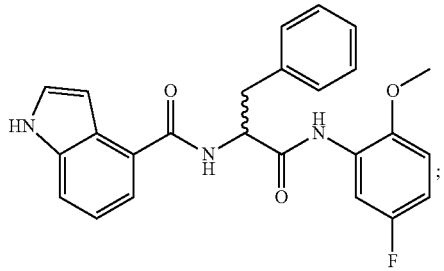

and salts thereof.

23. A compound selected from the group consisting of:
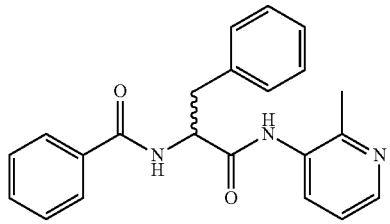
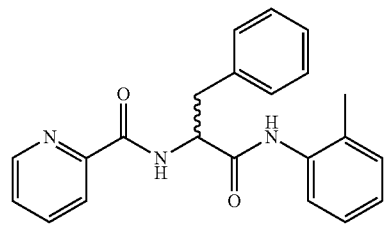
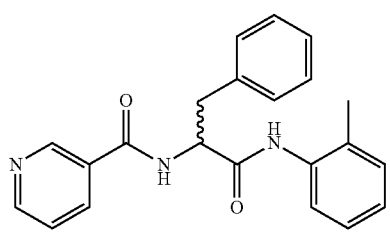
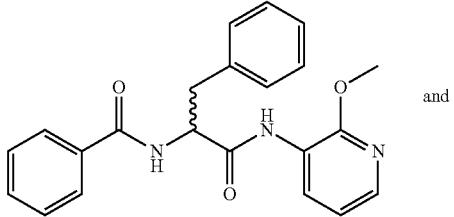
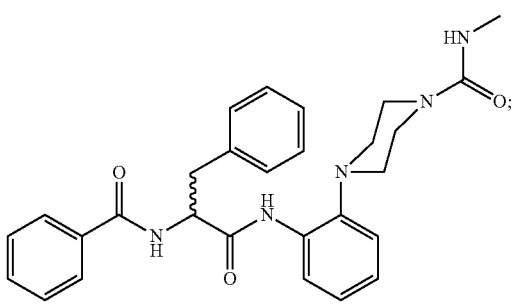
and salts thereof.

UNITED STATES PATENT AND TRADEMARK OFFICE
CERTIFICATE OF CORRECTION

PATENT NO. : 9,919,998 B2
APPLICATION NO. : 15/116787
DATED : March 20, 2018
INVENTOR(S) : Richard H. Ebright et al.

Page 1 of 1

It is certified that error appears in the above-identified patent and that said Letters Patent is hereby corrected as shown below:

In the Claims

Column 226, Line 42, Claim 1, please delete "hydroxy; -O-C(=O)-$C_1$-$C_4$alkyl," and insert
-- hydroxy, -O-C(=O)-$C_1$-$C_4$alkyl --;

Column 226, Line 44, Claim 1, please delete "phenyl, or morpholino" and insert
-- phenyl, or morpholino; --;

Column 226, Line 56, Claim 1, please delete "methyl group, $R^1$, $R^2$," and insert
-- methyl group, and $R^1$, $R^2$, --;

Column 236, Lines 37-47, Claim 3, please delete the following structure:

" 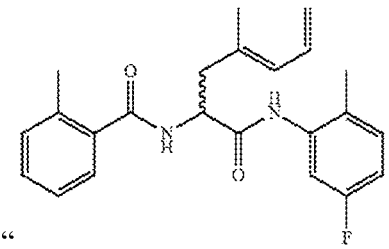 " and insert -- 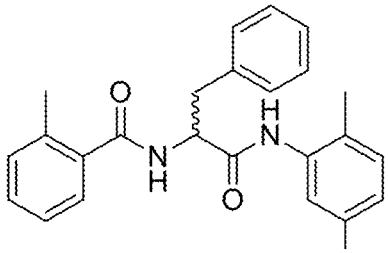 -- therefor.

Signed and Sealed this
Tenth Day of July, 2018

Andrei Iancu
*Director of the United States Patent and Trademark Office*

UNITED STATES PATENT AND TRADEMARK OFFICE
CERTIFICATE OF CORRECTION

PATENT NO. : 9,919,998 B2
APPLICATION NO. : 15/116787
DATED : March 20, 2018
INVENTOR(S) : Richard H. Ebright et al.

It is certified that error appears in the above-identified patent and that said Letters Patent is hereby corrected as shown below:

In the Specification

Column 1, Lines 16-19, please delete "This invention was made with government support under AI072766 and GM041376 awarded by the National Institutes of Health. The government has certain rights in the invention." and insert -- This invention was made with government support under grant numbers AI090837, AI072766, GM041376 awarded by the National Institutes of Health. The government has certain rights in the invention. -- therefor.

Signed and Sealed this
Twenty-fourth Day of January, 2023

Katherine Kelly Vidal
*Director of the United States Patent and Trademark Office*